United States Patent
Zhang et al.

(10) Patent No.: US 12,116,356 B2
(45) Date of Patent: *Oct. 15, 2024

(54) N-HETEROCYCLIC FIVE-MEMBERED RING-CONTAINING CAPSID PROTEIN ASSEMBLY INHIBITOR, PHARMACEUTICAL COMPOSITION THEREOF, AND USE THEREOF

(71) Applicant: CHIA TAI TIANQING PHARMACEUTICAL GROUP CO., LTD., Lianyungang (CN)

(72) Inventors: Yinsheng Zhang, Lianyungang (CN); Wangwei Ao, Lianyungang (CN); Yuan Li, Lianyungang (CN); Hui Wang, Lianyungang (CN); Hangzhou Shen, Lianyungang (CN); Jie Ni, Lianyungang (CN); Huan Zhang, Lianyungang (CN); Jie Wu, Lianyungang (CN); Li Zhang, Lianyungang (CN); Kai Cao, Lianyungang (CN); Peng Lu, Lianyungang (CN); Xushi Liu, Lianyungang (CN); Jie Wang, Lianyungang (CN); Tianxiao Zhao, Lianyungang (CN); Xingfeng Ge, Lianyungang (CN); Dandan Lu, Lianyungang (CN); Shuo Chen, Lianyungang (CN); Xueqin Ma, Lianyungang (CN); Wei Shi, Lianyungang (CN); Xiaojin Wang, Lianyungang (CN); Hongjiang Xu, Lianyungang (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 76 days.

This patent is subject to a terminal disclaimer.

(21) Appl. No.: 18/106,103

(22) Filed: Feb. 6, 2023

(65) Prior Publication Data
US 2023/0183208 A1  Jun. 15, 2023

Related U.S. Application Data

(63) Continuation of application No. 17/043,593, filed as application No. PCT/CN2019/080412 on Mar. 29, 2019, now Pat. No. 11,597,716.

(30) Foreign Application Priority Data

Mar. 30, 2018 (CN) .......................... 201810286111.1
Jul. 5, 2018 (CN) .......................... 201810730325.3
Jan. 25, 2019 (CN) .......................... 201910073465.2

(51) Int. Cl.
C07D 401/12 (2006.01)
C07D 207/34 (2006.01)
(Continued)

(52) U.S. Cl.
CPC ......... *C07D 401/12* (2013.01); *C07D 207/34* (2013.01); *C07D 405/12* (2013.01); *C07D 409/12* (2013.01)

(58) Field of Classification Search
None
See application file for complete search history.

(56) References Cited

U.S. PATENT DOCUMENTS 10,590,076 B2  3/2020  Burns et al.
11,597,716 B2  3/2023  Zhang et al.
(Continued)

FOREIGN PATENT DOCUMENTS

CN   105431413 A   3/2016
CN   105658624 A   6/2016
(Continued)

OTHER PUBLICATIONS

Nozaki, et al; Medicinal Drug Chemistry (Soyaku Kagaku); Jul. 1, 1995; 8 pgs.
(Continued)

*Primary Examiner* — Zinna Northington Davis
(74) *Attorney, Agent, or Firm* — Kilpatrick Townsend & Stockton LLP

(57) ABSTRACT

A N-heterocyclic five-membered ring-containing capsid protein assembly inhibitor, and a pharmaceutical composition and use thereof, specifically relating to a compound as represented by formula I, a stereoisomer, a tautomer, a geometrical isomer, a solvate, an active metabolite, a hydrate, a prodrug or a pharmaceutically acceptable salt thereof, a pharmaceutical composition thereof, and a medical use thereof. The medical use comprises the use in treating diseases benefiting from the capsid protein assembly inhibitor, and in particular, diseases caused by hepatitis B virus infection.

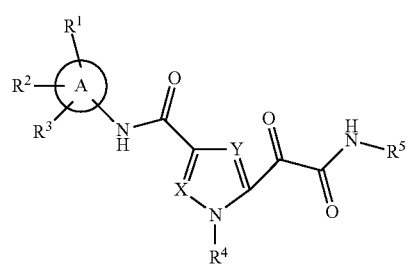

20 Claims, No Drawings

(51) Int. Cl.
   C07D 405/12   (2006.01)
   C07D 409/12   (2006.01)

(56) References Cited

U.S. PATENT DOCUMENTS

| | | |
|---|---|---|
| 2022/0185774 A1 | 6/2022 | Zhang et al. |
| 2022/0204510 A1 | 6/2022 | He et al. |

FOREIGN PATENT DOCUMENTS

| | | |
|---|---|---|
| CN | 105980378 A | 9/2016 |
| CN | 107721895 A | 2/2018 |
| CN | 109153640 A | 1/2019 |
| CN | 109790168 A | 5/2019 |
| CN | 112585118 A | 3/2021 |
| EP | 3915972 A1 | 12/2021 |
| RU | 2007107388 A | 9/2008 |
| WO | 2006012642 A2 | 2/2006 |
| WO | 2014184350 A1 | 11/2014 |
| WO | 2015011281 A1 | 1/2015 |
| WO | 2015059212 A1 | 4/2015 |
| WO | 2017156255 A1 | 9/2017 |
| WO | 2018039531 A1 | 3/2018 |
| WO | 2018050110 A1 | 3/2018 |
| WO | 2019154343 A1 | 8/2019 |
| WO | 2019165374 A1 | 8/2019 |
| WO | 2019185016 A1 | 10/2019 |
| WO | 2019223791 A1 | 11/2019 |
| WO | 2019241292 A1 | 12/2019 |
| WO | 2020151252 A1 | 7/2020 |
| WO | 2020156494 A1 | 8/2020 |
| WO | 2021058001 A1 | 4/2021 |
| WO | 2021058002 A1 | 4/2021 |

OTHER PUBLICATIONS

U.S. Appl. No. 17/043,593, Non-Final Office Action, Mailed On Dec. 17, 2021, 21 pages.
U.S. Appl. No. 17/043,593, Notice of Allowance, Mailed On Nov. 16, 2022, 10 pages.
U.S. Appl. No. 17/043,593, Notice of Allowance, Mailed On Jun. 1, 2022, 11 pages.
China National Intellectual Property Administration; Official Action; App. 2019800213174; Dec. 6, 2021; 3 pages.
European Patent Office; Extended European Search Report; App. No. 19777163.7; Nov. 25, 2021; 7 pages.
Banker et al., "Modern Pharmaceutics", Scientific & Technical Information, 3rd Edition, 1996, 2 pages.
Brahmania et al., "New Therapeutic Agents for Chronic Hepatitis B", The Lancet Infectious Diseases, vol. 16, No. 2, Jan. 2016, pp. e10-e21.
Bundgaard , "Design of prodrugs: Bioreversible Derivatives for Various Functional Groups and Chemical Entities", Design of Prodrugs, Chapter 1, 1985, 1 page.
Ettmayer et al., "Lessons Learned from Marketed and Investigational Prodrugs", Journal of Medicinal Chemistry, vol. 47, No. 10, May 2004, pp. 2393-2404.
Greene et al., "Protection for the Hydroxyl Group, Including 1,2-and 1,3-Diols", Hoboken, New Jersey: John Wiley & Sons, Inc., Greene's Protective Groups in Organic Synthesis, 4th Edition, Apr. 2006, 351 pages.
He, et al., Hepatitis B virus replication mechanisms and drug targets of chronic hepatitis B; Chinese Pharmacological Bulletin; Feb. 2015; 31 (2); pp. 152-156.
Jordan , "Tamoxifen: A Most Unlikely Pioneering Medicine", Nature Reviews, Drug Discovery, vol. 2, Issue 3, Mar. 2003, pp. 205-213.
Application No. PCT/CN2019/080412; International Search Report, Mailed on Jun. 27, 2019.
Application No. PCT/CN2019/108483 , International Search Report and Written Opinion, Mailed On Jan. 2, 2020, 28 pages.
Application No. PCT/CN2020/118426 , International Search Report and Written Opinion, Mailed On Jan. 5, 2021, 22 pages.
Application No. PCT/CN2020/118427 , International Search Report and Written Opinion, Mailed On Dec. 31, 2020, 22 pages.
Silverman , "The Organic Chemistry of Drug Design and Drug Action", Prodrugs and Drug Delivery Systems, Chapter 8, 1992, 522 pages.
Stella , "Prodrugs as Therapeutics", Expert Opinion on Therapeutic Patents, vol. 14, No. 3, 2004, pp. 277-280.
Testa, "Prodrug Research: Futile or Fertile?", Biochemical Pharmacology, vol. 68, Dec. 1, 2004, pp. 2097-2106.
Wolff et al., "Burger's Medicinal Chemistry and Drug Discovery", 5th Edition, vol. 1, Principles and Practice, Jan. 1995, pp. 949-982.
Wolff, "Burger's Medicinal Chemistry and Drug Discovery", Fifth Edition, vol. 1, 1996, pp. 975-976.
Alekseyev, Optical Isomerism and Drugs Pharmacological Activity, Soros Educational Journal, 1998, pp. 49-55.
Knunyants, Chemical Encyclopedic Dictionary, Moscow, Soviet Encyclopedia, 1983, pp. 130-131.
Kummerer, Pharmaceuticals in the environment; Annual Review of Environment and Resources; 2010, v.35, pp. 57-75, doi: 10.1146/annurev-environ-052809-161223.
Patent Office of the Russian Federation, Office Action of Application No. 2021123614/04(049497), dated Feb. 28, 2023, 27 pages with translation.

N-HETEROCYCLIC FIVE-MEMBERED RING-CONTAINING CAPSID PROTEIN ASSEMBLY INHIBITOR, PHARMACEUTICAL COMPOSITION THEREOF, AND USE THEREOF

CROSS-REFERENCE TO RELATED APPLICATIONS

The present application is a continuation of U.S. application Ser. No. 17/043,593, filed Sep. 29, 2020, which is a § 371 National Phase Application of PCT/CN2019/080412, filed Mar. 29, 2019, which application claims the priorities and benefits of Chinese Patent Application No. 201810286111.1 filed with the China National Intellectual Property Administration on Mar. 30, 2018, Chinese Patent Application No. 201810730325.3 filed with the China National Intellectual Property Administration on Jul. 5, 2018, and Chinese Patent Application No. 201910073465.2 filed with the China National Intellectual Property Administration on Jan. 25, 2019, the disclosures of which are incorporated herein by reference in their entireties, for all purposes herein.

TECHNICAL FIELD

The present application relates to a compound of Formula I, a stereoisomer, a tautomer, a geometric isomer, a solvate, an active metabolite, a hydrate, a prodrug or a pharmaceutically acceptable salt thereof, and a process for the preparation thereof, a pharmaceutical composition comprising the same, and use thereof as a medicament for treating hepatitis B virus infection.

BACKGROUND

Currently, chronic hepatitis B can not be cured and only controlled, and is limited to two types of drugs (interferons and nucleoside analogs/inhibitors of viral polymerases). The lower cure rate of HBV is partially due to the presence and persistence of covalently closed circular DNA (cccDNA) in the nucleus of infected hepatocytes. Current treatment protocols are unable to remove cccDNA from the repository, and some new targets for HBV such as Core inhibitors (such as viral capsid protein formation or assembly inhibitors, cccDNA inhibitors, interferon-stimulated gene activators, and etc.) is expected to bring hope to curing hepatitis B (Mayur Brahmania, et al. New therapeutic agents for chronic hepatitis B).

The HBV capsid is assembled from the core protein. HBV reverse transcriptase and pgRNA need to be correctly encapsulated before reverse transcription. Therefore, blocking capsid protein assembly, or accelerating capsid protein degradation would block the assembly process of the capsid protein, and thereby affecting viral replication. In recent years, researchers have begun to study inhibitors targeting capsid protein assembly, for example, WO2014184350, WO2015011281, WO2017156255, etc., disclose a series of related compounds. However, most of them are in the early stage of clinical research or the research has been terminated, and there is a need in the art for more alternative effective capsid protein assembly inhibitors for treating, ameliorating or preventing HBV infection. The present invention synthesized a series of novel derivatives and studied their HBV protein assembly activity.

DETAILED DESCRIPTION OF THE INVENTION

The present application relates to a compound of Formula I, a stereoisomer, a tautomer, a geometric isomer, a solvate, an active metabolite, a hydrate, a prodrug or a pharmaceutically acceptable salt thereof,

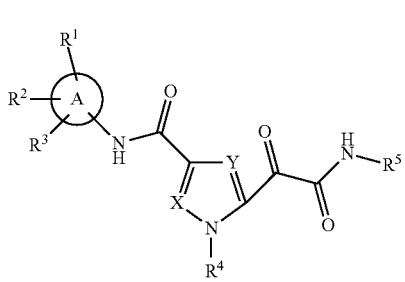

I wherein,
X and Y each independently represent $CR^7$, and said $R^7$ is independently selected from the group consisting of hydrogen, $C_{3-4}$ cycloalkyl, —CN, fluoro, chloro, bromo and $C_{1-3}$ alkyl, wherein said $C_{1-3}$ alkyl is optionally substituted with one or more groups selected from the group consisting of fluoro, chloro, bromo, $C_{1-6}$ alkoxy, —OH, —$NH_2$ and —CN;
ring A is selected from the group consisting of phenyl and 5- to 10-membered heteroaryl;
$R^1$, $R^2$ and $R^3$ are each independently selected from the group consisting of hydrogen, fluoro, chloro, bromo, —$CHF_2$, —$CH_2F$, —$CF_3$, —CN, $C_{1-3}$ alkyl, —$NH_2$, $C_{3-4}$ cycloalkyl, —$NHR^a$ and —$NR^bR^c$, wherein $R^a$, $R^b$ and $R^c$ are each independently selected from the group consisting of —$C(O)C_{1-6}$ alkyl, $C_{1-6}$ alkyl, —$S(O)_2C_{1-6}$ alkyl, 5- to 10-membered heteroaryl, $C_{6-10}$ aryl, $C_{3-6}$ cycloalkyl and 3- to 6-membered heterocycloalkyl;
$R^4$ is selected from the group consisting of hydrogen, $C_{1-3}$ alkyl and $C_{3-4}$ cycloalkyl;
$R^5$ is selected from the group consisting of $C_{1-6}$ alkyl, $C_{2-6}$ alkenyl, $C_{2-6}$ alkynyl, 3- to 7-membered cycloalkyl and 3- to 7-membered heterocycloalkyl, wherein said $C_{1-6}$ alkyl, $C_{2-6}$ alkenyl, $C_{2-6}$ alkynyl, 3- to 7-membered cycloalkyl and 3- to 7-membered heterocycloalkyl are optionally substituted with the group(s) selected from the group consisting of halo, 3- to 4-membered cycloalkyl, 3- to 4-membered heterocycloalkyl, —$OR^8$, oxo, —CN, —$C(O)OR^8$, —$SO_2R^8$, —$C(O)N(R^8)_2$, and $C_{1-3}$ alkyl, wherein $C_{1-3}$ alkyl is optionally substituted with one or more groups selected from the group consisting of fluoro, —CN and —OH; and
each $R^8$ is independently selected from the group consisting of hydrogen and $C_{1-3}$ alkyl.
In some embodiments, the above X and Y each independently represent $CR^7$, and said $R^7$ is independently selected from the group consisting of hydrogen, fluoro, chloro, bromo and $C_{1-3}$ alkyl, wherein said $C_{1-3}$ alkyl is optionally substituted with one or more groups selected from the group consisting of fluoro and $C_{1-3}$ alkoxy; in some embodiments, said $R^7$ is independently selected from the group consisting of hydrogen, fluoro, chloro, bromo, and $C_{1-3}$ alkyl, wherein $C_{1-3}$ alkyl is optionally substituted with one or more methoxy; in some embodiments, said $R^7$ is independently selected from the group consisting of hydrogen, fluoro, chloro, bromo, —$CH_2OCH_3$ and methyl; in some embodiments, said $R^7$ is independently selected from the group consisting of hydrogen, chloro, bromo and methyl.

In some other embodiments, X and Y each independently represent $CR^7$, and said $R^7$ is independently selected from the group consisting of hydrogen, $C_{3-4}$ cycloalkyl, —CN, fluoro, chloro, bromo, and $C_{1-3}$ alkyl, wherein $C_{1-3}$ alkyl is optionally substituted with one or more fluoro. In some other embodiments, the above X and Y each independently represent $CR^7$, and said $R^7$ is independently selected from the group consisting of hydrogen, fluoro, chloro, bromo, and $C_{1-3}$ alkyl, wherein $C_{1-3}$ alkyl is optionally substituted with one or more fluoro; in some other embodiments, the $R^7$ is independently selected from the group consisting of hydrogen, fluoro, chloro, bromo and $C_{1-3}$ alkyl; in some other embodiments, the $R^7$ is independently selected from the group consisting of hydrogen, fluoro, chloro, bromo and methyl.

In some embodiments, the above ring A is selected from the group consisting of phenyl, 5-membered heteroaryl, 6-membered heteroaryl, 7-membered heteroaryl, 8-membered heteroaryl, 9-membered heteroaryl and 10-membered heteroaryl; in some embodiments, ring A is selected from the group consisting of phenyl and 6-membered heteroaryl; in some embodiments, ring A is selected from the group consisting of phenyl and pyridyl. In some embodiments, the "heteroaryl" in the above definitions of ring A contains 1 or 2 N atoms.

In some other embodiments, ring A is selected from phenyl.

In some embodiments, $R^a$ is selected from the group consisting of —C(O)$C_{1-3}$ alkyl, $C_{1-3}$ alkyl, —S(O)$_2C_{1-3}$ alkyl, 5- to 6-membered heteroaryl, $C_{6-10}$ aryl, $C_{3-6}$ cycloalkyl, and 3- to 6-membered heterocycloalkyl; in some embodiments, $R^a$ is selected from the group consisting of —C(O)$C_{1-3}$ alkyl, $C_{1-3}$ alkyl, and —S(O)$_2C_{1-3}$ alkyl; in some embodiments, $R^a$ is selected from the group consisting of —C(O)CH$_3$, and —S(O)$_2$CH$_3$.

In some embodiments, $R^b$ and $R^c$ are each independently selected from the group consisting of —C(O)$C_{1-3}$ alkyl, $C_{1-3}$ alkyl, —S(O)$_2C_{1-3}$ alkyl, 5- to 6-membered heteroaryl, $C_{6-10}$ aryl, $C_{3-6}$ cycloalkyl, and 3- to 6-membered heterocycloalkyl; in some embodiments, $R^b$ and $R^c$ are each independently selected from the group consisting of —C(O)$C_{1-3}$ alkyl, $C_{1-3}$ alkyl, and —S(O)$_2C_{1-3}$ alkyl.

In still some other embodiments, $R^1$, $R^2$ and $R^3$ are each independently selected from the group consisting of hydrogen, fluoro, chloro, bromo, —CHF$_2$, —CH$_2$F, —CF$_3$, —CN, $C_{1-3}$ alkyl, —NH$_2$, and $C_{3-4}$ cycloalkyl.

In some embodiments, the above $R^1$ is selected from the group consisting of hydrogen, fluoro, chloro, —CHF$_2$, —CN, —CF$_3$ and methyl; in some embodiments, the above $R^1$ is selected from the group consisting of hydrogen and fluoro.

In some embodiments, the above $R^2$ is selected from the group consisting of hydrogen, fluoro, chloro, and bromo; in some embodiments, the above $R^2$ is selected from the group consisting of hydrogen and fluoro.

In some embodiments, the above $R^3$ is selected from the group consisting of hydrogen, fluoro, chloro, —CHF$_2$, —CN, —CF$_3$, methyl, —NH$_2$ and —NHR$^a$; in some embodiments, the above $R^3$ is selected from the group consisting of hydrogen, fluoro, chloro, —CHF$_2$, —CN, —CF$_3$, methyl, —NH$_2$, —NHC(O)CH$_3$, and —NHS(O)$_2$CH$_3$; in some embodiments, the above $R^3$ is selected from the group consisting of hydrogen, fluoro, chloro, —CHF$_2$, —CN, —CF$_3$, methyl, and —NH$_2$; in some embodiments, the above $R^3$ is selected from the group consisting of hydrogen, fluoro, chloro, —CN, methyl, and —NH$_2$.

In some embodiments, $R^1$ is selected from the group consisting of hydrogen, fluoro, chloro, —CHF$_2$, —CN, —CF$_3$ and methyl, and at least one of $R^1$ and $R^3$ is selected from the group consisting of fluoro and hydrogen.

In some embodiments, one of $R^1$ and $R^3$ is selected from the group consisting of hydrogen and fluoro, and the other is selected from the group consisting of hydrogen, fluoro, chloro, —CHF$_2$, —CN, —CF$_3$, methyl and —NH$_2$.

In some embodiments, the above $R^2$ is selected from the group consisting of fluoro, chloro, and bromo, and one of $R^1$ and $R^3$ is hydrogen, and the other is selected from the group consisting of hydrogen, fluoro, chloro, —CHF$_2$, —CN, —CF$_3$ and methyl; in some embodiments, the above $R^2$ is fluoro, and one of $R^1$ and $R^3$ is hydrogen, and the other is selected from the group consisting of fluoro, chloro and —CN; in some embodiments, the above $R^2$ is fluoro, $R^1$ is hydrogen, and $R^3$ is —CN or chloro. In some embodiments, above $R^2$ is fluoro, $R^1$ is hydrogen, and $R^3$ is —CN.

In some other embodiments, one of $R^1$ and $R^3$ is hydrogen, and the other is selected from the group consisting of fluoro, chloro, —CHF$_2$, —CN, —CF$_3$ and methyl.

In some other embodiments, X and Y are each independently represent $CR^7$, and said $R^7$ is independently selected from the group consisting of hydrogen, $C_{3-4}$ cycloalkyl, —CN, fluoro, chloro, bromo, and $C_{1-3}$ alkyl, wherein $C_{1-3}$ alkyl is optionally substituted with one or more fluoro; $R^1$, $R^2$ and $R^3$ are each independently selected from the group consisting of hydrogen, fluoro, chloro, bromo, —CHF$_2$, —CH$_2$F, —CF$_3$, —CN, $C_{1-3}$ alkyl and $C_{3-4}$ cycloalkyl.

In some embodiments, the above $R^4$ is selected from the group consisting of hydrogen and $C_{1-3}$ alkyl; in some embodiments, the above $R^4$ is methyl or hydrogen.

In some other embodiments, the above $R^4$ is methyl.

In some embodiments, the above $R^5$ is selected from the group consisting of $C_{1-4}$ alkyl, $C_{2-4}$ alkenyl, $C_{2-4}$ alkynyl, 3- to 6-membered cycloalkyl and 4- to 6-membered heterocycloalkyl, wherein said $C_{1-4}$ alkyl, $C_{2-4}$ alkenyl, $C_{2-4}$ alkynyl, 3- to 6-membered cycloalkyl or 4- to 6-membered heterocycloalkyl is optionally substituted with the group(s) selected from the group consisting of halo, 3- to 4-membered cycloalkyl, 3- to 4-membered heterocycloalkyl, —OR$^8$, oxo, —CN, —C(O)OR$^8$, —SO$_2$R$^8$, —C(O)N(R$^8$)$_2$, and $C_{1-3}$ alkyl, wherein $C_{1-3}$ alkyl is optionally substituted with one or more groups selected from the group consisting of fluoro, —CN and —OH; in some embodiments, the above $R^5$ is selected from the group consisting of $C_{1-4}$ alkyl, $C_{2-4}$ alkenyl, $C_{2-4}$ alkynyl, 3- to 6-membered cycloalkyl and 4- to 6-membered heterocycloalkyl, wherein said $C_{1-4}$ alkyl, $C_{2-4}$ alkenyl, $C_{2-4}$ alkynyl, 3- to 6-membered cycloalkyl or 4- to 6-membered heterocycloalkyl is optionally substituted with the group(s) selected from the group consisting of halo, oxo, —OH, —CN, —C(O)OR$^8$, —C(O)N(R$^8$)$_2$, and $C_{1-3}$ alkyl, wherein $C_{1-3}$ alkyl is optionally substituted with one or more groups selected from the group consisting of fluoro and OH; in some embodiments, the above $R^5$ is selected from the group consisting of $C_{1-4}$ alkyl, $C_{2-4}$ alkynyl, 3- to 6-membered cycloalkyl and 4- to 6-membered heterocycloalkyl, wherein said $C_{1-4}$ alkyl, $C_{2-4}$ alkynyl, 3- to 6-membered cycloalkyl or 4- to 6-membered heterocycloalkyl is optionally substituted with the group(s) selected from the group consisting of halo, oxo, —OH, —C(O)N(R$^8$)$_2$, —C(O)OR$^8$, and $C_{1-3}$ alkyl, wherein $C_{1-3}$ alkyl is optionally substituted with one or more groups selected from the group consisting of OH and fluoro; in some embodiments, the above $R^5$ is selected from the group consisting of $C_{1-4}$ alkyl, $C_{2-4}$ alkynyl, 3- to 6-membered cycloalkyl and 4- to 6-membered heterocycloalkyl, wherein said $C_{1-4}$ alkyl is optionally substituted with the group(s) selected from the group consisting of halo, —OH and —C(O)OR$^8$, wherein the 3- to 6-membered cycloalkyl or 4- to 6-membered heterocycloalkyl is optionally substituted with the group(s) selected from the group consisting of oxo, —OH, fluoro, —C(O)N(R$^8$)$_2$, and $C_{1-3}$ alkyl, wherein $C_{1-3}$ alkyl is optionally substituted with one or more groups selected from the group consisting of OH and fluoro; in some embodiments, the above R$^5$ is selected from the group consisting of $C_{1-4}$ alkyl, $C_3$ alkynyl, 3- to 6-membered cycloalkyl and 4- to 6-membered heterocycloalkyl, wherein said $C_{1-4}$ alkyl is optionally substituted with the group(s) selected from the group consisting of fluoro, —OH and —C(O)OCH$_3$, wherein said 3- to 6-membered cycloalkyl or 4- to 6-membered heterocycloalkyl is optionally substituted with the group(s) selected from the group consisting of oxo, —OH, fluoro, —C(O)NHCH$_3$, and methyl, wherein methyl is optionally substituted with one or more groups selected from the group consisting of OH and fluoro.

In some other embodiments, the above R$^5$ is selected from the group consisting of $C_{1-4}$ alkyl, $C_{2-4}$ alkenyl, $C_{2-4}$ alkynyl, 3- to 6-membered cycloalkyl and 4- to 6-membered heterocycloalkyl, wherein said $C_{1-4}$ alkyl, $C_{2-4}$ alkenyl, $C_{2-4}$ alkynyl, 3- to 6-membered cycloalkyl or 4- to 6-membered heterocycloalkyl is optionally substituted with the group(s) selected from the group consisting of halo, —OH, —CN, —C(O)OR$^8$, —C(O)N(R$^8$)$_2$, and $C_{1-3}$ alkyl, wherein $C_{1-3}$ alkyl is optionally substituted with one or more groups selected from the group consisting of fluoro and —OH; in some other embodiments, the above R$^5$ is selected from the group consisting of $C_{1-4}$ alkyl, $C_{2-4}$ alkynyl, 3- to 6-membered cycloalkyl and 4- to 6-membered heterocycloalkyl, wherein said $C_{1-4}$ alkyl, $C_{2-4}$ alkynyl, 3- to 6-membered cycloalkyl or 4- to 6-membered heterocycloalkyl is optionally substituted with the group(s) selected from the group consisting of halo, —OH, —C(O)N(R$^8$)$_2$, —C(O)OR$^8$, and $C_{1-3}$ alkyl, wherein $C_{1-3}$ alkyl is optionally substituted with one or more groups selected from the group consisting of OH and fluoro; in some other embodiments, the above R$^5$ is selected from the group consisting of $C_{1-4}$ alkyl, $C_{2-4}$ alkynyl, 3- to 6-membered cycloalkyl and 4- to 6-membered heterocycloalkyl, wherein said $C_{1-4}$ alkyl is optionally substituted with the group(s) selected from the group consisting of halo, —OH and —C(O)OR$^8$, wherein said 3- to 6-membered cycloalkyl or 4- to 6-membered heterocycloalkyl is optionally substituted with the group(s) selected from the group consisting of —OH, fluoro, —C(O)N(R$^8$)$_2$, and $C_{1-3}$ alkyl, wherein $C_{1-3}$ alkyl is optionally substituted with the group(s) selected from the group consisting of OH and fluoro; in some other embodiments, the above R$^5$ is selected from the group consisting of $C_{1-4}$ alkyl, $C_3$ alkynyl, 3- to 6-membered cycloalkyl and 4- to 6-membered heterocycloalkyl, wherein said $C_{1-4}$ alkyl is optionally substituted with the group(s) selected from the group consisting of fluoro, —OH and —C(O)OCH$_3$, wherein said 3- to 6-membered cycloalkyl or 4- to 6-membered heterocycloalkyl is optionally substituted with the group(s) selected from the group consisting of —OH, fluoro, —C(O)NHCH$_3$, and methyl, wherein methyl is optionally substituted with the group(s) selected from the group consisting of OH and fluoro.

In still some other embodiments, the above R$^5$ is selected from the group consisting of $C_{1-4}$ alkyl, $C_{2-4}$ alkenyl, $C_{2-4}$ alkynyl, 4- to 6-membered cycloalkyl and 4- to 6-membered heterocycloalkyl, wherein said $C_{1-4}$ alkyl, $C_{2-4}$ alkenyl, $C_{2-4}$ alkynyl, 4- to 6-membered cycloalkyl or 4- to 6-membered heterocycloalkyl is optionally substituted with the group(s) selected from the group consisting of halo, 3- to 4-membered cycloalkyl, 3- to 4-membered heterocycloalkyl, —OR$^8$, oxo, —CN, —C(O)OR$^8$, —SO$_2$R$^8$, —C(O)N(R$^8$)$_2$, and $C_{1-3}$ alkyl, wherein $C_{1-3}$ alkyl is optionally substituted with one or more groups selected from the group consisting of fluoro, —CN and —OH, each R$^8$ is independently selected from the group consisting of hydrogen and $C_{1-3}$ alkyl; in still some other embodiments, the above R$^5$ is selected from the group consisting of $C_{1-4}$ alkyl, $C_{2-4}$ alkenyl, $C_{2-4}$ alkynyl, 4- to 6-membered cycloalkyl and 4- to 6-membered heterocycloalkyl, wherein $C_{1-4}$ alkyl, $C_{2-4}$ alkenyl, $C_{2-4}$ alkynyl, 4- to 6-membered cycloalkyl or 4- to 6-membered heterocycloalkyl is optionally substituted with the group(s) selected from the group consisting of halo, —OH, —CN, —C(O)OR$^8$, —C(O)N(R$^8$)$_2$, and $C_{1-3}$ alkyl, wherein $C_{1-3}$ alkyl is optionally substituted with one or more groups selected from the group consisting of fluoro and OH, each R$^8$ is independently selected from the group consisting of hydrogen and $C_{1-3}$ alkyl; in still some other embodiments, the above R$^5$ is selected from the group consisting of $C_{1-4}$ alkyl, $C_{2-4}$ alkynyl, 4- to 6-membered cycloalkyl and 4- to 6-membered heterocycloalkyl, wherein $C_{1-4}$ alkyl, $C_{2-4}$ alkynyl, 4- to 6-membered cycloalkyl or 4- to 6-membered heterocycloalkyl is optionally substituted with the group(s) selected from the group consisting of halo, —OH, —C(O)OR$^8$, and $C_{1-3}$ alkyl, wherein $C_{1-3}$ alkyl is optionally substituted with OH, each R$^8$ is selected from the group consisting of hydrogen and $C_{1-3}$ alkyl; in still some other embodiments, the above R$^5$ is selected from the group consisting of $C_{1-4}$ alkyl, $C_{2-4}$ alkynyl, 4- to 6-membered cycloalkyl and 4- to 6-membered heterocycloalkyl, wherein $C_{1-4}$ alkyl is optionally substituted with the group(s) selected from the group consisting of halo, —OH, and —C(O)OR$^8$, wherein said 4- to 6-membered cycloalkyl or 4- to 6-membered heterocycloalkyl is optionally substituted with the group(s) selected from the group consisting of —OH, and methyl, wherein methyl is optionally substituted with OH.

In some embodiments, the "heterocycloalkyl" in the above definitions of R$^5$ contains 1 or 2 heteroatoms selected from the group consisting of N, O and S.

In some embodiments, each R$^8$ is independently selected from the group consisting of hydrogen and methyl.

In some embodiments, the structural unit

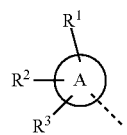

is selected from the group consisting of

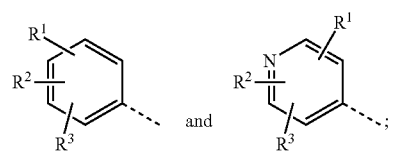

in some embodiments, the structural unit

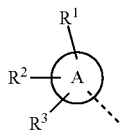

is selected from the group consisting of

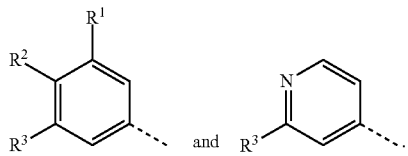

In some embodiments, the structural unit

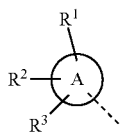

is selected from

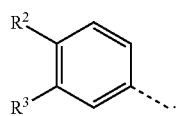

In some embodiments, the structural unit

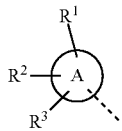

is selected from the group consisting of

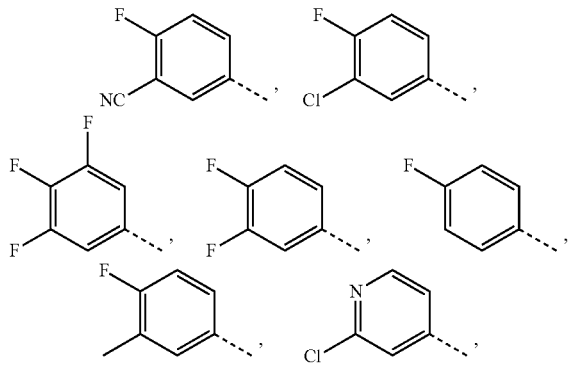

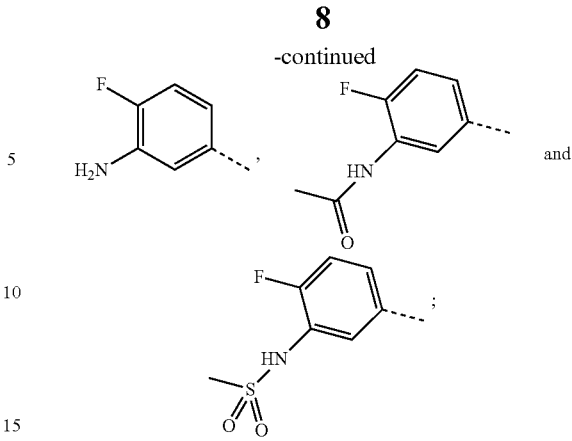

in some specific embodiments, the structural unit

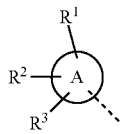

is selected from the group consisting of

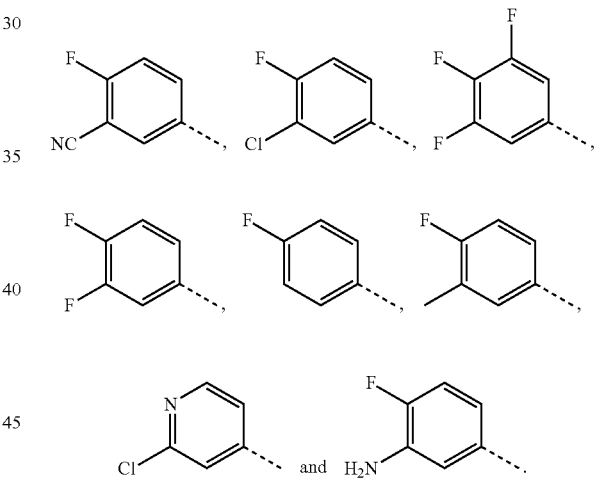

In some specific embodiments, the structural unit

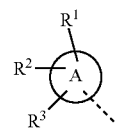

is selected from the group consisting of

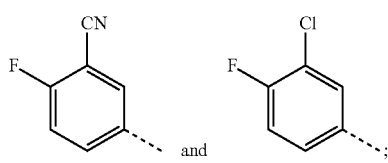

in some specific embodiments, the structural unit

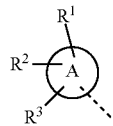

is

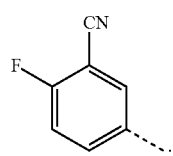

In some other embodiments, the structural unit

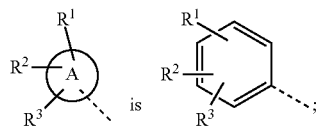

in some other embodiments, the structural unit

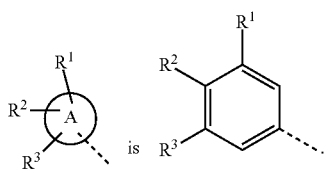

In some other specific embodiments, the structural unit

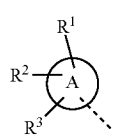

is selected from the group consisting of

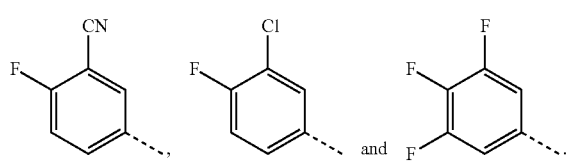

In some embodiments, the structural unit

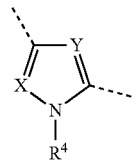

is selected from the group consisting of

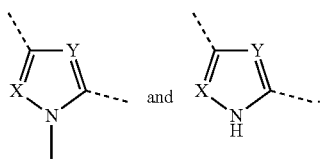

In some specific embodiments, the structural unit

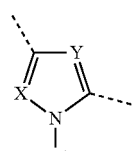

is selected from the group consisting of

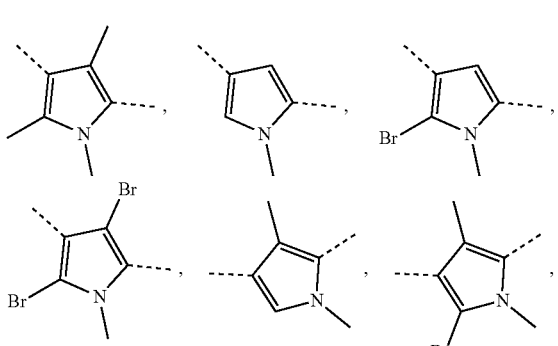

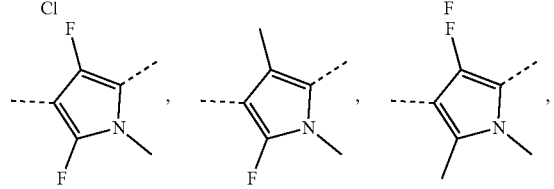

-continued
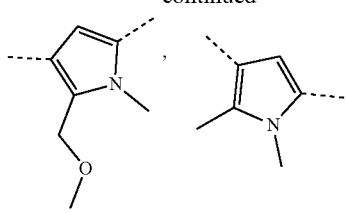, and
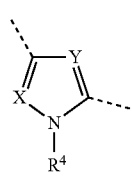;
in some specific embodiments, the structural unit
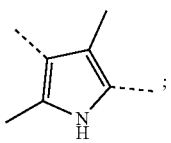
is selected from the group consisting of
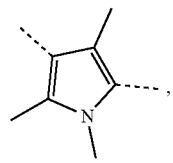, 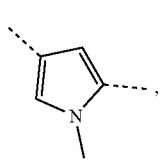, 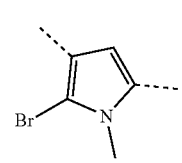,
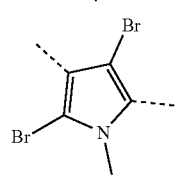, 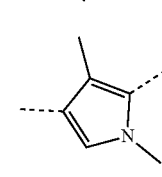, 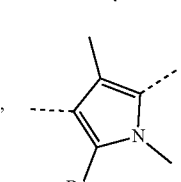,
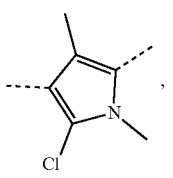, 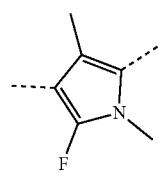, 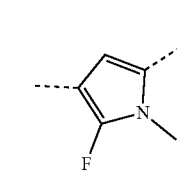,
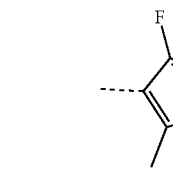, 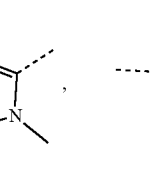,
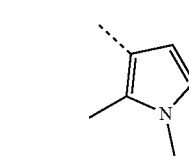 and 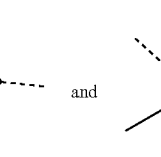;
In some other embodiments, the structural unit
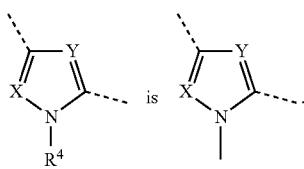 is
In some other specific embodiments, the structural unit
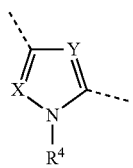
is selected from the group consisting of
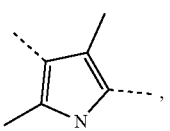, 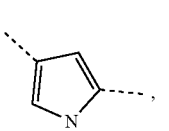, 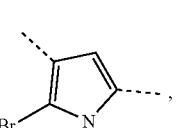,
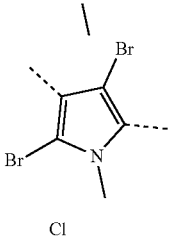, 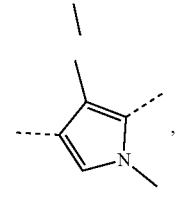, 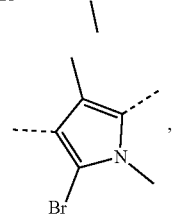,
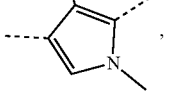, 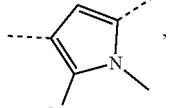, 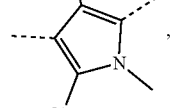,
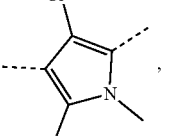, 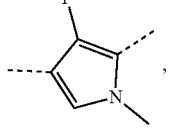, 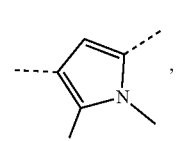,
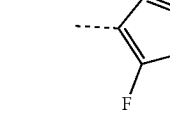 and 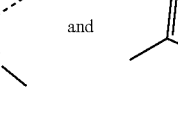;
in some other specific embodiments, the structural unit
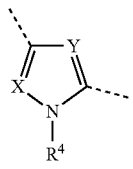

is selected from the group consisting of
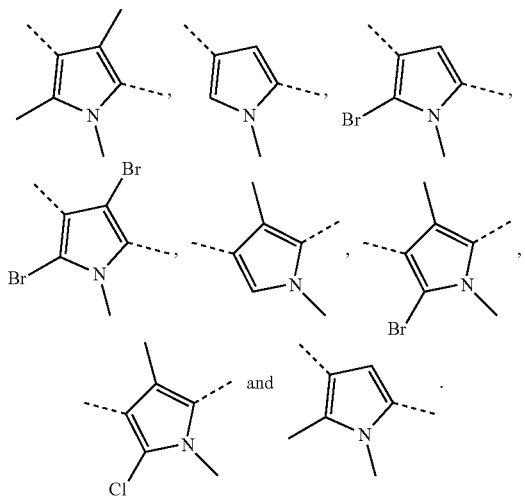
In some specific embodiments, the structural unit
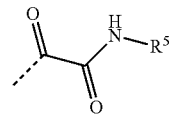
is selected from the group consisting of
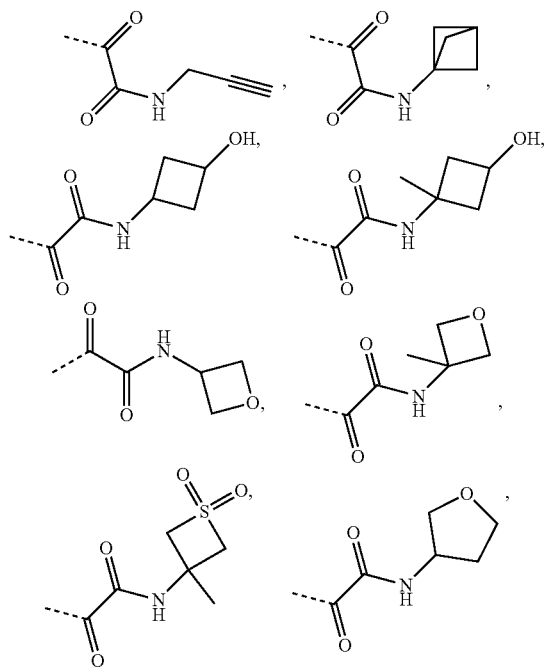
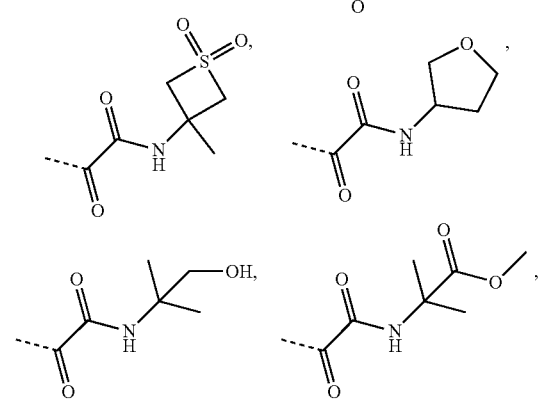
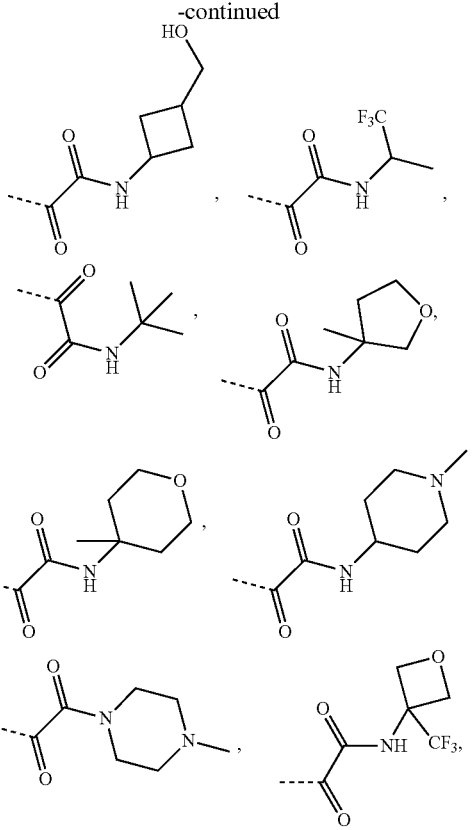
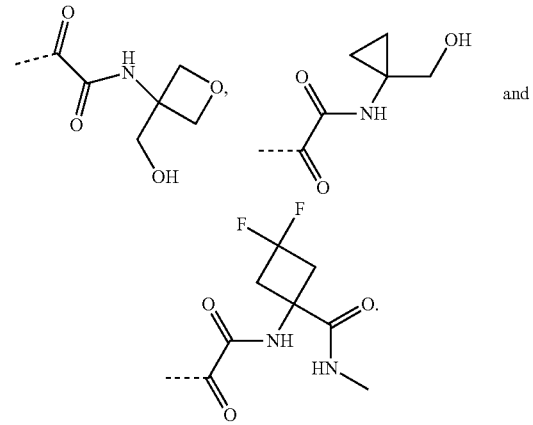
In some specific embodiments, the structural unit
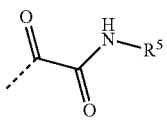
is selected from the group consisting of
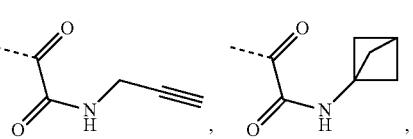

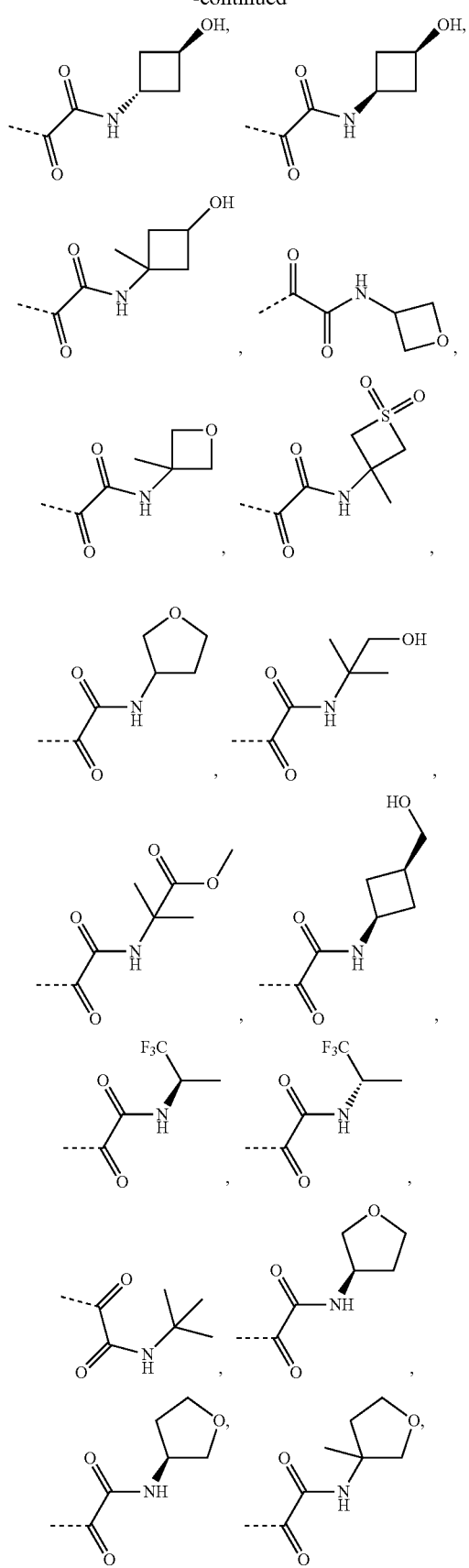
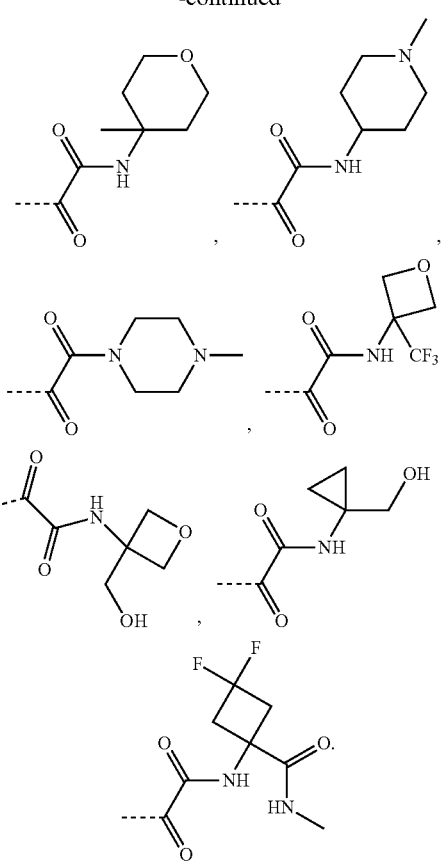
In some other specific embodiments, the structural unit
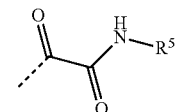
is selected from the group consisting of
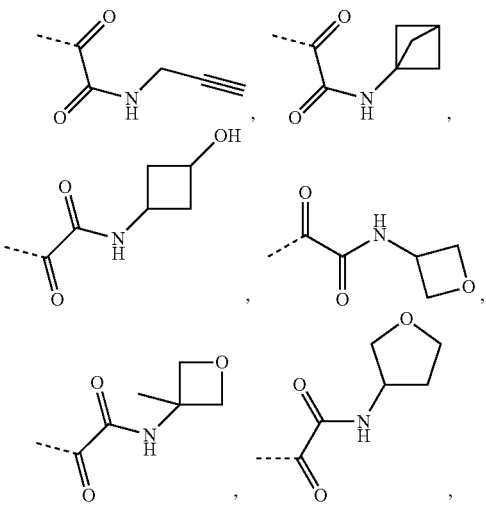

-continued
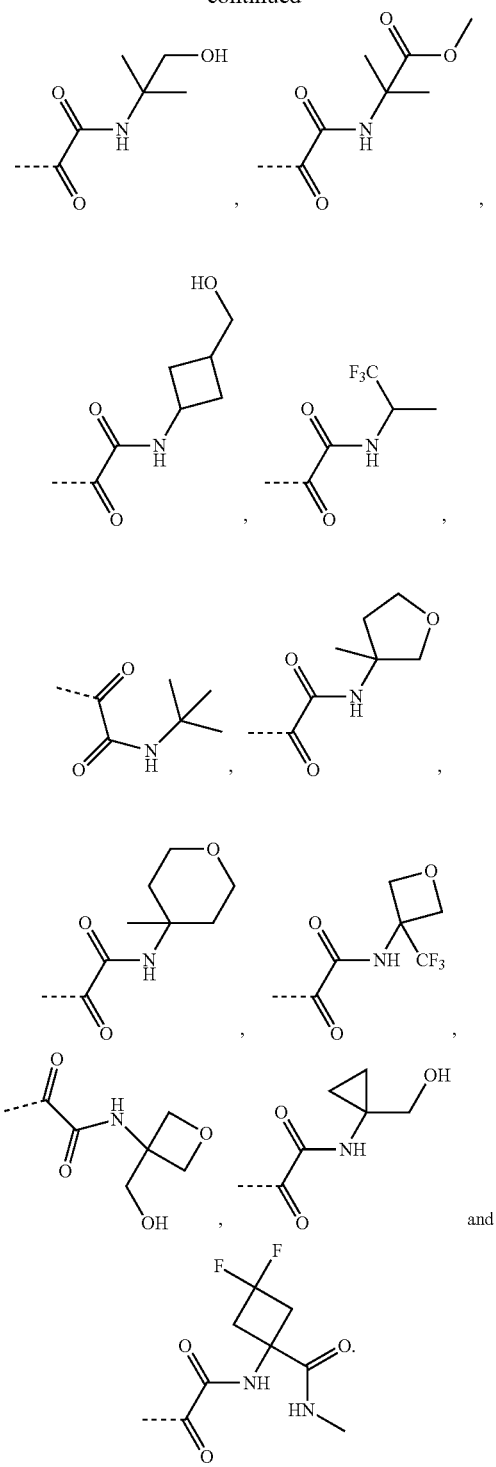
In some other specific embodiments, the structural unit is selected from the group consisting of
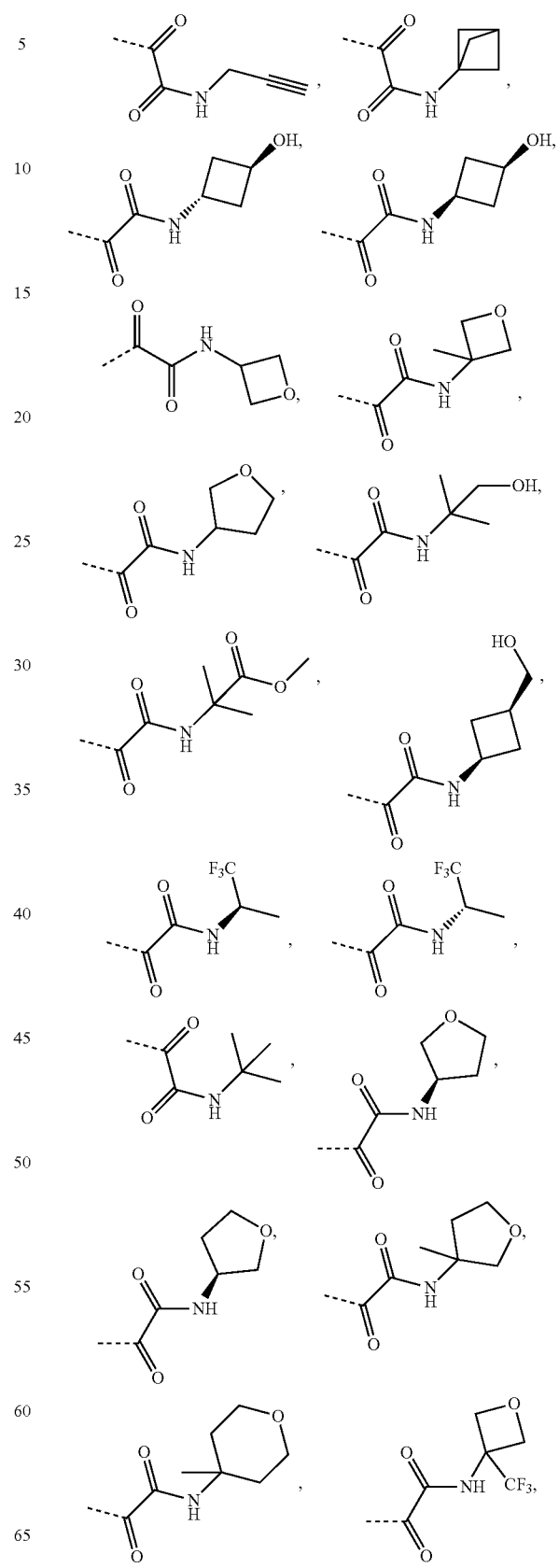

-continued
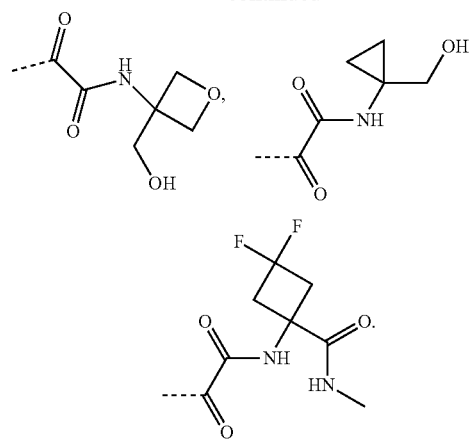
In still some other specific embodiments, the structural unit
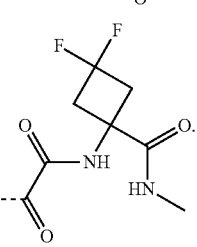
is selected from the group consisting of
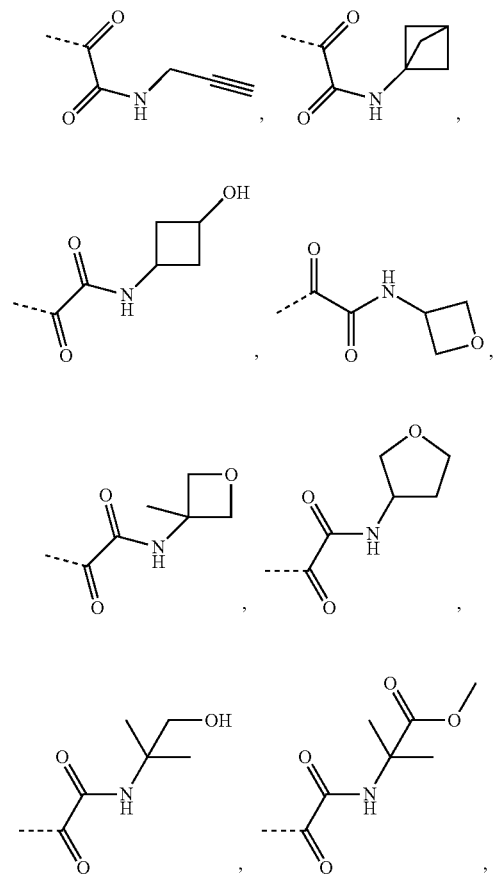
-continued
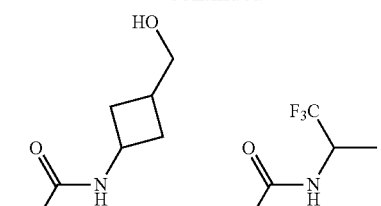
In still some other specific embodiments, the structural unit
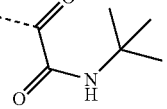
is selected from the group consisting of
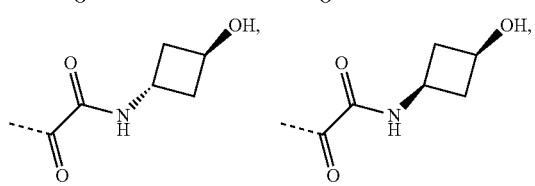
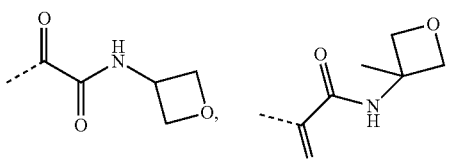
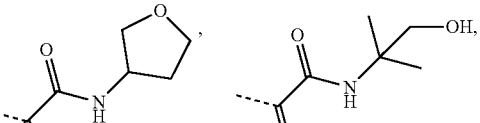
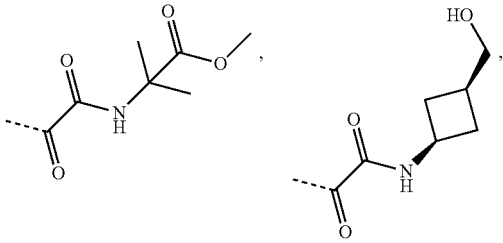

-continued

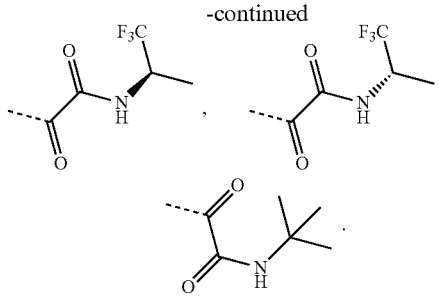

In some embodiments, the compound of Formula I, a stereoisomer, a tautomer, a geometric isomer, a solvate, an active metabolite, a hydrate, a prodrug or a pharmaceutically acceptable salt thereof of the present application is selected from a compound of Formula II, Formula III or Formula IV, or a stereoisomer, a tautomer, a geometric isomer, a solvate, an active metabolite, a hydrate, a prodrug or a pharmaceutically acceptable salt thereof,

II

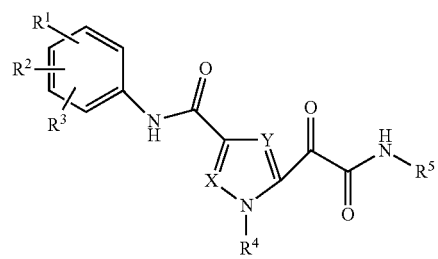

III

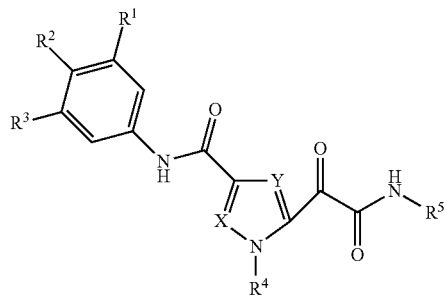

IV

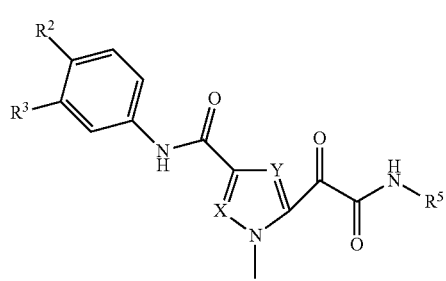

wherein $R^1$, $R^2$, $R^3$, $R^4$, $R^5$, X, and Y are as defined above; or $R^1$, $R^2$, $R^3$, X, and Y are as defined above; the structural unit

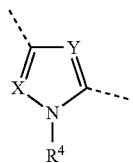

is selected from the group consisting of

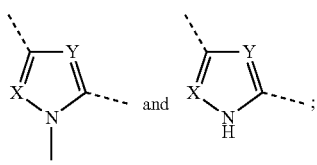

the structural unit

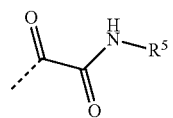

is selected from the group consisting of

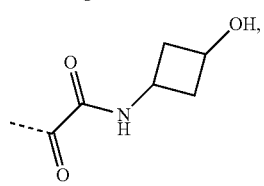

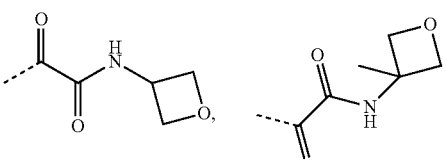

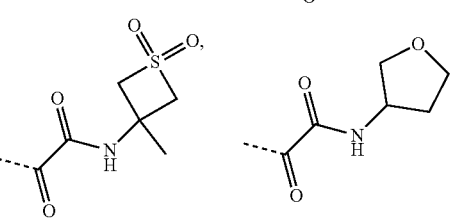

-continued
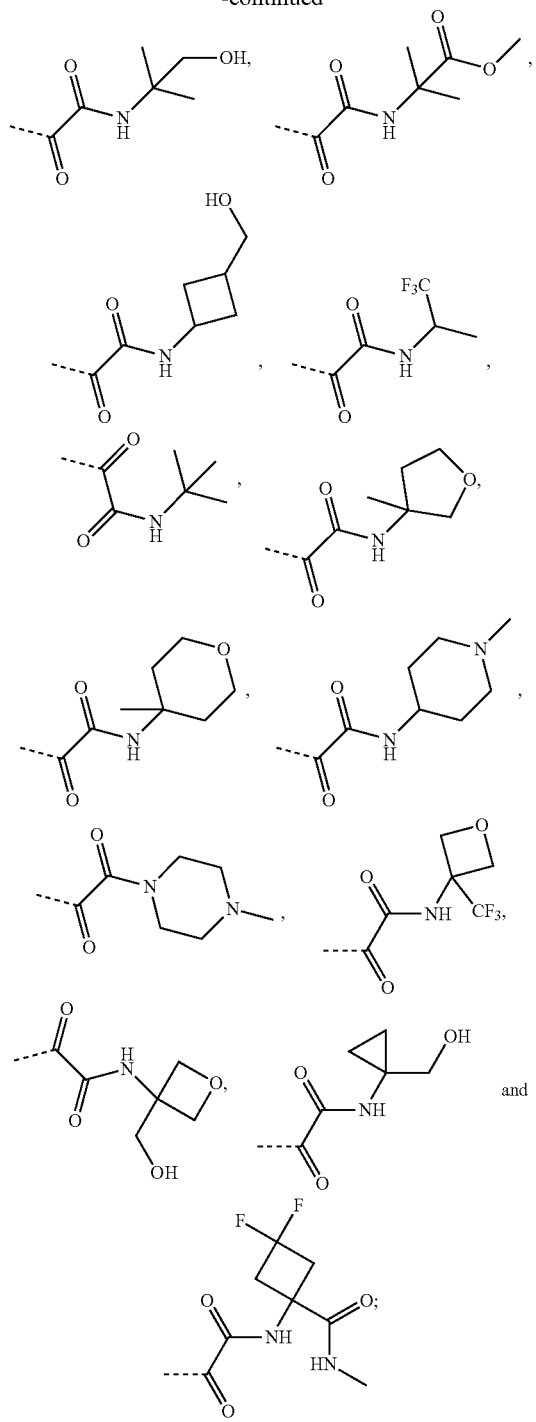
in some embodiments, the structural unit
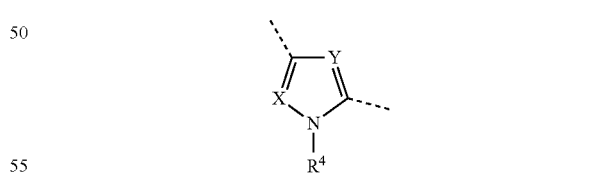
is selected from the group consisting of
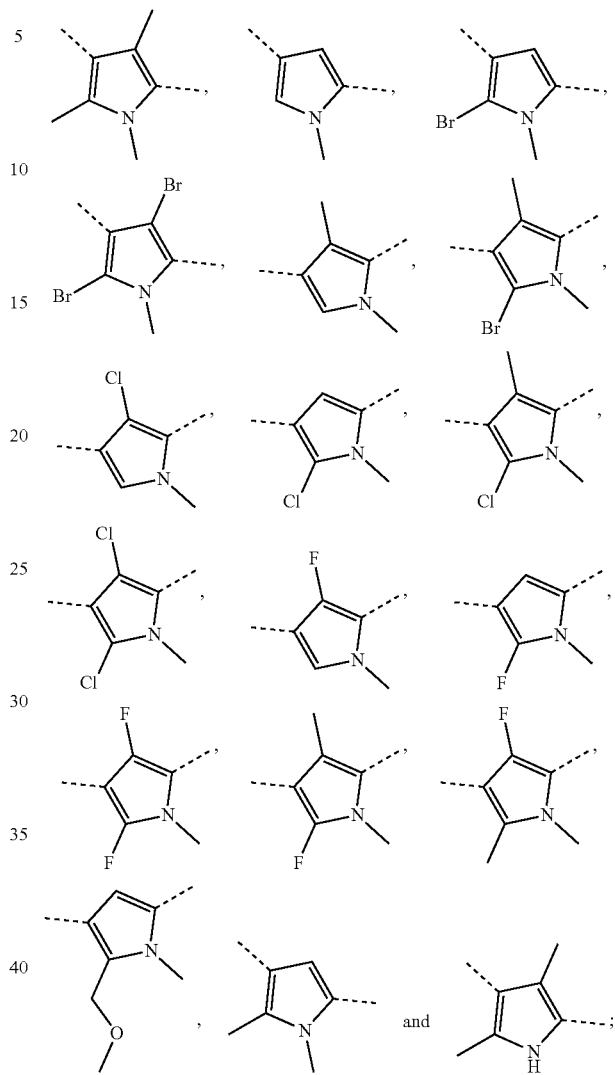
in some embodiments, the structural unit
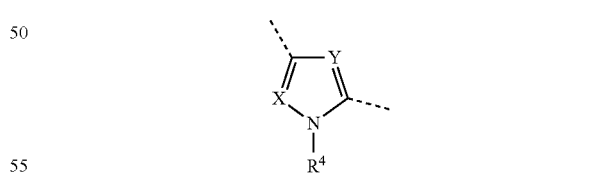
is selected from the group consisting of
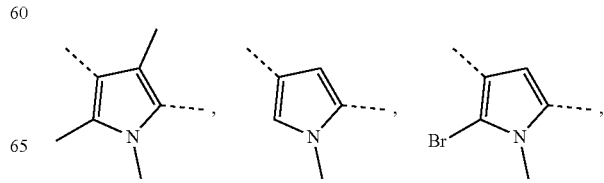

25
-continued
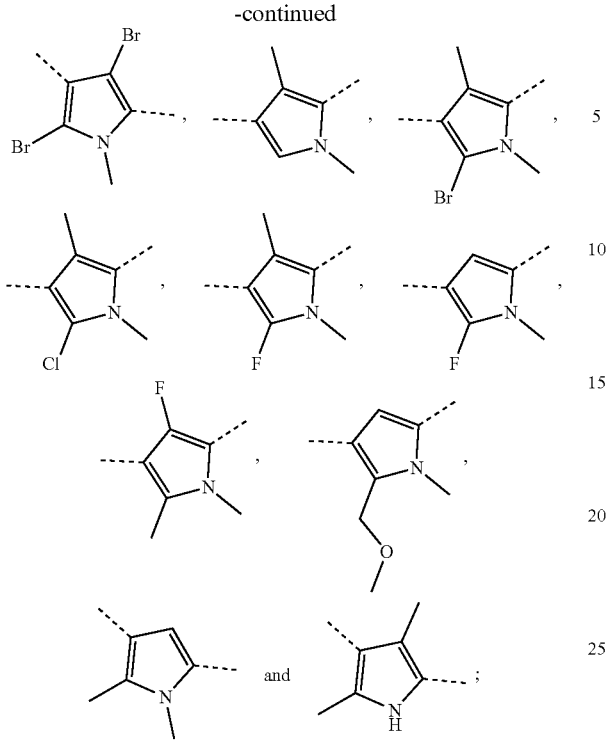
in some embodiments, the structural unit
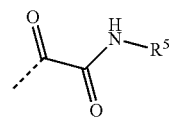
is selected from the group consisting of
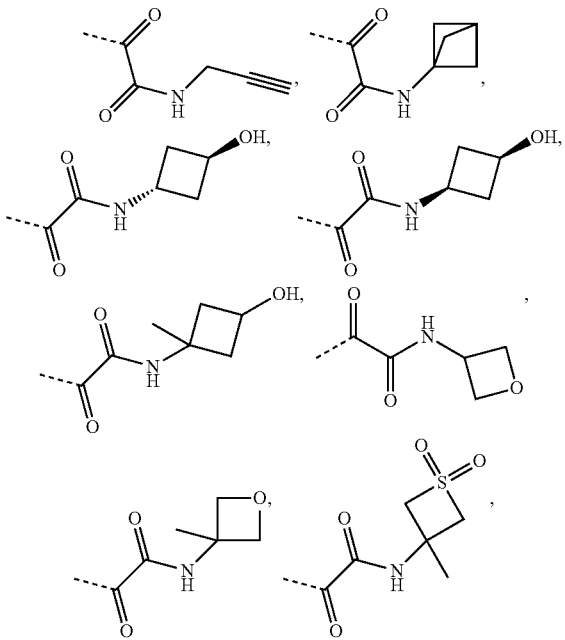
26
-continued
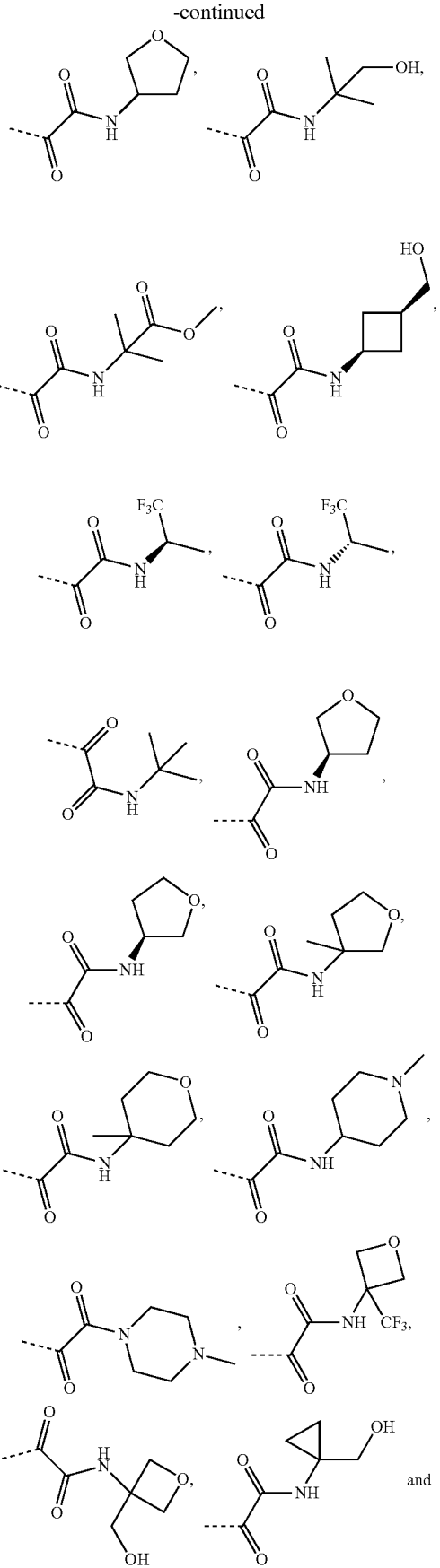

-continued

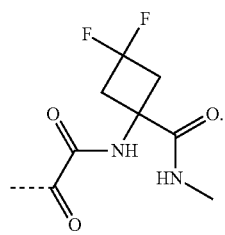

In some embodiments, the compound of Formula I, a stereoisomer, a tautomer, a geometric isomer, a solvate, an active metabolite, a hydrate, a prodrug or a pharmaceutically acceptable salt thereof of the present application is selected from a compound of Formula II, a stereoisomer, a tautomer, a geometric isomer, a solvate, an active metabolite, a hydrate, a prodrug or a pharmaceutically acceptable salt thereof,

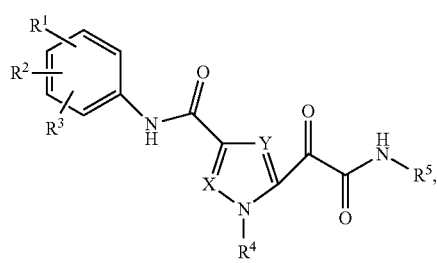

II wherein $R^1$, $R^2$, $R^3$, $R^4$, $R^5$, X, and Y are as defined above; or
$R^1$, $R^2$, $R^3$, the structural unit

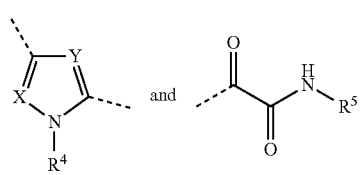

are as defined above.

In some embodiments, the compound of Formula I, a stereoisomer, a tautomer, a geometric isomer, a solvate, an active metabolite, a hydrate, a prodrug or a pharmaceutically acceptable salt thereof of the present application is selected from a compound of Formula III, a stereoisomer, a tautomer, a geometric isomer, a solvate, an active metabolite, a hydrate, a prodrug or a pharmaceutically acceptable salt thereof,

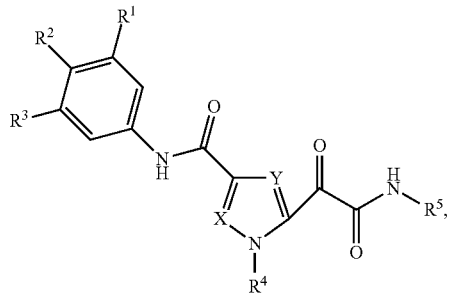

III wherein $R^1$, $R^2$, $R^3$, $R^4$, $R^5$, X, and Y are as defined above; or
$R^1$, $R^2$, $R^3$, the structural unit and are as defined above.

In some embodiments, the compound of Formula I, a stereoisomer, a tautomer, a geometric isomer, a solvate, an active metabolite, a hydrate, a prodrug or a pharmaceutically acceptable salt thereof of the present application is selected from a compound of Formula IV, a stereoisomer, a tautomer, a geometric isomer, a solvate, an active metabolite, a hydrate, a prodrug or a pharmaceutically acceptable salt thereof,

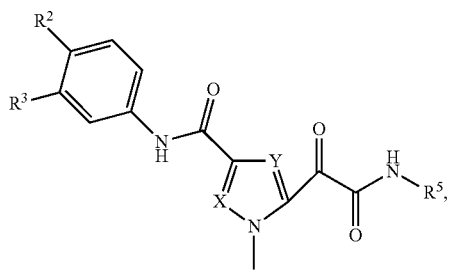

IV wherein $R^2$, $R^3$, $R^5$, X, and Y are as defined above; or
$R^2$, $R^3$, X, Y, and the structural unit

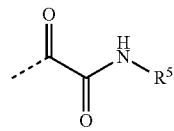

are as defined above.

In some embodiments, the compound of Formula I, a stereoisomer, a tautomer, a geometric isomer, a solvate, an active metabolite, a hydrate, a prodrug or a pharmaceutically acceptable salt thereof of the present application is selected from the following compounds, stereoisomers, tautomers, geometric isomers, solvates, active metabolites, hydrates, prodrugs or pharmaceutically acceptable salts thereof,
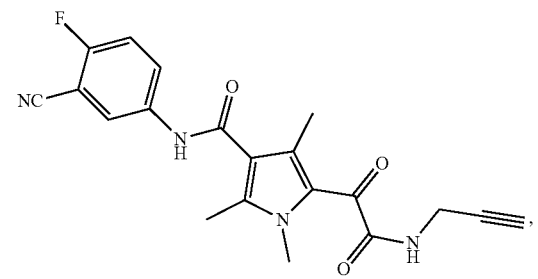
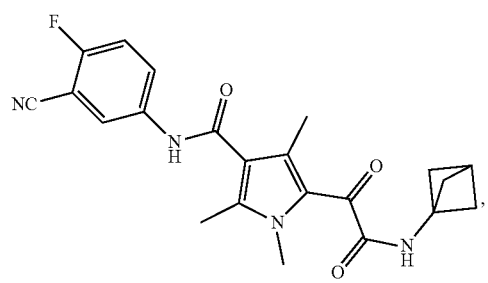
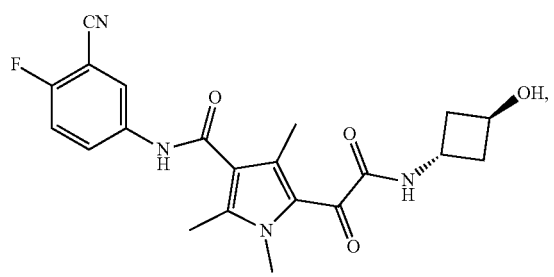
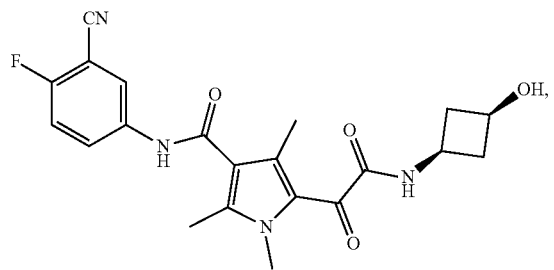
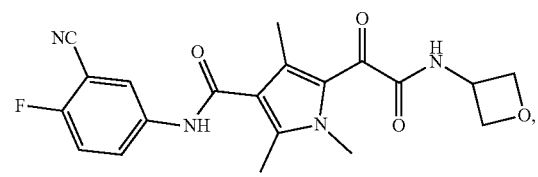
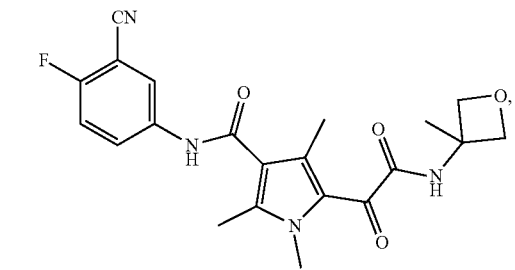
-continued
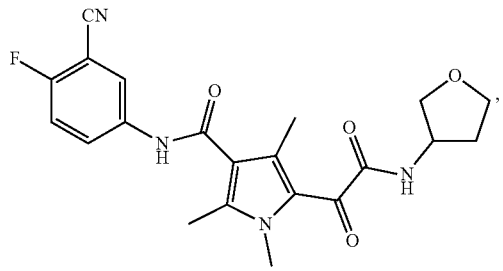
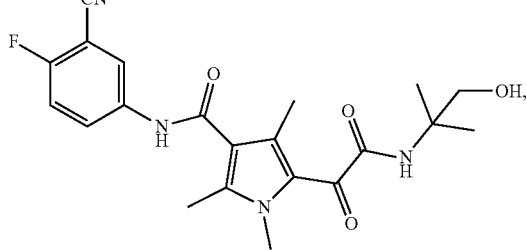
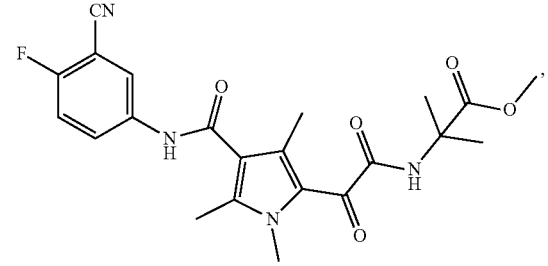
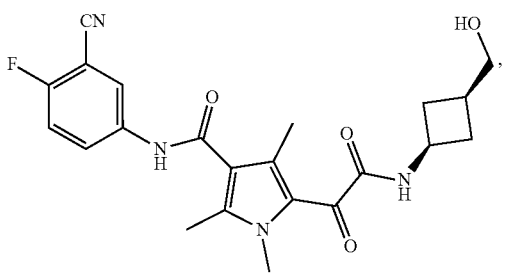
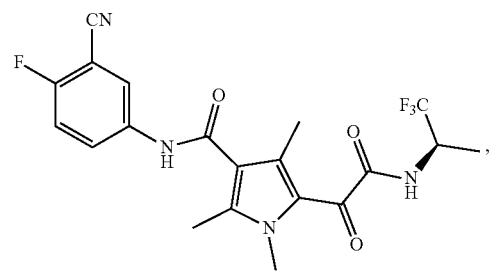
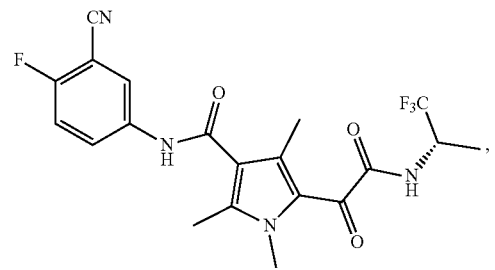

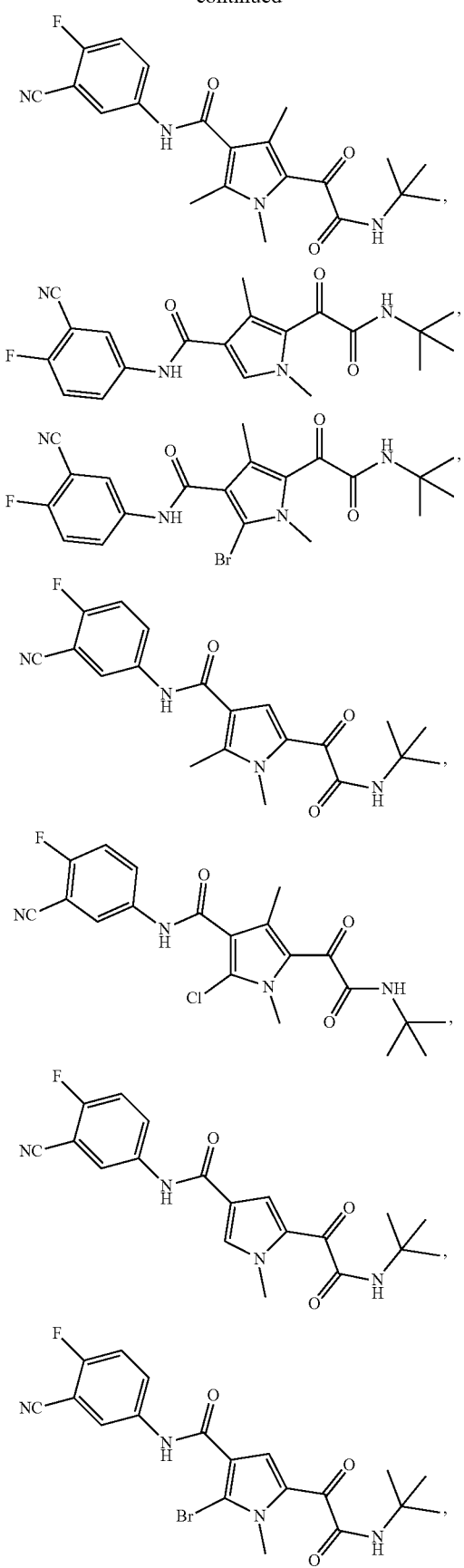
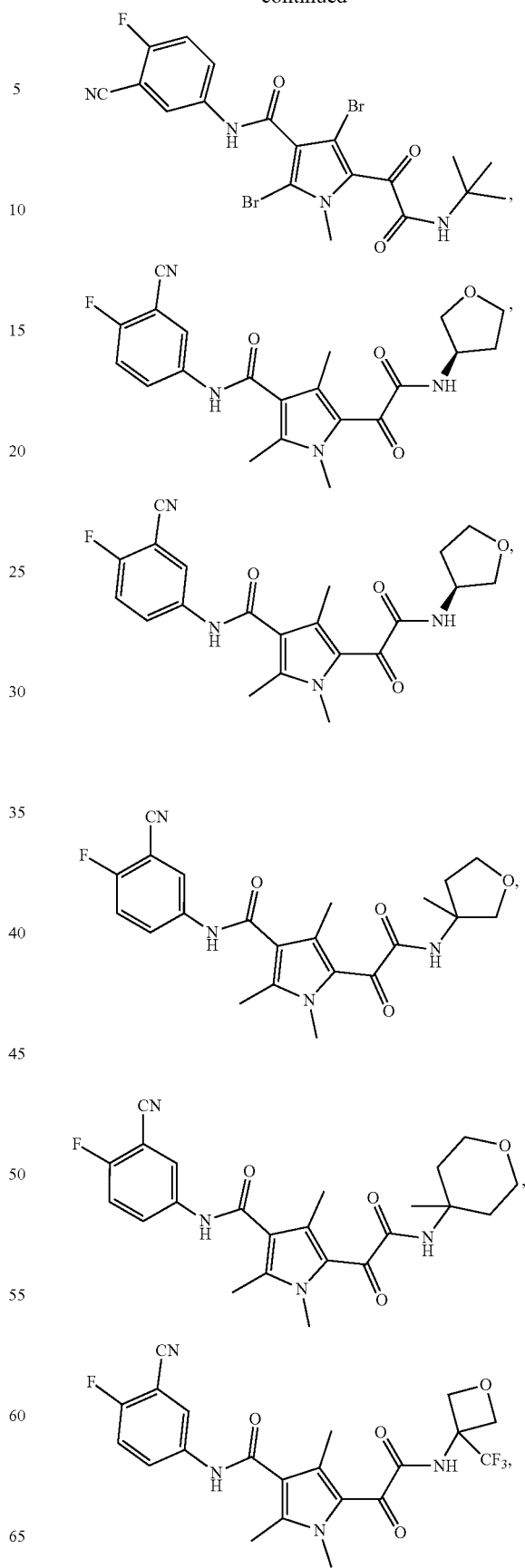

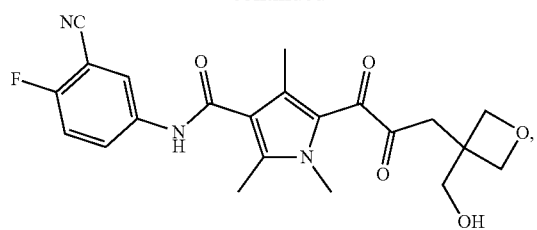
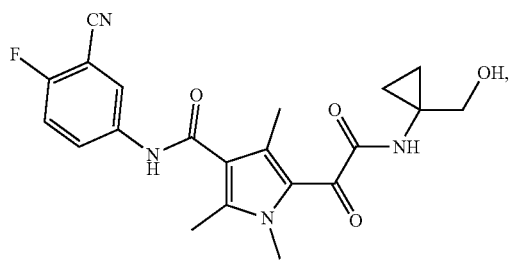
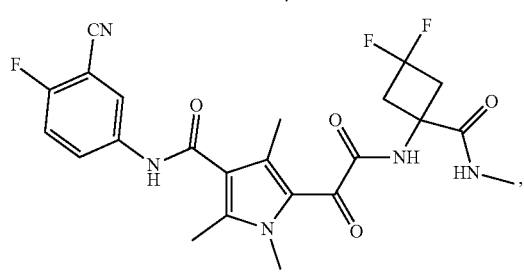
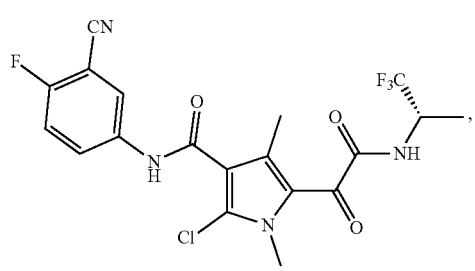
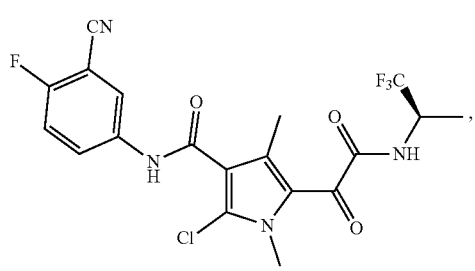
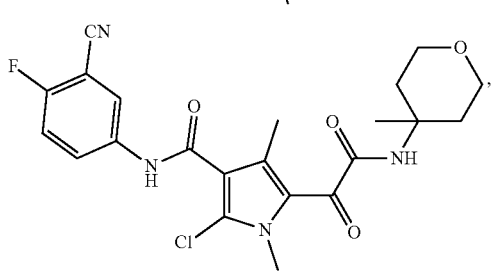
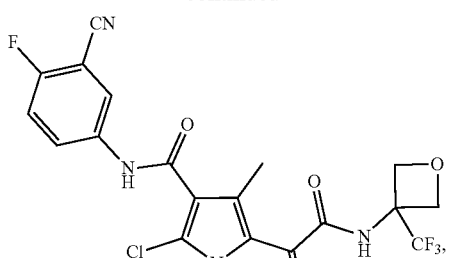
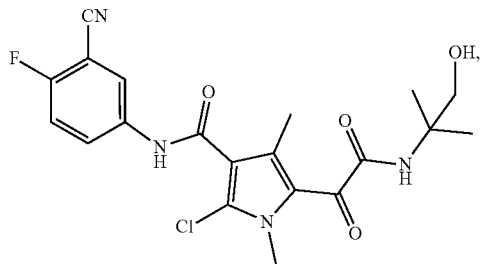
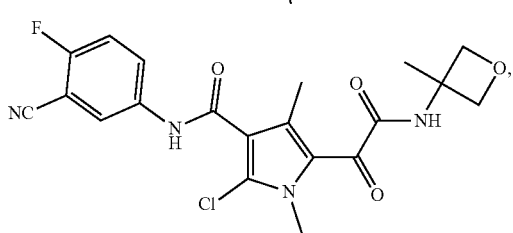
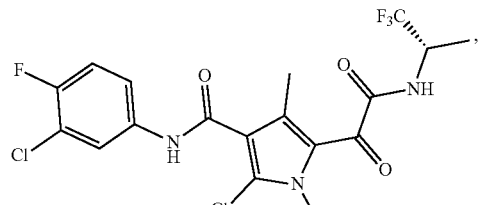
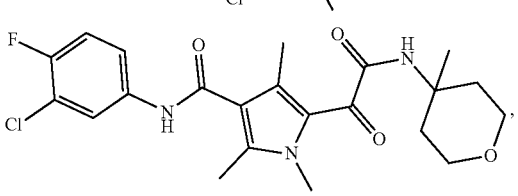
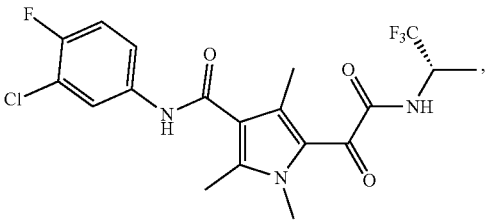
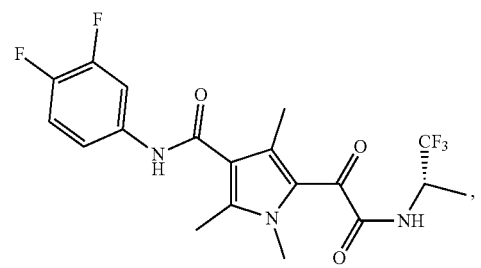

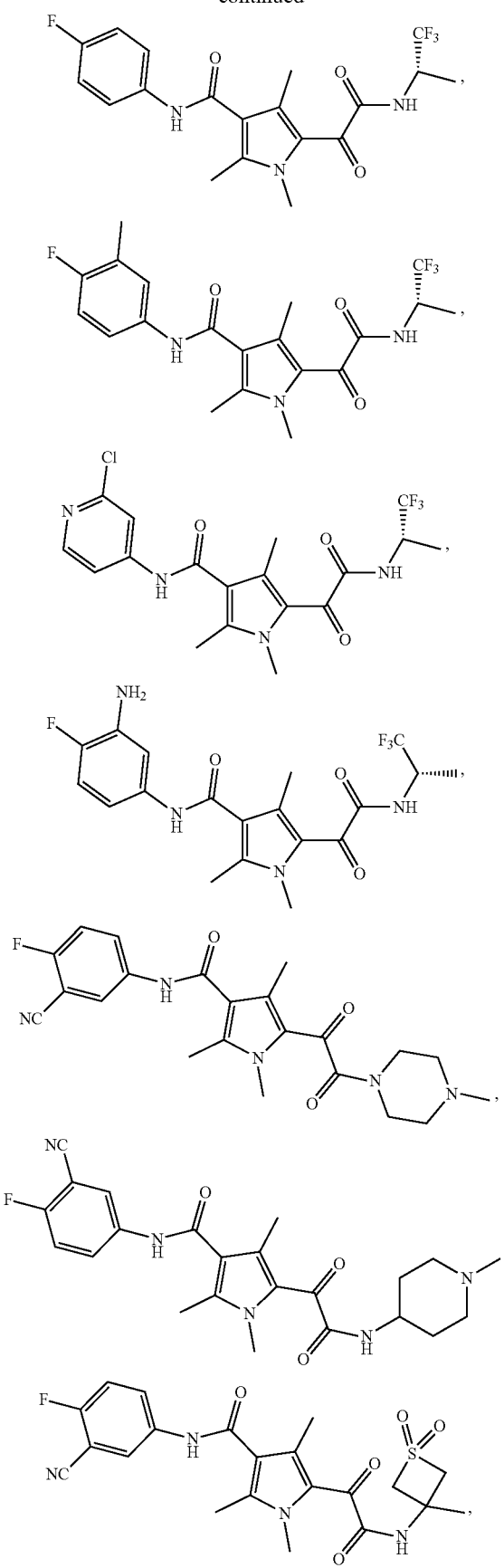
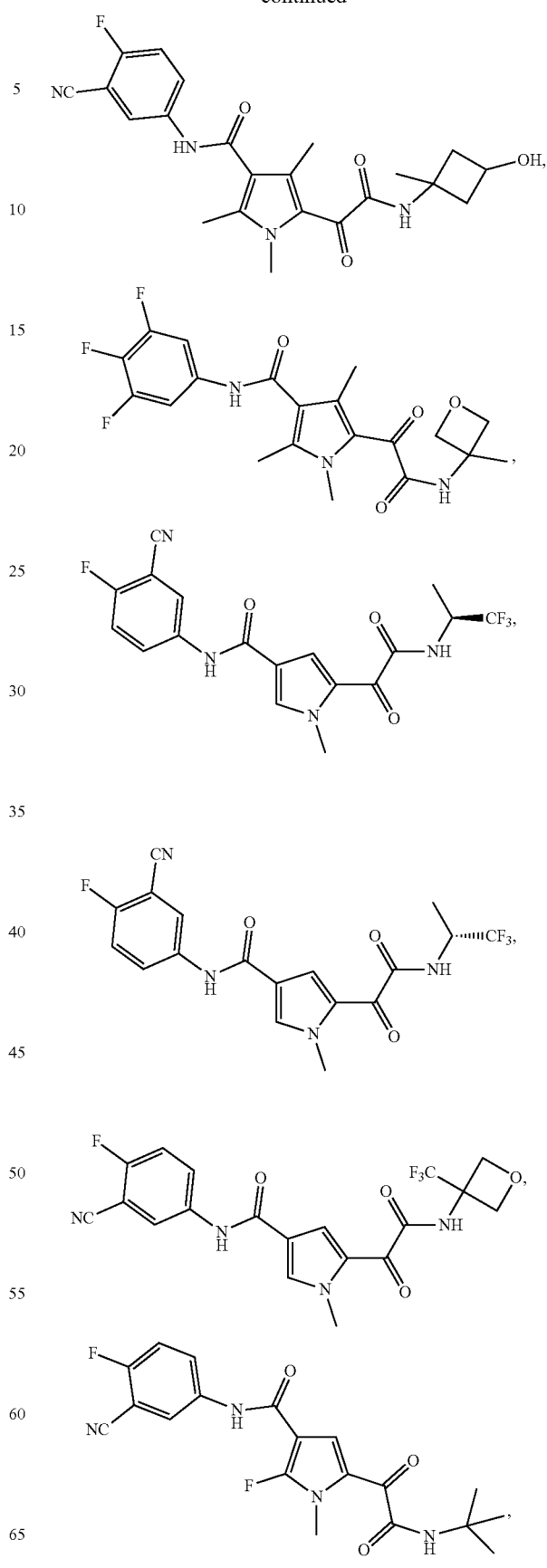

-continued

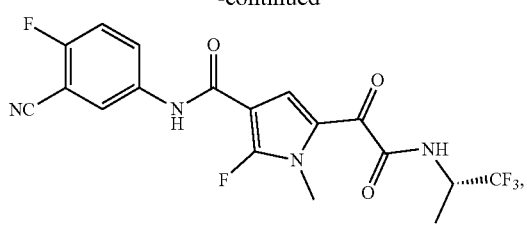
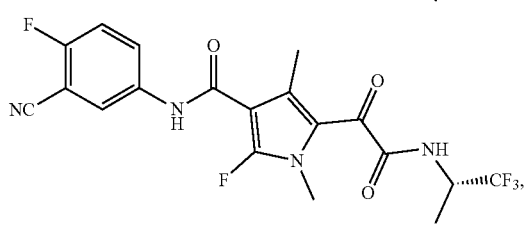
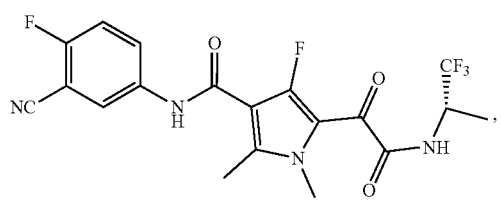
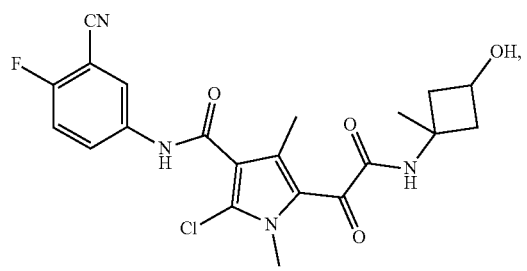
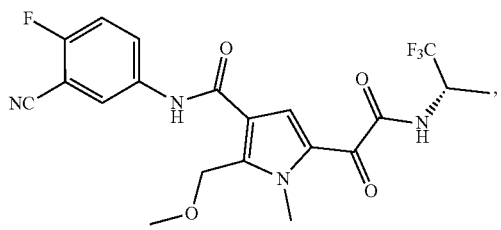
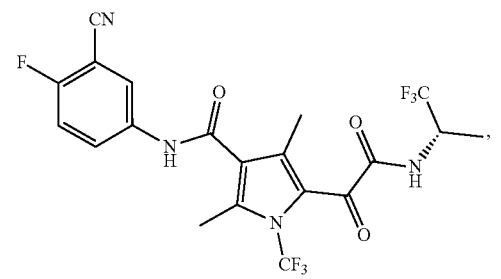
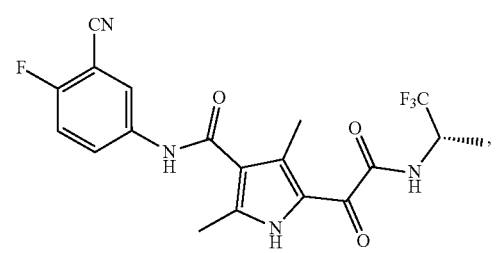

-continued

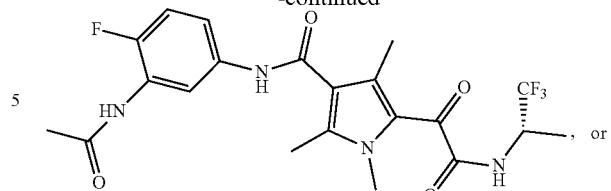
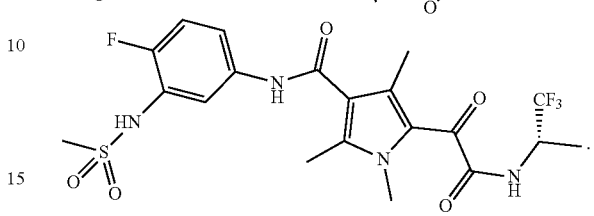

In another aspect, the application provides a pharmaceutical composition comprising a compound of Formula I, or a pharmaceutically acceptable salt thereof of the present application. In some embodiments, the pharmaceutical composition of the present application further comprises a pharmaceutically acceptable excipient.

In another aspect, the present application provides a method for treating a disease that benefits from the inhibition of capsid protein assembly, comprising administering to a mammal, preferably a human, in need of such treatment a therapeutically effective amount of a compound of the above Formula I, a pharmaceutically acceptable salt thereof or a pharmaceutical composition thereof.

In another aspect, the present application also provides use of a compound of the above Formula I, a pharmaceutically acceptable salt thereof, or a pharmaceutical composition thereof, in the preparation of a medicament for preventing or treating a disease that benefits from the inhibition of capsid protein assembly.

In another aspect, the present application provides use of a compound of the above Formula I, a pharmaceutically acceptable salt thereof, or a pharmaceutical composition thereof, for preventing or treating a disease that benefits from the inhibition of capsid protein assembly.

In another aspect, the present application provides a compound of the above Formula I, a pharmaceutically acceptable salt thereof, or a pharmaceutical composition thereof, for use in preventing or treating a disease that benefits from the inhibition of capsid protein assembly.

In another aspect, the application provides a pharmaceutical composition comprising a compound of Formula I, a stereoisomer, a tautomer, a geometric isomer, a solvate, an active metabolite, a hydrate, a prodrug or a pharmaceutically acceptable salt thereof of the present application. In some embodiments, the pharmaceutical composition of the present application further comprises a pharmaceutically acceptable excipient. In another aspect, the present application provides a method for inhibiting capsid protein assembly comprising administering to a subject in need thereof a therapeutically effective amount of a compound of Formula I, a stereoisomer, a tautomer, a geometric isomer, a solvate, an active metabolite, a hydrate, a prodrug, a pharmaceutically acceptable salt thereof or pharmaceutical composition thereof of the present application. In some embodiments, said subject is a mammal; in some embodiments, said subject is a human.

In another aspect, the present application provides a method for preventing or treating a disease that benefits from the inhibition of capsid protein assembly, comprising administering to a subject in need thereof a therapeutically effective amount of a compound of Formula I, a stereoisomer, a tautomer, a geometric isomer, a solvate, an active metabolite, a hydrate, a prodrug, a pharmaceutically acceptable salt thereof, or a pharmaceutical composition thereof of the present application. In some embodiments, said subject is a mammal; in some embodiments, said subject is a human. In another aspect, the present application provides use of a compound of Formula I, a stereoisomer, a tautomer, a geometric isomer, a solvate, an active metabolite, a hydrate, a prodrug or a pharmaceutically acceptable salt thereof, or a pharmaceutical composition thereof of the present application for inhibiting capsid protein assembly.

In another aspect, the present application also provides use of a compound of the Formula I, a stereoisomer, a tautomer, a geometric isomer, a solvate, an active metabolite, a hydrate, a prodrug, a pharmaceutically acceptable salt thereof, or a pharmaceutical composition thereof of the present application in the preparation of a medicament for inhibiting capsid protein assembly.

In another aspect, the present application also provides use of a compound of the Formula I, a stereoisomer, a tautomer, a geometric isomer, a solvate, an active metabolite, a hydrate, a prodrug, a pharmaceutically acceptable salt thereof, or a pharmaceutical composition thereof of the present application in the preparation of a medicament for preventing or treating a disease that benefits from the inhibition of capsid protein assembly.

In another aspect, the present application also provides use of a compound of the above Formula I, a stereoisomer, a tautomer, a geometric isomer, a solvate, an active metabolite, a hydrate, a prodrug or a pharmaceutically acceptable salt thereof, or a pharmaceutical composition thereof for preventing or treating a disease that benefits from the inhibition of capsid protein assembly.

In another aspect, the present application provides a compound of Formula I, a stereoisomer, a tautomer, a geometric isomer, a solvate, an active metabolite, a hydrate, a prodrug or a pharmaceutically acceptable salt thereof, or a pharmaceutical composition thereof of the present application for use in inhibiting capsid protein assembly.

In another aspect, the present application provides a compound of the above Formula I, a stereoisomer, a tautomer, a geometric isomer, a solvate, an active metabolite, a hydrate, a prodrug, a pharmaceutically acceptable salt thereof, or a pharmaceutical composition thereof for use in preventing or treating a disease that benefits from the inhibition of capsid protein assembly.

In some embodiments of the present application, the disease that benefits from the inhibition of capsid protein assembly is a disease caused by hepatitis B virus (HBV) infection.

In some embodiments of the present application, the disease that benefits from inhibition of capsid protein assembly is a liver disease caused by hepatitis B virus (HBV) infection.

In some embodiments of the present application, the treating disease that benefits from inhibition of capsid protein assembly is to control, reduce or eliminate HBV to prevent, alleviate or cure liver disease in an infected patient.

Definition

Unless stated otherwise, the terms and phrases used herein have the following meanings. A specific term or phrase shall not be considered as indefinite or unclear when it is not specifically defined, but should be understood according to the general meaning thereof. The trade names used herein refer to the corresponding products or the active ingredients thereof.

The dotted line ( - - - ) in a structural unit or a group in the present application represents a covalent bond.

When some of the structural units or covalent bonds in the groups are not linked to a specific atom, it means that the covalent bond can be attached to any atom in the structural units or groups, as long as the valence bond connection rule is not violated. Thus, for example, the structural unit

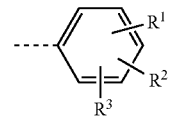

includes, but is not limited to

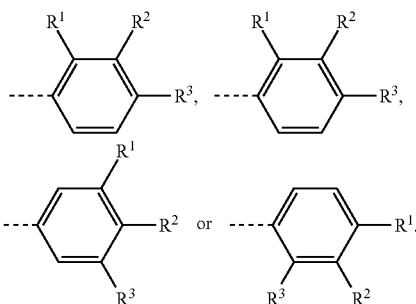

The term "substituted" means that any one or more of the hydrogen atoms on a specific atom are substituted by a substituent, as long as the valence state of the specific atom is normal and the substituted compound is stable. When the substituent is oxygen (i.e., =O), it means that two hydrogen atoms are substituted. Oxygen substitution does not occur on an aromatic group.

Term "optional" or "optionally" means that the subsequently described event or situation may or may not occur, and the description includes instances in which the event or situation occurs and instances in which the event or situation does not occur. For example, an ethyl group "optionally" substituted with halo means that the ethyl group may be unsubstituted ($CH_2CH_3$), monosubstituted (e.g., $CH_2CH_2F$), polysubstituted (e.g. $CHFCH_2F$, $CH_2CHF_2$, etc.) or completely substituted ($CF_2CF_3$). It will be understood by a person skilled in the art that for any group containing one or more substituents, no substitution or substitution pattern that is sterically impossible to exist and/or which cannot be synthesized is introduced.

The $C_{m-n}$ herein means that the moiety has an integer number of carbon atoms in a given range. For example, "$C_{1-6}$" means that a group may have 1 carbon atom, 2 carbon atoms, 3 carbon atoms, 4 carbon atoms, 5 carbon atoms or 6 carbon atoms. For example, $C_{1-3}$ means that a group may have 1 carbon atom, 2 carbon atoms, and 3 carbon atoms.

When any variable (e.g., R) occurs more than once in composition or structure of a compound, its definition in each occurrence is independent. Thus, for example, if a group is substituted with 2 R, and R in each case has an independent option.

When the number of a linking group is 0, such as —$(CH_2)_0$—, it means that the linking group is a single bond.

When one of the variables is selected from a covalent bond, it means that the two groups linked by the covalent bond are connected directly. For example, when L' in A-L'-Z represents a single bond, the structure is actually A-Z.

When a bond of a substituent is cross-linked to two atoms on a ring, the substituent may be bonded to any atom on the ring. For example, a structural unit

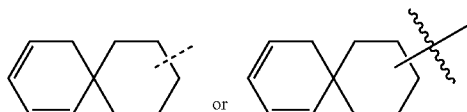

means it may be substituted at any position on cyclohexyl or cyclohexadiene

The term "halo" or "halogen" refers to fluoro, chloro, bromo, or iodo.

The term "alkyl" refers to a hydrocarbon group of the formula $C_nH_{2n+1}$. The alkyl group can be straight or branched. For example, the term "$C_{1-6}$ alkyl" refers to an alkyl group containing 1 to 6 carbon atoms (eg, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, etc.). Similarly, the alkyl moiety (i.e., alkyl) of an alkoxy group, an alkylamino group, a dialkylamino group, an alkylsulfonyl group, and an alkylthio group has the same definition as defined above. As another example, the term "$C_{1-3}$ alkyl" refers to an alkyl group containing 1 to 3 carbon atoms (eg, methyl, ethyl, propyl, and isopropyl).

The term "alkoxy" refers to —O-alkyl.

The term "alkenyl" refers to a straight or branched unsaturated aliphatic hydrocarbon group consisting of carbon atoms and hydrogen atoms, which has at least one double bond. Non-limiting examples of alkenyl groups include, but are not limited to, ethenyl, 1-propenyl, 2-propenyl, 1-butenyl, isobutenyl, 1,3-butadienyl, and the like.

The term "alkynyl" means a straight or branched unsaturated aliphatic hydrocarbon group consisting of carbon atoms and hydrogen atoms, which has at least one triple bond. Non-limiting examples of alkynyl groups include, but are not limited to, ethynyl (—C≡CH), 1-propynyl (—C≡C—CH₃), 2-propynyl (—CH₂—C≡CH), 1,3-butadiynyl (—C≡C—C≡CH), and the like.

The term "cycloalkyl" refers to a fully saturated carbocyclic ring that can exist as a single ring, bridged ring or spiro ring. Unless otherwise indicated, the carbocyclic ring is typically a 3- to 10-membered ring. Non-limiting examples of cycloalkyl includes, but are not limited to, cyclopropyl, cyclobutyl, cyclopentyl, cyclohexyl, norbornyl (bicyclo[2.2.1]heptyl), bicyclo[2.2.2]octyl, adamantyl, bicyclo[1.1.1]pent-1-yl and the like. For example, $C_{3-4}$ cycloalkyl includes cyclopropyl and cyclobutyl.

The term "heterocycloalkyl" refers to a fully saturated cyclic group that can exist as a single ring, bridged ring or spiro ring. Unless otherwise indicated, the heterocyclic ring is typically a 3- to 7-membered ring containing 1 to 3 heteroatoms (preferably 1 or 2 heteroatoms) independently selected from sulfur, oxygen and/or nitrogen. Examples of 3-membered heterocycloalkyl include, but are not limited to, oxiranyl, thiiranyl, and aziridinyl. Non-limiting examples of 4-membered heterocycloalkyl include, but are not limited to, azetidinyl, oxetanyl, and thietanyl. Examples of 5-membered heterocycloalkyl include, but are not limited to, tetrahydrofuranyl, tetrahydrothiophenyl, pyrrolidinyl, isoxazolidinyl, oxazolidinyl, isothiazolidinyl, thiazolidinyl, imidazolidinyl, and tetrahydropyrazolyl. Examples of 6-membered heterocycloalkyl include, but are not limited to, piperidinyl, tetrahydropyranyl, tetrahydrothiopyranyl, morpholinyl, piperazinyl, 1,4-thiaxyl, 1,4-dioxanyl, thiomorpholinyl, 1,3-dithiaalkyl, and 1,4-dithiaalkyl. Examples of 7-membered heterocycloalkyl include, but are not limited to azepanyl, oxepanyl, thiepanyl. The preferred heterocycloalkyl is a monocyclic heterocycloalkyl group having 5 or 6 ring atoms.

The term "aryl" refers to an all-carbon monocyclic or fused polycyclic aromatic ring group having a conjugated π-electron system. For example, an aryl group can have 6-20 carbon atoms, 6-14 carbon atoms or 6-12 carbon atoms. Non-limiting examples of aryl include, but are not limited to, phenyl, naphthyl, anthracenyl, 1,2,3,4-tetrahydronaphthalene, and the like.

The term "heteroaryl" refers to a monocyclic or fused polycyclic system, which contains at least one ring atom selected from the group consisting of N, O and S and the other ring atom(s) is(are) C, and has at least one aromatic ring. Preferred heteroaryl groups have a single 4- to 8-membered ring, especially a 5- to 8-membered ring, or a plurality of fused rings containing 6 to 14, especially 6 to 10 ring atoms. Non-limiting examples of heteroaryl groups include, but are not limited to, pyrrolyl, furyl, thienyl, imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl, and the like.

The term "treating" or "treatment" refers to the administration of a compound or formulation described in the present application to prevent, ameliorate or eliminate a disease or one or more symptoms associated with the disease, and comprises:

(i) preventing the occurrence of a disease or disease condition in a mammal, particularly when such mammal is susceptible to the disease condition but has not been diagnosed as suffering from the disease condition;

(ii) inhibiting the disease or disease condition, i.e, curbing its development;

(iii) alleviating the disease or disease condition, i.e., regressing the disease or disease condition.

The term "therapeutically effective amount" means an amount of a compound of the present application for (i) treating or preventing a particular disease, condition or disorder, (ii) alleviating, ameliorating or eliminating one or more symptoms of a particular disease, condition or disorder, or (iii) preventing or delaying the onset of one or more symptoms of disease, condition or disorder described herein. The "therapeutically effective amount" of a compound of this application varies depending on the compound, the disease condition and its severity, the mode of administration, and the age of the mammal to be treated, but can be routinely determined by those skilled in the art according to their own knowledge and the present disclosure.

The term "pharmaceutically acceptable" refers to those compounds, materials, compositions and/or dosage forms that are within the scope of sound medical judgment and are suitable for use in contact with human and animal tissues without excessive toxicity, irritation, allergic reactions or other problems or complications, and are commensurate with a reasonable benefit/risk ratio.

As a pharmaceutically acceptable salt, for example, a metal salt, an ammonium salt, a salt formed with an organic base, a salt formed with an inorganic acid, a salt formed with an organic acid, a salt formed with a basic or acidic amino acid, or the like can be mentioned.

The term "pharmaceutical composition" refers to a mixture of one or more compounds of the present application or a salt thereof and a pharmaceutically acceptable excipient. The purpose of the pharmaceutical composition is to facilitate the administration of the compounds of the present application to a subject.

The term "solvate" refers to a substance formed by combining a compound of the present invention with a pharmaceutically acceptable solvent. Pharmaceutically acceptable solvents include water, ethanol, acetic acid, and the like. Solvates include stoichiometric solvates and non-stoichiometric solvates.

The term "hydrate" refers to a solvate comprising a compound disclosed or claimed and a stoichiometric or non-stoichiometric amount of water.

The compounds of the present invention may also be prepared as prodrugs, such as pharmaceutically acceptable prodrugs. Since prodrugs are known to improve many desired properties of a drug (e.g., solubility, bioavailability, preparation, etc.), the compounds of the present invention can be delivered in the form of a prodrug. Accordingly, the present invention is intended to encompass prodrugs of currently claimed compounds, methods of delivery thereof, and compositions containing prodrugs.

The term "prodrug" is intended to include any covalently bonded carrier which, when administered to a mammalian subject, releases the active parent drug of the present invention in vivo. The prodrugs of the present invention are prepared by modifying a functional group present in the compound in such a manner that the modification cleaves into the parent compound in a conventional operation or in vivo.

In the present invention, the term "subject" includes humans and animals, for example, mammals (e.g., primates, cows, horses, pigs, dogs, cats, mice, rats, rabbits, goats, sheeps, birds, etc.). The term "active metabolite" refers to a biologically active derivative of a compound that is formed when the compound is metabolized.

The term "pharmaceutically acceptable excipient" refers to those excipients which have no significant irritating effect on the organism and do not impair the biological activity and properties of the active compound. Suitable excipients are well known to those skilled in the art, such as carbohydrates, waxes, water soluble and/or water swellable polymers, hydrophilic or hydrophobic materials, gelatin, oils, solvents, water, and the like.

The word "comprise" and its English variants such as "comprises" or "comprising" shall be understood in an open, non-exclusive sense, ie "including, but not limited to".

The compounds and intermediates of the present application may also exist in different tautomeric forms, and all such forms are encompassed within the scope of the present application. The term "tautomer" or "tautomeric form" refers to structural isomers with different energies that are interconvertible via a low energy barrier. For example, proton tautomers (also known as proton transfer tautomers) include interconversions via proton transfer, such as keto-enol and imine-enamine isomerization. A specific example of a proton tautomer is an imidazole moiety in which a proton can migrate between two ring nitrogen atoms. Valence tautomers include recombination tautomers through some of the bond-forming electrons.

Certain compounds of the present application may have asymmetric carbon atoms (stereocenters) or double bonds. Thus, racemates, diastereomers, enantiomers, geometric isomers, and individual isomers are included within the scope of the present application.

Unless otherwise specified, when the compounds of the present application contain olefinic double bonds or other centers of geometric asymmetry, they include the E and Z geometric isomers.

The compounds of the present application may exist in specific geometric or stereoisomeric forms. The present application contemplates all such compounds, including tautomers, cis and trans isomers, (−)- and (+)-enantiomers, (R)- and (S)-enantiomers, diastereoisomers, (D)-isomers, (L)-isomers, and racemic mixtures thereof, and other mixtures, such as enantiomers- or diastereomers-enriched mixtures, all of which fall within the scope of the present application. Additional asymmetric carbon atoms may be present in the substituents such as alkyl, etc. All these isomers and their mixtures are included within the scope of the present application.

The optically active (R)- and (S)-isomers as well as the D and L isomers can be prepared by chiral synthesis or chiral reagents or other conventional techniques. An enantiomer of a certain compound of the present application can be prepared by asymmetric synthesis or by derivatization with a chiral auxiliary, wherein the resulting diastereomeric mixture is separated and the auxiliary group is cleaved to provide the pure desired enantiomers. Alternatively, when a molecule contains a basic functional group (such as amino) or an acidic functional group (such as carboxyl), it forms a salt of diastereomer with a suitable optically active acid or base, and then a diastereomer resolution is performed by a conventional method well known in the art, then the pure enantiomer is recovered. In addition, the separation of the enantiomers and diastereomers is generally accomplished by using chromatography with a chiral stationary phase, and optionally in combination with chemical derivatization method (e.g., formation of carbamates from amines).

The present application also includes isotopically labeled compounds of the present application that are identical to those described herein, but in which one or more atoms are replaced by those having an atomic weight or mass number different from the atomic mass or mass number normally found in nature. Examples of isotopes that may be incorporated into the compounds of the present application include isotopes of hydrogen, carbon, nitrogen, oxygen, phosphorus, sulfur, fluorine, iodine, and chlorine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{123}I$, $^{125}I$, $^{36}Cl$ and the like, respectively.

Certain isotopically-labeled compounds of the present application (such as those labeled with $^{3}H$ and $^{14}C$) can be used in compound and/or substrate tissue distribution assays. Deuterated (i.e., $^{3}H$) and carbon-14 (i.e., $^{14}C$) isotopes are especially preferred for their ease of preparation and detectability. Positron emitting isotopes such as $^{15}O$, $^{13}N$, $^{11}C$ and $^{18}F$ can be used in positron emission tomography (PET) studies to determine substrate occupancy. Isotopically labeled compounds of the present application can generally be prepared by replacing an non-isotopically labeled reagent with an isotopically labeled reagent through procedures similar to those disclosed in the schemes and/or examples disclosed below.

Furthermore, substitution with heavier isotopes such as deuterium (ie, $^{2}H$) may provide certain therapeutic advantages resulting from higher metabolic stability (eg, increased in vivo half-life or reduced dosage requirements), and thus may be preferred in some cases, wherein the deuterium substitution may be partial or complete, and the partial deuterium substitution means that at least one hydrogen is substituted with at least one deuterium, and all such forms of the compounds are encompassed within the scope of the present application. For example, deuterium substitution may occur in the structural unit

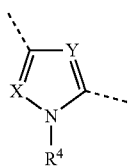

to obtain specific structures such as

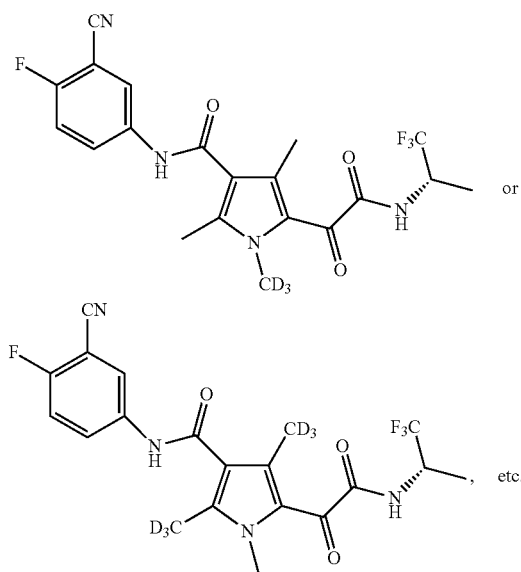

The pharmaceutical composition of the present application can be prepared by combining a compound of the present application with a suitable pharmaceutically acceptable excipient, and may be formulated into, for example, solid, semi-solid, liquid or gaseous formulations, such as tablets, pills, capsules, powders, granules, pastes, emulsions, suspensions, suppositories, injections, inhalants, gels, microspheres, aerosols and the like.

Typical administration routes of the compound of the present application or a pharmaceutically acceptable salt thereof, or a pharmaceutical composition comprising the same, include, but are not limited to, oral, rectal, topical, inhaled, parenteral, sublingual, intravaginal, intranasal, intraocular, intraperitoneal, intramuscular, subcutaneous, or intravenous administration.

The pharmaceutical composition of the present application can be manufactured through the well-known methods in the art, such as a conventional mixing method, dissolving method, granulation method, sugar-coated-pill method, grinding method, emulsification method, and freeze-drying method, etc.

In some embodiments, the pharmaceutical composition is in an oral administration form. For oral administration, the active compound can be mixed with the pharmaceutically acceptable carriers well-known in the art, to prepare the pharmaceutical composition. With these excipients, the compounds of the present application can be formulated into tablets, pills, lozenges, dragees, capsules, liquid, gels, syrup, or suspensions and the like, for oral administration to patients.

The solid oral composition can be prepared by conventional mixing, filling or tabletting method. For example, it can be obtained through the following method: mixing the active compound with a solid excipient; optionally grinding the resulting mixture, adding other suitable excipients if needed; and then processing the mixture into granules to obtain the core of tablets or dragees. Suitable excipients include, but are not limited to, adhesives, diluents, disintegrants, lubricants, glidants, sweeteners and/or flavoring agents, etc.

The pharmaceutical composition is also suitable for parenteral administration, such as sterile solutions, suspensions or freeze-dried products in an appropriate unit dose form.

The therapeutic dosage of the compounds of the present application can be determined according to, for example, the particular use of the treatment, the administration route of the compound, the health and condition of the patient, and the judgment of the prescribing physician. The proportion or concentration of the compounds of the present application in a pharmaceutical composition may vary depending on a variety of factors including dosage, chemical characteristics (e.g., hydrophobicity) and the route of administration. For example, the compound of the present application can be provided in a physiologically buffered aqueous solution containing about 0.1 to 10% w/v of the compound for parenteral administration. Some typical doses range from about 1 μg/kg to about 1 g/kg body weight per day. In certain embodiments, the dose range is from about 0.01 mg/kg to about 100 mg/kg body weight per day. The dosage is likely to depend on such variables as the type and progression extent of the disease or condition, the general health state of the particular patient, the relative biological efficacy of the selected compound, the formulation of the excipient, and the route of administration thereof. An effective dose can be obtained by extrapolation from a dose-response curve derived from an in vitro or animal model test system.

The compounds of the present application can be prepared through a variety of synthetic processes well-known to those skilled in the art, including the specific embodiments listed below, embodiments formed by combining the specific embodiments with other chemical synthetic processes, and equivalent alternatives known to a person skilled in the art. Preferred embodiments include, but are not limited to, the working examples of the present application.

The chemical reaction of a specific embodiment of the present application is carried out in a suitable solvent, which should be suitable for the chemical changes of the present application and the required reagents and materials in the present application. In order to obtain the compounds of the present application, a person skilled in the art sometimes needs to modify or select a synthesis step or a reaction process on the basis of the existing embodiments.

An important consideration in the design of synthetic routes in the art is the selection of a suitable protecting group for a reactive functional group (such as an amino group in this application), for example, reference may be made to Greene's Protective Groups in Organic Synthesis (4th Ed). Hoboken, New Jersey: John Wiley & Sons, Inc. All references cited in the present application are incorporated herein in their entireties.

In some embodiments, the compounds of Formula (I) of the present application can be prepared by one of ordinary skill in the field of organic synthesis using general or conventional methods in the art through the following schemes:

Scheme 1
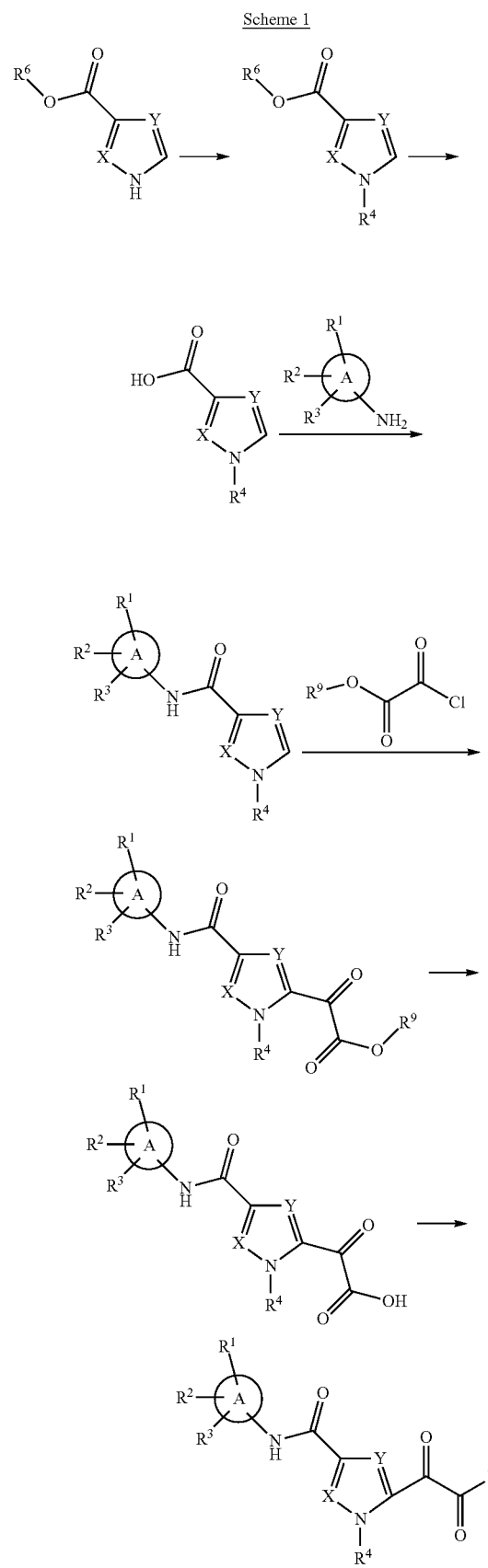
Scheme 2
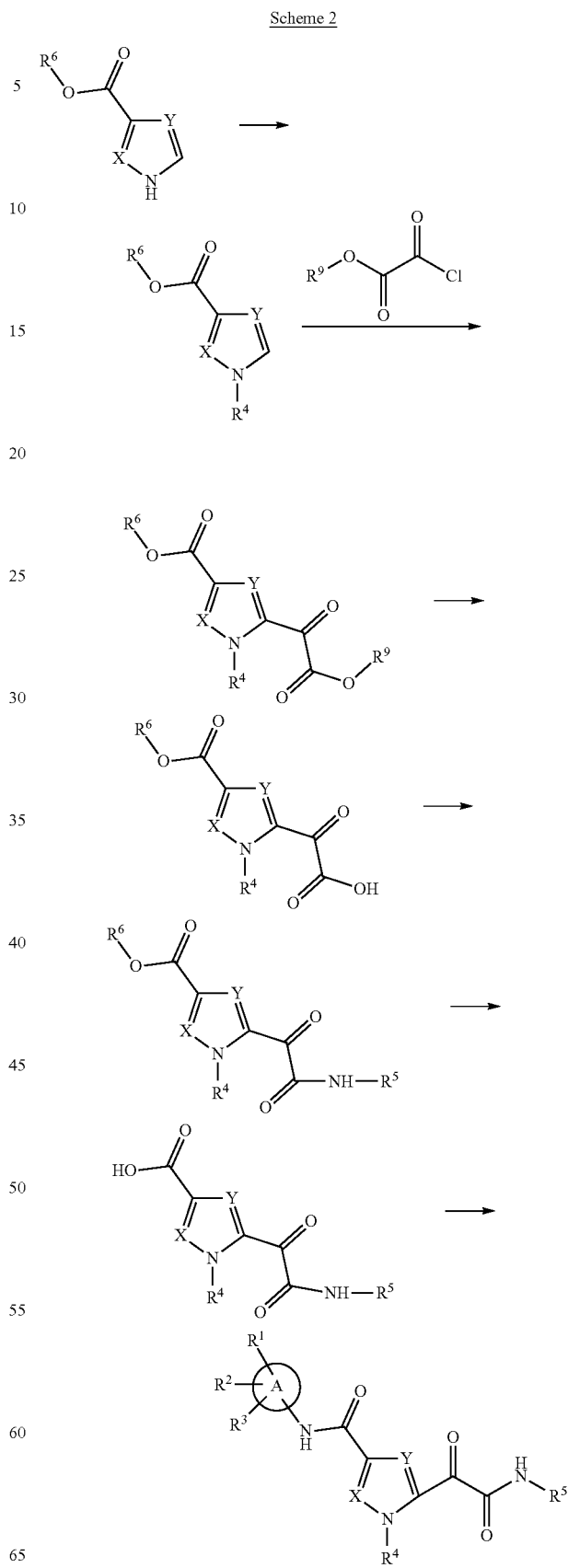

Scheme 3
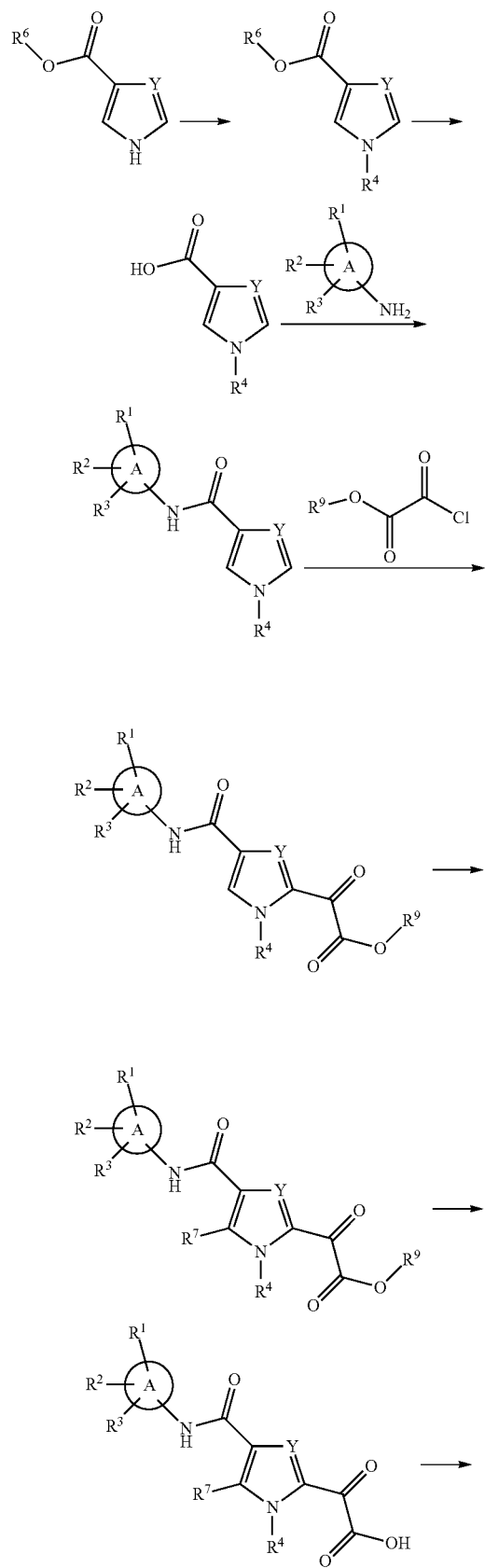
Scheme 4
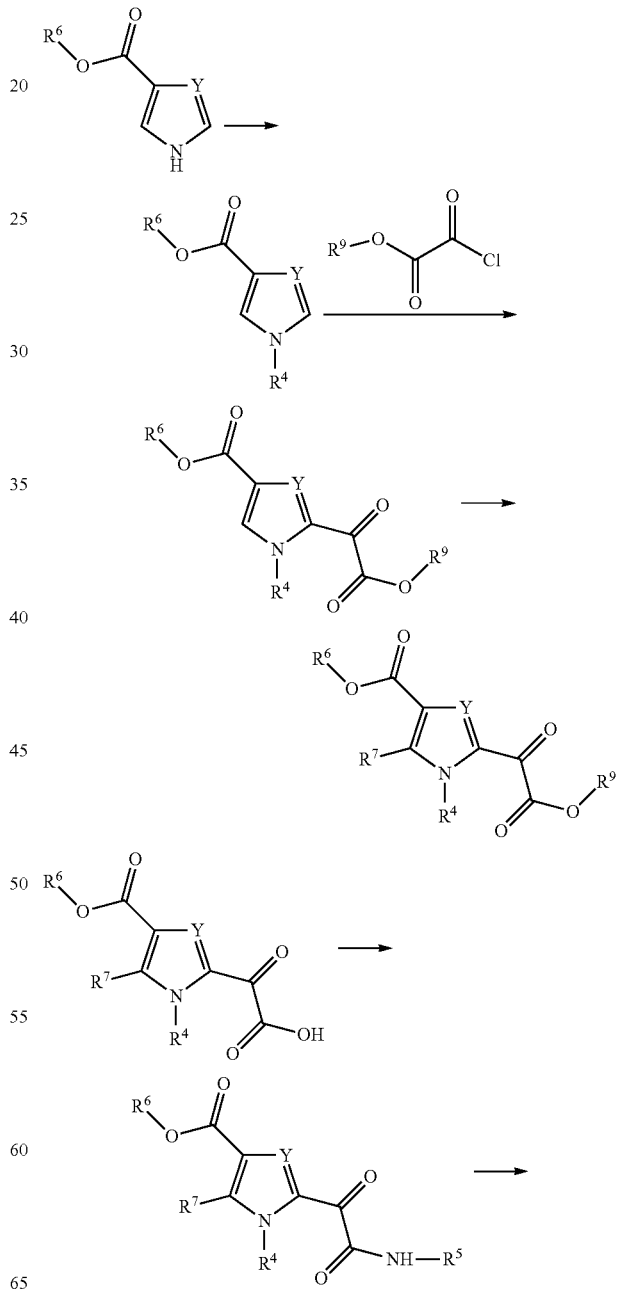

51
-continued
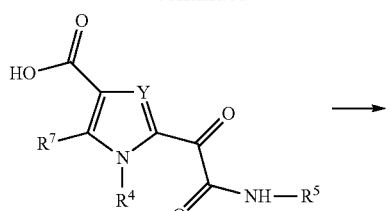
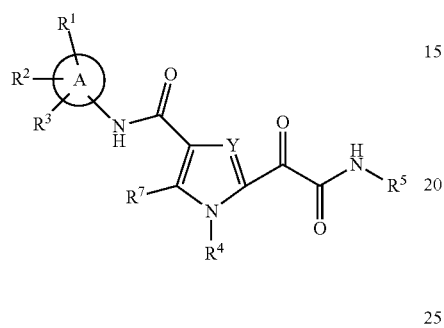
Scheme 5
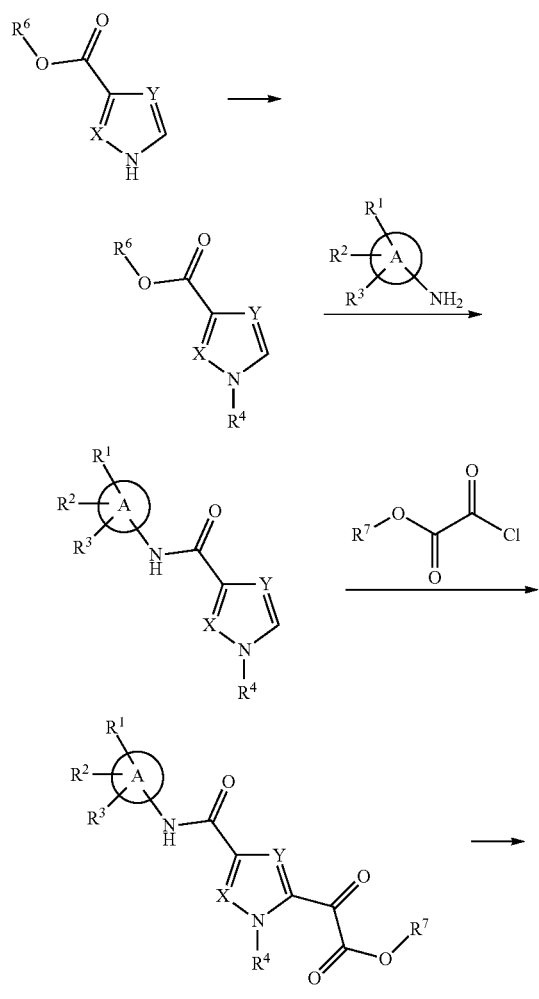
52
-continued
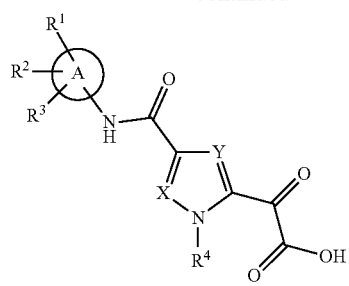
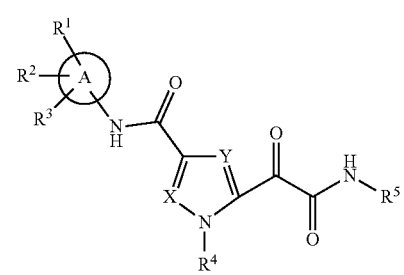
Scheme 6
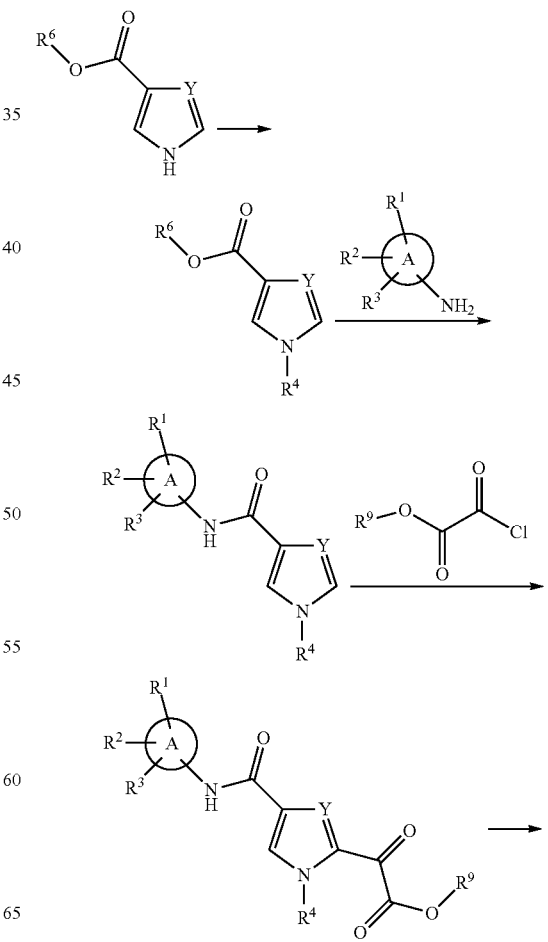

-continued

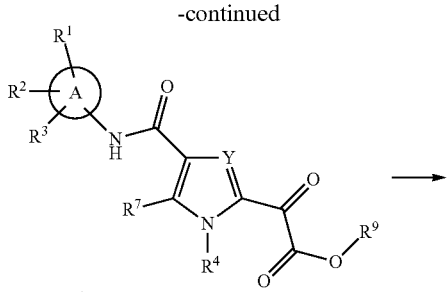

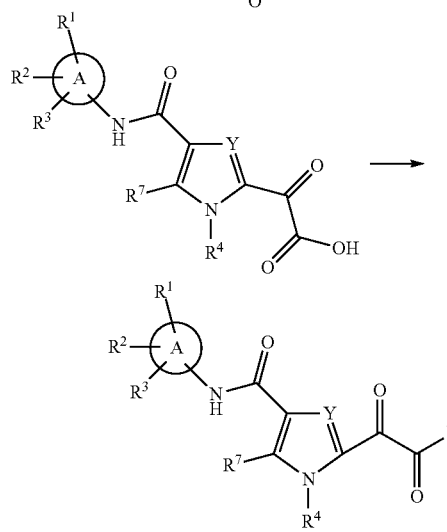

wherein $R^6$ and $R^9$ are selected from the group consisting of methyl and ethyl.

The present application employs the following abbreviations:

NBS represents N-bromosuccinimide; EA represents ethyl acetate; PE represents petroleum ether; NCS represents N-chlorosuccinimide; DMF represents N,N-dimethylformamide; HATU represents O-(7-azabenzotriazol-1-yl)-N,N,N', N'-tetramethyluronium hexafluorophosphate; h represents hour; DCM represents dichloromethane; DIPEA represents N,N-diisopropylethylamine; DMA represents dimethylacetamide; THF represents tetrahydrofuran; LiHDMS represents bistrimethylsilylamine lithium; PO represents oral administration; IV represents intravenous injection; MRT represents mean residence time; Ts represents p-toluenesulfonyl; selectfluor represents 1-chloromethyl-4-fluoro-1,4-diazonium dicyclo 2.2.2 octane bis(tetrafluoroborate) salt; DMSO represents dimethyl sulfoxide; HOBt represents 1-hydroxybenzotriazole; DCC represents dicyclohexylcarbodiimide; MeOH represents methanol.

For clarity, the present invention is further illustrated by the following examples, but the examples are not intended to limit the scope of the present application. All reagents used in this application are commercially available and can be used without further purification.

EXAMPLES

The nuclear magnetic resonance (NMR) of the present invention was detected by BRUKER-300 and BRUKER-500 nuclear magnetic resonance spectrometer, and tetramethylsilane (TMS=δ 0.00) was employed as an internal standard of the chemical shift, and the nuclear magnetic resonance data was recorded as: proton number, peak type (s, singlet; d, doublet; t, triplet; q, quartet; m, multiplet), coupling constant (in Hz). AB SCIEX Triple TOF 4600 or AB SCIEX 3200QTRAP was employed as mass spectrometry instrument.

Example 1

N-(3-cyano-4-fluorophenyl)-1,2,4-trimethyl-5-(2-oxo-2-(prop-2-yn-1-ylamino)acetyl)-1H-pyrrole-3-carboxamide

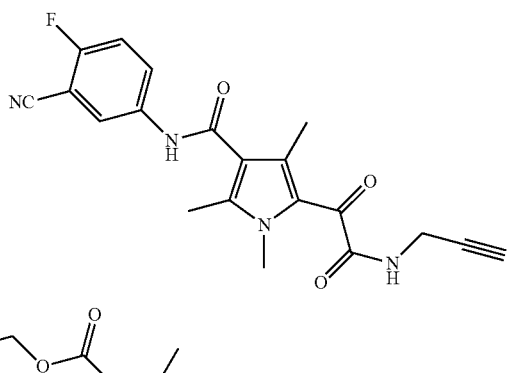

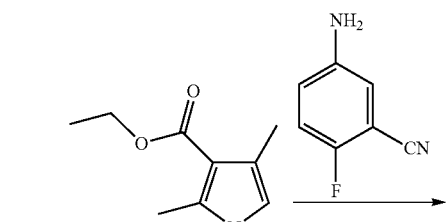

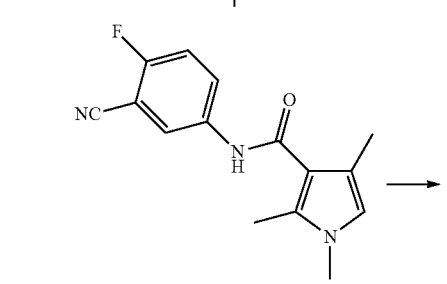

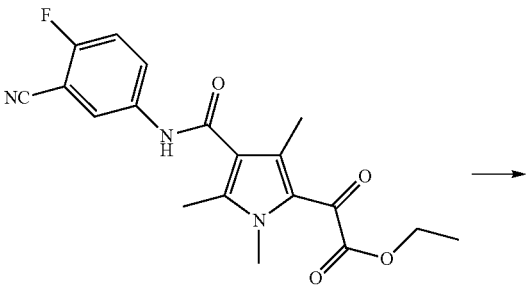

-continued

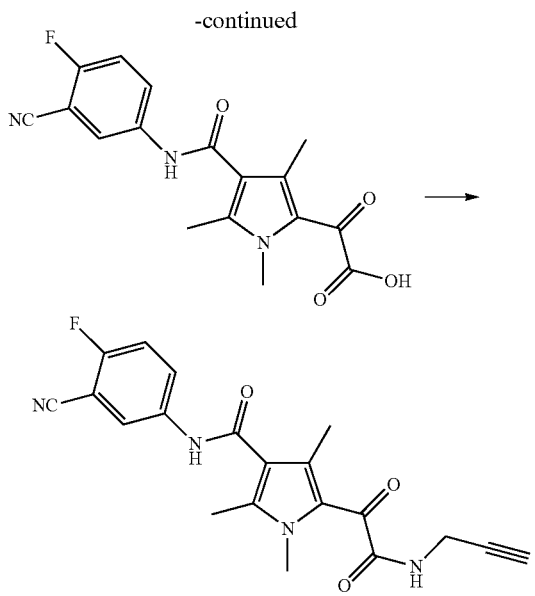

Step A: DMF (100 mL), ethyl 2,4-dimethyl-1H-pyrrole-3-carboxylate (8.0 g), and methyl iodide (8.15 g) were added to a 500 mL single-port flask under the protection of nitrogen gas. Sodium hydride (2.87 g) was added in batches in an ice bath, and then brought to room temperature after the addition and reacted for 2.5 h. After the reaction was finished, the reaction solution was slowly poured into 400 mL ice water for quenching, and then extracted with ethyl acetate (2*300 mL), and the organic layers were combined. The combined organic layer was washed with a saturated aqueous solution of sodium chloride, dried over anhydrous sodium sulfate and evaporated under reduced pressure to remove the solvent. The crude product was separated by silica gel column chromatography (PE:EA=20:1) to give ethyl 1,2,4-trimethyl-1H-pyrrole-3-carboxylate (4.87 g). $^1$H-NMR (500 MHz, DMSO-d6): δ 6.44 (s, 1H), 4.15 (q, J=7.5 Hz, 2H), 3.44 (s, 3H), 2.39 (s, 3H), 2.09 (s, 3H), 1.25 (t, J=7.0 Hz, 3H). $^{13}$C-NMR (125 MHz, DMSO-d6): δ 165.63, 136.13, 120.78, 118.91, 110.56, 58.76, 33.58, 14.85, 12.93, 11.60. MS(ESI+, [M+H]$^+$) m/z: 182.3.

Step B: THF (150 mL), ethyl 1,2,4-trimethyl-1H-pyrrole-3-carboxylic acid (15.0 g), and 5-amino-2-fluorobenzonitrile (14.08 g) were added to a 500 mL three-necked flask under the protection of nitrogen gas. Bi(trimethylsilyl)amide lithium (27.7 g, 166 mL solution in THF) was slowly added dropwise in an ice bath, and then brought to room temperature after the addition and reacted for 16.0 h. After the reaction was finished, the reaction solution was slowly poured into 500 mL ice water for quenching, and then extracted with ethyl acetate (2*400 mL), and the organic layers were combined. The combined organic layer was washed with a saturated aqueous solution of sodium chloride, dried over anhydrous sodium sulfate and evaporated under reduced pressure to remove the solvent. The crude product was separated by silica gel column chromatography (PE:EA=1:1) to give N-(3-cyano-4-fluorophenyl)-1,2,4-trimethyl-1H-pyrrole-3-carboxamide (6.73 g). $^1$H-NMR (500 MHz, DMSO-d6): δ 9.64 (s, 1H), 8.18 (t, J=3.5 Hz, 1H), 7.93-7.96 (m, 1H), 7.48 (t, J=9.0 Hz, 1H), 6.49 (s, 1H), 3.47 (s, 3H), 2.30 (s, 3H), 2.10 (s, 3H). $^{13}$C-NMR (125 MHz, DMSO-d6): δ 165.51, 159.30, 157.15, 137.56, 131.76, 126.97, 123.33, 120.33, 117.39, 116.77, 114.59, 100.19, 33.53, 11.63. MS(ESI-, [M-H]$^-$) m/z: 270.2.

Step C: DCM (240 mL), (N-(3-cyano-4-fluorophenyl)-1,2,4-trimethyl-1H-pyrrole-3-carboxamide (5.0 g), and monoethyl chloroacetonate (7.55 g) were added to a 500 mL one-necked flask under the protection of nitrogen gas. Aluminum chloride (12.29 g) was added in batches in an ice bath, and then brought to room temperature after the addition and reacted for 15.0 h. After the reaction was finished, the reaction solution was slowly poured into 300 mL ice water for quenching, and then extracted with DCM (2*300 mL), and the organic layers were combined. The combined organic layer was washed with a saturated aqueous solution of sodium chloride, dried over anhydrous sodium sulfate, and then suction-filtered. The filtrate was rotary-evaporated under reduced pressure to remove the solvent. To the crude product was added EtOAc (45 mL), and slurried at room temperature for 1.0 h. The resulting mixture was suction-filtered, and the filter cake was dried under vacuum to give ethyl 2-(4-((3-cyano-4-fluorophenyl)carbamoyl)-1,3,5-trimethyl-1H-pyrrol-2-yl)-2-oxoacetate (4.25 g). MS(ESI−, [M−H]$^-$) m/z: 370.2.

Step D: Methanol (30 mL), ethyl 2-(4-((3-cyano-4-fluorophenyl)carbamoyl)-1,3,5-trimethyl-1H-pyrrol-2-yl)-2-oxoacetate (4.00 g) and sodium hydroxide (0.862 g) in water (30 mL) were added into a 100 mL single-necked flask in an ice bath, and then brought to room temperature after the addition and reacted for 2.0 h. Water (200 mL) and DCM (150 mL) were added to the reaction mixture, and the resulting mixture was layered. The organic layer was discarded, and the aqueous layer was adjusted to pH 2 with concentrated hydrochloric acid and then extracted with ethyl acetate (2*150 mL). The organic layer was combined, washed with a saturated aqueous solution of sodium chloride, dried over anhydrous sodium sulfate, and then suction-filtered. The filtrate was evaporated under reduced pressure to remove the solvent to give 2-(4-(3-cyano-4-fluorophenyl)carbamoyl)-1,3,5-trimethyl-1H-pyrrol-2-yl)-2-oxoacetic acid (3.25 g). $^1$H-NMR (500 MHz, DMSO-d6): δ 10.32 (s, 1H), 8.19-8.21 (m, 1H), 7.93-7.97 (m, 1H), 7.52 (t, J=9.0 Hz, 1H), 3.81 (s, 3H), 2.36 (s, 3H), 2.27 (s, 3H). $^{13}$C-NMR (125 MHz, DMSO-d6): δ 178.85, 167.79, 163.98, 159.67, 157.66, 141.31, 136.80, 130.95, 127.26, 123.84, 117.60, 114.43, 100.41, 60.21, 33.73, 21.22, 14.55.

Step E: DMF (5.0 mL), 2-(4-(3-cyano-4-fluorophenyl)carbamoyl)-1,3,5-trimethyl-1H-pyrrol-2-yl)-2-oxoacetic acid (300 mg), HATU (399 mg), and DIPEA (169 mg) were added sequentially to a 50 mL one-necked flask, followed by adding propargylamine (52.9 mg), and then stirred at room temperature for 16.0 h. Water (200 mL) was added to the reaction mixture, and then extracted with ethyl acetate (2*100 mL), and the organic layers were combined. The combined organic layer was washed with a saturated aqueous solution of sodium chloride, dried over anhydrous sodium sulfate, and evaporated under reduced pressure to remove the solvent. The crude product was separated by silica gel column chromatography (PE:EA=1:1) to give N-(3-cyano-4-fluorophenyl)-1,2,4-trimethyl-5-(2-oxo-2-(prop-2-yn-1-ylamino)acetyl)-1H-pyrrole-3-carboxamide (142 mg). $^1$H-NMR (500 MHz, DMSO-d6): δ 10.31 (s, 1H), 9.19 (t, J=5.5 Hz, 1H), 8.20-8.21 (m, 1H), 7.93-7.97 (m, 1H), 7.51 (t, J=9.0 Hz, 1H), 4.01-4.02 (m, 2H), 3.78 (s, 3H), 3.17 (t, J=2.0 Hz, 1H), 2.35 (s, 3H), 2.22 (s, 3H). $^{13}$C-NMR (125 MHz, DMSO-d6): δ 181.35, 166.95, 164.16, 159.64, 157.63, 140.62, 136.85, 130.84, 127.27, 125.24, 123.76, 120.62, 117.58, 114.45, 100.39, 80.43, 73.99, 33.62, 28.18, 11.56. MS (ESI-, [M−H]$^-$) m/z: 379.2.

Example 2

5-(2-(Bicyclo[1.1.1]pentan-1-ylamino)-2-oxoacetyl)-N-(3-cyano-4-fluorophenyl)-1,2,4-trimethyl-1H-pyrrole-3-carboxamide

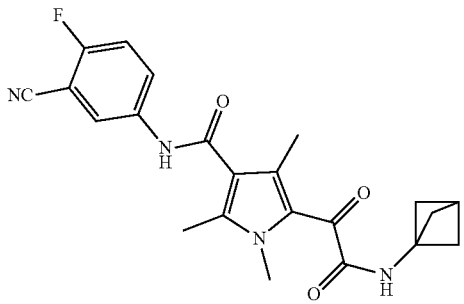 [SMILES: Cc1c(C(=O)Nc2ccc(F)c(C#N)c2)c(C)n(C)c1C(=O)C(=O)NC12CC(C1)C2]

According to Example 1, propargylamine was replaced with 1-bicyclo[1,1,1]pentylamine hydrochloride in step E to give 5-(2-(bicyclo[1.1.1]pent-1-ylamino)-2-oxoacetyl)-N-(3-cyano-4-fluorophenyl)-1,2,4-trimethyl-1H-pyrrole-3-carboxamide. $^1$H-NMR (500 MHz, DMSO-d$_6$): δ 10.31 (s, 1H), 9.28 (s, 1H), 8.20-8.22 (m, 1H), 7.94-7.97 (m, 1H), 7.52 (t, J=9.0 Hz, 1H), 3.77 (s, 3H), 2.48-2.50 (m, 1H), 2.34 (s, 3H), 2.22 (s, 3H), 2.06 (s, 6H). $^{13}$C-NMR (125 MHz, DMSO-d$_6$): δ 181.57, 167.47, 164.15, 159.62, 157.62, 140.52, 136.83, 130.51, 127.25, 125.04, 123.73, 120.52, 117.60, 114.48, 100.37, 52.63, 48.55, 33.60, 25.29, 11.54. MS (ESI-, [M-H]$^-$) m/z: 407.3.

Example 3

N-(3-cyano-4-fluorophenyl)-5-(2-((trans-3-hydroxycyclobutyl)amino)-2-oxoacetyl)-1,2,4-trimethyl-1H-pyrrole-3-carboxamide

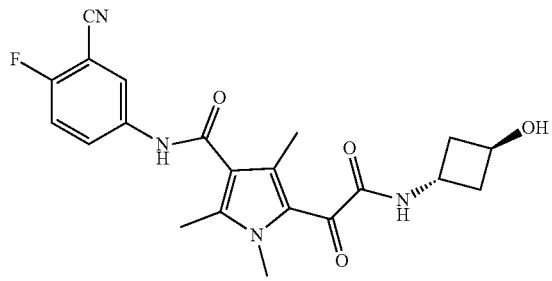 [SMILES: Cc1c(C(=O)Nc2ccc(F)c(C#N)c2)c(C)n(C)c1C(=O)C(=O)N[C@H]1C[C@H](O)C1]

According to Example 1, propargylamine was replaced with trans-3-aminocyclobutanol hydrochloride in step E to give N-(3-cyano-4-fluorophenyl)-5-(2-((trans-3-hydroxycyclobutyl)amino)-2-oxoacetyl)-1,2,4-trimethyl-1H-pyrrole-3-carboxamide. $^1$H-NMR (500 MHz, DMSO-d$_6$): δ 10.28 (s, 1H), 8.98 (d, J=7.0 Hz, 1H), 8.19-8.21 (m, 1H), 7.94-7.97 (m, 1H), 7.51 (t, J=9.0 Hz, 1H), 5.06 (d, J=5.5 Hz, 1H), 4.27-4.31 (m, 2H), 3.77 (s, 3H), 2.35 (s, 3H), 2.14-2.24 (m, 7H). $^{13}$C-NMR (125 MHz, DMSO-d$_6$): δ 182.10, 166.88, 164.19, 159.63, 157.63, 140.37, 136.84, 130.40, 127.29, 125.36, 123.77, 120.49, 117.58, 114.45, 100.38, 63.57, 33.59, 11.55. MS (ESI-, [M-H]$^-$) m/z: 411.3.

Example 4

N-(3-cyano-4-fluorophenyl)-5-(2-((cis-3-hydroxycyclobutyl)amino)-2-oxoacetyl)-1,2,4-trimethyl-1H-pyrrole-3-carboxamide

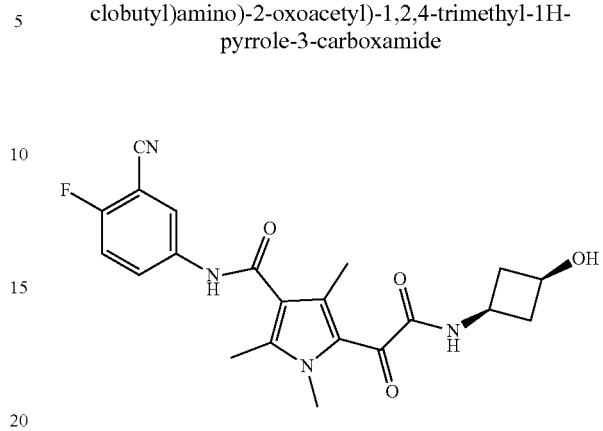

According to Example 1, propargylamine was replaced with cis-3-aminocyclobutanol hydrochloride in step E to give N-(3-cyano-4-fluorophenyl)-5-(2-((cis-3-hydroxycyclobutyl)amino)-2-oxoacetyl)-1,2,4-trimethyl-1H-pyrrole-3-carboxamide. $^1$H-NMR (500 MHz, DMSO-d6): δ 10.29 (s, 1H), 8.92 (d, J=7.0 Hz, 1H), 8.20 (d, J=3.5 Hz, 1H), 7.95 (d, J=3.0 Hz, 1H), 7.52 (t, J=9.0 Hz, 1H), 5.11 (d, J=5.5 Hz, 1H), 3.76-3.87 (m, 5H), 2.51-2.55 (m, 2H), 2.35 (s, 3H), 2.19 (s, 3H), 1.81-1.86 (m, 2H); $^{13}$C-NMR (125 MHz, DMSO-d6): δ 182.07, 166.64, 164.20, 159.63, 157.63, 140.32, 136.84, 130.40, 127.25, 125.32, 123.77, 120.50, 117.50, 114.45, 100.32, 59.78, 35.81, 33.58, 25.27, 11.43. MS (ESI-, [M-H]$^-$) m/z: 411.3.

Example 5

N-(3-cyano-4-fluorophenyl)-1,2,4-trimethyl-5-(2-(oxetan-3-ylamino)-2-oxoacetyl)-1H-pyrrole-3-carboxamide

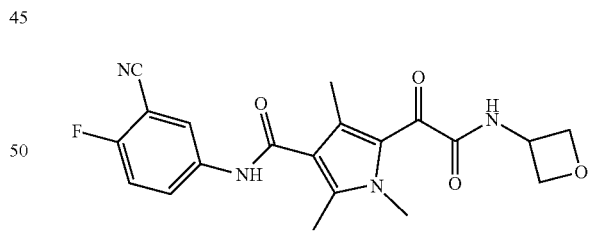

According to Example 1, propargylamine was replaced with 3-oxetanamine in step E to give N-(3-cyano-4-fluorophenyl)-1,2,4-trimethyl-5-(2-(oxetan-3-ylamino)-2-oxoacetyl)-1H-pyrrole-3-ca rboxamide. $^1$H NMR (500 MHz, DMSO-d$_6$): δ 10.30 (s, 1H), 9.51-9.52 (m, 1H), 8.20-8.21 (m, 1H), 7.95-7.96 (m, 1H), 7.50-7.53 (m, 1H), 4.92-4.95 (m, 1H), 4.77-4.80 (t, J=13.5 Hz, 2H), 4.52-4.55 (t, J=12 Hz, 2H), 3.78 (s, 3H), 2.36 (s, 3H), 2.19 (s, 3H); $^{13}$C NMR (125 MHz, DMSO-d$_6$): δ 164.12, 159.64, 157.64, 140.69, 136.84, 136.82, 130.64, 127.27, 127.21, 120.63, 117.58, 117.41, 114.44, 76.88, 44.31, 33.63, 11.56, 11.47. MS(ESI-, [M-H]$^-$) m/z: 397.3.

Example 6

N-(3-cyano-4-fluorophenyl)-1,2,4-trimethyl-5-(2-(3-methyloxetan-3-ylamino)-2-oxoacetyl)-1H-pyrrole-3-carboxamide

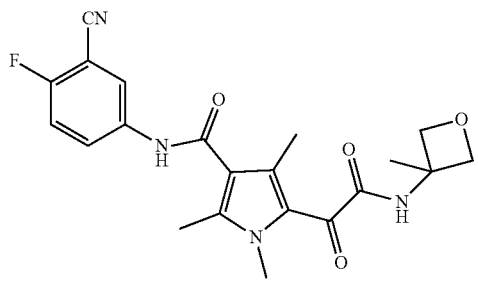 [SMILES: Cc1c(C(=O)Nc2ccc(F)c(C#N)c2)c(C)n(C)c1C(=O)C(=O)NC1(C)COC1]

According to Example 1, propargylamine was replaced with 3-methyl-3-aminooxetane in step E to give N-(3-cyano-4-fluorophenyl)-1,2,4-trimethyl-5-(2-((3-methyloxetane-3-yl)amino)-2-oxoacetyl)-1H-pyrrole-3-carboxamide.
$^1$H-NMR (500 MHz, DMSO-d6): δ 10.29 (s, 1H), 9.24 (s, 1H), 8.21 (d, J=3.5 Hz, 1H), 7.96 (s, 1H), 7.52 (t, J=9.0 Hz, 1H), 4.69 (d, J=6.5 Hz, 2H), 4.39 (d, J=6.0 Hz, 2H), 3.78 (s, 3H), 2.36 (s, 3H), 2.28 (s, 3H), 1.60 (s, 3H). $^{13}$C-NMR (125 MHz, DMSO-d6): δ 181.41, 166.23, 164.14, 159.64, 157.64, 140.70, 136.85, 130.46, 127.26, 125.41, 123.78, 120.51, 117.50, 114.45, 100.32, 80.79, 53.55, 33.62, 23.38, 11.64. MS (ESI–, [M–H]$^-$) m/z: 411.3.

Example 7

N-(3-cyano-4-fluorophenyl)-1,2,4-trimethyl-5-(2-oxo-2-((tetrahydrofuran-3-yl)amino)acetyl)-1H-pyrrole-3-carboxamide

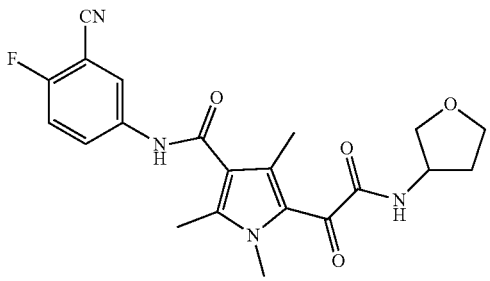 [SMILES: Cc1c(C(=O)Nc2ccc(F)c(C#N)c2)c(C)n(C)c1C(=O)C(=O)NC1CCOC1]

According to Example 1, propargylamine was replaced with 3-aminotetrahydrofuran in step E to give N-(3-cyano-4-fluorophenyl)-1,2,4-trimethyl-5-(2-oxo-2-((tetrahydrofuran-3-yl)amino)acetyl)-1H-pyrrole-3-carboxamide.
$^1$H-NMR (500 MHz, DMSO-d$_6$): δ 10.29 (s, 1H), 8.98 (d, J=6.0 Hz, 1H), 8.20 (d, J=2.5 Hz, 1H), 7.94-7.96 (m, 1H), 7.51 (t, J=9.5 Hz, 1H), 4.35 (s, 1H), 3.69-3.83 (m, 6H), 3.56-3.58 (m, 1H), 2.35 (s, 3H), 2.22 (s, 3H), 2.12-2.20 (m, 1H), 1.83-1.85 (m, 1H). $^{13}$C-NMR (125 MHz, DMSO-d$_6$): δ 181.80, 167.32, 164.18, 159.64, 157.63, 140.44, 136.86, 130.42, 127.28, 125.29, 123.77, 120.52, 117.58, 114.45, 100.39, 72.28, 66.83, 50.00, 33.61, 32.04, 11.55. MS (ESI–, [M–H]$^-$) m/z: 411.3.

Example 8

N-(3-cyano-4-fluorophenyl)-5-(2-((1-hydroxy-2-methylpropan-2-yl)amino)-2-oxoacetyl)-1,2,4-trimethyl-1H-pyrrole-3-carboxamide

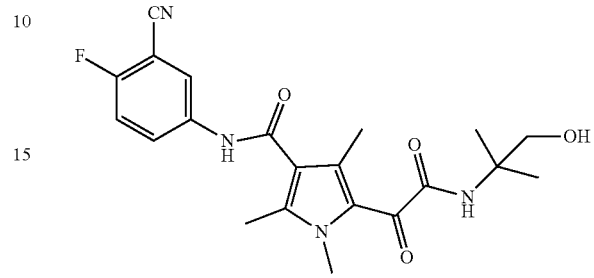

According to Example 1, propargylamine was replaced with 2-amino-2-methyl-1-propanol in step E to give N-(3-cyano-4-fluorophenyl)-5-(2-((1-hydroxy-2-methylpropane-2-yl)amino)-2-oxoacetyl)-1,2,4-trimethyl-1H-pyrrole-3-carboxamide. $^1$H-NMR (500 MHz, DMSO-d$_6$): δ 10.26 (s, 1H), 8.20-8.21 (m, 1H), 8.08 (m, 1H), 7.95-7.97 (m, 1H), 7.51 (t, J=9.0 Hz, 1H), 4.85 (t, J=5.5 Hz, 1H), 3.76 (s, 3H), 3.45 (d, J=5.5 Hz, 2H), 2.35 (s, 3H), 2.28 (s, 3H), 1.29 (s, 6H). $^{13}$C-NMR (125 MHz, DMSO-d$_6$): δ 181.94, 167.14, 164.28, 159.61, 157.60, 140.04, 136.91, 130.12, 127.25, 125.44, 123.74, 120.28, 117.56, 114.46, 100.37, 67.75, 55.38, 33.56, 23.52, 11.61. MS (ESI–, [M–H]$^-$) m/z: 413.4.

Example 9 Methyl (2-(4-((3-cyano-4-fluorophenyl)carbamoyl)-1,3,5-trimethyl-1H-pyrrol-2-yl)-2-oxoacetamido)-2-methylpropionate

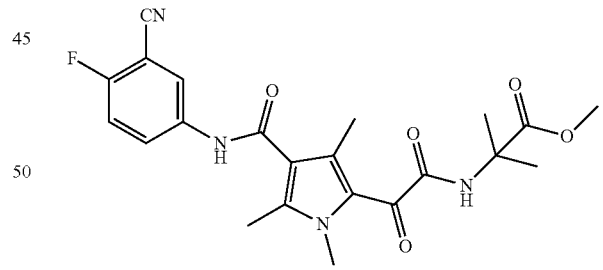

According to Example 1, propargylamine was replaced with methyl 2-aminoisobutyrate hydrochloride in step E to give methyl (2-(4-((3-cyano-4-fluorophenyl)carbamoyl)-1,3,5-trimethyl-1H-pyrrole-2-yl)-2-oxoacetylamino)-2-methylpropionate. $^1$H-NMR (500 MHz, DMSO-d6): δ 10.28 (s, 1H), 9.07 (s, 1H), 8.21 (d, J=3.5 Hz, 1H), 7.96 (s, 1H), 7.52 (t, J=9.0 Hz, 1H), 3.76 (s, 3H), 3.62 (s, 3H), 2.36 (s, 3H), 2.26 (s, 3H), 1.44 (s, 6H). $^{13}$C-NMR (125 MHz, DMSO-d6): δ 174.12, 166.24, 164.24, 162.77, 157.62, 140.51, 136.89, 130.67, 127.25, 125.57, 123.76, 120.40, 117.49, 114.46, 100.31, 55.67, 52.41, 36.24, 33.60, 25.06, 11.58. MS (ESI–, [M–H]$^-$) m/z: 441.4.

Example 10

N-(3-cyano-4-fluorophenyl)-5-(2-((cis-3-(hydroxymethyl)cyclobutyl)amino)-2-oxoacetyl)-1,2,4-trimethyl-1H-pyrrole-3-carboxamide

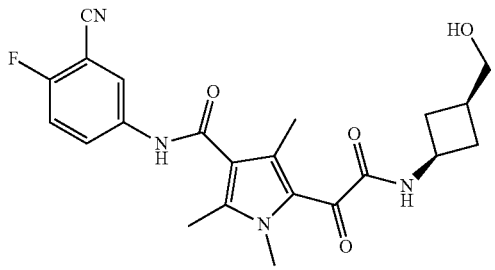 [SMILES: Cc1c(C(=O)Nc2ccc(F)c(C#N)c2)c(C)n(C)c1C(=O)C(=O)N[C@H]1C[C@@H](CO)C1]

According to Example 1, propargylamine was replaced with cis-3-amino-cyclobutanemethanol in step E to give N-(3-cyano-4-fluorophenyl)-5-(2-((cis-3-(hydroxymethyl)cyclobutyl)amino)-2-oxoacetyl)-1,2,4-tri methyl-1H-pyrrole-3-carboxamide. $^1$H-NMR (500 MHz, DMSO-$d_6$): δ 10.28 (s, 1H), 8.90 (d, J=7.5 Hz, 1H), 8.20 (s, 1H), 7.95 (t, J=4.0 Hz, 1H), 7.52 (t, J=9.5 Hz, 1H), 4.48 (t, J=5.0 Hz, 1H), 4.17 (m, 1H), 3.77 (s, 3H), 3.35 (t, J=5.5 Hz, 2H), 2.35 (s, 3H), 2.25 (m, 2H), 2.10 (s, 3H), 1.75 (m, 2H). $^{13}$C-NMR (125 MHz, DMSO-$d_6$): δ 182.14, 166.41, 164.21, 159.63, 157.62, 140.27, 136.85, 130.35, 127.24, 125.35, 123.76, 120.48, 117.50, 114.45, 100.31, 65.26, 60.21, 33.58, 32.66, 31.00, 11.44. MS (ESI-, [M−H]$^-$) m/z: 425.3.

Example 11

(R)—N-(3-cyano-4-fluorophenyl)-1,2,4-trimethyl-5-(2-oxo-2-((1,1,1-)trifluoropropan-2-yl)amino)acetyl)-1H-pyrrole-3-carboxamide

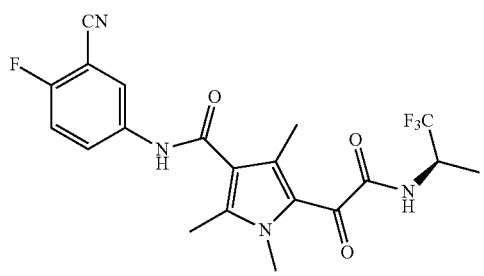 [SMILES: Cc1c(C(=O)Nc2ccc(F)c(C#N)c2)c(C)n(C)c1C(=O)C(=O)N[C@H](C)C(F)(F)F]

According to Example 1, propargylamine was replaced with (R)-1,1,1-trifluoroisopropylamine hydrochloride in step E to give (R)—N-(3-cyano-4-fluorophenyl)-1,2,4-trimethyl-5-(2-oxo-2-((1,1,1-trifluoropropane)-2-yl)amino)acetyl)-1H-pyrrole-3-carboxamide. $^1$H-NMR (500 MHz, DMSO-$d_6$): δ 10.31 (s, 1H), 9.38 (d, J=8.5 Hz, 1H), 8.19 (d, J=4.0 Hz, 1H), 7.95 (t, J=4.5 Hz, 1H), 7.52 (t, J=9.0 Hz, 1H), 4.67-4.75 (m, 1H), 3.79 (s, 3H), 2.36 (s, 3H), 2.12 (s, 3H), 1.31 (d, J=6.5 Hz, 3H). $^{13}$C-NMR (125 MHz, DMSO-$d_6$): δ 180.80, 167.24, 164.08, 140.92, 136.82, 130.81, 127.32, 125.02, 123.82, 120.71, 117.59, 114.44, 100.27, 33.66, 13.76, 11.58. MS(ESI-, [M−H]$^-$) m/z: 437.3.

Example 12

(S)—N-(3-cyano-4-fluorophenyl)-1,2,4-trimethyl-5-(2-oxo-2-((1,1,1-)trifluoropropan-2-yl)amino)acetyl)-1H-pyrrole-3-carboxamide

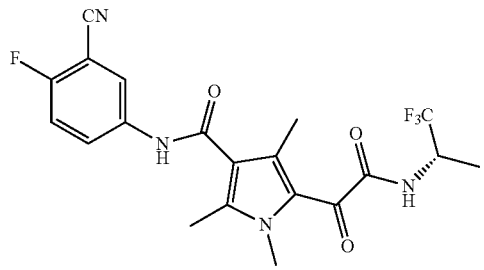 [SMILES: Cc1c(C(=O)Nc2ccc(F)c(C#N)c2)c(C)n(C)c1C(=O)C(=O)N[C@@H](C)C(F)(F)F]

Step A: According to Example 1, propargylamine was replaced with (S)-1,1,1-trifluoroisopropylamine hydrochloride in step E to give (S)—N-(3-cyano-4-fluorophenyl)-1,2,4-trimethyl-5-(2-oxo-2-((1,1,1-trifluoropropane)-2-yl)amino)acetyl)-1H-pyrrole-3-carboxamide. $^1$H-NMR (500 MHz, DMSO-$d_6$): δ 10.31 (s, 1H), 9.38 (d, J=9.0 Hz, 1H), 8.19-8.21 (m, 1H), 7.93-7.97 (m, 1H), 7.51 (t, J=9.5 Hz, 1H), 4.68-4.75 (m, 1H), 3.79 (s, 3H), 2.36 (s, 3H), 2.21 (s, 3H), 1.31 (d, J=7.0 Hz, 3H). $^{13}$C-NMR (125 MHz, DMSO-$d_6$): δ 180.80, 167.24, 164.08, 159.66, 157.65, 140.92, 136.82, 130.81, 127.31, 125.02, 123.81, 120.71, 117.58, 114.44, 100.40, 46.04, 33.66, 13.75, 11.57. MS(ESI-, [M−H]$^-$) m/z: 437.3.

Example 13

5-(2-(tert-butylamino)-2-oxoacetyl)-N-(3-cyano-4-fluorophenyl)-1,2,4-trimethyl-1H-pyrrole-3-carboxamide

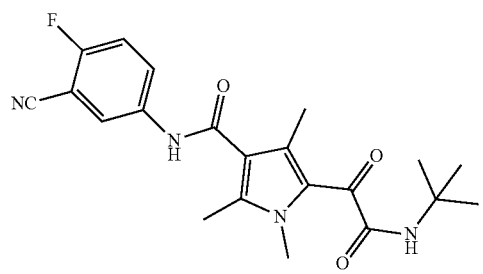

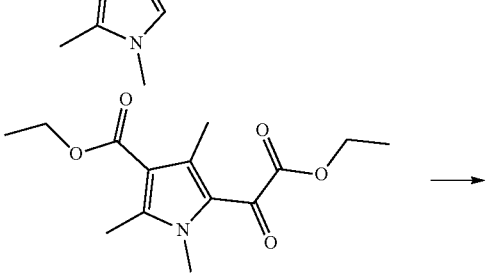

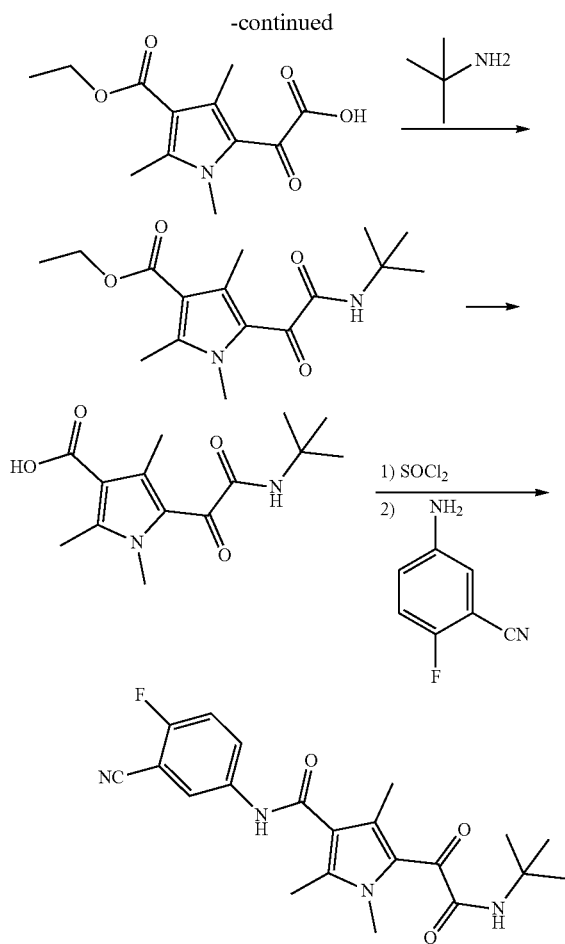

Step A: DCM (250 mL), ethyl 1,2,4-trimethyl-1H-pyrrole-3-carboxylate (2.0 g), and monoethyl chlorooxalate (4.52 g) were added into a 500 mL one-necked flask under the protection of nitrogen gas. Anhydrous aluminum chloride (7.36 g) was added slowly in an ice bath, and then the reaction solution was brought to room temperature after the addition and reacted for 5.5 h. After the reaction is finished, the resulting mixture was slowly poured into 200 mL ice water for quenching, and then extracted with DCM (2*200 mL), and the organic layers were combined. The combined organic layer was washed with a saturated aqueous solution of sodium chloride, dried over anhydrous sodium sulfate and then evaporated under reduced pressure to remove the solvent. The crude product was eluted by silica gel column chromatography (PE:EA=10:1) to give ethyl 5-(2-ethoxy-2-oxoacetyl)-1,2,4-trimethyl-1H-pyrrole-3-carboxylate (2.14 g). $^1$H-NMR (500 MHz, DMSO-d6): δ 4.35 (q, J=7.0 Hz, 2H), 4.24 (q, J=7.0 Hz, 2H), 3.77 (s, 3H), 2.50 (s, 3H), 2.30 (s, 3H), 1.27-1.32 (m, 6H). $^{13}$C-NMR (125 MHz, DMSO-d6): δ 177.03, 165.34, 164.38, 146.14, 134.75, 124.72, 113.85, 62.66, 60.09, 33.76, 14.59, 14.12, 12.06, 11.59.

Step B: Methanol (10 mL), and ethyl 5-(2-ethoxy-2-oxoacetyl)-1,2,4-trimethyl-1H-pyrrole-3-carboxylate (1.20 g) were added into a 100 mL one-necked flask, followed by slowly adding a solution of sodium hydroxide (0.34 g) in water (10 mL) in an ice bath, and then reacted for 15 minutes in an ice bath. After the reaction is finished, to the reaction system was added water (30 mL), and the resulting mixture was adjusted to pH 2 with concentrated hydrochloric acid, and then extracted with ethyl acetate (2*50 mL), and the organic layers were combined. The combined organic layer was washed with a saturated aqueous solution of sodium chloride, dried over anhydrous sodium sulfate and evaporated under reduced pressure to remove the solvent to give crude 2-(4-(ethoxycarbonyl)-1,3,5-trimethyl-1H-pyrrol-2-yl)-2-oxoacetic acid (897 mg) which was used directly in the next reaction.

MS (ESI-, [M−H]$^−$) m/z: 252.1.

Step C: At room temperature, DMF (15 mL), 2-(4-(ethoxycarbonyl)-1,3,5-trimethyl-1H-pyrrol-2-yl)-2-oxoacetic acid (700 mg), HATU (1366 mg), and DIPEA (464 mg) were added sequentially to a 25 mL one-necked flask, stirred at room temperature for 10 minutes, and then tert-butylamine (202 mg) was added thereto. The resulting mixture was stirred at room temperature to react for 0.5 h. After the reaction was finished, to the reaction system was added water (100 mL), and then extracted with ethyl acetate (2*100 mL), and the organic layers were combined. The combined organic layer was washed with a saturated aqueous solution of sodium chloride, dried over anhydrous sodium sulfate and evaporated under reduced pressure to remove the solvent. The crude product was eluted by silica gel column chromatography (PE:EA=3:1) to give ethyl 5-(2-(tert-butylamino)-2-oxoacetyl)-1,2,4-trimethyl-1H-pyrrole-3-carboxylate (719 mg). $^1$H-NMR (500 MHz, DMSO-d6): δ 8.28 (s, 1H), 4.23 (q, J=7.0 Hz, 2H), 3.73 (s, 3H), 2.51 (s, 3H), 2.37 (s, 3H), 1.34 (s, 9H), 1.29 (t, J=7.0 Hz, 3H). $^{13}$C-NMR (125 MHz, DMSO-d6): δ 182.55, 166.89, 164.78, 144.19, 132.84, 126.23, 113.01, 59.86, 51.26, 33.55, 28.59, 14.67, 12.05. MS (ESI+, [M+H]$^+$) m/z: 309.4.

Step D: Methanol (9 mL), and ethyl 5-(2-(tert-butylamino)-2-oxoacetyl)-1,2,4-trimethyl-1H-pyrrole-3-carboxylate (500 mg) were added sequentially to a 50 mL one-necked flask, followed by adding a solution of sodium hydroxide (259 mg) in water (9 mL) at room temperature, and then the reaction mixture was heated to 90° C. and reacted for 3.0 h. After the reaction is finished, the resulting mixture was adjusted to pH 2 with concentrated hydrochloric acid, and then extracted with ethyl acetate (2*50 mL), and the organic layers were combined. The combined organic layer was washed with a saturated aqueous solution of sodium chloride, dried over anhydrous sodium sulfate and evaporated under reduced pressure to remove the solvent to give crude 5-(2-(tert-butylamino)-2-oxoacetyl)-1,2,4-trimethyl-1H-pyrrole-3-carboxylic acid (260 mg) which was used directly in the next reaction. $^1$H-NMR (500 MHz, DMSO-d6): δ 12.28 (s, 1H), 8.26 (s, 1H), 3.73 (s, 3H), 2.50 (s, 3H), 2.38 (s, 3H), 1.33 (s, 9H). $^{13}$C-NMR (125 MHz, DMSO-d6): δ 182.50, 167.00, 166.39, 144.35, 133.30, 126.12, 113.61, 51.23, 33.50, 28.61, 12.04. MS (ESI+, [M+H]$^+$) m/z: 281.3.

Step E: Toluene (15 mL), 5-(2-(tert-butylamino)-2-oxoacetyl)-1,2,4-trimethyl-1H-pyrrole-3-carboxylic acid (360 mg), and thionyl chloride (3.05 g) were added sequentially into a 50 mL one-necked flask, and then the system was heated to 115° C. to react for 1.0 h under the protection of nitrogen gas. After the reaction was finished, the reaction solution was cooled to room temperature, and then evaporated to remove the solvent. Acyl chloride intermediate (339 mg) was collected. Then the acyl chloride intermediate (339 mg) was dissolved in N,N-dimethylacetamide (12 mL) at room temperature, followed by adding 5-amino-2-fluorobenzonitrile (309 mg), and then heated to 100° C. to react for 0.5 h. After the reaction was finished, the resulting mixture was cooled to room temperature, and then extracted with ethyl acetate (2*50 mL), and the organic layers were combined. The combined organic layer was washed with a saturated aqueous solution of sodium chloride, dried over anhydrous sodium sulfate and then rotary-evaporated under reduced pressure to remove the solvent. The crude product was eluted by silica gel column chromatography (PE:EA=2:1) to give 5-(2-(tert-butylamino)-2-oxoacetyl)-N-(3-cyano-4-fluorophenyl)-1,2,4-trimethyl-1H-pyrrole-3-carboxamide (280 mg). $^{1}$H-NMR (500 MHz, DMSO-d6): δ 10.26 (s, 1H), 8.29 (s, 1H), 8.20-8.21 (m, 1H), 7.95-7.98 (m, 1H), 7.51 (t, J=9.0 Hz, 1H), 3.77 (s, 3H), 2.35 (s, 3H), 2.88 (s, 3H), 1.35 (s, 9H). $^{13}$C-NMR (125 MHz, DMSO-d6): δ 182.06, 167.12, 164.27, 159.61, 157.61, 140.07, 136.90, 130.03, 127.27, 125.36, 123.75, 120.27, 117.56, 114.46, 100.37, 51.23, 33.57, 28.66, 11.57. MS (ESI-, [M-H]$^{-}$) m/z: 397.3.

Example 14

5-(2-(tert-butylamino)-2-oxoacetyl)-N-(3-cyano-4-fluorophenyl)-1,4-dimethyl-1H-pyrrole-3-carboxamide

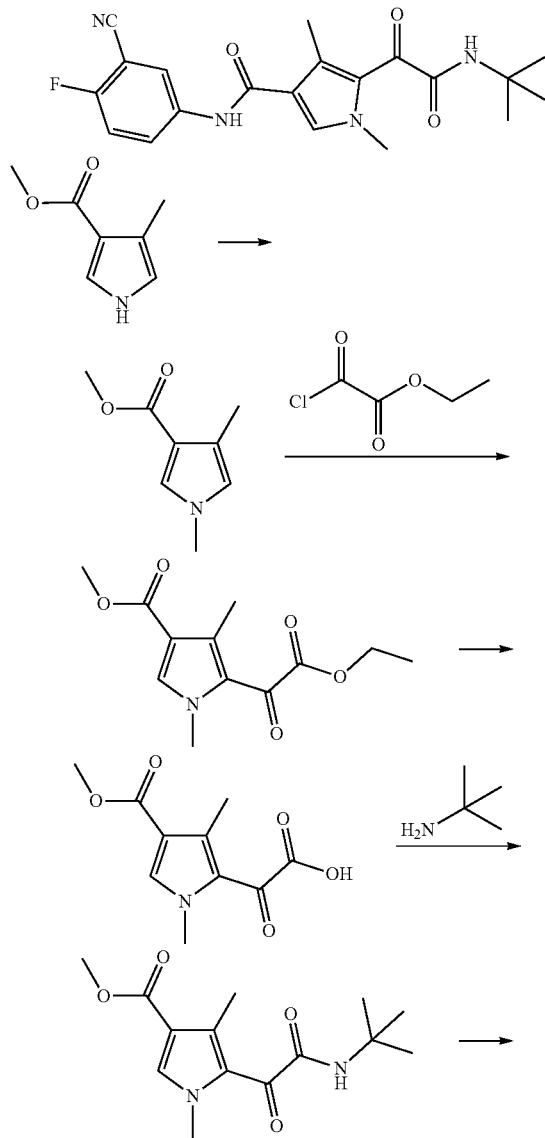

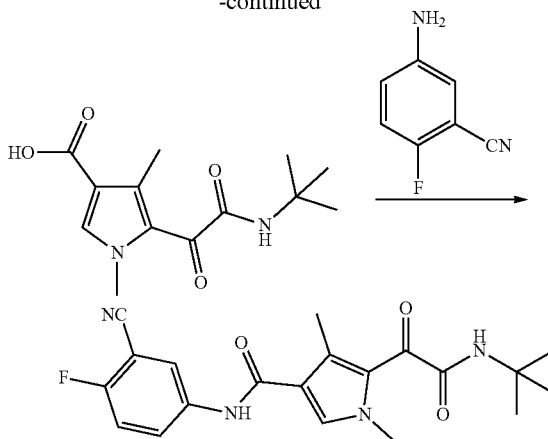

Step A: According to Example 1, ethyl 2,4-dimethyl-1H-pyrrole-3-carboxylate was replaced with methyl 4-methyl-1H-pyrrole-3-carboxylate in step A to give methyl 1,4-dimethyl-1H-pyrrole-3-carboxylate. $^{1}$H-NMR (500 MHz, DMSO-d$_{6}$): δ 7.30-7.31 (d, J=2 Hz, 1H), 6.56 (s, 1H), 3.66 (s, 3H), 23.57 (s, 3H), 2.13 (s, 3H); $^{13}$C-NMR (125 MHz, DMSO-d$_{6}$): δ 165.14, 128.24, 122.40, 120.50, 113.04, 50.72, 36.34, 11.96.

Step B: According to Example 13, ethyl 1,2,4-trimethyl-1H-pyrrole-3-carboxylate was replaced with methyl 1,4-dimethyl-1H-pyrrole-3-carboxylate in step A to give methyl 5-(2-ethoxy-2-oxoacetyl)-1,4-dimethyl-1H-pyrrole-3-carboxylate. MS(ESI+, [M+Na]$^{+}$) m/z: 276.3.

Step C: According to Example 13, ethyl 5-(2-ethoxy-2-oxoacetyl)-1,2,4-trimethyl-1H-pyrrole-3-carboxylate was replaced with methyl 5-(2-ethoxy-2-oxoacetyl)-1,4-dimethyl-1H-pyrrole-3-carboxylate in step B to give 2-(4-(methoxycarbonyl)-1,3-dimethyl-1H-pyrrol-2-yl)-2-oxoacetic acid. $^{1}$H-NMR (500 MHz, DMSO-d$_{6}$): δ 7.91 (s, 1H), 3.87 (s, 3H), 3.74 (s, 3H), 2.43 (s, 3H); $^{13}$C-NMR (125 MHz, DMSO-d$_{6}$): δ 179.71, 167.42, 164.00, 137.43, 134.14, 125.72, 113.93, 51.43, 38.52, 10.81.

Step D: According to Example 13, 2-(4-(ethoxycarbonyl)-1,3,5-trimethyl-1H-pyrrol-2-yl)-2-oxoacetic acid was replaced with 2-(4-(methoxycarbonyl)-1,3-dimethyl-1H-pyrrol-2-yl)-2-oxoacetic acid in step C to give methyl 5-(2-(tert-butylamino)-2-oxoacetyl)-1,4-dimethyl-1H-pyrrole-3-carboxylate. MS(ESI+, [M+Na]$^{+}$) m/z: 303.3.

Step E: According to Example 13, ethyl 5-(2-(tert-butylamino)-2-oxoacetyl)-1,2,4-trimethyl-1H-pyrrole-3-carboxylate was replaced with methyl 5-(2-(tert-butylamino)-2-oxoacetyl)-1,4-dimethyl-1H-pyrrole-3-carboxylate in step D to give 5-(2-(tert-butylamino)-2-oxoacetyl)-1,4-dimethyl-1H-pyrrole-3-carboxylic acid. $^{1}$H-NMR (500 MHz, DMSO-d$_{6}$): δ 8.32 (s, 1H), 7.75 (s, 1H), 3.83 (s, 3H), 2.43 (s, 3H), 1.34 (s, 9H); $^{13}$C-NMR (125 MHz, DMSO-d$_{6}$): δ 182.74, 166.86, 165.41, 136.65, 133.37, 127.10, 114.68, 51.28, 38.24, 28.63, 11.25.

Step F: According to Example 13, 5-(2-(tert-butylamino)-2-oxoacetyl)-1,2,4-trimethyl-1H-pyrrole-3-carboxylic acid was replaced with 5-(2-(tert-butylamino)-2-oxoacetyl)-1,4-dimethyl-1H-pyrrole-3-carboxylic acid in step E to give 5-(2-(tert-butylamino)-2-oxoacetyl)-N-(3-cyano-4-fluorophenyl)-1,4-dimethyl-1H-pyrrole-3-carboxamide. $^{1}$H-NMR (500 MHz, DMSO-d$_{6}$): δ 10.11 (s, 1H), 8.36 (s, 1H), 8.21 (s, 1H), 7.96-7.97 (m, 1H), 7.84 (s, 1H), 7.50-7.53 (m, 1H), 3.87 (s, 3H), 2.43 (s, 3H), 1.35 (s, 9H); $^{13}$C-NMR (125 MHz, DMSO-d$_{6}$): δ 166.83, 163.09, 159.48, 157.47, 137.01, 133.74, 132.59, 127.41, 127.35, 127.00, 123.87, 117.82, 117.50, 117.34, 114.49, 51.31, 38.34, 28.64, 11.32. MS(ESI–, [M–H]⁻) m/z: 383.3.

Example 15

2-bromo-5-(2-(tert-butylamino)-2-oxoacetyl)-N-(3-cyano-4-fluorophenyl)-1,4-dimethyl-1H-pyrrole-3-carboxamide

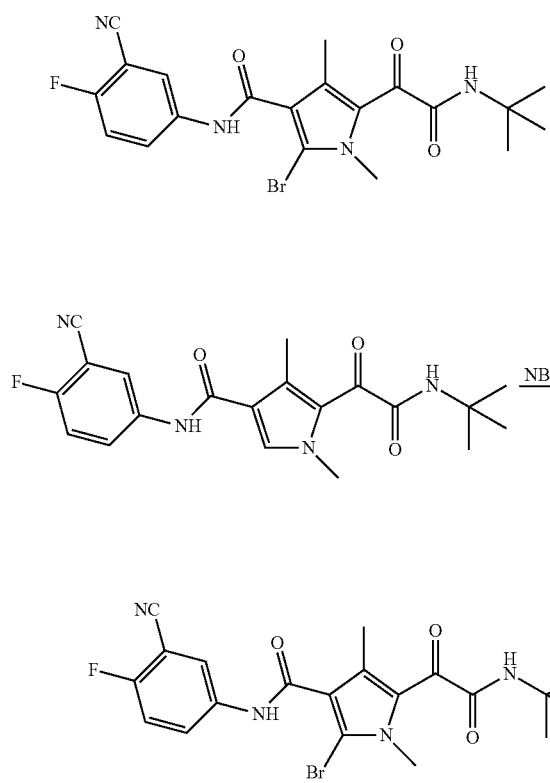

5-(2-(tert-butylamino)-2-oxoacetyl)-N-(3-cyano-4-fluorophenyl)-1,4-dimethyl-1H-pyrrole-3-carboxamide (0.3 g), DMF (8 mL), and acetonitrile (4 mL) were added into a 100 mL one-necked flask, followed by adding NBS (0.153 g) in an ice bath, and then warmed to room temperature and reacted for 3 hours. After the reaction was finished, to the reaction solution was added ethyl acetate (100 mL), washed with water (3*100 mL) for three times, dried, concentrated, and then slurried with a mixed solvent (2 mL) of PE:EA=3:1. The resulting mixture was filtered, and dried to give 2-bromo-5-(2-(tert-butylamino)-2-oxoacetyl)-N-(3-cyano-4-fluorophenyl)-1,4-dimethyl-1H-pyrrole-3-carboxamide (79 mg). ¹H-NMR (500 MHz, DMSO-d₆): δ 10.56 (s, 1H), 8.41 (s, 1H), 8.20 (s, 1H), 7.96-7.97 (m, 1H), 7.52-7.56 (m, 1H), 3.87 (s, 3H), 2.28 (s, 3H), 1.35 (s, 9H); ¹³C-NMR (125 MHz, DMSO-d₆): δ 162.45, 159.83, 157.82, 136.55, 130.30, 129.13, 127.16, 123.67, 122.42, 117.59, 116.05, 114.36, 51.40, 35.97, 28.60, 11.50. MS(ESI–, [M–H]⁻) m/z: 461.3.

Example 16

5-(2-(tert-butylamino)-2-oxoacetyl)-N-(3-cyano-4-fluorophenyl)-1,2-dimethyl-1H-pyrrole-3-carboxamide

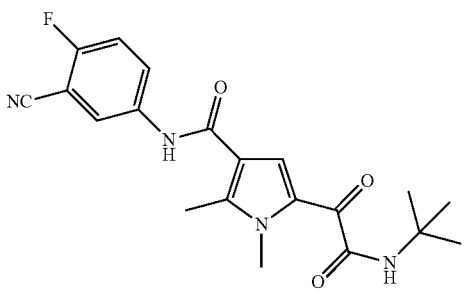

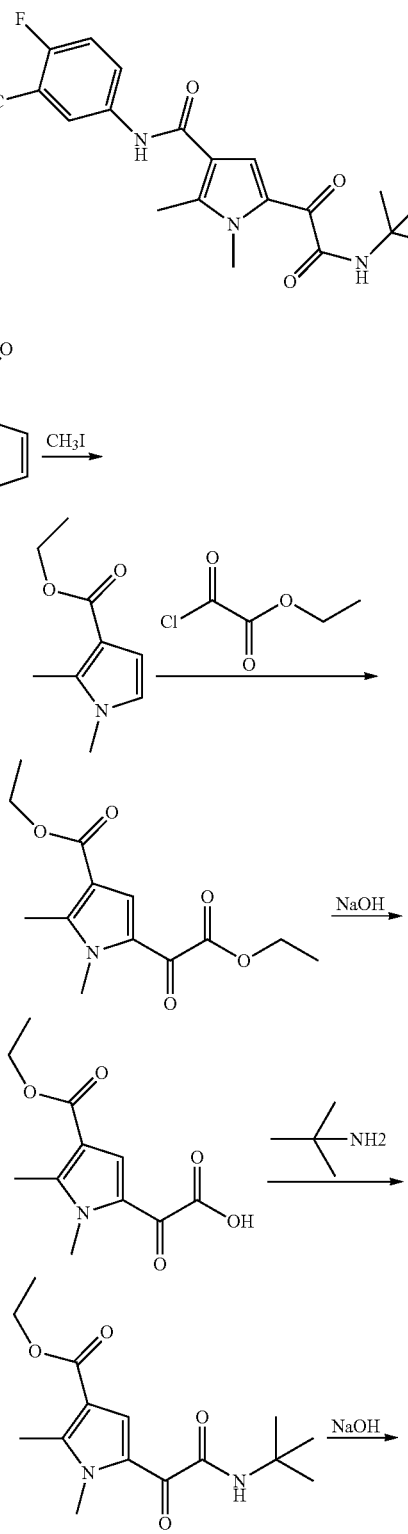

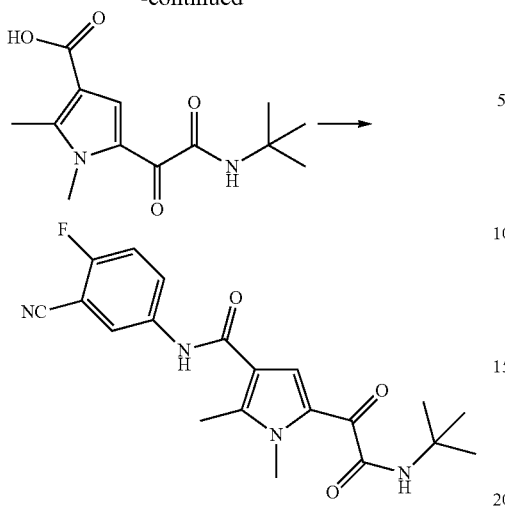

Example 17

5-(2-(tert-butylamino)-2-oxoacetyl)-2-chloro-N-(3-cyano-4-fluorophenyl)-1,4-dimethyl-1H-pyrrole-3-carboxamide

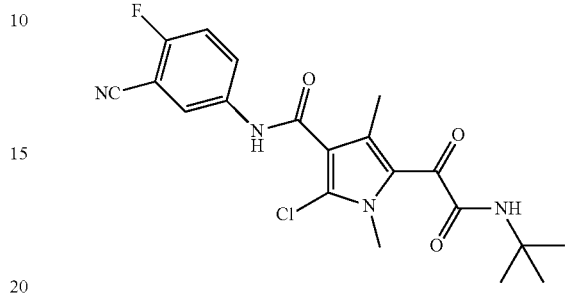

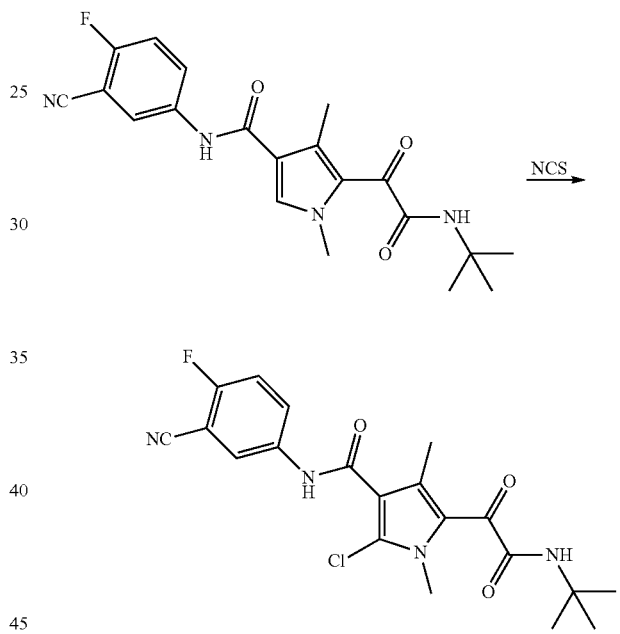

Step A: According to Example 1, ethyl 2,4-dimethyl-1H-pyrrole-3-carboxylate was replaced with ethyl 2-methyl-1H-pyrrole-3-carboxylate in step A to give ethyl 1,2-dimethyl-1H-pyrrole-3-carboxylate.

Step B: According to Example 13, ethyl 1,2,4-trimethyl-1H-pyrrole-3-carboxylate was replaced with ethyl 1,2-dimethyl-1H-pyrrole-3-carboxylate in step A to give ethyl 5-(2-ethoxy-2-oxoacetyl)-1,2-dimethyl-1H-pyrrole-3-carboxylate. $^1$H-NMR (500 MHz, DMSO-d$_6$): δ 7.44 (s, 1H), 4.36 (q, J=7.0 Hz, 2H), 4.22 (q, J=7.0 Hz, 2H), 3.86 (s, 3H), 2.56 (s, 3H), 1.30 (m, 6H); $^{13}$C-NMR (125 MHz, DMSO-d$_6$): δ 175.07, 163.61, 163.53, 147.08, 126.13, 125.73, 113.98, 62.52, 60.12, 33.53, 14.67, 14.29, 11.45.

Step C: According to Example 13, ethyl 5-(2-ethoxy-2-oxoacetyl)-1,2,4-trimethyl-1H-pyrrole-3-carboxylate was replaced with ethyl 5-(2-ethoxy-2-oxoacetyl)-1,2-dimethyl-1H-pyrrole-3-carboxylate in step B to give 2-(4-(ethoxycarbonyl)-1,5-dimethyl-1H-pyrrol-2-yl)-2-oxoacetic acid. MS(ESI$^-$, [M−H]$^-$) m/z: 238.2.

Step D: According to Example 13, 2-(4-(ethoxycarbonyl)-1,3,5-trimethyl-1H-pyrrol-2-yl)-2-oxoacetic acid was replaced with 2-(4-(ethoxycarbonyl)-1,5-dimethyl-1H-pyrrol-2-yl)-2-oxoacetic acid in step C to give ethyl 5-(2-(tert-butylamino)-2-oxoacetyl)-1,2-dimethyl-1H-pyrrole-3-carboxylate. MS(ESI+, [M+Na]$^+$) m/z: 317.3.

Step E: According to Example 13, ethyl 5-(2-(tert-butylamino)-2-oxoacetyl)-1,2,4-trimethyl-1H-pyrrole-3-carboxylate was replaced with ethyl 5-(2-(tert-butylamino)-2-oxoacetyl)-1,2-dimethyl-1H-pyrrole-3-carboxylate in step D to give 5-(2-(tert-butylamino)-2-oxoacetyl)-1,2-dimethyl-1H-pyrrole-3-carboxylic acid. MS(ESI$^-$, [M−H]$^-$) m/z: 265.3.

Step F: According to Example 13, 5-(2-(tert-butylamino)-2-oxoacetyl)-1,2,4-trimethyl-1H-pyrrole-3-carboxylic acid was replaced with 5-(2-(tert-butylamino)-2-oxoacetyl)-1,2-dimethyl-1H-pyrrole-3-carboxylic acid in step E to give 5-(2-(tert-butylamino)-2-oxoacetyl)-N-(3-cyano-4-fluorophenyl)-1,2-dimethyl-1H-pyrrole-3-carboxamide. $^1$H-NMR (500 MHz, DMSO-d$_6$): δ 10.28 (s, 1H), 8.25 (m, 1H), 8.11 (s, 1H), 8.05 (m, 1H), 7.91 (s, 1H), 7.50 (t, J=9.0 Hz, 1H), 3.88 (s, 3H), 2.59 (s, 3H), 1.38 (s, 9H); $^{13}$C-NMR (125 MHz, DMSO-d$_6$): δ 179.71, 164.45, 163.28, 159.51, 157.51, 145.38, 136.99, 127.97, 126.33, 124.49, 123.28, 117.29, 116.54, 114.51, 100.51, 51.32, 33.32, 28.77. MS(ESI$^-$, [M−H]$^-$) m/z: 383.3.

5-(2-(tert-butylamino)-2-oxoacetyl)-N-(3-cyano-4-fluorophenyl)-1,4-dimethyl-1H-pyrrole-3-carboxamide (0.1 g), NCS (52 mg), glacial acetic acid (5 mL), and trifluoroacetic anhydride (42 μL) were added into a 50 mL one-necked flask, and then reacted at room temperature for 10 hours. After the reaction was finished, the reaction solution was poured into 50 mL saturated sodium bicarbonate aqueous solution, and then extracted with 50 mL*3 ethyl acetate. The organic layer was separated, dried, concentrated, slurried with a mixed solvent (2 ml) of petroleum ether:ethyl acetate=1:1, and then filtered. The filter cake was dried to give 5-(2-(tert-butylamino)-2-oxoacetyl)-2-chloro-N-(3-cyano-4-fluorophenyl)-1,4-dimethyl-1H-pyrrole-3-ca rboxamide (16.9 mg). $^1$H NMR (500 MHz, DMSO-d$_6$): δ 10.55 (s, 1H), 8.42 (s, 1H), 8.20 (m, 1H), 7.96 (s, 1H), 7.52-7.56 (t, J=18 Hz, 1H), 3.85 (s, 3H), 2.29 (s, 3H), 1.35 (s, 9H). $^{13}$C NMR (125 MHz, DMSO-d$_6$): δ 181.83, 166.43, 161.78, 136.45, 130.14, 127.32, 126.14, 125.90, 123.80, 118.99, 117.73, 117.56, 114.36, 100.30, 51.41, 34.17, 28.60, 11.45. MS (ESI−, [M−H]−) m/z: 417.4.

Example 18

5-(2-(tert-butylamino)-2-oxoacetyl)-N-(3-cyano-4-fluorophenyl)-1-methyl-1H-pyrrole-3-carboxamide

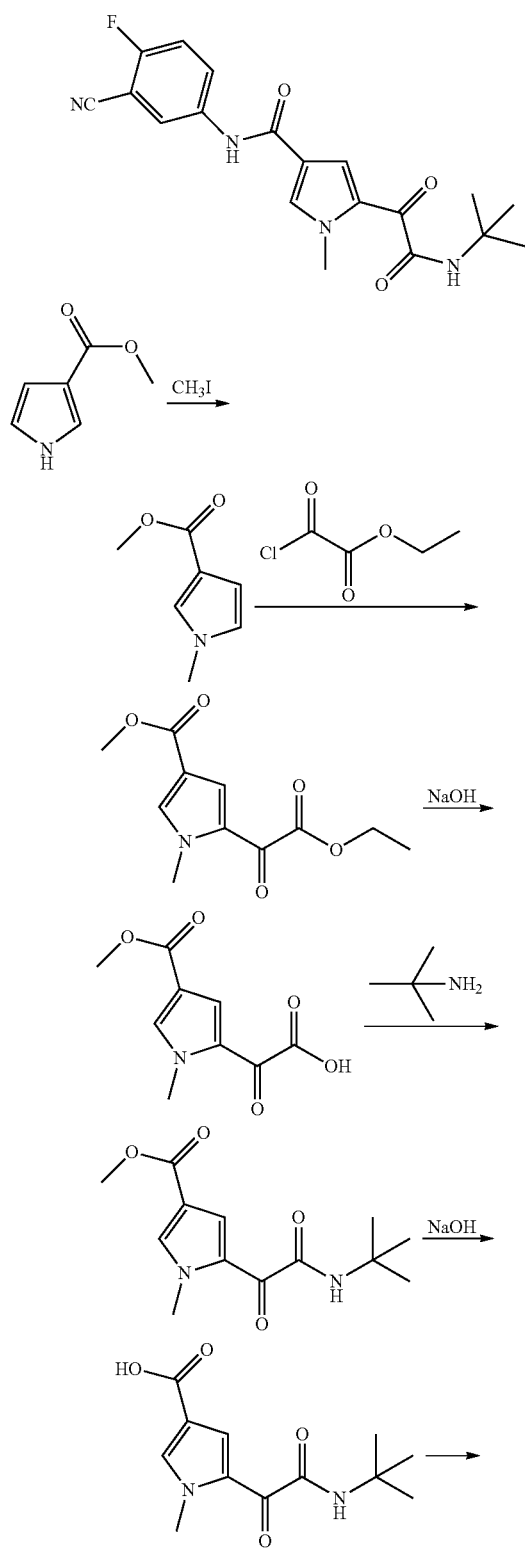

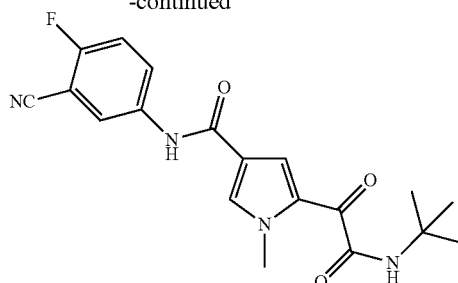

Step A: methyl 1H-pyrrole-3-carboxylate (3.0 g), and 20 mL DMF were added sequentially into a reaction flask. After dissolving, to the resulting solution were added 1.16 g sodium hydride in batches at 0° C., and then 1.67 mL methyl iodide, and reacted at room temperature for 0.5 h After the addition. After the reaction was finished, to the reaction solution were added 50 mL water and 50 mL DCM. The organic layer was separated, dried over anhydrous sodium sulfate, and then filtered. The filtrate was concentrated to give methyl 1-methyl-1H-pyrrole-3-carboxylate (3.12 g) which was used in the next reaction without purification. $^{1}$H-NMR (500 MHz, DMSO-d$_6$): δ 7.40 (s, 1H), 6.77 (s, 1H), 6.41 (s, 1H), 3.69 (s, 3H), 3.66 (s, 3H); $^{13}$C-NMR (125 MHz, DMSO-d$_6$): δ 162.69, 127.59, 123.74, 115.01, 109.71, 50.88, 31.09.

Step B: DCM (2 mL), and 200 mg methyl 1-methyl-1H-pyrrole-3-carboxylate were added sequentially into a reaction flask, and then cooled down to 0° C. To the resulting mixture were added 0.52 mL monoethyl chlorooxalate, and then 958 mg aluminum trichloride in batches. After the addition, the reaction solution reacted at room temperature for 3 hours. After the reaction was finished, to the reaction solution were added 50 mL ethyl acetate and 50 mL purified water. The organic layer was separated, dried over anhydrous sodium sulfate, and then filtered, and the filtrate was concentrated. The crude product was separated and purified by column chromatography (PE:EA=5:1) to give methyl 5-(2-ethoxy-2-oxoacetyl)-1-methyl-1H-pyrrole-3-carboxylate (104 mg). $^{1}$H-NMR (500 MHz, DMSO-d6): δ 8.02 (s, 1H), 7.50 (s, 1H), 4.36 (m, 2H), 3.94 (s, 3H), 3.76 (s, 3H), 1.32 (t, J=7.0 Hz, 3H); $^{13}$C-NMR (125 MHz, DMSO-d6): δ 175.50, 163.36, 163.09, 137.81, 127.88, 124.63, 115.80, 62.67, 51.78, 28.12, 14.29.

Step C: methyl 5-(2-ethoxy-2-oxoacetyl)-1-methyl-1H-pyrrole-3-carboxylate (3.35 g), and THF (4 mL) were added sequentially into a reaction flask. The reaction solution was stirred at room temperature for 10 minutes, followed by slowly adding a solution of sodium hydroxide (1.68 g) in water (4.00 ml) and reacted at room temperature for 1 hour. After the reaction was finished, the pH of the solution was adjusted to 3-4, and then 50 mL ethyl acetate and 50 mL purified water were added. The organic layer was separated, dried over anhydrous sodium sulfate, and then filtered, and the filtrate was concentrated to give 2.46 g 2-(4-(methoxy)carbonyl)-1-methyl-1H-pyrrol-2-yl)-2-oxoacetic acid. $^{1}$H-NMR (500 MHz, DMSO-d6): δ 7.97 (s, 1H), 7.45 (s, 1H), 3.94 (s, 3H), 3.76 (s, 3H); $^{13}$C-NMR (125 MHz, DMSO-d6): δ 177.66, 165.22, 163.43, 137.45, 127.84, 124.11, 115.57, 51.74, 38.06. MS (ESI–, [M–H]⁻) m/z: 210.2.

Step D: 2-(4-(methoxy)carbonyl)-1-methyl-1H-pyrrol-2-yl)-2-oxoacetic acid (2.46 g), ethyl acetate (2 mL), tert-butylamine (2.55 g) and 1-propyl phosphoric anhydride (50% w/v solution in ethyl acetate, 7.5 mL) were added into a reaction flask, and reacted at room temperature for 1 hour. After the reaction was finished, to the reaction solution were added 100 mL ethyl acetate and 100 mL water. The organic layer was separated, washed with saturated brine (2*50 mL), dried over anhydrous sodium sulfate, filtered, and concentrated. The crude product was separated and purified by column chromatography (PE:EA=3:1) to give methyl 5-(2-(tert-butylamino)-2-oxoacetyl)-1-methyl-1H-pyrrole-3-carboxylate (2.60 g). $^1$H-NMR (500 MHz, DMSO-d$_6$): δ 8.17 (s, 1H), 7.94 (s, 1H), 7.49 (s, 1H), 3.93 (s, 3H), 3.76 (s, 3H), 1.36 (s, 9H); $^{13}$C-NMR (125 MHz, DMSO-d$_6$): δ 180.44, 164.20, 157.50, 136.63, 128.32, 123.93, 115.26, 51.40, 38.02, 29.83, 28.6. MS (ESI$^+$, [M+Na]$^+$) m/z: 289.3.

Step E: methyl 5-(2-(tert-butylamino)-2-oxoacetyl)-1-methyl-1H-pyrrole-3-carboxylate (1.17 g), and methanol (5 mL) were added sequentially into a reaction flask. After stirring for 10 minutes, a solution of sodium hydroxide (0.53 g) in water (5.00 ml) was added, and then reacted at room temperature for 1 hour. After the reaction was finished, the resulting mixture was adjusted to pH 3~4 with 2N HCl, and then 100 mL ethyl acetate and 100 mL water were added thereto. The organic phase was separated, washed with saturated brine (2*50 mL), dried over anhydrous sodium sulfate, and then filtered. The filtrate was concentrated to dryness to give 5-(2-(t-butylamino)-2-oxoacetyl)-1-methyl-1H-pyrrole-3-carboxylic acid (1.11 g). MS (ESI$^-$, [M–H]$^-$) m/z: 251.2.

Step F: 5-(2-(t-butylamino)-2-oxoacetyl)-1-methyl-1H-pyrrole-3-carboxylic acid (100 mg), toluene (2 mL), and thionyl chloride (189 mg) were added into a reaction flask, heated to 110° C. and reacted for 1 h under the protection of N$_2$. The solvent was removed by concentration, and to the obtained crude product were added N,N-dimethylacetamide (2 mL) and 5-amino-2-fluorophenylacetonitrile (108 mg), and the mixture was heated to 100° C. and reacted for 2 h. After the reaction was finished, 60 mL ethyl acetate and 60 mL water were added. The organic phase was separated, washed with saturated brine (2*50 mL), dried over anhydrous sodium sulfate, filtered, and concentrated. The crude product was subjected to column chromatography (PE:EA=1:1) to give 5-(2-(tert-butylamino)-2-oxoacetyl)-N-(3-cyano-4-fluorophenyl)-1-methyl-1H-pyrrole-3-carboxamide (118 mg). $^1$H-NMR (500 MHz, DMSO-d$_6$): δ 10.29 (s, 1H), 8.25 (d, J=4.0 Hz 1H), 8.15 (s, 1H), 8.05 (t, J=4.0 Hz 1H), 7.96 (s, 1H), 7.89 (s, 1H), 7.52 (t, J=9.0 Hz 1H), 3.96 (s, 3H), 1.39 (s, 9H); $^{13}$C-NMR (125 MHz, DMSO-d$_6$): δ 180.31, 164.12, 161.83, 159.58, 157.58, 136.87, 128.07, 124.30, 122.66, 119.46, 117.44, 114.48, 100.27, 51.38, 38.14, 28.72. MS (ESI$^-$, [M–H]$^-$) m/z: 369.3.

Example 19

2-bromo-5-(2-(tert-butylamino)-2-oxoacetyl)-N-(3-cyano-4-fluorophenyl)-1-methyl-1H-pyrrole-3-carboxamide

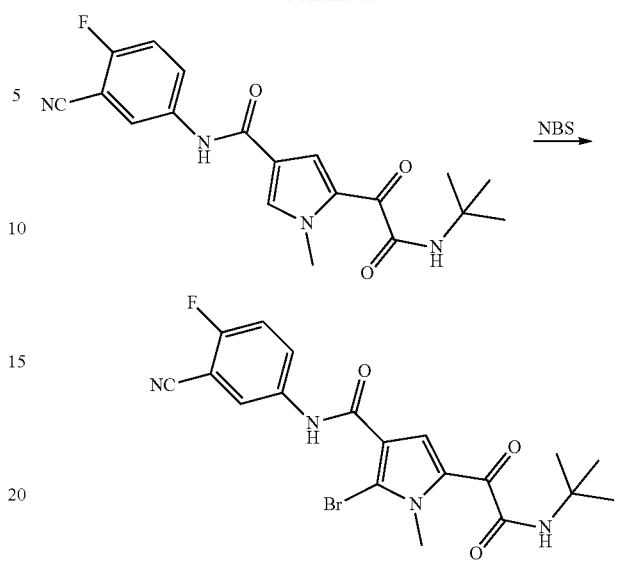

Step A: 100 mg 5-(2-(tert-butylamino-2-oxoacetyl)-N-(3-cyano-4-fluorophenyl)-1-methyl-1H-pyrrole-3-carboxamide, 1 mL DMF, 4 mL acetonitrile, and 48.1 mg NBS were added sequentially into a reaction flask, and reacted at 80° C. for 24 hours. After the reaction was finished, 100 mL ethyl acetate and 100 mL water were added. The organic phase was separated, washed with saturated brine (2*50 mL), dried over anhydrous sodium sulfate, and then filtered, and the filtrate was concentrated. The obtained crude product was purified by column chromatography (PE:EA=1:1) to give 2-bromo-5-(2-(tert-butylamino)-2-oxoacetyl)-N-(3-cyano-4-fluorophenyl)-1-methyl-1H-pyrrole-3-carboxamide (81 mg). $^1$H-NMR (500 MHz, DMSO-d$_6$): δ 10.44 (s, 1H), 8.23 (m, 2H), 8.03 (m, 1H), 7.94 (s, 1H), 7.53 (t, J=9.0 Hz 1H), 3.97 (s, 3H), 1.38 (s, 9H); $^{13}$C-NMR (125 MHz, DMSO-d6): δ 179.52, 163.76, 161.11, 159.72, 157.71, 136.65, 128.62, 124.58, 123.08, 120.55, 118.44, 117.43, 117.27, 114.42, 100.29, 51.51, 35.74, 28.73; MS (ESI$^-$, [M–H]$^-$) m/z: 447.3.

Example 20

2,4-dibromo-5-(2-(tert-butylamino)-2-oxoacetyl)-N-(3-cyano-4-fluorophenyl)-1-methyl-1H-pyrrole-3-carboxamide

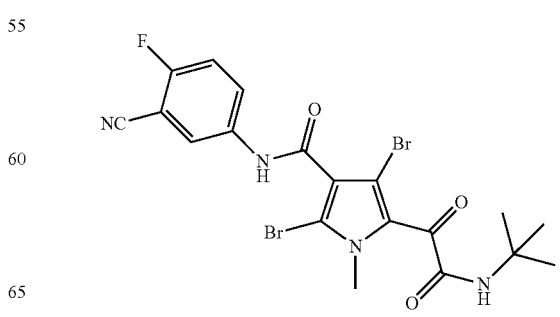

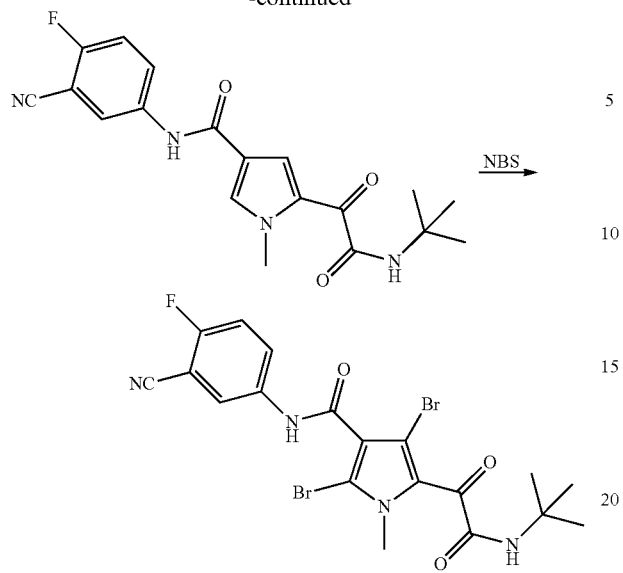

Step A: 100 mg 5-(2-(tert-butylamino-2-oxoacetyl)-N-(3-cyano-4-fluorophenyl)-1-methyl-1H-pyrrole-3-carboxamide, 1 mL DMF and 4 mL acetonitrile were added to a reaction flask, and then 144.3 mg NBS was added under stirring and reacted at 110° C. for 24 hours. After the stirring was stopped, to the resulting solution were added 100 mL ethyl acetate and 100 mL water. The organic phase was separated, washed with saturated brine (2*50 mL), dried over anhydrous sodium sulfate, and then filtered. The filtrate was concentrated, and then purified by column chromatography (PE/EA=1/1) to give 19.4 mg 2,4-dibromo-5-(2-(tert-butylamino)-2-oxoacetyl)-N-(3-cyano-4-fluorophenyl)-1-methyl-1H-pyrrole-3-carboxamide. $^1$H-NMR (500 MHz, DMSO-d$_6$): δ 10.80 (s, 1H), 8.42 (s, 1H), 8.19 (s, 1H), 7.96 (s, 1H), 7.56 (t, J=8.5 Hz, 1H), 3.86 (s, 3H), 1.37 (s, 9H); $^{13}$C-NMR (125 MHz, DMSO-d$_6$): δ 181.55, 179.82, 164.62, 160.93, 139.18, 136.31, 127.96, 127.09, 123.56, 117.92, 115.79, 114.29, 105.28, 100.87, 51.45, 36.46, 28.67; MS (ESI−, [M−H]−) m/z: 525.2.

Example 21

(R)—N-(3-cyano-4-fluorophenyl)-1,2,4-trimethyl-5-(2-oxo-2-((tetrahydrofuran-3-yl)amino)acetyl)-1H-pyrrole-3-carboxamide

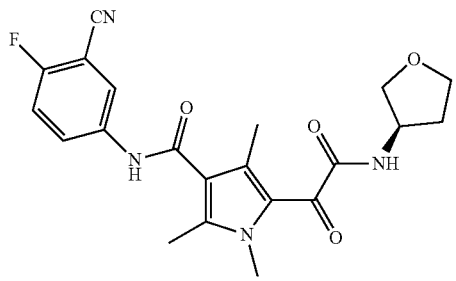 [SMILES: Cc1c(C(=O)Nc2ccc(F)c(C#N)c2)c(C)n(C)c1C(=O)C(=O)N[C@@H]1CCOC1]

According to Example 1, propargylamine was replaced with (R)-3-aminotetrahydrofuran in step E to give (R)—N-(3-cyano-4-fluorophenyl)-1,2,4-trimethyl-5-(2-oxo-2-((tet- rahydrofuran-3-yl)amino)acetyl)-1H-pyrrole-3-carboxamide. $^1$H-NMR (500 MHz, DMSO-d$_6$): δ 10.30 (s, 1H), 8.99 (s, 1H), 8.20-8.21 (m, 1H), 7.95-7.97 (m, 1H), 7.50-7.54 (m, 1H), 4.35-4.36 (m, 1H), 3.80-3.84 (m, 2H), 3.78 (s, 3H), 3.71-3.74 (m, 1H), 3.56-3.59 (m, 1H), 2.36 (s, 3H), 2.22 (s, 3H), 2.16-2.19 (m, 1H), 1.84-2.15 (m, 1H); $^{13}$C-NMR (125 MHz, DMSO-d$_6$): δ 164.18, 159.64, 157.63, 140.44, 136.85, 136.83, 130.43, 127.28, 125.29, 123.77, 120.51, 117.58, 117.41, 114.45, 72.28, 66.82, 50.00, 33.61, 32.04, 11.55, 11.40. MS(ESI−, [M−H]−) m/z: 411.4.

Example 22

(S)—N-(3-cyano-4-fluorophenyl)-1,2,4-trimethyl-5-(2-oxo-2-((tetrahydrofuran-3-yl))amino)acetyl)-1H-pyrrole-3-carboxamide

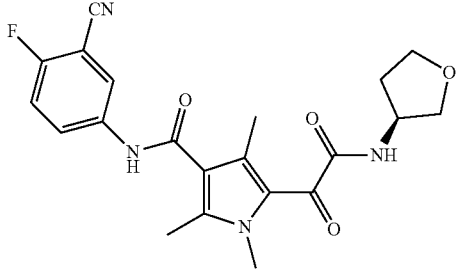 [SMILES: Cc1c(C(=O)Nc2ccc(F)c(C#N)c2)c(C)n(C)c1C(=O)C(=O)N[C@H]1CCOC1]

According to Example 1, propargylamine was replaced with (S)-3-aminotetrahydrofuran in step E to give (S)—N-(3-cyano-4-fluorophenyl)-1,2,4-trimethyl-5-(2-oxo-2-((tetrahydrofuran-3-yl)amino)acetyl)-1H-pyrrole-3-carboxamide. $^1$H-NMR (500 MHz, DMSO-d$_6$): δ 10.30 (s, 1H), 8.98 (d, J=6.5 Hz, 1H), 8.20 (s, 1H), 7.96 (d, J=7.0 Hz, 1H), 7.52 (t, J=9.0 Hz, 1H), 4.35 (d, J=2.5 Hz, 1H), 3.83 (t, J=6.5 Hz, 2H), 3.74 (s, 3H), 3.71 (m, 1H), 3.57 (m, 1H), 2.51 (s, 3H), 2.36 (s, 3H), 2.17 (m, 1H), 1.85 (m, 1H); $^{13}$C-NMR (125 MHz, DMSO-d$_6$): δ 181.80, 167.33, 164.18, 159.64, 157.63, 140.44, 136.86, 130.43, 127.25, 125.30, 123.77, 120.52, 117.50, 100.32, 72.28, 66.83, 50.00, 33.61, 32.04, 11.55. MS(ESI−, [M−H]−) m/z: 411.4.

Example 23

N-(3-cyano-4-fluorophenyl)-1,2,4-trimethyl-5-(2-((3-methyltetrahydrofuran-3-yl)amino)-2-(oxoacetyl)-1H-pyrrole-3-carboxamide

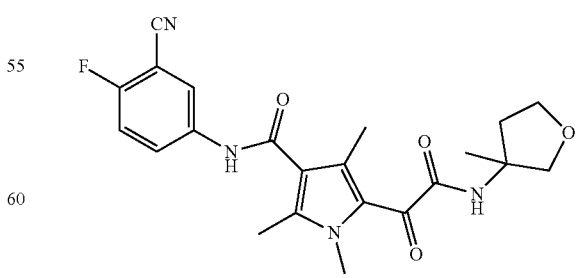

According to Example 1, propargylamine was replaced with 3-amino-3-methyltetrahydrofuran in step E to give N-(3-cyano-4-fluorophenyl)-1,2,4-trimethyl-5-(2-((3-methyltetrahydrofuran-3-yl)amino)-2-(oxoacetyl)-1H-pyrrole-3-carboxamide. $^1$H-NMR (500 MHz, DMSO-d6): δ 10.28 (s, 1H), 8.76 (s, 1H), 8.20-8.21 (m, 1H), 7.95-7.98 (m, 1H), 7.52 (t, J=9.0 Hz, 1H), 3.99 (d, J=9.0 Hz, 1H), 3.78-3.82 (m, 5H), 3.54 (d, J=8.5 Hz, 1H), 2.36 (s, 3H), 2.31-2.33 (m, 1H), 2.27 (s, 3H), 1.86-1.91 (m, 1H), 1.46 (s, 3H); $^{13}$C-NMR (125 MHz, DMSO-d6): δ 181.80, 167.41, 164.20, 159.62, 157.63, 140.42, 136.85, 130.30, 127.26, 125.29, 123.78, 120.41, 117.50, 114.45, 100.32, 76.77, 66.85, 59.96, 38.70, 33.60, 22.80, 11.53. MS (ESI−, [M−H]$^-$) m/z: 425.4.

Example 24

N-(3-cyano-4-fluorophenyl)-1,2,4-trimethyl-5-(2-((4-methyltetrahydro-2H-pyran-4-yl)amino)-2-oxoacetyl)-1H-pyrrole-3-carboxamide

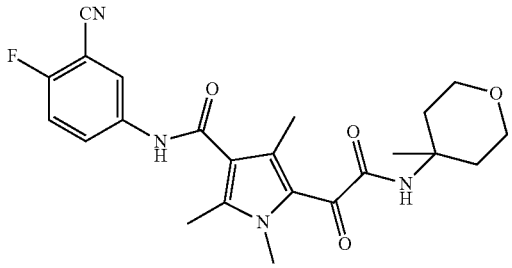 [SMILES: Cc1c(C(=O)Nc2ccc(F)c(C#N)c2)c(C)n(C)c1C(=O)C(=O)NC1(C)CCOCC1]

According to Example 1, propargylamine was replaced with tetrahydro-4-methyl-2H-pyran-4-amine in step E to give N-(3-cyano-4-fluorophenyl)-1,2,4-trimethyl-5-(2-((4-methyltetrahydro-2H-pyran-4-yl)amino)-2-oxoacetyl)-1H-pyrrole-3-carboxamide. $^1$H-NMR (500 MHz, DMSO-d$_6$): δ 10.26 (s, 1H), 8.33 (s, 1H), 8.21 (s, 1H), 7.96 (d, J=4.5 Hz, 1H), 7.51 (t, J=9.0 Hz, 1H), 3.78 (s, 3H), 3.58-3.60 (m, 4H), 2.35 (s, 3H), 2.29 (s, 3H), 2.07-2.10 (m, 2H), 1.55-1.59 (m, 2H), 1.40 (s, 3H). $^{13}$C-NMR (125 MHz, DMSO-d$_6$): δ 181.94, 167.53, 164.40, 140.26, 136.84, 130.12, 127.30, 125.28, 123.79, 120.30, 117.40, 114.43, 100.51, 93.69, 63.46, 60.42, 51.33, 36.40, 33.60, 25.76, 11.72. MS(ESI−, [M−H]$^-$) m/z: 439.5.

Example 25

N-(3-cyano-4-fluorophenyl)-1,2,4-trimethyl-5-(2-oxo-2-((3-(trifluoromethyl)oxetan-3-yl)amino)acetyl)-1H-pyrrole-3-carboxamide

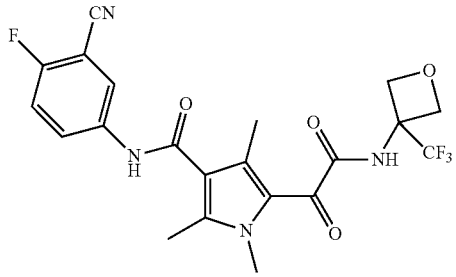 [SMILES: Cc1c(C(=O)Nc2ccc(F)c(C#N)c2)c(C)n(C)c1C(=O)C(=O)NC1(C(F)(F)F)COC1]

According to Example 1, propargylamine was replaced with 3-(trifluoromethyl)oxetane-3-amine hydrochloride in step E to give N-(3-cyano-4-fluorophenyl)-1,2,4-trimethyl-5-(2-oxo-2-((3-(trifluoromethyl) oxetan-3-yl)amino)acetyl)-1H-pyrrole-3-carboxamide. $^1$H-NMR (500 MHz, DMSO-d$_6$): δ 10.32 (s, 1H), 9.93 (s, 1H), 8.20-8.22 (m, 1H), 7.95-7.98 (m, 1H), 7.50-7.54 (m, 1H), 4.82 (q, J=8.0 Hz, 4H), 3.79 (s, 3H), 2.37 (s, 3H), 2.28 (s, 3H); $^{13}$C-NMR (125 MHz, DMSO-d$_6$): δ 180.07, 166.20, 164.00, 159.68, 157.67, 141.38, 136.80, 131.00, 127.31, 125.10, 123.85, 120.80, 117.51, 114.44, 100.33, 73.37, 57.28, 57.03, 33.70, 11.62, 11.55. MS(ESI−, [M−H]$^-$) m/z: 465.4.

Example 26

N-(3-cyano-4-fluorophenyl)-5-(2-(3-(hydroxymethyl)oxetan-3-yl)amino)-2-oxoacetyl)-1,2,4-trimethyl-1H-pyrrole-3-carboxamide

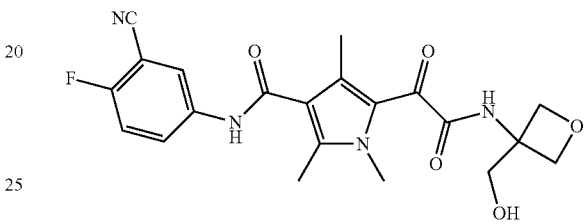

According to Example 1, propargylamine was replaced with 3-(3-aminooxetan-3-yl)methanol in step E to give N-(3-cyano-4-fluorophenyl)-5-(2-(3-(hydroxymethyl) oxetan-3-yl)amino)-2-oxoacetyl)-1,2,4-trimethyl-1H-pyrrole-3-carboxamide. $^1$H-NMR (500 MHz, DMSO-d$_6$): δ 10.30 (s, 1H), 9.23 (s, 1H), 8.21 (d, J=3.5 Hz, 1H), 7.96 (t, J=3.5 Hz, 1H), 7.52 (t, J=9.0 Hz, 1H), 5.23 (t, J=5.0 Hz, 1H), 4.61 (d, J=6.0 Hz, 2H), 4.56 (d, J=6.0 Hz, 2H), 3.77 (s, 3H), 3.72 (t, J=5.0 Hz, 2H), 2.36 (s, 3H), 2.29 (s, 3H); $^{13}$C-NMR (125 MHz, DMSO-d$_6$): δ 181.31, 170.78, 166.50, 164.17, 159.64, 157.63, 140.57, 136.84, 130.52, 127.27, 125.44, 123.77, 120.50, 117.57, 114.45, 100.39, 76.45, 57.63, 33.61, 21.22, 11.61. MS(ESI−, [M−H]$^-$) m/z: 427.4.

Example 27

N-(3-cyano-4-fluorophenyl)-5-(2-((1-(hydroxymethyl)cyclopropyl)amino)-2-oxoacetyl)-1,2,4-trimethyl-1H-pyrrole-3-carboxamide

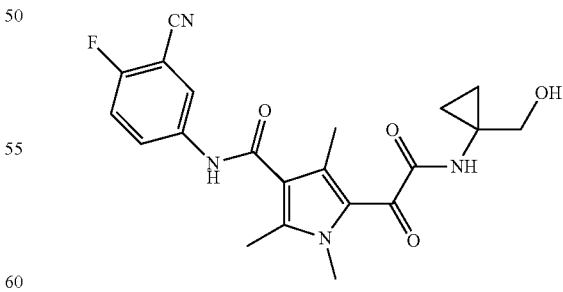

According to Example 1, propargylamine was replaced with (1-aminocyclopropyl)methanol in step E to give N-(3-cyano-4-fluorophenyl)-5-(2-((1-(hydroxymethyl)cyclopropyl)amino)-2-oxoacetyl)-1,2,4-trimethyl-1H-pyrrole-3-carboxamide. $^1$H-NMR (500 MHz, DMSO-d$_6$): δ 10.28 (s, 1H), 8.92 (s, 1H), 8.20-8.21 (m, 1H), 7.94-7.97 (m, 1H), 7.50-

7.53 (m, 1H), 4.71-4.73 (t, J=11 Hz, 1H), 3.75 (s, 3H), 3.53 (s, 3H), 2.35 (s, 3H), 2.32 (s, 3H), 0.77-0.70 (t, J=11 Hz, 1H), 0.65-0.67 (t, J=11 Hz, 1H); $^{13}$C-NMR (125 MHz, DMSO-$d_6$): δ 168.07, 164.23, 159.62, 157.62, 140.25, 136.88, 130.31, 127.26, 127.19, 125.44, 123.74, 120.38, 117.57, 117.41, 114.45, 63.83, 34.49, 33.55, 11.55, 11.42, 10.45. MS(ESI-, [M-H]-) m/z: 411.4.

Example 28

N-(3-cyano-4-fluorophenyl)-5-(2-((3,3-difluoro-1-(methylcarbamoyl)cyclobutyl)amino)-2-(oxoacetyl)-1,2,4-trimethyl-1H-pyrrole-3-carboxamide

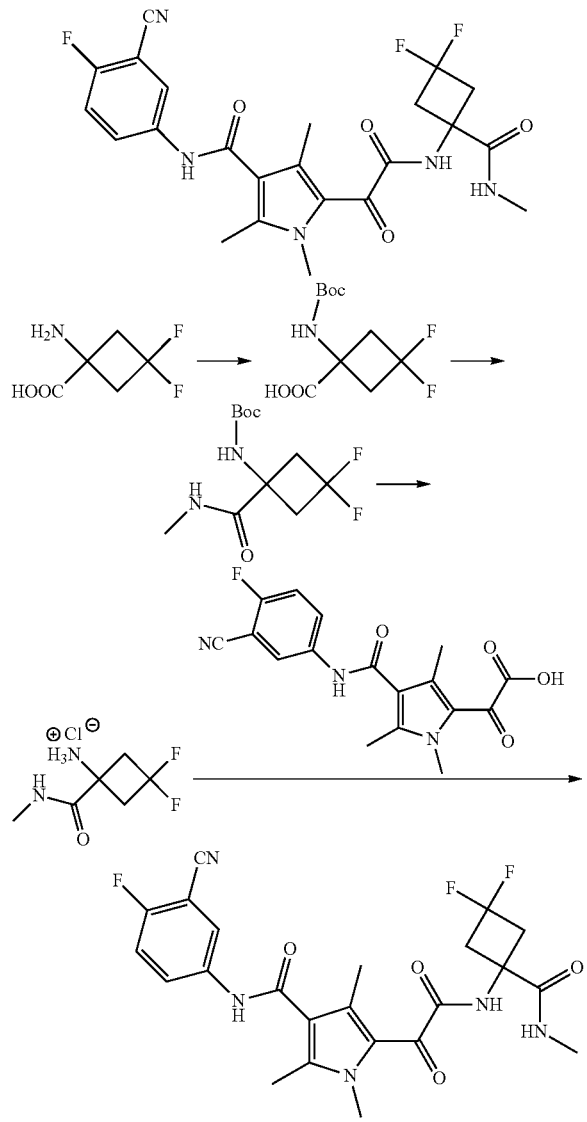

Step A: water (10.00 mL), and sodium hydroxide (1.416 g) were added sequentially into a reaction flask at 0° C., followed by slowly adding dropwise a solution of 1-amino-3,3-difluorocyclobutane-1-carboxylic acid (5 g) in methanol (50 mL). After the dropwise addition, di-tert-butyl dicarbonate (9.10 g) was added, and the reaction mixture was warmed to room temperature after the addition and stirred for 16 h. After the reaction is finished, the resulting mixture was adjusted to pH2~3 with 2 N HCl, and then filtered, and the filter cake was dried to give 1-((tert-butoxycarbonyl)amino)-3,3-difluorocyclobutane-1-carboxylic acid (7.80 g). $^1$H NMR (500 MHz, DMSO-$d_6$): δ 12.81 (s, 1H), 7.82 (s, 1H), 3.08-3.16 (m, 2H), 2.72-2.79 (m, 2H), 1.39 (s, 9H); $^{13}$C NMR (125 MHz, DMSO-$d_6$): δ 174.03, 155.49, 79.05, 47.73, 44.84, 44.66, 44.48, 28.61, 28.33.

Step B: 1-((tert-butoxycarbonyl)amino)-3,3-difluorocyclobutane-1-carboxylic acid (7.6 g), HATU (17.25 g), DMF (50 mL), methylamine (4.79 g) and DIPEA (42.3 mL) were added sequentially into a reaction flask, and reacted for 3 h at room temperature. After the reaction was finished, to the reaction solution was added 300 mL water, and then extracted with ethyl acetate (200 mL*3). The organic layers were combined, dried, filtered, and concentrated to give tert-butyl (3,3-difluoro-1-(methylcarbamoyl)cyclobutyl)carbamate. $^1$H NMR (500 MHz, DMSO-$d_6$): δ 7.65-7.73 (m, 2H), 3.08-3.09 (m, 2H), 2.89 (s, 3H), 2.60-2.61 (m, 2H), 1.40 (s, 9H); $^{13}$C NMR (125 MHz, DMSO-$d_6$): δ 172.41, 154.97, 79.32, 48.55, 43.98, 28.57, 26.81.

Step C: tert-butyl (3,3-difluoro-1-(methylcarbamoyl)cyclobutyl)carbamate (7.38 g), and dioxane (50 mL) were added sequentially into a reaction flask, followed by slowly adding dropwise a solution of 4M HCl in dioxane (69.8 mL), and stirred at room temperature for 12 h. After the reaction was finished, the reaction solution was adjusted to pH 10~11 with 2 M sodium hydroxide solution, and then filtered, and the filter cake was dried under vacuum at 40° C. to give 1-amino-3,3-difluoro-N-methylcyclobutane-1-carboxamide hydrochloride (5.19 g). $^1$H NMR (500 MHz, DMSO-$d_6$): δ$^1$H NMR (500 MHz, DMSO-$d_6$): δ 9.32 (s, 3H), 8.72 (s, 1H), 3.23-3.32 (m, 2H), 3.11-3.19 (m, 2H), 2.69-2.70 (d, J=4.5 Hz, 3H); $^{13}$C NMR (125 MHz, DMSO-$d_6$): δ 168.26, 117.74, 48.12, 48.05, 43.73, 26.78.

Step D: According to Example 1, propargylamine was replaced with 1-amino-3,3-difluoro-N-methylcyclobutane-1-carboxamide hydrochloride in step E to give N-(3-cyano-4-fluorophenyl)-5-(2-((3,3-difluoro-1-(methylcarbamoyl)cyclobutyl)amino)-2-(oxoacetyl)-1,2,4-trimethyl-1H-pyrrole-3-carboxamide. $^1$H-NMR (500 MHz, DMSO-$d_6$): δ 10.30 (s, 1H), 9.57 (s, 1H), 8.20-8.22 (m, 1H), 7.94-7.97 (m, 1H), 7.68 (s, 1H), 7.50-7.54 (m, 1H), 3.75 (s, 3H), 3.22-3.30 (m, 2H), 2.90-2.97 (m, 2H), 2.63 (s, 3H), 2.36 (s, 3H), 2.22 (s, 3H); $^{13}$C-NMR (125 MHz, DMSO-$d_6$): δ 180.49, 170.89, 166.39, 164.16, 159.64, 157.64, 140.67, 136.83, 130.92, 127.23, 125.76, 123.80, 120.60, 119.47, 117.41, 114.45, 100.39, 48.92, 43.91, 33.68, 26.72, 11.65. MS(ESI+, [M+Na]+) m/z: 512.4.

Example 29

(S)-2-chloro-N-(3-cyano-4-fluorophenyl)-1,4-dimethyl-5-(2-oxo-2-((1,1,1-trifluoroprop-2-yl)amino)acetyl)-1H-pyrrole-3-carboxamide

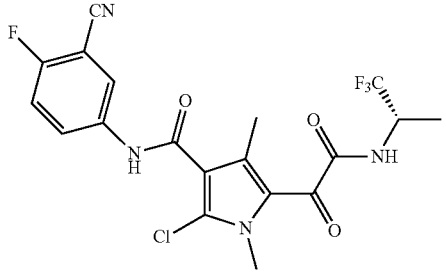

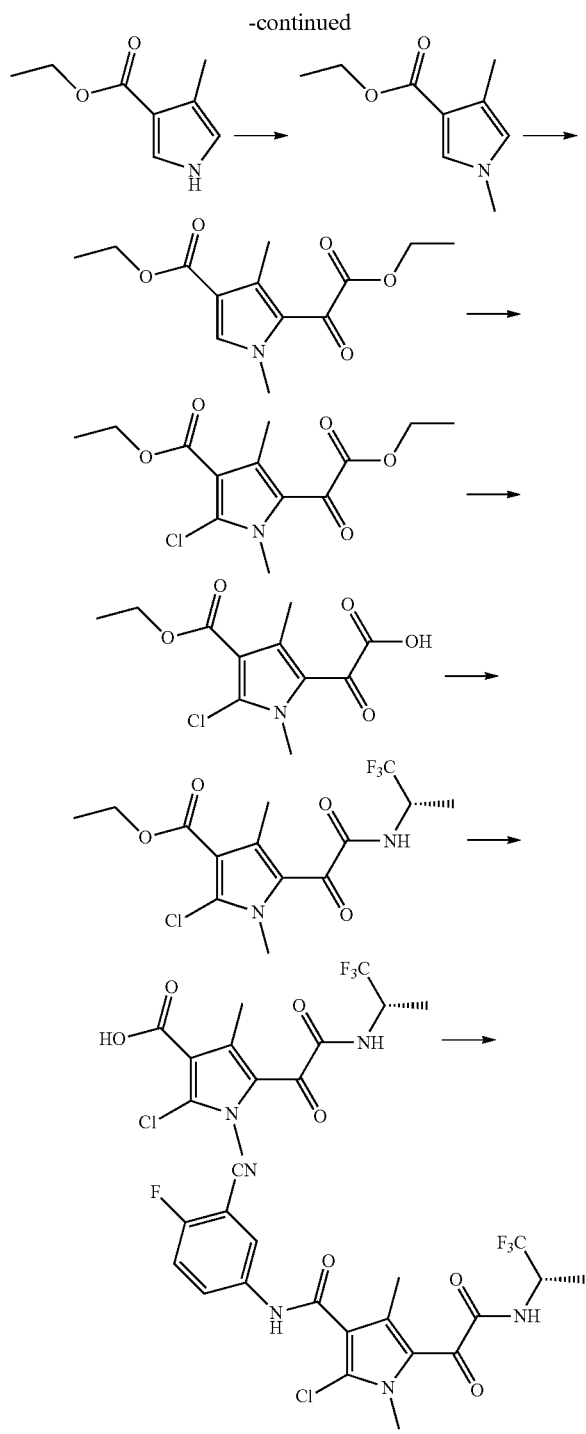

Step A: DMF (100 mL), and ethyl 4-methyl-1H-pyrrole-3-carboxylate (20 g) were added sequentially into a reaction flask, and NaH (7.83 g) was slowly added in an ice bath under the protection of $N_2$. After the addition, the resulting mixture was stirred for 30 min. Then methyl iodide (23.17 g) was slowly added to the stirred solution. After the addition, the reaction solution was stirred at room temperature for 2.0 h, and then poured into a saturated ammonium chloride solution (1000 mL) containing crushed ice, and extracted with ethyl acetate (3*1000 mL). The organic layers were combined, washed with saturated brine, dried over anhydrous sodium sulfate, and then filtered, and the filtrate was concentrated to give ethyl 1,4-dimethyl-1H-pyrrole-3-carboxylate (21.34 g). $^1$H-NMR (500 MHz, DMSO-$d_6$): δ 7.28 (s, 1H), 6.54 (s, 1H), 4.12-4.16 (q, J=21 Hz, 2H), 3.57 (s, 3H), 2.14 (s, 3H), 1.23-1.26 (t, J=14.5 Hz, 3H); $^{13}$C-NMR (125 MHz, DMSO-$d_6$): δ 164.73, 128.16, 122.34, 120.49, 113.43, 58.91, 36.29, 14.88, 11.95.

Step B: ethyl 1,4-dimethyl-1H-pyrrole-3-carboxylate (10 g), and DCM (200 mL) were added into a reaction flask, followed by adding $AlCl_3$ (32 g) in an ice bath. After the addition, a solution of monoethyl oxalyl chloride (24.5 g) in DCM (100 mL) was added dropwise, and after the addition, the reaction mixture was stirred at room temperature and reacted for 5.0 h. Then the reaction solution was poured into 500 mL ice water, and extracted with DCM (200 mL*3). The organic layers were combined, washed with saturated brine, dried over anhydrous sodium sulfate, and then filtered, and the filtrate was purified by column chromatography (PE:EA=12:1) to give ethyl 5-(2-ethoxy-2-oxoacetyl)-1,4-dimethyl-1H-pyrrole-3-carboxylate (11.5 g). $^1$H-NMR (500 MHz, DMSO-$d_6$): δ 7.92 (s, 1H), 4.37 (q, J=7.0 Hz, 1H), 4.21 (q, J=7.0 Hz, 1H), 8.16 (s, 1H), 3.87 (s, 3H), 2.36 (s, 2H), 1.32 (t, J=7.5 Hz, 3H), 1.27 (t, J=7.5 Hz, 3H); $^{13}$C-NMR (125 MHz, DMSO-$d_6$): δ 177.54, 165.14, 163.47, 138.01, 134.82, 125.79, 114.52, 62.83, 59.98, 38.48, 14.71, 14.14, 10.86. MS(ESI+, [M+Na]$^+$) m/z: 290.4.

Step C: ethyl 5-(2-ethoxy-2-oxoacetyl)-1,4-dimethyl-1H-pyrrole-3-carboxylate (6 g), DMF (100 mL), and NCS (4.5 g) were added into a reaction flask, and the reaction solution was stirred at room temperature for 8.0 h after the addition. Then the reaction solution was poured into 500 mL water, and extracted with ethyl acetate (200 mL*3). The organic layers were combined, washed with saturated brine, dried over anhydrous sodium sulfate, and then filtered. The filtrate was concentrated to dryness, and purified by column chromatography (PE:EA=50:1) to give ethyl 2-chloro-5-(2-ethoxy-2-oxoacetyl)-1,4-dimethyl-1H-pyrrole-3-carboxylate (3.5 g). $^1$H-NMR (500 MHz, DMSO-$d_6$): δ 4.38 (q, J=7.0 Hz, 2H), 4.26 (q, J=7.0 Hz, 2H), 3.84 (s, 3H), 2.33 (s, 3H), 1.32 (t, J=7.0 Hz, 3H), 1.30 (t, J=7.0 Hz, 3H); $^{13}$C-NMR (125 MHz, DMSO-$d_6$): δ 176.88, 164.71, 162.33, 134.29, 132.17, 125.12, 112.75, 63.06, 60.64, 34.52, 14.50, 14.10, 11.60.

Step D: ethyl 2-chloro-5-(2-ethoxy-2-oxoacetyl)-1,4-dimethyl-1H-pyrrole-3-carboxylate (3.2 g), and methanol (30 mL) were added into a reaction flask, followed by adding dropwise NaOH (0.85 g) aqueous solution (10 mL) in an ice bath. After the addition, the reaction solution was stirred at room temperature and reacted for 5 minutes. The resulting mixture was adjusted to pH 2-3 with 2 N HCl, and then extracted with ethyl acetate (200 mL*3). The organic layers were combined, washed with saturated brine, dried over anhydrous sodium sulfate, and then filtered. The filtrate was concentrated to dryness to give 2-(5-chloro-4-(ethoxycarbonyl)-1,3-dimethyl-1H-pyrrol-2-yl)-2-oxoacetic acid (2.6 g). MS(ESI-, [M-H]$^-$) m/z: 272.1.

Step E: 2-(5-chloro-4-(ethoxycarbonyl)-1,3-dimethyl-1H-pyrrol-2-yl)-2-oxoacetic acid (400 mg), DMF (10 mL), HATU (834 mg), and DIPEA (416 mg) were added into a reaction flask, and the reaction solution was stirred at room temperature for 10 min after the addition. Then (S)-1,1,1-trifluoroisopropylamine hydrochloride (200 mg) was added, and stirred at room temperature for 2.0 h after the addition. Then the reaction solution was poured into 100 mL water and extracted with ethyl acetate (50 mL*3). The organic layers were combined, washed with saturated brine, dried over anhydrous sodium sulfate, and then filtered. The filtrate was concentrated to dryness and purified by column chromatography (PE:EA=9:1) to give ethyl (S)-2-chloro-1,4-dimethyl-5-(2-oxo-2-((1,1,1-trifluoroprop-2-yl)amino)acetyl)-1H-pyrrole-3-carboxylate (380 mg). $^1$H-NMR (500 MHz, DMSO-d$_6$): δ 9.49 (s, 1H), 4.72 (q, J=7.5 Hz, 1H), 4.26 (q, J=7.0 Hz, 2H), 3.83 (s, 3H), 2.34 (s, 3H), 1.32 (t, J=7.0 Hz, 3H), 1.30 (t, J=7.0 Hz, 3H); $^{13}$C-NMR (125 MHz, DMSO-d$_6$): δ 181.10, 166.38, 162.55, 133.17, 130.95, 126.29, 112.45, 60.56, 46.21, 45.97, 34.38, 14.56, 13.69, 11.72. MS(ESI−, [M−H]$^−$) m/z: 367.3.

Step F: ethyl (S)-2-chloro-1,4-dimethyl-5-(2-oxo-2-((1,1,1-trifluoroprop-2-yl)amino)acetyl)-1H-pyrrole-3-carboxylate (360 mg) and methanol (20 mL) were added into a reaction flask. After the addition, to the reaction solution was added NaOH (0.85 g) aqueous solution (5 mL) and reacted at 80° C. for 8.0 h. The resulting mixture was adjusted to pH 2-3 with 2N HCl, and then extracted with ethyl acetate (100 mL*3). The organic layers were combined, washed with saturated brine, dried over anhydrous sodium sulfate, and filtered. The filtrate was concentrated to dryness to give (S)-2-chloro-1,4-dimethyl-5-(2-oxo-2-((1,1,1-trifluoroprop-2-yl)amino)acetyl)-1H-pyrrole-3-carboxylic acid (320 mg). MS(ESI−, [M−H]$^−$) m/z: 339.3.

Step G: (S)-2-chloro-1,4-dimethyl-5-(2-oxo-2-((1,1,1-trifluoroprop-2-yl)amino)acetyl)-1H-pyrrole-3-carboxylic acid (320 mg), toluene (10 mL) and dichlorosulfoxide (2.3 g) were added into a reaction flask, After the addition, the reaction solution reacted at 115° C. for 2.0 h under N$_2$ protection. Then the reaction solution was concentrated to dryness to give a crude product, and thereto were added DMA (10 mL) and 5-amino-2-fluorobenzonitrile (256 mg), reacted at 100° C. for 2.0 h. The reaction solution was poured into 100 mL water and extracted with ethyl acetate (50 mL*3). The organic layers were combined, washed with saturated brine, dried over anhydrous sodium sulfate, and then filtered, and the filtrate was concentrated to dryness, and purified by column chromatography (PE:EA=4:1) to give (S)-2-chloro-N-(3-cyano-4-fluorophenyl)-1,4-dimethyl-5-(2-oxo-2-((1,1,1-trifluoroprop-2-yl)amino)acetyl)-1H-pyrrole-3-carboxamide (125 mg). $^1$H-NMR (500 MHz, DMSO-d$_6$): δ 10.57 (s, 1H), 9.51 (d, J=9.0 Hz, 1H), 8.20 (m, 1H), 7.96 (m, 1H), 7.54 (t, J=9.0 Hz, 1H), 4.72 (m, 1H), 3.86 (s, 3H), 2.23 (s, 3H), 1.33 (d, J=7.0 Hz, 3H); $^{13}$C-NMR (125 MHz, DMSO-d$_6$): δ 180.70, 166.56, 161.60, 159.87, 157.87, 136.42, 134.88, 127.28, 125.53, 124.90, 123.84, 119.35, 117.67, 114.34, 100.51, 46.17, 34.28, 13.75, 11.19. MS(ESI−, [M−H]$^−$) m/z: 457.3.

Example 30

(R)-2-chloro-N-(3-cyano-4-fluorophenyl)-1,4-dimethyl-5-(2-oxo-2-((1,1,1-trifluoroprop-2-yl) amino)acetyl)-1H-pyrrole-3-carboxamide

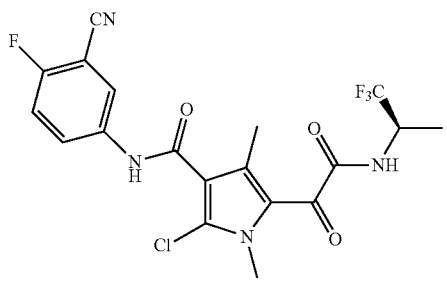

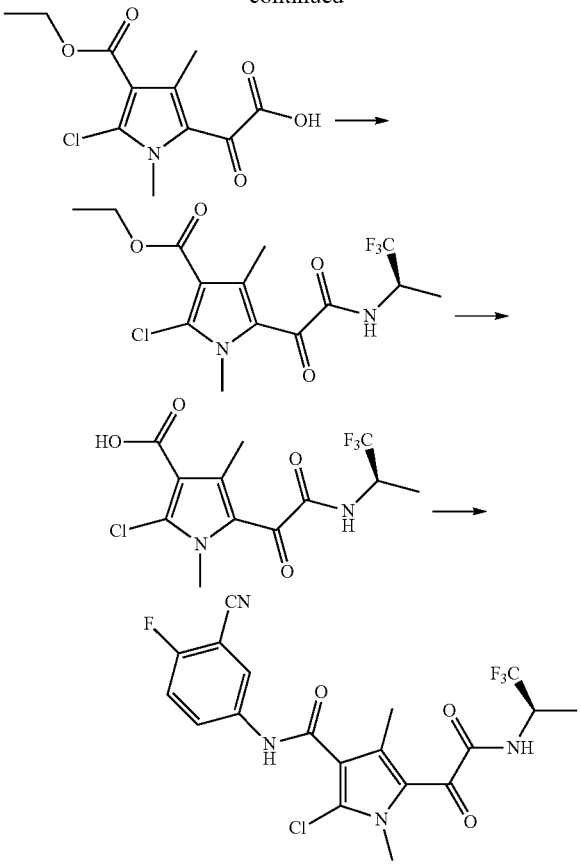

Step A: According to Example 29, (S)-1,1,1-trifluoroisopropylamine hydrochloride was replaced with (R)-1,1,1-trifluoroisopropylamine hydrochloride in step E to give ethyl (R)-2-chloro-1,4-dimethyl-5-(2-oxo-2-((1,1,1-trifluoroprop-2-yl) amino) acetyl)-1H-pyrrole-3-carboxylate. $^1$H NMR (500 MHz, DMSO-d$_6$): δ 9.47-9.49 (d, J=8.5 Hz, 1H), 4.70-7.75 (m, 1H), 4.24-4.28 (q, J=21 Hz, 2H), 3.83 (s, 3H), 2.34 (s, 3H), 1.28-1.36 (m, 6H); $^{13}$C NMR (125 MHz, DMSO-d$_6$): δ 181.11, 166.38, 162.55, 133.17, 130.95, 127.13, 126.29, 124.89, 112.45, 60.56, 34.38, 14.56, 13.69, 11.72. MS(ESI−, [M−H]$^−$) m/z: 367.3.

Step B: According to Example 29, ethyl (S)-2-chloro-1,4-dimethyl-5-(2-oxo-2-((1,1,1-trifluoroprop-2-yl) amino) acetyl)-1H-pyrrole-3-carboxylate was replaced with ethyl (R)-2-chloro-1,4-dimethyl-5-(2-oxo-2-((1,1,1-trifluoroprop-2-yl) amino) acetyl)-1H-pyrrole-3-carboxylate in step F to give (R)-2-chloro-1,4-dimethyl-5-(2-oxo-2-((1,1,1-trifluoroprop-2-yl) amino) acetyl)-1H-pyrrole-3-carboxylic acid. $^1$H NMR (500 MHz, DMSO-d$_6$): δ 12.79 (s, 1H), 9.45-9.47 (m, 1H), 4.68-4.76 (m, 1H), 3.82 (s, 3H), 2.35 (s, 3H), 1.32 (s, 3H); $^{13}$C NMR (125 MHz, DMSO-d$_6$): δ 181.09, 166.50, 164.11, 133.54, 131.09, 127.13, 126.19, 124.90, 113.17, 34.31, 13.69, 11.70. MS(ESI−, [M−H]$^−$) m/z: 339.3.

Step C: According to Example 29, (S)-2-chloro-1,4-dimethyl-5-(2-oxo-2-((1,1,1-trifluoroprop-2-yl) amino)acetyl)-1H-pyrrole-3-carboxylic acid was replaced with (R)-2-chloro-1,4-dimethyl-5-(2-oxo-2-((1,1,1-trifluoroprop-2-yl) amino)acetyl)-1H-pyrrole-3-carboxylic acid in step G to give (R)-2-chloro-N-(3-cyano-4-fluorophenyl)-1,4-dimethyl-5-(2-oxo-2-((1,1,1-trifluoroprop-2-yl)amino)acetyl)-1H-pyrrole-3-carboxamide. $^1$H NMR (500 MHz, DMSO-d$_6$): δ 10.58 (s, 1H), 9.51-9.52 (d, J=8.5 Hz, 1H), 8.19-8.20 (m, 1H), 7.94-7.97 (m, 1H), 7.52-7.56 3.82 (m, 1H), 4.70-4.77 (m, 1H), 3.86 (s, 3H), 2.23 (s, 3H), 1.34 (s, 3H); $^{13}$C NMR (125 MHz, DMSO-d$_6$): δ 166.57, 161.61, 159.88, 157.87, 136.43, 136.41, 130.89, 127.07, 125.54, 124.90, 123.84, 119.35, 117.74, 117.58, 114.34, 34.27, 13.73, 11.18. MS(ESI−, [M−H]$^−$) m/z: 457.4.

Example 31

2-chloro-N-(3-cyano-4-fluorophenyl)-1, 4-dimethyl-5-(2-((4-methyltetrahydro-2H-pyran-4)-yl)amino)-2-oxoacetyl)-1H-pyrrole-3-carboxamide

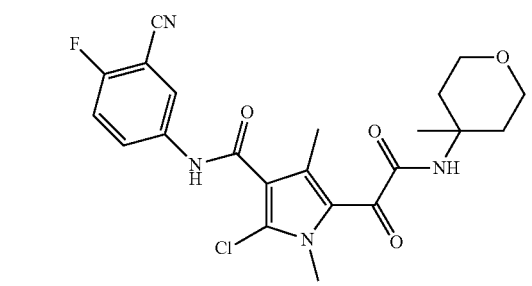

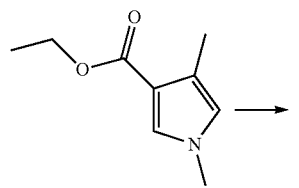

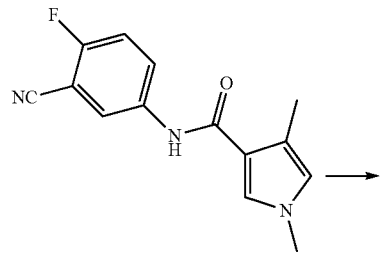

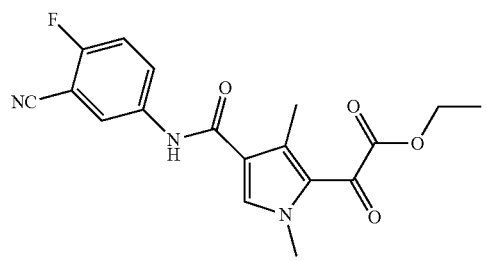

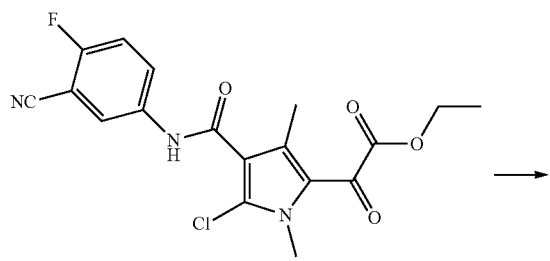

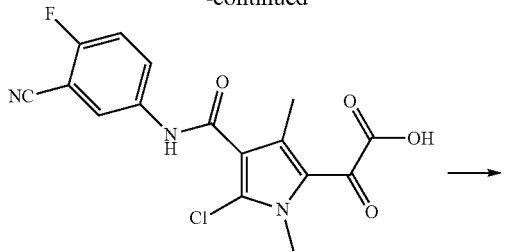

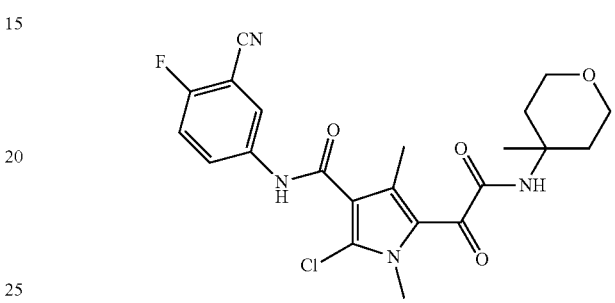

Step A: ethyl 1,4-dimethyl-1H-pyrrole-3-carboxylate (40 g), 5-fluoro-2-aminophenylcyanide (40.7 g) and THF (200 ml) were added to a reaction flask, followed by adding a solution (1 M, 600 mL) of LiHDMS in THF in an ice bath. After the addition, the reaction solution was stirred at room temperature for 2 h, and then poured into ice water (1500 mL). A large amount of solid was precipitated, and filtered, and the filter cake was slurried with 200 mL mixed solvent of PE:EA=1:1 to give N-(3-cyano-4-fluorophenyl)-1,4-dimethyl-1H-pyrrole-3-carboxamide (52.01 g). $^1$H NMR (500 MHz, DMSO-d$_6$): δ 9.73 (s, 1H), 8.22-8.23 (m, 1H), 7.95-7.98 (m, 1H), 7.45-7.49 (m, 1H), 6.58 (s, 1H), 3.62 (s, 3H), 2.18 (s, 3H); $^{13}$C NMR (125 MHz, DMSO-d$_6$): δ 164.07, 127.07, 127.00, 125.22, 123.46, 122.48, 120.45, 117.31, 117.15, 116.95, 114.61, 36.43, 11.98. MS(ESI−, [M−H]$^−$) m/z: 256.3.

Step B: zinc oxide (4.11 g) was added to a reaction flask, followed by adding oxalyl chloride monoethyl ester (310 g) in an ice bath, and then N-(3-cyano-4-fluorophenyl)-1,4-dimethyl-1H-pyrrole-3-carboxamide (26 g) was added. The reaction solution was stirred in an ice bath for 20 min, and then at room temperature for 3.0 h. To the reaction solution was added DCM (300 ml) under an ice bath, and stirred for 30 min. Then the reaction solution was poured into ice water, and extracted with DCM (300 ml*3). The organic layers were combined, washed with saturated brine, dried over anhydrous sodium sulfate, and then filtered, and the filtrate was concentrated to dryness to give ethyl 2-(4-((3-cyano-4-fluorophenyl)carbamoyl)-1,3-dimethyl-1H-pyrrol-2-yl)-2-oxoacetate (16.31 g). $^1$H-NMR (500 MHz, DMSO-d$_6$): δ 10.20 (s, 1H), 8.20 (q, J=2.5 Hz, 1H), 7.94 (m, 2H), 7.52 (t, J=9.0 Hz, 1H), 4.38 (q, J=7.0 Hz, 2H), 3.91 (s, 3H), 2.36 (s, 3H), 1.33 (t, J=7.0 Hz, 3H); $^{13}$C-NMR (125 MHz, DMSO-d$_6$): δ 177.50, 165.22, 162.71, 159.57, 157.57, 136.84, 135.49, 134.22, 127.45, 125.56, 123.95, 117.47, 114.46, 100.28, 62.82, 38.61, 14.18, 10.88. MS(ESI−, [M−H]−) m/z: 356.4.

Step C: ethyl 2-(4-((3-cyano-4-fluorophenyl)carbamoyl)-1,3-dimethyl-1H-pyrrol-2-yl)-2-oxoacetate (10 g), and DMF (400 mL) were added into a reaction flask. After the addition, to the reaction solution was added dropwise NCS (4.86 g) dissolved in DMF (20 mL), and stirred at room temperature for 30 h. Then the reaction solution was poured into 1000 mL water and extracted with ethyl acetate (300 mL*3). The organic layers were combined, washed with saturated brine, dried over anhydrous sodium sulfate, and then filtered, and the filtrate was purified by column chromatography to give ethyl 2-(5-chloro-4-((3-cyano-4-fluorophenyl)carbamoyl)-1,3-dimethyl-1H-pyrrol-2-yl)-2-oxoacetate (4.6 g). $^1$H-NMR (500 MHz, DMSO-$d_6$): δ 10.62 (s, 1H), 8.19 (q, J=2.5 Hz, 1H), 7.94 (m, 1H), 7.55 (t, J=8.0 Hz, 1H), 4.39 (q, J=7.0 Hz, 2H), 3.89 (s, 3H), 2.22 (s, 3H), 1.33 (t, J=7.0 Hz, 3H); $^{13}$C-NMR (125 MHz, DMSO-$d_6$): δ 176.51, 164.91, 161.34, 159.91, 157.90, 136.34, 131.82, 128.43, 127.28, 124.36, 123.82, 119.77, 114.34, 100.53, 63.07, 34.48, 14.16, 11.14. MS(ESI−, [M−H]−) m/z: 390.3.

Step D: ethyl 2-(5-chloro-4-((3-cyano-4-fluorophenyl)carbamoyl)-1,3-dimethyl-1H-pyrrol-2-yl)-2-oxoacetate (4 g), and THF (100 mL) were added into a reaction flask. An aqueous solution of LiOH (0.857 g, 15 mL) was added slowly in an ice bath, and stirred to react for 10 min in the ice bath. The reaction solution was adjusted to pH 3-4 with 2 N dilute hydrochloric acid, and then extracted with ethyl acetate (100 mL*3). The organic layers were combined, washed with saturated brine, dried over anhydrous sodium sulfate, and then filtered, and the filtrate was concentrated to give 2-(5-chloro-4-((3-cyano-4-fluorophenyl)carbamoyl)-1,3-dimethyl-1H-pyrrol-2-yl)-2-oxoacetic acid (3.0 g). $^1$H-NMR (500 MHz, DMSO-$d_6$): δ 10.59 (s, 1H), 8.19 (q, J=2.5 Hz, 1H), 7.95 (m, 2H), 7.54 (t, J=9.0 Hz, 1H), 3.87 (s, 2H), 2.29 (s, 3H); $^{13}$C-NMR (125 MHz, DMSO-$d_6$): δ 178.90, 167.25, 161.52, 159.88, 157.87, 136.40, 131.05, 127.29, 124.39, 123.78, 119.48, 117.68, 114.35, 100.61, 34.36, 11.08.

Step E: 2-(5-chloro-4-((3-cyano-4-fluorophenyl)carbamoyl)-1,3-dimethyl-1H-pyrrol-2-yl)-2-oxoacetic acid, DMF (6 mL), HATU (235 mg), and DIPEA (160 mg) were added into a reaction flask, stirred at room temperature for 5 min, and then 4-methyltetrahydro-2H-pyran-4-amine (50 mg) was added. The reaction solution reacted for 2.0 h at room temperature, and then thereto was added 50 mL water, and extracted with ethyl acetate (60 mL*3). The organic layers were combined, washed with saturated brine, dried over anhydrous sodium sulfate, and then filtered, and the filter was purified by column chromatography to give 2-chloro-N-(3-cyano-4-fluorophenyl)-1,4-dimethyl-5-(2-((4-methyltetrahydro-2H-pyran-4-yl)amino)-2-oxoacetyl)-1H-pyrrole-3-carboxamide (43 mg). $^1$H-NMR (500 MHz, DMSO-$d_6$): δ 10.58 (s, 1H), 8.46 (s, 1H), 8.21 (q, J=2.5 Hz, 1H), 7.98 (m, 1H), 7.54 (t, J=9.0 Hz, 1H), 3.86 (s, 3H), 3.59 (m, 4H), 2.31 (s, 3H), 2.08 (m, 2H), 1.61 (m, 2H), 1.41 (s, 3H); $^{13}$C-NMR (125 MHz, DMSO-$d_6$): δ 181.53, 166.82, 161.75, 159.84, 157.83, 136.52, 130.24, 127.32, 126.31, 125.81, 123.83, 119.03, 117.72, 117.56, 114.37, 100.46, 63.44, 51.50, 36.35, 34.20, 25.66, 11.61. MS(ESI−, [M−H]−) m/z: 459.5.

Example 32

2-chloro-N-(3-cyano-4-fluorophenyl)-1,4-dimethyl-5-(2-oxo-2-((3-(trifluoromethyl))oxetan-3-yl) amino)acetyl)-1H-pyrrole-3-carboxamide

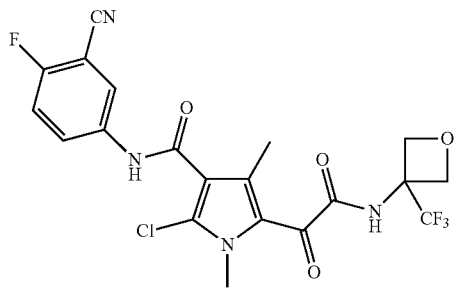 [SMILES: Cc1c(C(=O)Nc2ccc(F)c(C#N)c2)c(Cl)n(C)c1C(=O)C(=O)NC1(C(F)(F)F)COC1]

Step A: According to Example 31, 4-methyltetrahydro-2H-pyran-4-amine was replaced with 3-(trifluoromethyl)oxetane-3-amine hydrochloride in step E to give 2-chloro-N-(3-cyano-4-fluorophenyl)-1,4-dimethyl-5-(2-oxo-2-((3-(trifluoromethyl))oxetan-3-yl)amino)acetyl)-1H-pyrrole-3-carboxamide. $^1$H-NMR (500 MHz, DMSO-$d_6$): δ 10.58 (s, 1H), 10.06 (s, 1H), 8.20 (s, 1H), 7.96 (s, 1H), 7.55 (s, 1H), 4.93 (s, 4H), 3.85 (s, 3H), 2.29 (s, 3H); $^{13}$C-NMR (125 MHz, DMSO-$d_6$): δ 179.98, 165.34, 161.56, 160.05, 142.91, 136.41, 131.06, 127.32, 123.87, 119.41, 117.76, 117.59, 114.36, 100.58, 96.90, 73.33, 57.37, 34.33, 11.53. MS(ESI+, [M+Na]+) m/z: 485.4.

Example 33

2-chloro-N-(3-cyano-4-fluorophenyl)-5-(2-((1-hydroxy-2-methylpropan-2-yl)amino)-2-oxoacetyl)-1,4-dimethyl-1H-pyrrole-3-carboxamide

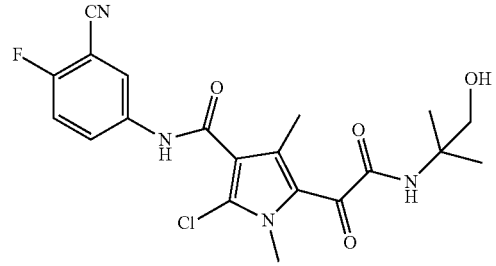 [SMILES: Cc1c(C(=O)Nc2ccc(F)c(C#N)c2)c(Cl)n(C)c1C(=O)C(=O)NC(C)(C)CO]

Step A: According to Example 31, 4-methyltetrahydro-2H-pyran-4-amine was replaced with 2-amino-2-methylpropan-1-ol in step E to give 2-chloro-N-(3-cyano-4-fluorophenyl)-5-(2-((1-hydroxy-2-methylpropan-2-yl)amino)-2-oxoacetyl)-1,4-dimethyl-1H-pyrrole-3-carboxamide. $^1$H-NMR (500 MHz, DMSO-d6): δ 10.55 (s, 1H), 8.23 (s, 1H), 8.20-8.21 (m, 1H), 7.94-7.97 (m, 1H), 7.54 (t, J=9.0 Hz, 1H), 4.89 (t, J=5.5 Hz, 1H), 3.83 (s, 3H), 3.47 (d, J=5.5 Hz, 2H), 2.29 (s, 3H), 1.29 (s, 6H); $^{13}$C-NMR (125 MHz, DMSO-d6): δ 181.74, 166.45, 161.79, 159.83, 157.82, 136.50, 130.20, 127.25, 126.02, 123.76, 118.97, 117.66, 114.37, 100.49, 67.54, 55.49, 34.17, 23.48, 11.48. MS(ESI−, [M−H]−) m/z: 433.4.

Example 34

2-chloro-N-(3-cyano-4-fluorophenyl)-1,4-dimethyl-5-(2-((3-methyloxetan-3-yl)amino)-2-oxoacetyl)-1H-pyrrole-3-carboxamide

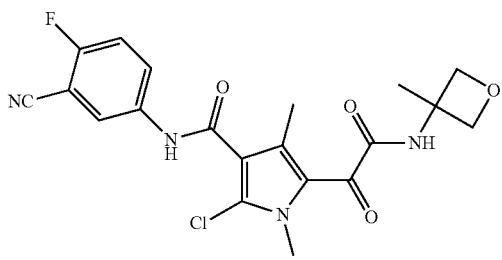 [SMILES: Cc1c(C(=O)Nc2ccc(F)c(C#N)c2)c(Cl)n(C)c1C(=O)C(=O)NC1(C)COC1]

Step A: According to Example 31, 4-methyltetrahydro-2H-pyran-4-amine was replaced with 3-methyl-3-aminooxetane in step E to give 2-chloro-N-(3-cyano-4-fluorophenyl)-1,4-dimethyl-5-(2-((3-methyloxetan-3-yl)amino)-2-oxoacetyl)-1H-pyrrole-3-carboxamide. $^1$H NMR (500 MHz, DMSO-d$_6$): δ 10.57 (s, 1H), 9.38 (s, 1H), 8.19-8.20 (m, 1H), 7.94-7.97 (m, 1H), 7.52-7.56 (m, 1H), 4.68-4.70 (t, J=6.5 Hz, 2H), 4.39-4.41 (t, J=6.5 Hz, 2H), 3.86 (s, 3H), 2.29 (s, 3H), 1.60 (s, 3H); $^{13}$C NMR (125 MHz, DMSO-d$_6$): δ 181.26, 165.40, 161.66, 159.85, 157.84, 136.46, 130.55, 127.30, 126.70, 125.94, 123.79, 119.17, 117.74, 114.36, 100.56, 80.72, 53.62, 34.25, 23.30, 11.65. MS(ESI–, [M–H]$^-$) m/z: 431.4.

Example 35

(S)-2-chloro-N-(3-chloro-4-fluorophenyl)-1,4-dimethyl-5-(2-oxo-2-((1,1,1-trifluoroprop-2-yl) amino)acetyl)-1H-pyrrole-3-carboxamide

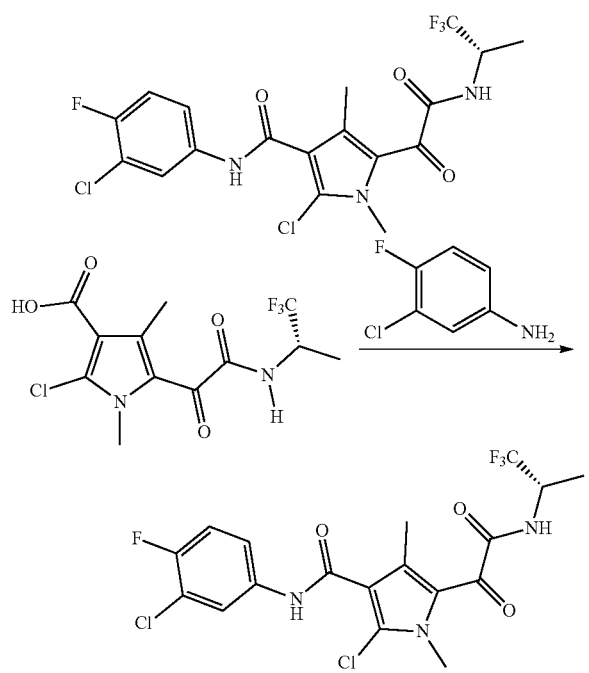

Step A: According to Example 29, 5-amino-2-fluorobenzonitrile was replaced with 3-chloro-4-fluoroaniline in step G to give (S)-2-chloro-N-(3-chloro-4-fluorophenyl)-1,4-dimethyl-5-(2-oxo-2-((1,1,1-trifluoroprop-2-yl)amino)acetyl)-1H-pyrrole-3-carboxamide. $^1$H-NMR (500 MHz, DMSO-d$_6$): δ 10.42 (s, 1H), 9.50 (d, J=8.5 Hz, 1H), 7.99 (m, 1H), 7.59 (m, 1H), 7.41 (t, J=9.0 Hz, 1H), 4.73 (m, 1H), 3.86 (s, 3H), 2.22 (s, 3H), 1.33 (d, J=7.0 Hz, 3H); $^{13}$C-NMR (125 MHz, DMSO-d$_6$): δ 180.68, 166.60, 161.42, 154.81, 152.88, 136.57, 136.55, 130.85, 126.98, 125.47, 121.38, 120.34, 119.66, 117.57, 46.16, 34.25, 13.73, 11.17; MS(ESI$^-$, [M–H]$^-$) m/z: 466.3.

Example 36

N-(3-chloro-4-fluorophenyl)-1,2,4-trimethyl-5-(2-((4-methyltetrahydro-2H-pyran-4-yl)amino)-2-oxoacetyl)-1H-pyrrole-3-carboxamide

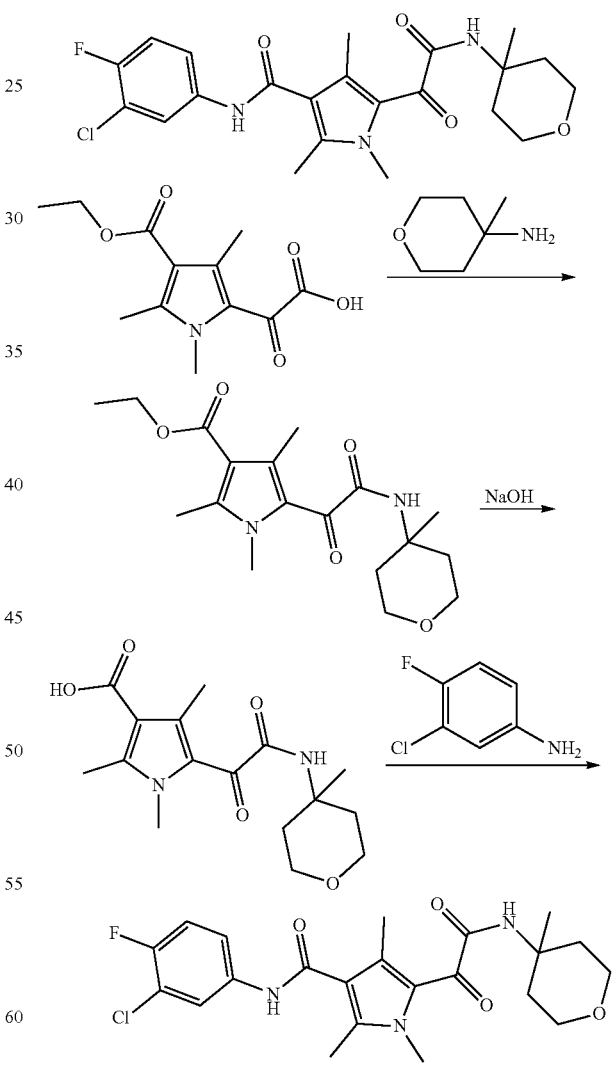

Step A: 2-(4-(ethoxycarbonyl)-1,3,5-trimethyl-1H-pyrrol-2-yl)-2-oxoacetic acid (800 mg, 3.16 mmol), and DMF (5 ml) were added sequentially into a reaction flask, and stirred for 10 minutes. Then N,N-diisopropylethylamine (1225 mg, 1.66 ml, 9.48 mmol), and HATU (1441 mg, 3.79 mmol) were added and reacted at room temperature for 3 hours. To the solution were added 100 mL ethyl acetate and 100 mL water. The organic phase was separated, washed with saturated brine (2×50 mL), and then dried over anhydrous sodium sulfate and filtered, and the filtrate was concentrated and subjected to column chromatography (PE/EA=1/1) to give the compound ethyl 1,2,4-trimethyl-5-(2-((4-methyltetrahydro-2H-pyran-4-yl)amino)-2-oxoacetyl)-1H-pyrrole-3-carboxylate (817.5 mg). MS(ESI⁺, [M+Na]⁺) m/z: 373.4.

Step B: ethyl 1,2,4-trimethyl-5-(2-((4-methyltetrahydro-2H-pyran-4-yl)amino)-2-oxoacetyl)-1H-pyrrole-3-carboxylate (954 mg, 2.72 mmol), and methanol (8 ml) were added sequentially to a reaction flask, and stirred at room temperature for 10 minutes, and then a solution of sodium hydroxide (0.327 g, 8.17 mmol) dissolved in water (8.00 ml) was added. The resulting mixture reacted at room temperature for 1 hour under N₂ protection. Then the pH of the solution was adjusted to 3-4, and 200 mL ethyl acetate and 200 mL purified water were added to the reaction. The organic layer was separated, dried over anhydrous sodium sulfate, and then filtered, and the filtrate was concentrated to give 1,2,4-trimethyl-5-(2-((4-methyltetrahydro-2H-pyran-4-yl)amino)-2-oxoacetyl)-1H-pyrrole-3-carboxylic acid (0.508 mg). MS(ESI⁻, [M–H]⁻) m/z: 321.6.

Step C: 1,2,4-trimethyl-5-(2-((4-methyltetrahydro-2H-pyran-4-yl)amino)-2-oxoacetyl)-1H-pyrrole-3-carboxylic acid (280 mg), toluene (5 ml), and thionyl chloride (0.25 ml, 3.47 mmol) were added sequentially into a reaction flask, reacted at 115° C. for 1 hour under N₂ protection and then concentrated. To the residue was added 5.0 mL of toluene, and then concentrated to obtain a 268 mg solid. To a reaction flask were added sequentially the above solid, N,N-dimethylacetamide (10 ml), and 3-chloro-4-fluoroaniline (160 mg, 1.101 mmol), and reacted for 2 hours at 100° C. under N₂ protection. To the solution were added 300 mL ethyl acetate and 300 mL water. The organic phase was separated, washed with saturated brine (2×50 mL), and then dried over anhydrous sodium sulfate and filtered, and the filtrate was concentrated and purified by column chromatography (PE/EA=1/1) to give N-(3-chloro-4-fluorophenyl)-1,2,4-trimethyl-5-(2-((4-methyltetrahydro-2H-pyran-4-yl)amino)-2-oxoacetyl)-1H-pyrrole-3-carboxamide (69 mg). ¹H-NMR (500 MHz, DMSO-d₆): δ 10.13 (s, 1H), 8.34 (s, 1H), 8.01 (d, J=5.0 Hz, 1H), 7.60 (m, 1H), 7.39 (t, J=9.0 Hz, 1H), 3.78 (s, 3H), 3.60 (m, 4H), 2.35 (s, 3H), 2.29 (s, 3H), 2.09 (m, 2H), 1.58 (m, 2H), 1.40 (s, 3H); ¹³C-NMR (125 MHz, DMSO-d₆): δ 181.71, 167.58, 164.06, 154.55, 152.62, 140.13, 137.01, 130.12, 125.18, 121.31, 120.62, 120.24, 119.58, 117.41, 63.46, 51.31, 36.38, 33.59, 25.76, 11.71, 11.56. MS(ESI+, [M+Na]+) m/z: 472.4.

Example 37

(S)—N-(3-chloro-4-fluorophenyl)-1,2,4-trimethyl-5-(2-oxo-2-((1,1,1-trifluoroprop-2-yl)amino) acetyl)-1H-pyrrole-3-carboxamide

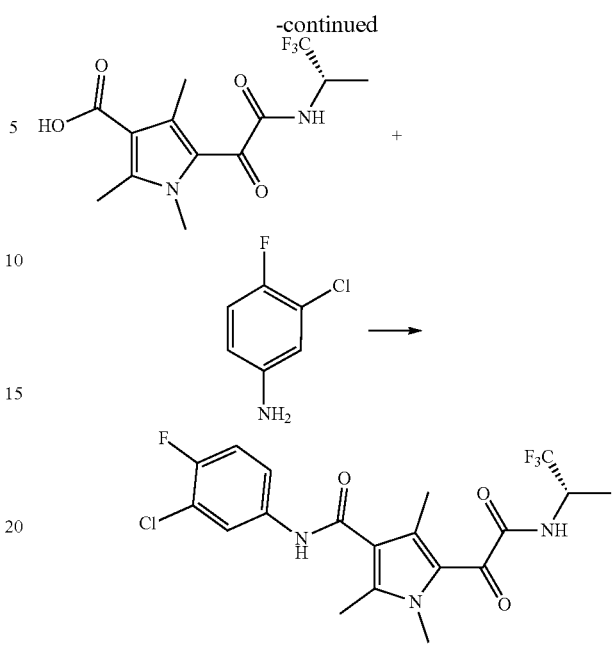

To a reaction flask were added (S)-1,2,4-trimethyl-5-(2-oxo-2-((1,1,1-trifluoroprop-2-yl)amino) acetyl))-1H-pyrrole-3-carboxylic acid (0.3 g), toluene (10 ml), and thionyl chloride (0.68 mL), and reacted at 115° C. for 2 h. After the reaction was completed, the resulting mixture was concentrated, and then thereto were added 3-chloro-4-fluoroaniline (0.27 g), and N,N-dimethylacetamide (10 ml), and reacted at 100° C. for 3 h. After the reaction was finished, ethyl acetate (30 mL) was added, and the resulting mixture was washed with water (3*20 mL) for three times, dried, and then concentrated. The residue was slurried with a mixed solvent (5 ml) of petroleum ether:ethyl acetate=3:1, filtered, and dried to give (S)—N-(3-chloro-4-fluorophenyl)-1,2,4-trimethyl-5-(2-oxo-2-((1,1,1-trifluoroprop-2-yl)amino)acetyl)-1H-pyrrole-3-carboxamide (0.19 g). ¹H NMR (500 MHz, DMSO-d₆): δ 10.18 (s, 1H), 9.39-9.41 (m, 1H), 8.00-8.02 (m, 1H), 7.58-7.61 (m, 1H), 7.37-7.41 (m, 1H), 4.69-4.76 (m, 1H), 3.79 (s, 3H), 2.36 (s, 3H), 2.21 (s, 3H), 1.32-1.33 (d, J=7 Hz, 3H); ¹³C NMR (125 MHz, DMSO-d₆): δ 180.76, 167.27, 163.90, 154.58, 152.65, 140.80, 136.95, 127.20, 124.93, 121.33, 120.25, 119.60, 117.42, 46.01, 33.65, 13.75, 11.57. MS(ESI–, [M–H]⁻) m/z: 446.4.

Example 38

(S)—N-(3,4-difluorophenyl)-1,2,4-trimethyl-5-(2-oxo-2-((1,1,1-trifluoroprop-2-yl)amino)acetyl)-1H-pyrrole-3-carboxamide

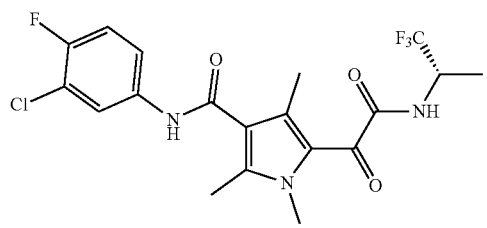

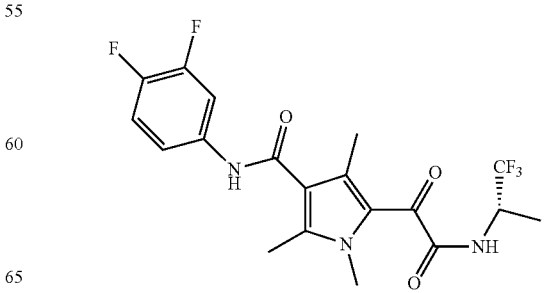

According to Example 37, 3-chloro-4-fluoroaniline was replaced with 3,4-difluoroaniline to give (S)—N-(3,4-difluorophenyl)-1,2,4-trimethyl-5-(2-oxo-2-((1,1,1-trifluoroprop-2-yl)amino)acetyl)-1H-pyrrole-3-carboxamide. $^1$H-NMR (DMSO-d$_6$, 500 MHz): δ 10.20 (s, 1H), 9.39 (d, J=8.5 Hz, 1H), 7.86 (q, J=8.0 Hz, 1H), 7.40 (q, J=6.5 Hz, 2H), 4.75-4.68 (m, 1H), 3.79 (s, 3H), 2.35 (s, 3H), 2.20 (s, 3H), 1.31 (d, J=7.0 Hz, 3H). MS (ESI$^-$, [M–H]$^-$) m/z: 430.4.

Example 39

(S)—N-(4-fluorophenyl)-1,2,4-trimethyl-5-(2-oxo-2-((1,1,1-trifluoroprop-2-yl)amino)acetyl)-1H-pyrrole-3-carboxamide

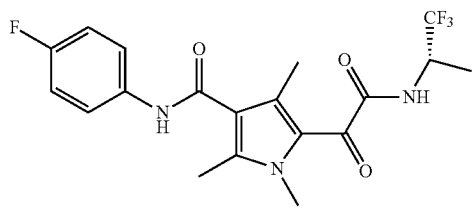 [SMILES: Cc1c(C(=O)Nc2ccc(F)cc2)c(C)n(C)c1C(=O)C(=O)N[C@@H](C)C(F)(F)F]

According to Example 37, 3-chloro-4-fluoroaniline was replaced with 4-fluoroaniline to give (S)—N-(4-fluorophenyl)-1,2,4-trimethyl-5-(2-oxo-2-((1,1,1-trifluoroprop-2-yl)amino)acetyl)-1H-pyrrole-3-carboxamide. $^1$H-NMR (DMSO-d$_6$, 500 MHz): δ 10.03 (s, 1H), 9.38 (d, J=8.0 Hz, 1H), 7.70 (s, 2H), 7.16 (t, J=8.0 Hz, 2H), 4.71 (d, J=6.5 Hz, 1H), 3.78 (s, 3H), 2.35 (s, 3H), 2.20 (s, 3H), 1.31 (d, J=6.0 Hz, 3H). $^{13}$C-NMR (DMSO-d$_6$, 125 MHz): δ 180.70, 167.33, 163.65, 159.50, 157.60, 140.62, 136.10, 130.76, 124.97, 124.84, 121.77, 121.71, 121.47, 115.77, 115.59, 33.63, 13.75, 11.57, 11.24. MS (ESI$^+$, [M+Na]$^+$) m/z: 436.2.

Example 40

(S)—N-(4-fluoro-3-methylphenyl)-1,2,4-trimethyl-5-(2-oxo-2-((1,1,1-trifluoroprop-2-yl)amino)acetyl)-1H-pyrrole-3-carboxamide

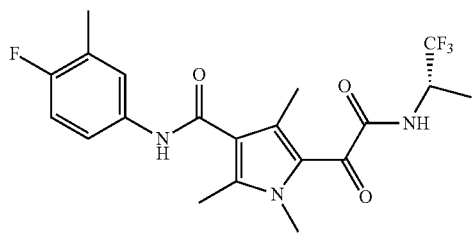 [SMILES: Cc1cc(NC(=O)c2c(C)c(C(=O)C(=O)N[C@@H](C)C(F)(F)F)n(C)c2C)ccc1F]

According to Example 37, 3-chloro-4-fluoroaniline was replaced with 2-fluoro-5-aminotoluene to give (S)—N-(4-fluoro-3-methylphenyl)-1,2,4-trimethyl-5-(2-oxo-2-((1,1,1-trifluoroprop-2-yl)amino)acetyl)-1H-pyrrole-3-carboxamide. $^1$H-NMR (DMSO-d$_6$, 500 MHz): δ 9.95 (s, 1H), 9.36 (s, 1H), 8.85 (s, 1H), 7.66 (d, J=3.95 Hz, 1H), 7.51 (d, J=4.0 Hz, 1H), 4.75-4.66 (m, 1H), 3.84 (s, 3H), 3.74 (s, 3H), 2.67 (s, 3H), 2.45 (s, 3H), 2.32 (s, 3H). $^{13}$C-NMR (DMSO-d$_6$, 125 MHz): δ 181.26, 167.16, 166.26, 153.10, 145.19, 140.09, 134.25, 134.12, 130.31, 129.28, 125.77, 121.14, 114.00, 106.94, 33.58, 13.17, 12.75, 12.18, 12.05, 11.76. MS (ESI$^+$, [M+Na]$^+$) m/z: 450.1.

Example 41

(S)—N-(2-chloropyridin-4-yl)-1,2,4-trimethyl-5-(2-oxo-2-((1,1,1-trifluoroprop-2-yl)amino)acetyl)-1H-pyrrole-3-carboxamide

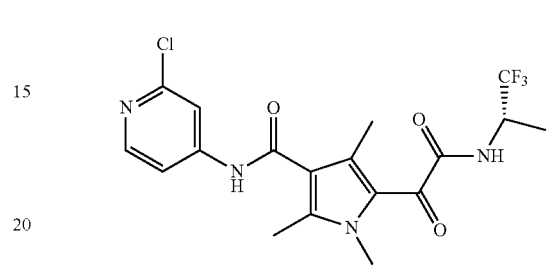

According to Example 37, 3-chloro-4-fluoroaniline was replaced with 2-chloro-4-aminopyridine to give (S)—N-(2-chloropyridin-4-yl)-1,2,4-trimethyl-5-(2-oxo-2-((1,1,1-trifluoroprop-2-yl)amino)acetyl)-1H-pyrrole-3-carboxamide.
$^1$H-NMR (500 MHz, DMSO-d$_6$): δ 9.55 (d, J=8.3 Hz, 1H), 8.85 (s, 1H), 8.74 (d, J=8.0 Hz, 1H), 7.72-7.62 (m, 1H), 4.80-4.67 (m, 1H), 3.84 (s, 3H), 3.75 (s, 1H), 2.68 (s, 3H), 2.45 (s, 3H), 1.34 (d, J=6.0 Hz, 3H). $^{13}$C-NMR (125 MHz, DMSO-d$_6$): δ 181.75, 166.41, 160.75, 153.08, 147.73, 140.60, 134.91, 134.24, 130.30, 122.17, 106.93, 34.23, 33.58, 13.70, 12.75, 12.18, 12.05.

Example 42

(S)—N-(3-amino-4-fluorophenyl)-1,2,4-trimethyl-5-(2-oxo-2-((1,1,1-trifluoroprop-2-yl)amino)acetyl)-1H-pyrrole-3-carboxamide

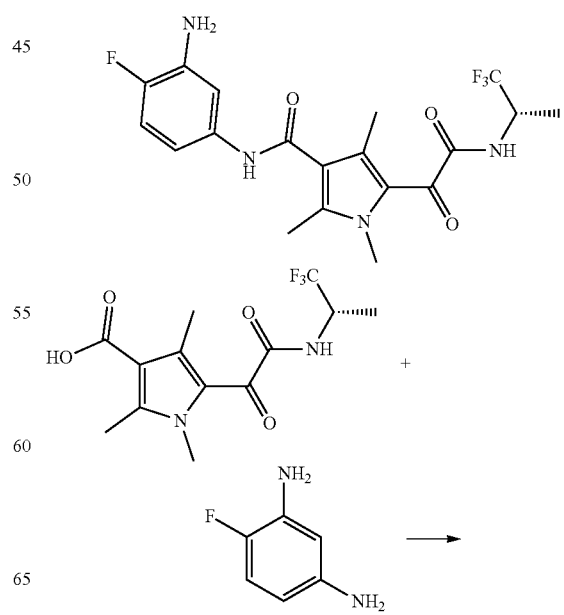

-continued

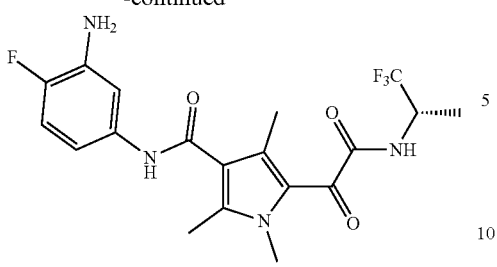

Step A: According to Example 37, in step A, 3-chloro-4-fluoroaniline was replaced with 4-fluorobenzene-1,3-diamine to give (S)—N-(3-amino-4-fluorophenyl)-1,2,4-trimethyl-5-(2-oxo-2-((1,1,1-trifluoroprop-2-yl)amino)acetyl)-1H-pyrrole-3-carboxamide.

$^1$H-NMR (500 MHz, DMSO-$d_6$): δ 9.76 (s, 1H), 9.37 (d, J=9.0 Hz, 1H), 7.25 (d, J=8.0 Hz, 1H), 6.92-6.88 (m, 1H), 6.75 (d, J=8.5 Hz, 1H), 5.13 (s, 2H), 4.71 (q, J=7.5 Hz, 1H), 3.78 (s, 3H), 2.34 (s, 3H), 2.19 (s, 3H), 1.32 (d, J=7.0 Hz, 3H). MS (ESI-, [M-H]$^-$) m/z: 427.4.

Example 43

N-(3-cyano-4-fluorophenyl)-1,2,4-trimethyl-5-(2-(4-methylpiperazin-1-yl)-2-oxoacetyl)-1H-pyrrole-3-carboxamide

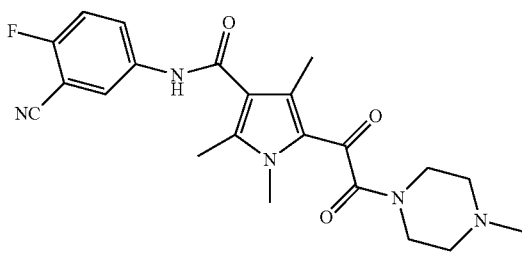 [SMILES: Cc1c(C(=O)Nc2ccc(F)c(C#N)c2)c(C)n(C)c1C(=O)C(=O)N1CCN(C)CC1]

According to Example 1, propynamine was replaced with 1-methylpiperazine in step E to give N-(3-cyano-4-fluorophenyl)-1,2,4-trimethyl-5-(2-(4-methylpiperazin-1-yl)-2-oxoacetyl)-1H-pyrrole-3-carboxamide. $^1$H-NMR (DMSO-$d_6$, 500 MHz): δ 10.35 (s, 1H), 8.20 (q, J=2.5 Hz, 1H), 7.96-7.93 (m, 1H), 7.53 (t, J=9.0 Hz, 1H), 3.85 (s, 3H), 3.56 (s, 2H), 3.33 (s, 2H), 2.36 (d, J=9.0 Hz, 5H), 2.32 (d, J=4.0 Hz, 2H), 2.22 (d, J=5.5 Hz, 6H). $^{13}$C-NMR (DMSO-$d_6$, 125 MHz): δ 181.14, 166.00, 164.05, 141.17, 136.77, 131.02, 127.27, 127.20, 124.84, 123.75, 120.96, 117.63, 117.46, 114.44, 54.59, 54.12, 46.06, 45.67, 40.78, 33.92, 11.56, 11.33. MS (ESI-, [M-H]$^-$) m/z: 424.4.

Example 44

N-(3-cyano-4-fluorophenyl)-1,2,4-trimethyl-5-(2-((1-methylpiperidin-4-yl)amino)-2-oxoacetyl)-1H-pyrrole-3-carboxamide

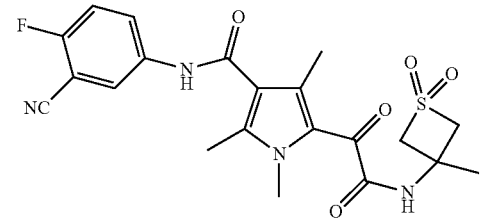 [SMILES: Cc1c(C(=O)Nc2ccc(F)c(C#N)c2)c(C)n(C)c1C(=O)C(=O)NC1(C)CS(=O)(=O)C1]

According to Example 1, propynamine was replaced with 1-methylpiperidine-4-amine in step E to give N-(3-cyano-4-fluorophenyl)-1,2,4-trimethyl-5-(2-((1-methylpiperidin-4-yl)amino)-2-oxoacetyl)-1H-pyrrole-3-carboxamide.

$^1$H-NMR (500 MHz, DMSO-$d_6$): δ 10.30 (s, 1H), 8.69 (d, J=8.0 Hz, 1H), 8.19-8.21 (m, 1H), 7.93-7.97 (m, 1H), 7.51 (t, J=9.0 Hz, 1H), 3.77 (s, 3H), 3.60-3.66 (br, 1H), 2.74-2.77 (m, 2H), 2.35 (s, 3H), 2.22 (s, 3H), 2.18 (s, 3H), 2.01 (t, J=10.5 Hz, 2H), 1.762-1.782 (m, 2H), 1.50-1.55 (m, 2H). $^{13}$C-NMR (125 MHz, DMSO-$d_6$): δ 182.06, 166.78, 164.20, 159.62, 157.62, 140.31, 136.87, 130.33, 127.26, 125.32, 123.73, 120.45, 117.58, 114.46, 100.37, 54.42, 46.22, 33.60, 31.41, 11.56. MS(ESI-, [M-H]$^-$) m/z: 438.5.

Example 45

N-(3-cyano-4-fluorophenyl)-1,2,4-trimethyl-5-(2-((3-methyl-1,1-dioxidothietan-3-yl)amino)-2-oxoacetyl)-1H-pyrrole-3-carboxamide According to Example 1, propynamine was replaced with 3-amino-3-methylthietane 1,1-dioxide in step E to give N-(3-cyano-4-fluorophenyl)-1,2,4-trimethyl-5-(2-((3-methyl-1,1-dioxidothietan-3-yl)amino)-2-oxoacetyl)-1H-pyrrole-3-carboxamide. $^1$H-NMR (DMSO-$d_6$, 500 MHz): δ 10.32 (s, 1H), 9.52 (s, 1H), 8.20 (s, 1H), 7.95 (d, J=8.5 Hz, 1H), 7.52 (d, J=9.0 Hz, 1H), 4.45 (d, J=14.5 Hz, 2H), 4.35 (d, J=14.5 Hz, 2H), 3.78 (s, 3H), 2.36 (s, 3H), 2.26 (s, 3H), 1.70 (s, 3H). $^{13}$C-NMR (DMSO-$d_6$, 125 MHz): δ 180.75, 166.98, 164.06, 159.65, 157.64, 141.04, 136.82, 130.81, 127.28, 125.16, 123.78, 120.65, 117.59, 117.43, 114.45, 100.39, 74.66, 41.80, 33.68, 26.10, 11.71. MS (ESI-, [M-H]$^-$) m/z: 459.4.

Example 46

N-(3-cyano-4-fluorophenyl)-5-(2-((3-hydroxy-1-methylcyclobutyl)amino)-2-oxoacetyl)-1,2,4-trimethyl-1H-pyrrole-3-carboxamide

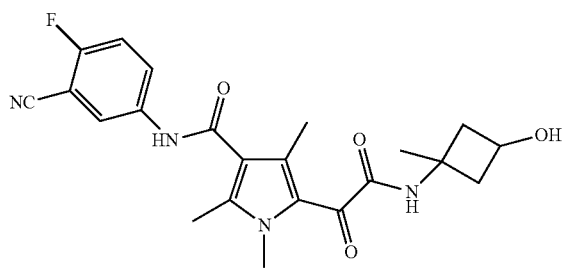 [SMILES: Cc1c(C(=O)Nc2ccc(F)c(C#N)c2)c(C)n(C)c1C(=O)C(=O)NC1(C)CC(O)C1]

According to Example 1, propynamine was replaced with 3-amino-3-methylcyclobutan-1-ol in step E to give N-(3-cyano-4-fluorophenyl)-5-(2-((3-hydroxy-1-methylcyclobutyl)amino)-2-oxoacetyl)-1,2,4-trimethyl-1H-pyrrole-3-carboxamide. $^1$H-NMR (500 MHz, DMSO-$d_6$): δ 10.29 (s, 1H), 8.84 (s, 1H), 8.21~8.20 (m, 1H), 7.96 (t, J=4.0 Hz, 1H), 7.52 (t, J=4.0 Hz, 1H), 5.06 (d, J=7.0 Hz, 1H), 4.01 (t, J=7.0 Hz, 1H), 3.77 (s, 3H), 2.40~2.35 (m, 5H), 2.28 (s, 3H), 2.09 (t, J=9.5 Hz, 2H), 1.37 (s, 3H). $^{13}$C-NMR (125 MHz, DMSO-$d_6$): δ 182.14, 166.00, 164.24, 159.62, 157.61, 140.25, 136.88, 130.18, 127.26, 125.47, 123.74, 120.31, 117.58, 114.47, 100.37, 100.24, 60.88, 45.70, 33.58, 25.98, 11.68. MS(ESI$^-$, [M−H]$^-$) m/z: 425.4.

Example 47

1,2,4-trimethyl-5-(2-((3-methyloxetan-3-yl)amino)-2-oxoacetyl)-N-(3,4,5-trifluorophenyl)-1H-pyrrole-3-carboxamide

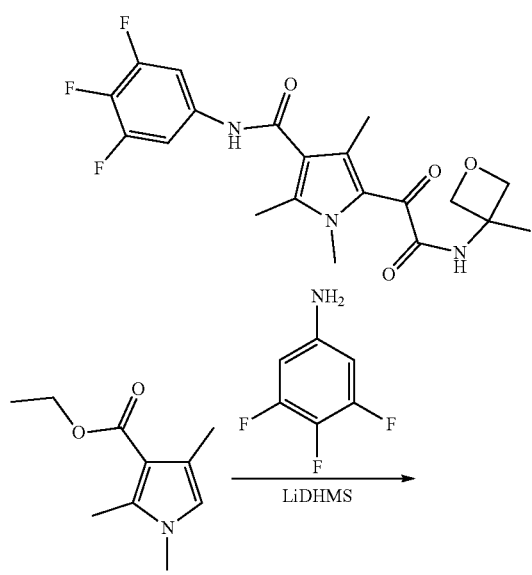

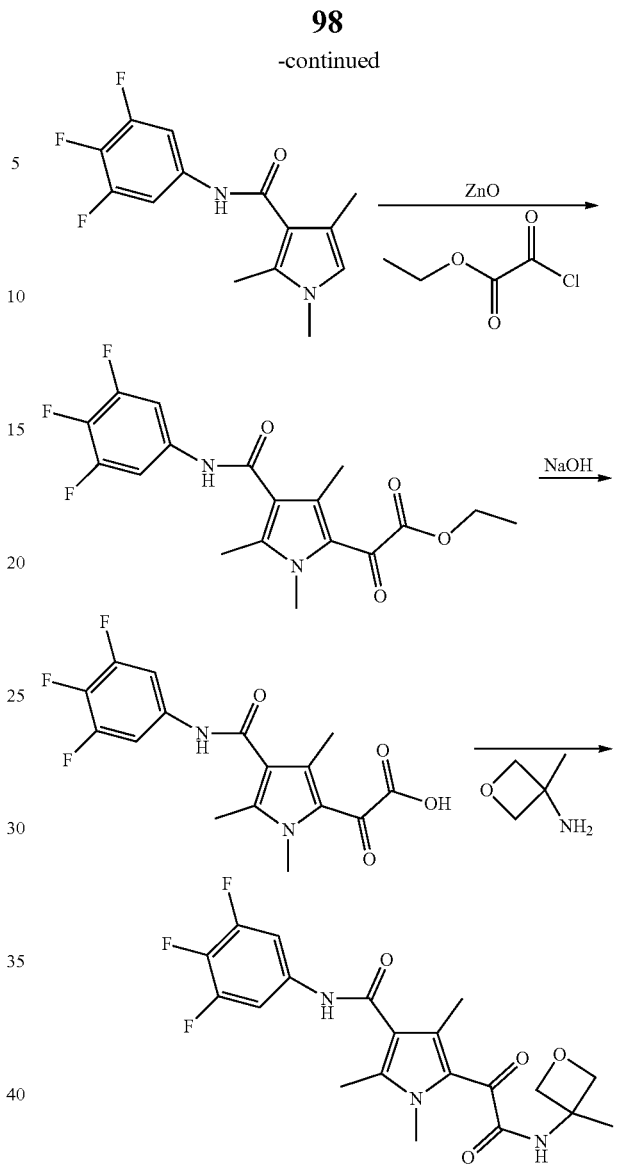

Step A: According to Example 1, 5-amino-3-fluorobenzonitrile was replaced with 3,4,5-trifluoroaniline in step B to give 1,2,4-trimethyl-N-(3,4,5-trifluorophenyl)-1H-pyrrole-3-carboxamide.

Step B: monoethyl chlorooxalate (447 g), and zinc oxide (5.28 g) were added into a reaction flask, followed by adding 1,2,4-trimethyl-N-(3,4,5-trifluorophenyl)-1H-pyrrole-3-carboxamide (36.6 g) in batches in an ice bath. After the addition, the reaction solution was brought to room temperature, and stirred to react for 2.0 h. After the reaction was finished, the resulting mixture was slowly poured into 500 mL ice water for quenching, and then extracted with DCM (2*500 mL). The combined organic layer was washed with a saturated sodium chloride aqueous solution, dried over anhydrous sodium sulfate, and then filtered, and the filtrate was concentrated under reduced pressure to remove the solvent. To the obtained crude product was added ethyl acetate (100 mL), and the resulting mixture was slurried at room temperature for 1.0 h and then suction-filtered. The filter cake was dried under vacuum to give ethyl 2-oxo-2-(1,3,5-trimethyl-4-((3,4,5-trifluorophenyl)carbamoyl)-1H-pyrrole-2-yl)acetate (28.8 g). MS(ESI-, [M−H]$^-$) m/z: 381.3.

Step C: MeOH (120 mL), ethyl 2-oxo-2-(1,3,5-trimethyl-4-((3,4,5-trifluorophenyl)carbamoyl)-1H-pyrrole-2-yl)acetate (28.8 g), and a solution of sodium hydroxide (6.93 g) in water (60 mL) were added into a reaction flask in an ice bath. After the addition, the reaction solution was brought to room temperature and reacted for 2.0 h, and then thereto were added water (200 mL) and DCM (150 mL). The resulting mixture was layered, and the organic layer was discarded. The aqueous layer was adjusted to pH about 3 with concentrated hydrochloric acid, and then extracted with ethyl acetate (2*500 mL). The organics were combined, washed with a saturated aqueous solution of sodium chloride, dried over anhydrous sodium sulfate, and then suction-filtered, and the filtrate was evaporated under reduced pressure to remove the solvent to give 2-oxo-2-(1,3,5-trimethyl-4-((3,4,5-trifluorophenyl) carbamoyl)-1H-pyrrol-2-yl)acetic acid (22.77 g). $^1$H-NMR (500 MHz, DMSO-d$_6$): δ 14.35 (s, 1H), 10.33 (s, 1H), 7.62 (dd, J=10 Hz, 2H), 3.82 (s, 3H), 2.35 (s, 3H), 2.26 (s, 3H). $^{13}$C-NMR (125 MHz, DMSO-d$_6$): δ 178.69, 167.72, 164.04, 151.51, 149.61, 149.49, 141.38, 136.27, 134.32, 130.95, 123.79, 120.90, 104.19, 60.21, 33.74, 11.47. MS (ESI−, [M−H]$^-$) m/z: 353.5.

Step D: DMF (5.0 mL), 2-oxo-2-(1,3,5-trimethyl-4-((3,4,5-trifluorophenyl)carbamoyl)-1H-pyrrol-2-yl) acetic acid (600 mg), HATU (773 mg), and DIPEA (657 mg) were added sequentially into a reaction flask, followed by adding 3-methyl-3-epoxybutylamine (162 mg), and then the reaction solution was stirred at room temperature for 16.0 h. Water (200 mL) was added into the reaction solution, and the mixture was extracted with ethyl acetate (2*200 mL). The organic layers were combined, washed with a saturated sodium chloride aqueous solution, dried over anhydrous sodium sulfate, and then evaporated under reduced pressure to remove the solvent. The obtained crude product was separated by silica gel column chromatography (PE:EA=1:1) to give 1,2,4-trimethyl-5-(2-((3-methyloxetan-3-yl)amino)-2-oxoacetyl)-N-(3,4,5-trifluorophenyl)-1H-pyrrole-3-carboxamide (700 mg). $^1$H-NMR (500 MHz, DMSO-d$_6$): δ 10.30 (s, 1H), 9.26 (s, 1H), 7.63~7.60 (m, 2H), 4.68 (d, J=6 Hz, 2H), 4.39 (d, J=6 Hz, 2H), 3.77 (s, 3H), 2.35 (s, 3H), 2.27 (s, 3H), 1.60 (s, 3H). 13C-NMR (125 MHz, DMSO-d6): δ 181.42, 166.19, 164.22, 151.47, 151.43, 149.61, 149.53, 140.70, 136.10, 136.03, 134.15, 130.40, 125.41, 120.50, 104.19, 80.79, 53.53, 33.63, 23.37, 11.68. MS(ESI−, [M−H]−) m/z: 422.3.

Example 48

(S)—N-(3-cyano-4-fluorophenyl)-1-methyl-5-(2-oxo-2-(1,1,1-trifluoroprop-2-yl)amino)acetyl)-1H-pyrrole-3-carboxamide

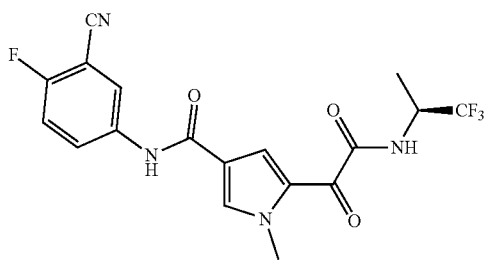

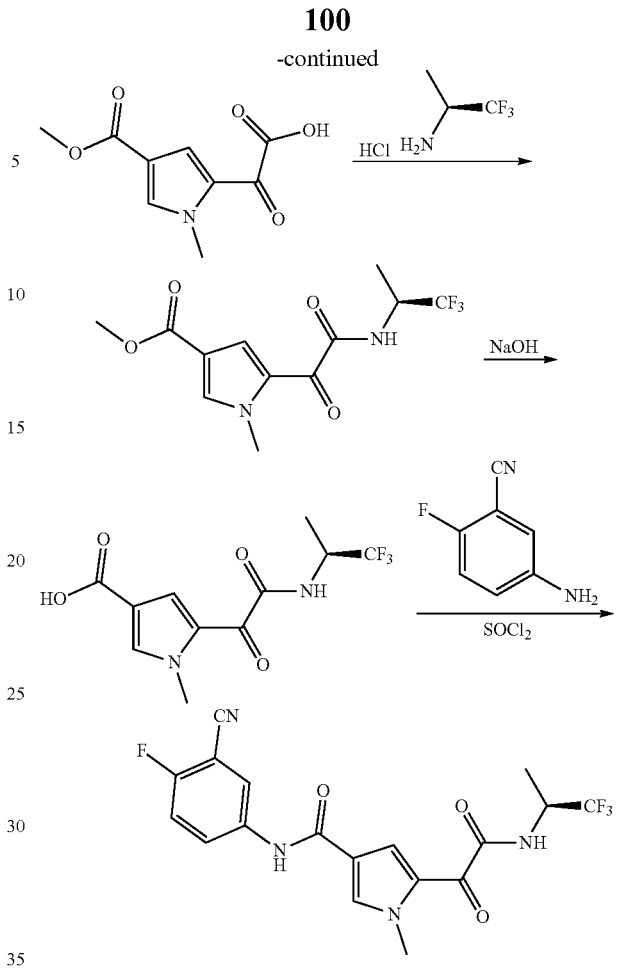

Step A: According to Example 18, tert-butylamine was replaced with (S)-1,1,1-trifluoropropan-2-amine hydrochloride in step D to give methyl (S)-1-methyl-5-(2-oxo-2-((1,1,1-trifluoroprop-2-yl)amino)acetyl)-1H-pyrrole-3-carboxylate. MS (ESI+, [M+H]$^+$) m/z: 307.2.

Step B: According to Example 18, methyl 5-(2-(tert-butylamino)-2-oxoacetyl)-1-methyl-1H-pyrrole-3-carboxylate was replaced with methyl (S)-1-methyl-5-(2-oxo-2-((1,1,1-trifluoroprop-2-yl)amino)acetyl)-1H-pyrrole-3-carboxylate in step E to give (S)-1-methyl-5-(2-oxo-2-((1,1,1-trifluoroprop-2-yl)amino)acetyl)-1H-pyrrole-3-carboxylic acid.

MS (ESI+, [M+H]$^+$) m/z: 293.3.

Step C: According to Example 18, 5-(2-(tert-butylamino)-2-oxoacetyl)-1-methyl-1H-pyrrole-3-carboxylic acid was replaced with methyl (S)-1-methyl-5-(2-oxo-2-((1,1,1-trifluoroprop-2-yl)amino)acetyl)-1H-pyrrole-3-carboxylic acid in step F to give (S)—N-(3-cyano-4-fluorophenyl)-1-methyl-5-(2-oxo-2-(1,1,1-trifluoroprop-2-yl)amino)acetyl)-1H-pyrrole-3-carboxamide. $^1$H-NMR (500 MHz, DMSO-d$_6$): δ 10.30 (s, 1H), 9.41 (d, J=9.0 Hz, 1H), 8.25 (q, J=3.0 Hz, 1H), 8.03-8.05 (m, 2H), 7.94 (d, J=2.0 Hz, 1H), 7.53 (t, J=9.0 Hz, 1H), 4.69-4.77 (m, 1H), 3.98 (s, 3H), 1.36 (d, J=7.0 Hz, 3H); $^{13}$C-NMR (125 MHz, DMSO-d$_6$): δ 178.70, 164.31, 161.68, 159.60, 157.60, 136.80, 127.70, 127.17, 124.93, 124.26, 123.21, 119.71, 117.40, 114.49, 100.23, 46.24, 38.23, 13.56.

MS (ESI−, [M−H]$^-$) m/z: 409.3.

Example 49

(R)—N-(3-cyano-4-fluorophenyl)-1-methyl-5-(2-oxo-2-((1,1,1-trifluoroprop-2-yl)amino)acetyl)-1H-pyrrole-3-carboxamide

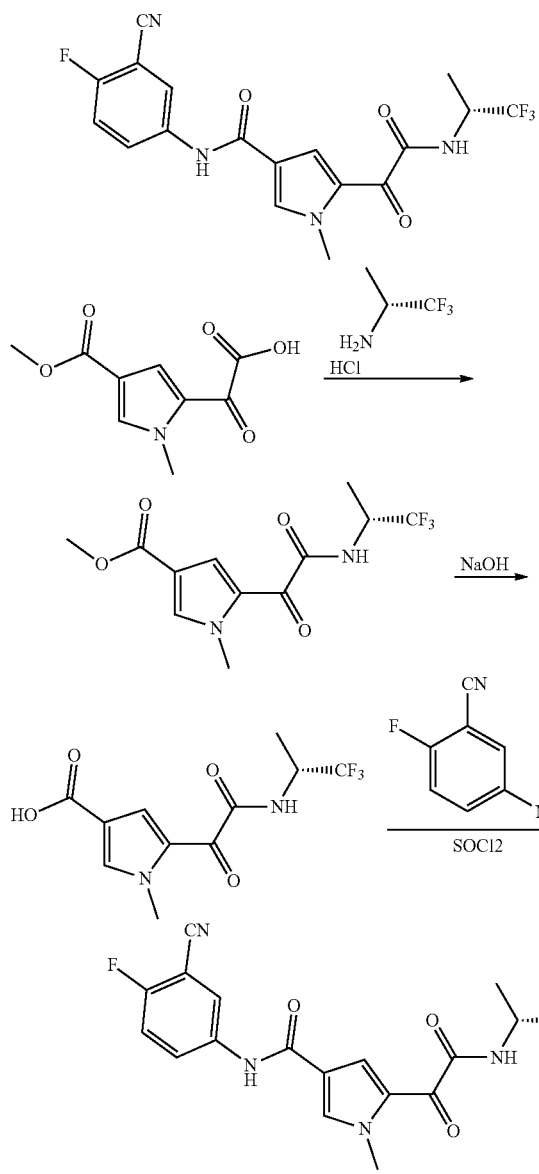

Step A: According to Example 18, tert-butylamine was replaced with (R)-1,1,1-trifluoropropan-2-amine hydrochloride in step D to give methyl (R)-1-methyl-5-(2-oxo-2-((1,1,1-trifluoroprop-2-yl)amino)acetyl)-1H-pyrrole-3-carboxylate. MS (ESI−, [M−H]⁻) m/z: 305.3.

Step B: According to Example 18, methyl 5-(2-(tert-butylamino)-2-oxoacetyl)-1-methyl-1H-pyrrole-3-carboxylate was replaced with methyl (R)-1-methyl-5-(2-oxo-2-((1,1,1-trifluoroprop-2-yl)amino)acetyl)-1H-pyrrole-3-carboxylate in step E to give (R)-1-methyl-5-(2-oxo-2-((1,1,1-trifluoroprop-2-yl)amino)acetyl)-1H-pyrrole-3-carboxylic acid. MS (ESI−, [M−H]⁻) m/z: 291.3.

Step C: According to Example 18, 5-(2-(tert-butylamino)-2-oxoacetyl)-1-methyl-1H-pyrrole-3-carboxylic acid was replaced with (R)-1-methyl-5-(2-oxo-2-((1,1,1-trifluoroprop-2-yl)amino)acetyl)-1H-pyrrole-3-carboxylic acid in step F to give (R)—N-(3-cyano-4-fluorophenyl)-1-methyl-5-(2-oxo-2-(1,1,1-trifluoroprop-2-yl)amino)acetyl)-1H-pyrrole-3-carboxamide. $^1$H-NMR (500 MHz, DMSO-$d_6$): δ 10.30 (s, 1H), 9.41 (d, J=9.0 Hz, 1H), 8.25 (q, J=2.5 Hz, 1H), 8.02-8.05 (m, 2H), 7.94 (d, J=1.5 Hz, 1H), 7.52 (t, J=9.0 Hz, 1H), 4.69-4.77 (m, 1H), 3.98 (s, 3H), 1.36 (d, J=7.0 Hz, 3H). $^{13}$C-NMR (125 MHz, DMSO-$d_6$): δ 178.69, 164.31, 161.68, 159.60, 157.59, 136.80, 127.70, 127.17, 124.92, 124.26, 123.22, 119.72, 117.39, 114.48, 100.23, 45.99, 38.23, 13.56. MS (ESI−, [M−H]⁻) m/z: 409.3.

Example 50

N-(3-cyano-4-fluorophenyl)-1-methyl-5-(2-oxo-2-((3-(trifluoromethyl)oxetan-3-yl)amino)acetyl)-1H-pyrrole-3-carboxamide

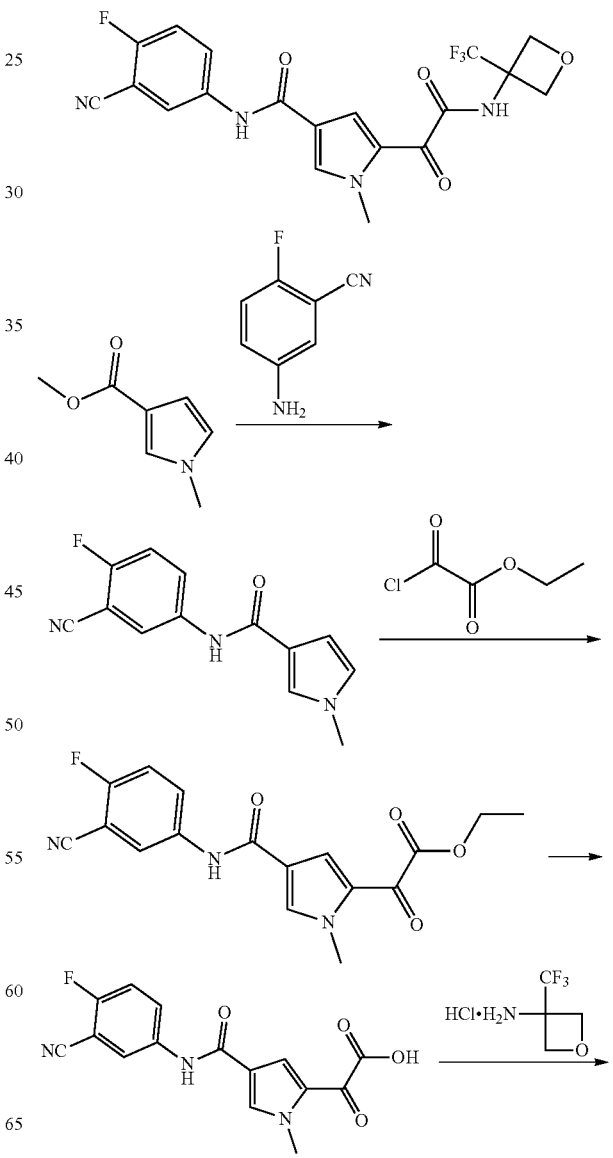

-continued

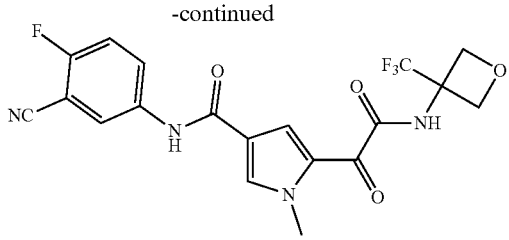

Step A: methyl 1-methyl-1H-pyrrole-3-carboxylate (33 g), 2-fluoro-5-aminobenzonitrile (40.4 g), and tetrahydrofuran (200 mL) were added sequentially into a reaction flask, followed by adding lithium bis(trimethylsilyl)amide (90 g, 538 mL solution in tetrahydrofuran) in an ice bath over 30 minutes, and then the reaction solution was warmed to room temperature and stirred for an additional hour. After the reaction was finished, the reaction solution was poured into 2000 mL of ice-water, stirred vigorously for 10 minutes, and then filtered, and the filter cake was dried overnight to obtain N-(3-cyano-4-fluorophenyl)-1-methyl-1H-pyrrole-3-carboxamide (51.48 g).

Step B: N-(3-cyano-4-fluorophenyl)-1-methyl-1H-pyrrole-3-carboxamide (20.0 g), and dichloromethane (250 mL) were added into a reaction flask, followed by adding ethyl 2-chloro-2-oxoacetate (33.7 g) under stirring and adding anhydrous aluminum trichloride (10.96 g) in batches. After the addition, the reaction solution was brought to room temperature and reacted for 2 hours. After the reaction was finished, the reaction solution was slowly poured into 2000 mL of ice water for quenching, and extracted with dichloromethane (1000 mL*2). The organic layers were combined, washed with a saturated sodium chloride aqueous solution, dried over anhydrous sodium sulfate, and evaporated under reduced pressure to remove the solvent. The obtained crude product was separated by silica gel column chromatography (PE:EA=3:1) to give ethyl 2-(4-((3-cyano-4-fluorophenyl) carbamoyl)-1-methyl-1H-pyrrol-2-yl)-2-oxoacetate (7.16 g). $^1$H NMR (500 MHz, DMSO-d$_6$): δ 10.26 (s, 1H), 8.22-8.23 (m, 1H), 8.01-8.06 (m, 2H), 7.80 (s, 1H), 7.52-7.55 (m, 1H), 4.39 (q, J=21.0 Hz, 2H), 3.97 (s, 3H), 1.34 (t, J=14.0 Hz, 3H); $^{13}$C NMR (125 MHz, DMSO-d$_6$): δ 175.60, 163.46, 161.48, 159.66, 157.66, 137.25, 136.68, 127.77, 124.33, 123.20, 120.00, 117.53, 114.46, 100.34, 62.64, 38.15, 14.36.

Step C: ethyl 2-(4-((3-cyano-4-fluorophenyl)carbamoyl)-1-methyl-1H-pyrrol-2-yl)-2-oxoacetate (2.16 g), and tetrahydrofuran (10 mL) were added into a reaction flask. The reaction solution was placed under an ice bath, and then thereto was added dropwise a solution of lithium hydroxide monohydrate (0.53 g) dissolved in water (5 mL). The mixture was stirred and reacted under an ice bath for 30 minutes. After the reaction was finished, the resulting mixture was diluted by adding 50 mL water, adjusted to pH 5-6 with 2 mol/L dilute hydrochloric acid, washed with ethyl acetate (50 mL*3), dried, and then concentrated to give 2-(4-((3-cyano-4-fluorophenyl) carbamoyl)-1-methyl-1H-pyrrol-2-yl)-2-oxoacetic acid (1.03 g), which was used directly in the next reaction.

Step D: 2-(4-((3-cyano-4-fluorophenyl)carbamoyl)-1-methyl-1H-pyrrol-2-yl)-2-oxoacetic acid (0.2 g), 3-(trifluoromethyl)oxetane-3-amine hydrochloride (0.169 g), HATU (0.362 g), and N,N-dimethylformamide (5 mL) were added sequentially into a reaction flask, followed by adding DIPEA (0.246 g) under N$_2$ protection, and then the mixture was stirred at room temperature and reacted for 2 hours. After the reaction was finished, 100 mL ethyl acetate was added to the reaction solution, and the mixture was washed twice with 100 mL*2 water. Then the resulting mixture was dried, concentrated, slurried with a 5 mL mixed solvent of petroleum ether:ethyl acetate=3:1 for 3 hours, and then filtered. The filter cake was dried under vacuum for 4 h to give N-(3-cyano-4-fluorophenyl)-1-methyl-5-(2-oxo-2-((3-(trifluoromethyl)oxetan-3-yl)amino)acetyl)-1H-pyrrole-3-carboxamide (115 mg). $^1$H-NMR (500 MHz, DMSO-d$_6$): δ 10.30 (s, 1H), 9.98 (s, 1H), 8.24-8.26 (m, 1H), 8.13 (m, 1H), 8.04-8.06 (m, 2H), 7.52 (t, J=18.0 Hz, 1H), 4.92 (d, J=8.0 Hz, 2H), 4.77 (d, J=8.0 Hz, 2H), 3.99 (s, 3H). $^{13}$C-NMR (125 MHz, DMSO-d$_6$): δ 176.97, 162.91, 161.70, 159.60, 157.60, 137.07, 127.75, 124.67, 123.90, 119.76, 117.28, 114.49, 100.28, 73.51, 57.09, 38.41. MS(ESI–, [M–H]–) m/z: 437.4.

Example 51

5-(2-(tert-butylamino)-2-oxoacetyl)-N-(3-cyano-4-fluorophenyl)-2-fluoro-1-methyl-1H-pyrrole-3-carboxamide

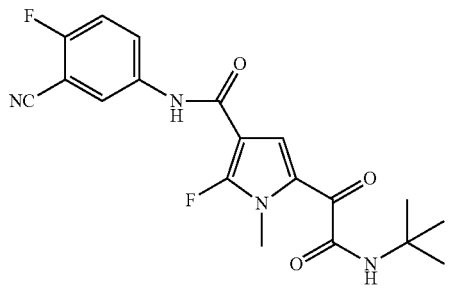

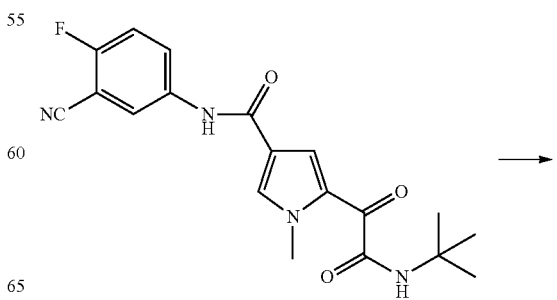

-continued

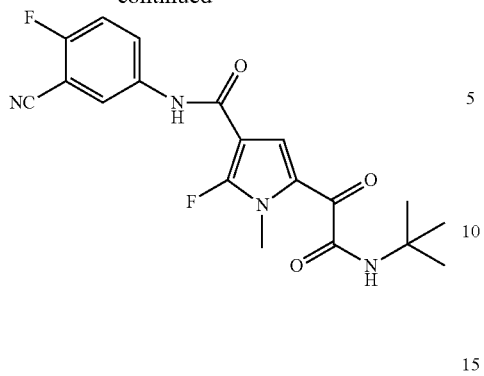

5-(2-(tert-butylamino)-2-oxoacetyl)-N-(3-cyano-4-fluorophenyl)-1-methyl-1H-pyrrole-3-carboxamide (100 mg), selectfluor (115 mg), acetonitrile (2 mL), and DMF (0.5 mL) were added into a reaction flask, and then reacted at 65° C. in oil bath overnight. After the reaction was finished, the reaction solution was poured into a 50 mL saturated aqueous solution of sodium chloride, and then extracted with ethyl acetate (50 mL*2). The organic layer was separated, dried, concentrated, and then separated by column chromatography (PE:EA=3:1) to give 5-(2-(tert-butylamino)-2-oxoacetyl)-N-(3-cyano-4-fluorophenyl)-2-fluoro-1-methyl-1H-pyrrole-3-carboxamide (38.1 mg). $^1$H-NMR (500 MHz, DMSO-d$_6$): δ 10.35 (s, 1H), 8.22 (t, J=3.0 Hz, 1H), 8.15 (s, 1H), 8.05~8.02 (m, 1H), 7.98 (d, J=6.5 Hz, 1H), 7.52 (t, J=9.0 Hz, 1H), 3.81 (s, 3H), 1.83 (s, 9H). $^{13}$C-NMR (125 MHz, DMSO-d$_6$): δ 179.54, 163.36, 159.97, 157.72, 153.45, 151.19, 136.50, 128.01, 124.60, 121.35, 119.46, 117.45, 117.29, 114.42, 100.68, 100.29, 51.42, 31.97, 28.70. MS(ESI$^-$, [M−H]$^-$) m/z: 387.3.

Example 52

(S)—N-(3-cyano-4-fluorophenyl)-2-fluoro-1-methyl-5-(2-oxo-2-((1,1,1-trifluoroprop-2-yl) amino) acetyl)-1H-pyrrole-3-carboxamide

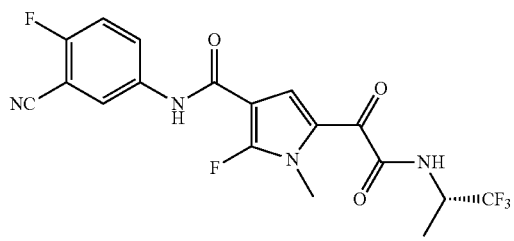 [SMILES: C[C@H](NC(=O)C(=O)c1cc(C(=O)Nc2ccc(F)c(C#N)c2)c(F)n1C)C(F)(F)F]

According to Example 51, 5-(2-(tert-butylamino)-2-oxoacetyl)-N-(3-cyano-4-fluorophenyl)-1-methyl-1H-pyrrole-3-carboxamide was replaced with (S)—N-(3-cyano-4-fluorophenyl)-1-methyl-5-(2-oxo-2-((1, 1, 1-trifluoroprop-2-yl) amino) acetyl)-1H-pyrrole-3-carboxamide to give (S)—N-(3-cyano-4-fluorophenyl)-2-fluoro-1-methyl-5-(2-oxo-2-((1, 1, 1-trifluoroprop-2-yl)amino)acetyl)-1H-pyrrole-3-carboxamide. $^1$H-NMR (500 MHz, DMSO-d$_6$): δ 10.34 (s, 1H), 9.43 (d, J=9.0 Hz, 1H), 8.21 (q, J=3.0 Hz, 1H), 8.05-8.00 (m, 2H), 7.53 (t, J=9.0 Hz, 1H), 4.76-4.70 (m, 1H), 3.83 (s, 3H), 1.36 (d, J=7.0 Hz, 3H). $^{13}$C-NMR (125 MHz, DMSO-d$_6$): δ 177.83, 163.62, 159.88, 157.74, 153.80, 151.54, 136.47, 127.89, 124.56, 121.96, 119.33, 117.49, 114.42, 101.06, 100.19, 46.04, 32.08, 13.53. MS(ESI$^-$, [M−H]$^-$) m/z: 427.3.

Example 53

(S)—N-(3-cyano-4-fluorophenyl)-2-fluoro-1,4-dimethyl-5-(2-oxo-2-((1,1,1-trifluoroprop-2-yl) amino) acetyl)-1H-pyrrole-3-carboxamide

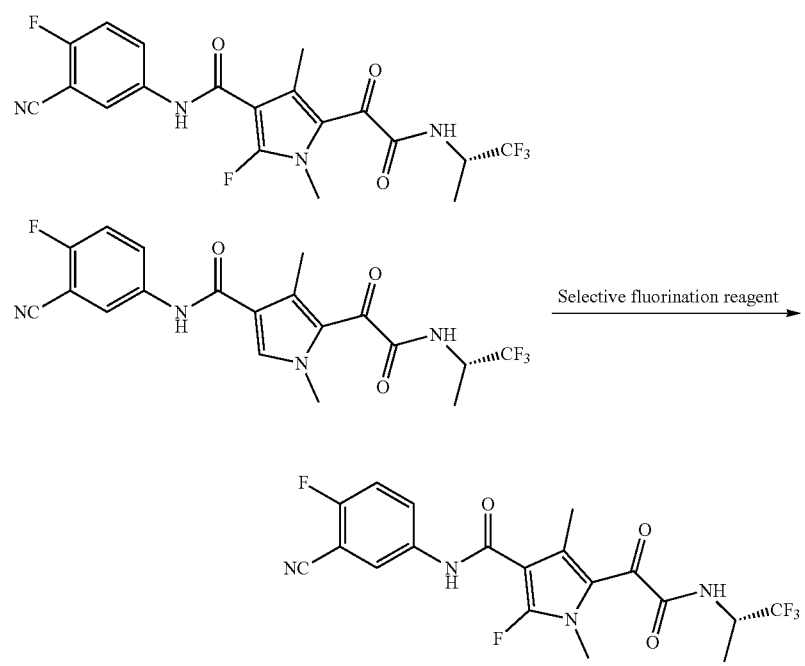

According to Example 51, 5-(2-(tert-butylamino)-2-oxoacetyl)-N-(3-cyano-4-fluorophenyl)-1-methyl-1H-pyrrole-3-carboxamide was replaced with (S)—N-(3-cyano-4-fluorophenyl)-1,4-dimethyl-5-(2-oxo-2-((1,1,1-trifluoroprop-2-yl)amino)acetyl)-1H-pyrrole-3-carboxamide to give (S)—N-(3-cyano-4-fluorophenyl)-2-fluoro-1,4-dimethyl-5-(2-oxo-2-((1,1,1-trifluoroprop-2-yl)amino)acetyl)-1H-pyrrole-3-carboxamide. $^1$H-NMR (500 MHz, DMSO-d$_6$): δ10.34 (s, 1H), 9.49 (d, J=9.0 Hz, 1H), 8.16 (q, J=3.0 Hz, 1H), 7.93-7.90 (m, 1H), 7.53 (t, J=9.0 Hz, 1H), 4.77-4.69 (m, 1H), 3.76 (s, 3H), 2.30 (s, 3H), 1.33 (d, J=7.0 Hz, 3H). $^{13}$C-NMR (125 MHz, DMSO-d$_6$): δ 181.09, 166.79, 160.33, 157.80, 151.02, 148.81, 136.43, 131.67, 127.57, 124.10, 118.58, 117.66, 114.37, 101.62, 100.49, 45.86, 32.01, 13.72, 11.16. MS(ESI$^-$, [M–H]$^-$) m/z: 440.9.

Example 54

(S)—N-(3-cyano-4-fluorophenyl)-4-fluoro-1,2-dimethyl-5-(2-oxo-2-((1,1,1-trifluoroprop-2-yl) amino)acetyl)-1H-pyrrole-3-carboxamide

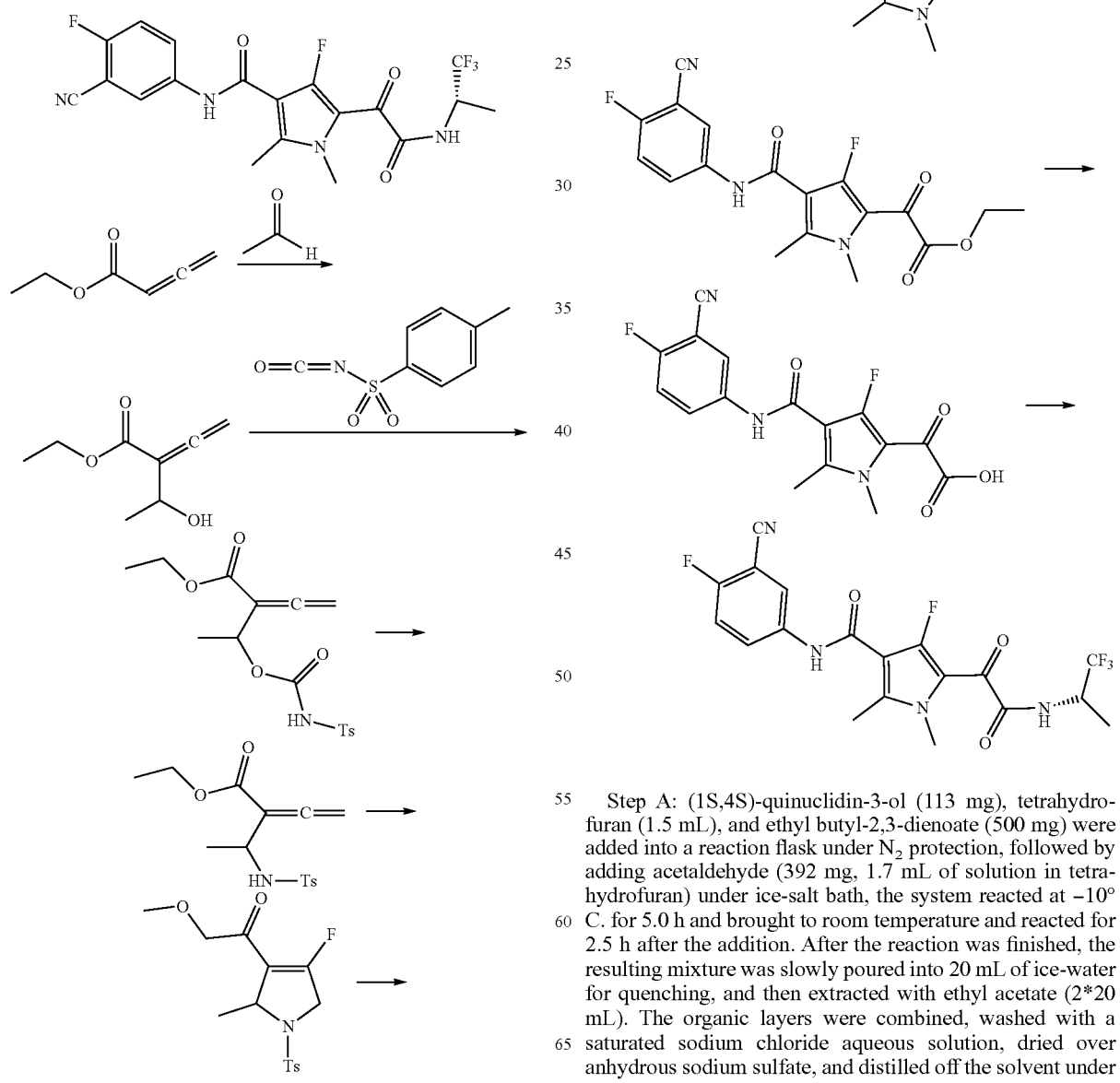

Step A: (1S,4S)-quinuclidin-3-ol (113 mg), tetrahydrofuran (1.5 mL), and ethyl butyl-2,3-dienoate (500 mg) were added into a reaction flask under N$_2$ protection, followed by adding acetaldehyde (392 mg, 1.7 mL of solution in tetrahydrofuran) under ice-salt bath, the system reacted at −10° C. for 5.0 h and brought to room temperature and reacted for 2.5 h after the addition. After the reaction was finished, the resulting mixture was slowly poured into 20 mL of ice-water for quenching, and then extracted with ethyl acetate (2*20 mL). The organic layers were combined, washed with a saturated sodium chloride aqueous solution, dried over anhydrous sodium sulfate, and distilled off the solvent under reduced pressure. The obtained crude product was separated by silica gel column chromatography (PE:EA=10:1) to give ethyl 2-(1-hydroxyethyl)but-2,3-dienoate (210 mg). $^1$H-NMR (500 MHz, DMSO-d$_6$): δ 5.42 (d, J=1.5 Hz, 2H), 4.94 (d, J=5.0 Hz, 1H), 4.48 (q, J=5.5 Hz, 1H), 4.15-4.10 (m, 2H), 1.20 (dd, J$_1$=5.5 Hz, J$_2$=7.0 Hz, 6H). $^{13}$C-NMR (125 MHz, DMSO-d$_6$): δ 212.31, 166.11, 105.77, 81.94, 63.23, 60.78, 22.99, 14.59.

Step B: dichloromethane (10.0 mL), and ethyl 2-(1-hydroxyethyl) butane-2,3-dienoate (210 mg) were added into a reaction flask under N$_2$ protection, followed by adding 4-methylbenzenesulfonyl isocyanate (292 mg) under an ice bath. After the addition, the reaction mixture was brought to room temperature and reacted for 1.0 h. After the reaction was finished, the resulting mixture was slowly poured into 50 mL ice-water for quenching, and then extracted with DCM (2*50 mL). The organic layer was combined, washed with a saturated sodium chloride aqueous solution, and the organic phase was dried over anhydrous sodium sulfate, and then distilled off the solvent under reduced pressure. The obtained crude product was separated by silica gel column chromatography (PE:EA=4:1) to give ethyl 2-(1-((toluenesulfonylamino)oxy)ethyl)buta-2,3-dienoate (270 mg). $^1$H-NMR (500 MHz, CDCl$_3$): δ 7.92 (d, J=8.5 Hz, 2H), 7.70 (br, 1H), 7.33 (d, J=8.0 Hz, 2H), 5.55-5.58 (m, 1H), 5.22-5.30 (m, 2H), 4.12 (q, J=7.5 Hz, 2H), 2.44 (s, 3H), 1.37 (d, J=6.5 Hz, 3H), 1.20 (t, J=7.0 Hz, 3H). $^{13}$C-NMR (125 MHz, CDCl$_3$): δ 212.95, 164.70, 149.52, 144.97, 135.60, 129.54, 128.44, 102.01, 82.23, 69.79, 61.32, 21.66, 19.10, 14.06. MS(ESI+, [M+H]$^+$) m/z: 354.3.

Step C: benzene (8.0 mL), and ethyl 2-(1-((toluenesulfonylamino)oxy)ethyl)buta-2,3-dienoate (270 mg) were added into a reaction flask under N$_2$ protection, followed by slowly adding dropwise a solution of 1,4-diazabicyclo[2.2.2] octane (83 mg) in benzene (8.0 mL) at room temperature over 5.0 h. After the dropwise addition, the reaction solution reacted for 16.0 h. After the reaction was finished, the resulting mixture was slowly poured into 50 mL ice-water for quenching, and then extracted with ethyl acetate (2*50 mL). The organic layers were combined, washed with a saturated sodium chloride aqueous solution, dried over anhydrous sodium sulfate and then evaporated under reduced pressure to remove the solvent. The obtained crude product was separated by silica gel column chromatography (PE:EA=5:1) to give ethyl 2-(1-((4-methylphenyl)sulfonamido)ethyl) buta-2,3-dienoate (110 mg). $^1$H-NMR (500 MHz, DMSO-d$_6$): δ 7.70 (d, J=8.0 Hz, 2H), 7.26 (t, J=4.0 Hz, 2H), 5.28 (d, J=10.0 Hz, 1H), 5.05 (dd, J$_1$=14.5 Hz, 17.0 Hz, 2H), 4.26-4.20 (m, 1H), 4.08 (dd, J$_1$=7.0 Hz, 14.0 Hz, 2H), 2.41 (s, 3H), 1.35 (d, J=7.0 Hz, 3H), 1.20 (t, J=7.0 Hz, 3H). $^{13}$C-NMR (125 MHz, DMSO-d$_6$): δ 212.14, 165.46, 143.17, 138.08, 129.42, 127.23, 101.44, 80.60, 61.15, 49.86, 22.09, 21.51, 14.09. MS(ESI+, [M+Na]$^+$) m/z: 332.3.

Step D: diethyl ether (80 mL), ethyl 2-(1-((4-methylphenyl)sulfonamido)ethyl)buta-2,3-dienoate (6.26 g), N-fluoro-N-(benzenesulfonyl)benzenesulfonamide (9.57 g), silver nitrate (0.687 g), and potassium carbonate (5.59 g) were added into a 250 mL one-necked reaction flask under N$_2$ protection. The system was light-shielded, stirred at room temperature and reacted overnight. After the reaction was finished, the reaction mixture was poured into water (100 ml), and then extracted with ethyl acetate (100 ml*2). The organic layers were combined, washed with saturated brine, dried over anhydrous sodium sulfate and evaporated under reduced pressure to remove the solvent. The obtained crude product was separated by silica gel column chromatography (PE:EA=10:1) to give ethyl 4-fluoro-2-methyl-1-toluenesulfonyl-2,5-dihydro-1H-pyrrole-3-carboxylate (4.1 g). $^1$H-NMR (500 MHz, DMSO-d$_6$): δ 7.72 (d, J=8.0 Hz, 2H), 7.33 (d, J=7.5 Hz, 2H), 4.68 (d, J=4.5 Hz, 1H), 4.28-4.15 (m, 4H), 2.44 (s, 3H), 1.56 (d, J=6.0 Hz, 3H), 1.27 (t, J=6.5 Hz, 3H). $^{13}$C-NMR (125 MHz, DMSO-d$_6$): δ 161.09, 160.62, 158.70, 144.24, 134.01, 130.08, 129.86, 127.50, 110.60, 60.97, 50.48, 50.26, 22.37, 21.57, 14.09. MS(ESI+, [M+Na]$^+$) m/z: 350.08.

Step E: dimethyl sulfoxide (70 mL), ethyl 4-fluoro-2-methyl-1-toluenesulfonyl-2,5-dihydro-1H-pyrrole-3-carboxylate (3.52 g), and potassium tert-butoxide (3.62 g) were added into a reaction flask, and then the reaction system was heated to 50° C. and reacted for 1 h. After the reaction was finished, the reaction solution was added into water (100 mL), and extracted with dichloromethane (100 mL*2). The organic layers were combined, washed with saturated brine, dried over anhydrous sodium sulfate and then evaporated under reduced pressure to remove the solvent. The obtained crude product was separated by silica gel column chromatography (PE:EA=4:1) to give ethyl 4-fluoro-2-methyl-1H-pyrrole-3-carboxylate (0.2 g). $^1$H-NMR (500 MHz, DMSO-d$_6$): δ 11.40 (s, 1H), 7.28 (s, 1H), 4.45 (s, 2H), 2.80 (s, 3H), 1.49 (s, 3H). $^{13}$C-NMR (125 MHz, DMSO-d$_6$): δ 168.09, 137.93, 124.48, 109.14, 103.49, 60.01, 15.26, 14.60. MS (ESI+, [M+Na]$^+$) m/z: 194.04.

Step F: DMF (20 mL), ethyl 4-fluoro-2-methyl-1H-pyrrole-3-carboxylate (0.2 g), and methyl iodide (199 mg) were added into a reaction flask, followed by adding slowly sodium hydrogen (56 mg) in an ice bath. After the addition, the reaction mixture was brought to room temperature and reacted for 1.0 h. After the reaction was finished, the reaction solution was added into ice water (50 mL), and extracted with ethyl acetate (50 mL*2). The organic layers were combined, washed with saturated brine, dried over anhydrous sodium sulfate, and then evaporated under reduced pressure to remove the solvent. The obtained crude product was separated by silica gel column chromatography (PE:EA=20:1) to give ethyl 4-fluoro-1,2-dimethyl-1H-pyrrole-3-carboxylate (169 mg). $^1$H-NMR (500 MHz, CDCl$_3$): δ 6.27 (s, 1H), 4.30 (d, J=6.5 Hz, 2H), 3.47 (s, 3H), 2.46 (s, 3H), 1.35 (d, J=6.5 Hz, 3H). $^{13}$C-NMR (125 MHz, CDCl3): δ 164.04, 151.11, 149.14, 132.92, 104.86, 59.46, 33.67, 14.46, 10.94. MS (ESI$^+$, [M+Na]$^+$) m/z: 208.7.

Step G: Tetrahydrofuran (12 mL), ethyl 4-fluoro-1,2-dimethyl-1H-pyrrole-3-carboxylate (200 mg), and 5-amino-2-fluorobenzonitrile (170 mg) were added into a reaction flask, followed by adding slowly lithium bis(trimethylsilyl) amide (415 mg, 2.7 mL solution in tetrahydrofuran) in an ice bath. After the addition, the mixture was brought to room temperature and reacted for 2.0 hours. After the reaction was finished, the reaction solution was added into ice water (50 mL), and then extracted with ethyl acetate (50 mL*2). The combined organic layer was washed with saturated brine, and the organic phase was dried over sodium sulfate, and then evaporated under reduced pressure to remove the solvent. The obtained crude product was separated by silica gel column chromatography (PE:EA=1:1) to give N-(3-cyano-4-fluorophenyl)-4-fluoro-1,2-dimethyl-1H-pyrrole-3-carboxamide (200 mg). $^1$H-NMR (500 MHz, DMSO-d6): δ 9.53 (s, 1H), 8.19 (d, J=3.0 Hz, 1H), 7.97 (d, J=4.0 Hz, 1H), 7.49 (t, J=9.0 Hz, 1H), 6.74 (s, 1H), 3.49 (s, 3H), 2.36

(s, 3H). $^{13}$C-NMR (125 MHz, DMSO-d$_6$): δ 148.76, 146.25, 136.94, 131.34, 127.72, 124.14, 117.36, 114.53, 105.51, 104.07, 33.84, 10.89. MS (ESI$^+$, [M+H]$^+$) m/z: 276.03.

Step H: Zinc oxide (20 mg), and monoethyl chlorooxalate (1.38 g) were added into a reaction flask under N$_2$ protection, followed by adding N-(3-cyano-4-fluorophenyl)-4-fluoro-1,2-dimethyl-1H-pyrrole-3-carboxamide (140 mg) in batches in an ice bath. After the addition, the reaction solution reacted for 2.0 h. After the reaction was finished, the resulting mixture was slowly poured into 50 mL ice-water for quenching, and then extracted with DCM (2*50 mL). The organic layers were combined, washed with a saturated sodium chloride aqueous solution, dried over anhydrous sodium sulfate, and then suction-filtered, and the filtrate was rotary-evaporated under reduced pressure to remove the solvent. The obtained crude product was separated by silica gel column chromatography (DCM:MeOH=10:1) to give ethyl 2-(4-((3-cyano-4-fluorophenyl)carbamoyl)-3-fluoro-1,5-dimethyl-1H-pyrrol-2-yl)-2-oxoacetate (120 mg). MS (ESI+, [M+Na]$^+$) m/z: 398.10.

Step I: Tetrahydrofuran (3.0 mL), and ethyl 2-(4-((3-cyano-4-fluorophenyl)carbamoyl)-3-fluoro-1,5-dimethyl-1H-pyrrol-2-yl)-2-oxoacetate (120 mg) were added into a reaction flask under an ice bath, followed by adding dropwise a solution of lithium hydroxide monohydrate (19.2 mg) in water (5.0 mL). After the addition, the reaction solution was brought to room temperature and reacted for 10 minutes, and then thereto were added water (40 mL) and ethyl acetate (30 mL). The resulting mixture was layered, and the organic layer was discarded. The aqueous layer was adjusted to pH about 2 with concentrated hydrochloric acid, and then extracted with ethyl acetate (2*50 mL). The organic layers were combined, washed with a saturated sodium chloride aqueous solution, dried over anhydrous sodium sulfate, and then suction-filtered. The filtrate was evaporated under reduced pressure to remove the solvent to give 2-(4-(3-cyano-4-fluorophenyl)carbamoyl)-3-fluoro-1,5-dimethyl-1H-pyrrol-2-yl)-2-oxoacetic acid (38.0 mg). MS(ESI−, [M−H]$^−$) m/z: 346.3.

Step J: N,N-dimethylformamide (5.0 mL), 2-(4-(3-cyano-4-fluorophenyl)carbamoyl)-3-fluoro-1,5-dimethyl-1H-pyrrol-2-yl)-2-oxoacetic acid (38.0 mg), HATU (54 mg), and DIPEA (32.5 mg) were added sequentially into a reaction flask, followed by adding (S)-1,1,1-trifluoropropan-2-amine hydrochloride (20 mg). The reaction solution was then stirred at room temperature for 2.0 h. Water (50 mL) was added thereto, and the resulting mixture was extracted with ethyl acetate (2*50 mL). The organic layers were combined, washed with a saturated sodium chloride aqueous solution, dried over anhydrous sodium sulfate, and then evaporated under reduced pressure to remove the solvent. The obtained crude product was separated by silica gel column chromatography (PE:EA=1:1) to give (S)—N-(3-cyano-4-fluorophenyl)-4-fluoro-1,2-dimethyl-5-(2-oxo-2-((1,1,1-trifluoroprop-2-yl)amino)acetyl)-1H-pyrrole-3-carboxamide (21 mg). $^1$H-NMR (500 MHz, DMSO-d$_6$): δ 10.25 (s, 1H), 9.36 (d, J=8.5 Hz, 1H), 8.17 (d, J=3.0 Hz, 1H), 7.95 (d, J=4.5 Hz, 1H), 7.52 (t, J=9.0 Hz, 1H), 4.67 (d, J=6.5 Hz, 1H), 3.83 (s, 3H), 2.47 (s, 3H), 1.30 (d, J=6.5 Hz, 3H). $^{13}$C-NMR (125 MHz, DMSO-d$_6$): δ 165.87, 160.43, 159.84, 142.17, 136.38, 128.03, 124.58, 117.55, 114.40, 112.50, 105.68, 100.33, 93.06, 88.16, 45.75, 33.16, 13.78, 11.38. MS (ESI−, [M−H]$^−$) m/z: 441.4.

Example 55

2-chloro-N-(3-cyano-4-fluorophenyl)-5-(2-((3-hydroxy-1-methylcyclobutyl)amino)-2-oxoacetyl)-1,4-dimethyl-1H-pyrrole-3-carboxamide

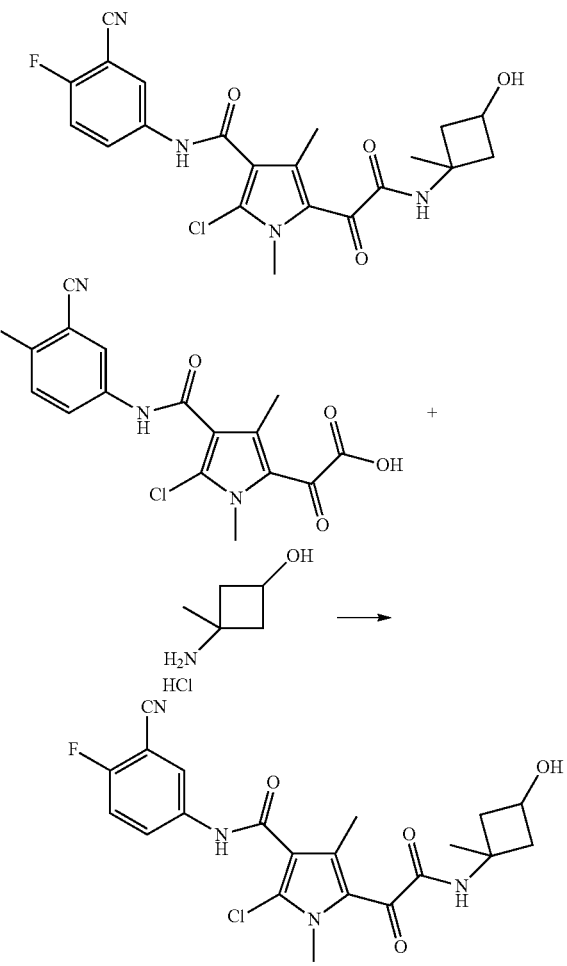

2-(5-chloro-4-((3-cyano-4-fluorophenyl)carbamoyl)-1,3-dimethyl-1H-pyrrole-2-)-2-oxoacetic acid (500 mg), DCM (25 mL) and HOBt (211 mg) were added sequentially into a reaction flask at room temperature. After the addition, the reaction solution was continuously stirred for 30 minutes at room temperature. Then, DMAP (16.79 mg), 3-amino-3-methylcyclobut-1-ol hydrochloride (189 mg), and DIPEA (0.24 mL) were added into the reaction solution, and the resulting mixture was cooled in an ice bath, and stirred for 20 minutes. A solution of DCC (312 mg) in DCM (20 mL) was added into the above reaction solution, and the mixture was stirred at room temperature overnight after removing the ice bath. After the reaction was finished, the resulting mixture was concentrated to remove the solvent. To the residue were added EA (150 mL) and water (30 mL). The organic layer was separated, washed with 1N hydrochloric acid (30 mL*2) and then water (30 mL*3), respectively, dried over anhydrous sodium sulfate, and then suction-filtered. The filtrate was concentrated, and then purified by column chromatography to give 2-chloro-N-(3-cyano-4-fluorophenyl)-5-(2-((3-hydroxy-1-methylcyclobutyl)

amino)-2-oxoacetyl)-1,4-dimethyl-1H-pyrrole-3-carboxamide (201 mg). $^1$H-NMR (500 MHz, DMSO-d$_6$): δ 10.56 (s, 1H), 8.97 (s, 1H), 8.20-8.19 (m, 1H), 7.95-7.94 (m, 1H), 7.54 (t, J=9.5 Hz, 1H), 5.58-5.57 (d, J=8.0 Hz, 1H), 5.10-5.08 (m, 1H), 3.84 (s, 3H), 2.29 (s, 3H), 1.73-1.71 (m, 2H), 1.63-1.61 (m, 2H), 1.37 (s, 3H). $^{13}$C-NMR (125 MHz, DMSO-d$_6$): δ 181.94, 165.27, 161.76, 159.85, 157.84, 157.11, 136.47, 130.28, 127.26, 126.33, 123.79, 119.01, 117.75, 114.37, 100.55, 61.49, 45.82, 34.18, 25.90, 24.92, 11.58. MS(ESI+, [M+H]$^+$) m/z: 447.1.

Example 56

((S)—N-(3-cyano-4-fluorophenyl)-2-(methoxymethyl)-1-methyl-5-(2-oxo-2-(1,1,1-trifluoroprop-2-yl)amino)acetyl)-1H-pyrrole-3-carboxamide

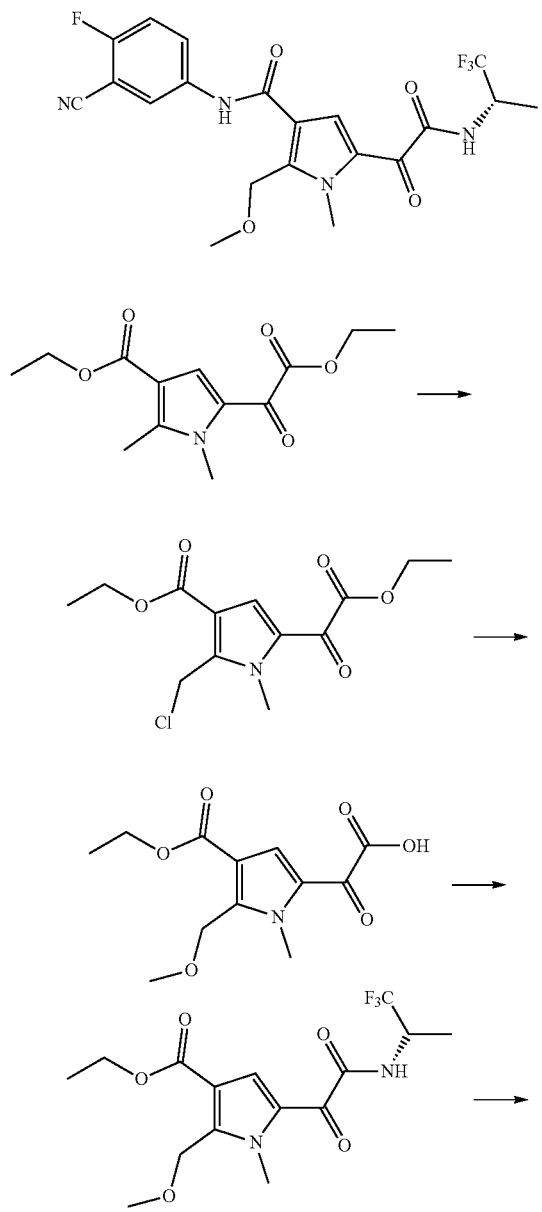

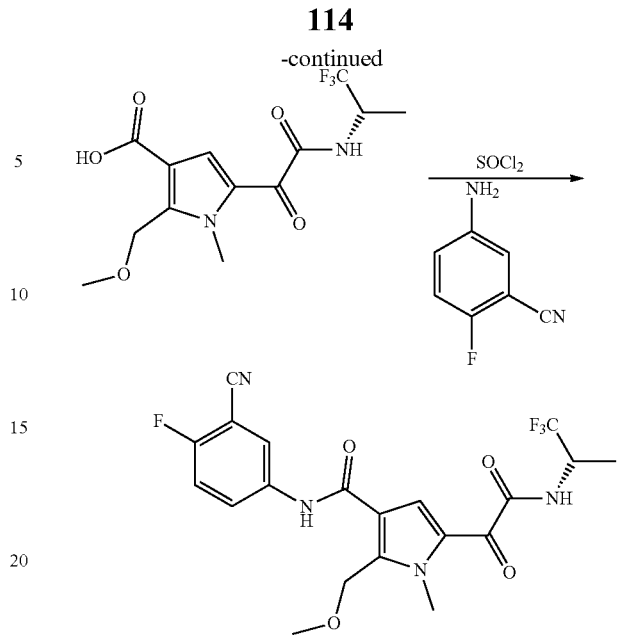

Step A: N,N-dimethylformamide (15 mL), ethyl 5-(2-ethoxy-2-oxoacetyl)-1,2-dimethyl-1H-pyrrole-3-carboxylate (1.0 g), and 1-chloropyrrolidine-2,5-dione (0.6 g) were added into a reaction flask and reacted at room temperature for 24.0 h. After the reaction was finished, the reaction solution was added into ice water (50 mL), and then extracted with ethyl acetate (50 mL*2). The organic layers were combined, washed with saturated brine, dried over anhydrous sodium sulfate and evaporated under reduced pressure to remove the solvent. The obtained crude product was separated by silica gel column chromatography (PE: EA=20:1) to give ethyl 2-(chloromethyl)-5-(2-ethoxy-2-oxoacetyl)-1-methyl-1H-pyrrole-3-carboxylate (350 mg).

$^1$H-NMR (500 MHz, DMSO-d$_6$): δ 7.52 (s, 1H), 5.22 (s, 2H), 4.36 (q, J=7.0 Hz, 2H), 4.27 (q, J=7.0 Hz, 2H), 3.96 (s, 3H), 1.29-1.33 (m, 6H). $^{13}$C-NMR (125 MHz, DMSO-d$_6$): δ 175.76, 162.87, 142.45, 127.70, 124.76, 114.78, 62.79, 60.70, 34.23, 14.59.

Step B: MeOH (9.0 mL), ethyl 2-(chloromethyl)-5-(2-ethoxy-2-oxoacetyl)-1-methyl-1H-pyrrole-3-carboxylate (1.00 g), and a solution of lithium hydroxide monohydrate (0.143 g) in water (9.0 mL) were added into a reaction flask under an ice bath. After the addition, the reaction solution was brought to room temperature and reacted for 10 minutes, and then thereto were added water (100 mL) and ethyl acetate (100 mL). The resulting mixture was layered, and the organic layer was discarded. The aqueous layer was adjusted to pH about 2 with concentrated hydrochloric acid and then extracted with ethyl acetate (2*100 mL). The organic layers were combined, washed with a saturated aqueous solution of sodium chloride, dried over anhydrous sodium sulfate, and then suction-filtered, and the filtrate was evaporated under reduced pressure to remove the solvent to give 2-(4-(ethoxycarbonyl)-5-(methoxymethyl)-1-methyl-1H-pyrrol-2-yl)-2-oxoacetic acid (684 mg). MS(ESI–, [M–H]$^-$) m/z: 268.3.

Step C: N,N-dimethylformamide (3.0 mL), 2-(4-(ethoxycarbonyl)-5-(methoxymethyl)-1-methyl-1H-pyrrol-2-yl)-2-oxoacetic acid (100 mg), HATU (184 mg), and DIPEA (106 mg) were added sequentially into a reaction flask, followed by adding (S)-1,1,1-trifluoropropan-2-amine hydrochloride (66 mg), and then the reaction solution was stirred at room temperature for 2.0 h, and then thereto was added water (50 mL). The resulting mixture was extracted with ethyl acetate (2*50 mL). The organic layers were combined, washed with a saturated sodium chloride aqueous solution, dried over anhydrous sodium sulfate, evaporated under reduced pressure to remove the solvent. The obtained crude product was separated by silica gel column chromatography (PE:EA=5:1) to give ethyl (S)-2-(methoxymethyl)-1-methyl-5-(2-oxo-2-((1,1,1-trifluoroprop-2-yl)amino)acetyl)-1H-pyrrole-3-carboxylate. $^1$H-NMR (500 MHz, DMSO-d$_6$): δ 9.38 (d, J=9.0 Hz, 1H), 7.54 (s, 1H), 4.86 (s, 2H), 4.69-4.76 (m, 1H), 4.22-4.26 (m, 2H), 3.93 (s, 3H), 3.29 (s, 3H), 1.33 (d, J=7.0 Hz, 3H), 1.28 (d, J=7.0 Hz, 3H). $^{13}$C-NMR (125 MHz, DMSO-d6): δ179.38, 164.51, 163.30, 143.21, 129.44, 127.52, 124.96, 122.71, 115.32, 62.15, 60.39, 58.07, 64.44, 34.21, 14.60. MS(ESI–, [M–H]⁻) m/z: 363.4.

Step D: MeOH (5.0 mL), and ethyl (S)-2-(methoxymethyl)-1-methyl-5-(2-oxo-2-((1,1,1-trifluoroprop-2-yl)amino)acetyl)-1H-pyrrole-3-carboxylate (150 mg) were added sequentially into a reaction flask, followed by adding a solution of sodium hydroxide (33 mg) in water (5 mL) at room temperature. The mixture was heated to 80° C. and reacted for 4.0 h. After the reaction was finished, the resulting mixture was adjusted to pH 2 with concentrated hydrochloric acid, and then extracted with ethyl acetate (2*50 mL). The organic layers were combined, washed with a saturated sodium chloride aqueous solution, dried over anhydrous sodium sulfate, and evaporated under reduced pressure to remove the solvent to give (S)-2-(methoxymethyl)-1-methyl-5-(2-oxo-2-((1,1,1-trifluoroprop-2-yl)amino)acetyl)-1H-pyrrole-3-carboxylic acid (256 mg). $^1$H-NMR (500 MHz, DMSO-d$_6$): δ12.57 (s, 1H), 9.37 (d, J=9.0 Hz, 1H), 7.48 (s, 1H), 4.87 (s, 2H), 4.70-4.74 (m, 1H), 3.29 (s, 3H), 3.28 (s, 3H), 1.33 (d, J=7.0 Hz, 3H). $^{13}$C-NMR (125 MHz, DMSO-d$_6$): δ179.59, 164.89, 143.21, 127.34, 125.17, 116.24, 62.13, 58.03, 46.15, 34.17, 13.50. MS (ESI–, [M–H]⁻) m/z: 335.3.

Step E: Toluene (10 mL), (S)-2-(methoxymethyl)-1-methyl-5-(2-oxo-2-((1,1,1-trifluoroprop-2-yl)amino)acetyl)-1H-pyrrole-3-carboxylic acid (250 mg), and thionyl chloride (1.84 g) were sequentially added into a reaction flask, and the system was heated to 115° C. and reacted for 1.0 h under nitrogen protection. After the reaction was finished, the resulting mixture was cooled to room temperature, and then rotary-evaporated under reduced pressure to remove the solvent, and an acyl chloride intermediate (297 mg) was collected. The acyl chloride intermediate (297 mg) was dissolved in N,N-dimethylacetamide (5 mL) at room temperature, followed by adding 5-amino-2-fluorobenzonitrile (100 mg) into the system. Then the resulting mixture was heated to 100° C. and reacted for 0.5 h. After the reaction was finished, the resulting mixture was cooled to room temperature, and then extracted with ethyl acetate (2*50 mL). The organic layers were combined, washed with a saturated sodium chloride aqueous solution, dried over anhydrous sodium sulfate, and then evaporated under reduced pressure to remove the solvent. The obtained crude product was eluted by column chromatography (PE:EA=3:1) to give (S)—N-(3-cyano-4-fluorophenyl)-2-(methoxymethyl)-1-methyl-5-(2-oxo-2-(1,1,1-trifluoroprop-2-yl)amino)acetyl)-1H-pyrrole-3-carboxamide (280 mg). $^1$H-NMR (500 MHz, DMSO-d$_6$): δ 10.37 (s, 1H), 9.40 (d, J=9.0 Hz, 1H), 8.23-8.24 (m, 1H), 8.01-8.04 (m, 1H), 7.92 (s, 1H), 7.52 (t, J=9.5 Hz, 1H), 4.90-4.95 (m, 2H), 4.70-4.76 (m, 1H), 3.95 (s, 3H), 3.29 (s, 3H), 1.36 (d, J=7.0 Hz, 3H). $^{13}$C-NMR (125 MHz, DMSO-d6): δ 179.16, 164.49, 162.69, 159.69, 157.69, 143.05, 136.68, 128.12, 127.18, 124.70, 122.77, 118.66, 117.40, 114.45, 100.26, 62.28, 58.10, 46.27, 34.21, 13.63. MS(ESI–, [M–H]⁻) m/z: 453.4.

Example 57

(S)—N-(3-cyano-4-fluorophenyl)-2,4-dimethyl-5-(2-oxo-2-((1,1,1-trifluoroprop-2-yl)amino)acetyl)-1H-pyrrole-3-carboxamide

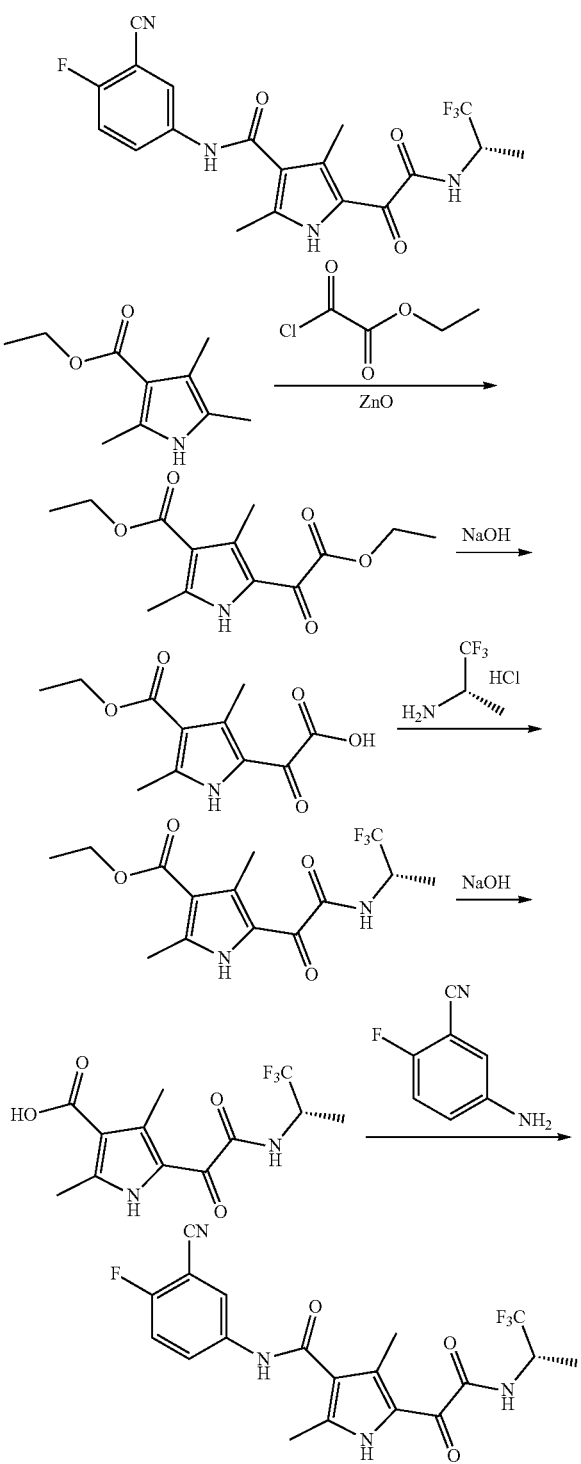

Step A: Ethyl 2-chloro-2-oxoacetate (40.8 g) and zinc oxide (1.22 g) were added sequentially into a reaction flask in an ice bath under N₂ protection, followed by adding ethyl 2,4-dimethyl-1H-pyrrole-3-carboxylate (5 g). After the addition, the mixture was stirred for 10 minutes in an ice bath, and then stirred at room temperature after removing the ice bath. After the reaction was finished, the reaction solution was slowly added dropwise into a 200 mL ice-water mixture, followed by adding EA (200 mL). The resulting mixture was layered. The organic phase was dried over anhydrous sodium sulfate, concentrated, and subjected to column chromatography to give ethyl 5-(2-ethoxy-2-oxoacetyl)-2,4-dimethyl-1H-pyrrole-3-carboxylate (4.5 g). MS (ESI+, [M+Na]⁺) m/z: 290.07.

Step B: ethyl 5-(2-ethoxy-2-oxoacetyl)-2,4-dimethyl-1H-pyrrole-3-carboxylate (3.5 g), and MeOH (40 mL) were added sequentially into a reaction flask. Then a solution of sodium hydroxide (1.05 g) in water (20 mL) was added dropwise under an ice bath, and the mixture was stirred at room temperature. After the reaction was finished, the aqueous phase was adjusted to pH 3-4 with a 2N hydrochloric acid aqueous solution, and then extracted with EA (100 mL*2). The organic phase was washed with water (30 mL) and concentrated to give 2-(4-(ethoxycarbonyl)-3,5-dimethyl-1H-pyrrol-2-yl)-2-oxoacetic acid (2.7 g). MS (ESI–, [M–H]⁻) m/z: 238.1.

Step C: 2-(4-(ethoxycarbonyl)-3,5-dimethyl-1H-pyrrol-2-yl)-2-oxoacetic acid (1 g), DMF (20 mL), HATU (2.07 g) and DIPEA (1.08 g) were sequentially added into a reaction flask at room temperature. After the addition, the reaction solution was stirred at room temperature for 10 minutes, followed by adding (S)-1,1,1-trifluoropropan-2-hydrochloride (0.63 g). After the reaction was finished, the reaction solution was poured into 50 mL water, and then extracted with EA (50 mL*3). The organic phase was washed with a saturated sodium sulfate aqueous solution (50 mL*3), dried over anhydrous sodium sulfate, and then filtered. The filtrate was collected, concentrated, and then purified by column chromatography to give ethyl (S)-2,4-dimethyl-5-(2-oxo-2-((1,1,1-trifluoroprop-2-yl)amino)acetyl)-1H-pyrrole-3-carboxylate (0.5 g). MS (ESI–, [M–H]⁻) m/z: 333.4.

Step D: ethyl (S)-2,4-dimethyl-5-(2-oxo-2-((1,1,1-trifluoroprop-2-yl)amino)acetyl)-1H-pyrrole-3-carboxylate (300 mg), and MeOH (2 mL) were added into a reaction flask, followed by adding a solution of NaOH (72 mg) in water (1 mL). After the addition, the reaction solution was heated to 80° C. and reacted overnight. After the reaction was finished, the resulting mixture was concentrated, and then thereto were added water (20 mL) and EA (60 mL) were added. The aqueous layer was separated. The organic phase was washed with water (30 mL) and layered. The aqueous phases were combined, adjusted to pH about 3 with 2N hydrochloric acid, extracted by adding EA (100 mL*2) and then layered. The organic phase was concentrated to give (S)-2,4-dimethyl (2-oxo-2-((1,1,1-trifluoroprop-2-yl)amino)acetyl)-1H-pyrrole-3-carboxylic acid (230 mg). MS (ESI–, [M–H]⁻) m/z: 305.4.

Step E: (S)-2,4-dimethyl-5-(2-oxo-2-((1,1,1-trifluoroprop-2-yl)amino)acetyl)-1H-pyrrole-3-carboxylic acid (230 mg), DMF (5 mL), HATU (428 mg) and DIPEA (194 mg) were added sequentially into a reaction flask at room temperature. After the addition, the reaction solution was stirred for 10 minutes, followed by adding 5-amino-2-fluorobenzonitrile (123 mg). The resulting mixture was heated to 40° C. and stirred to react for 20 hours. After the reaction was finished, water (20 mL) and EA (60 mL) were added, and the mixture was layered. The organic layer was dried over anhydrous sodium sulfate, and then filtered. The filtrate was collected, rotary-evaporated to dryness, sampled and purified by column chromatography to give (S)—N-(3-cyano-4-fluorophenyl)-2,4-dimethyl-5-(2-oxo-2-((1,1,1-trifluoroprop-2-yl)amino)acetyl)-1H-pyrrole-3-carboxamide (180 mg). MS (ESI–, [M–H]⁻) m/z: 423.0.

Example 58

(S)—N-(4-fluoro-3-(methylsulfonylamino)phenyl)-1,2,4-trimethyl-5-(2-oxo-2-((1,1,1-trifluoroprop-2-yl)amino)acetyl)-1H-pyrrole-3-carboxamide

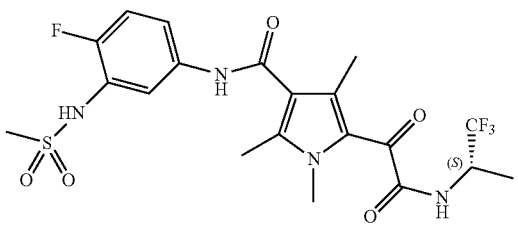

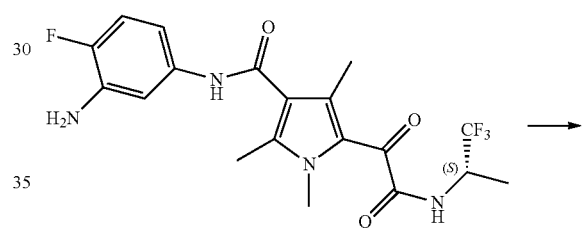

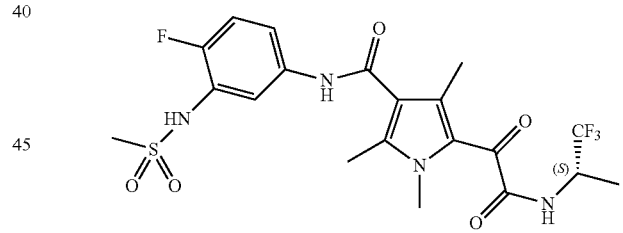

(S)—N-(3-amino-4-fluorophenyl)-1,2,4-trimethyl-5-(2-oxo-2-((1,1,1)-trifluoroprop-2-yl)amino) acetyl)-1H-pyrrole-3-carboxamide (compound of Example 42, 150 mg), DMF (5 mL), and methylsulfonyl chloride (50 mg) were added into a reaction flask, and then stirred at room temperature overnight. After the reaction was finished, the resulting mixture was slowly poured into 20 mL water, and then extracted with ethyl acetate (3*20 mL). The organic layers were combined, washed with a saturated sodium chloride aqueous solution, dried over anhydrous sodium sulfate, and then evaporated under reduced pressure to remove the solvent. The obtained crude product was separated by silica gel column chromatography (DCM: MeOH=20:1) to give (S)—N-(4-fluoro-3-(methylsulfonylamino) phenyl)-1,2,4-trimethyl-5-(2-oxo-2-((1,1,1-trifluoroprop-2-yl)amino)acetyl)-1H-pyrrole-3-carboxamide (45 mg). MS(ESI–, [M–H]⁻) m/z: 505.3.

Example 59

(S)—N-(3-acetamino-4-fluorophenyl)-1,2,4-trimethyl-5-(2-oxo-2-((1,1,1-trifluoroprop-2-yl)amino)acetyl)-1H-pyrrole-3-carboxamide

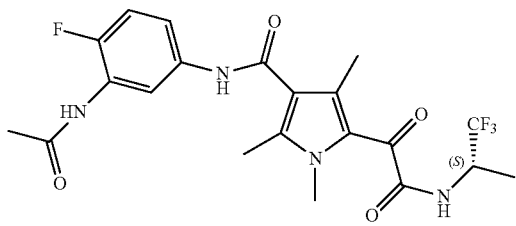

Step E: According to Example 58, methanesulfonyl chloride was replaced with acetyl chloride to give (S)—N-(3-acetamino-4-fluorophenyl)-1,2,4-trimethyl-5-(2-oxo-2-((1,1,1-trifluoroprop-2-yl)amino)acetyl)-1H-pyrrole-3-carboxamide. MS(ESI–, [M–H]⁻) m/z: 469.3.

Example 60

(S)—N-(3-cyano-4-fluorophenyl)-2,4-dimethyl-1-(methyl-d3)-5-(2-oxo-2-((1,1,1-trifluoroprop-2-yl)amino)acetyl)-1H-pyrrole-3-carboxamide

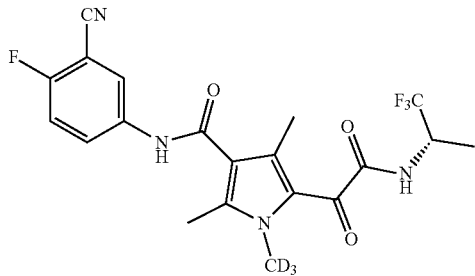

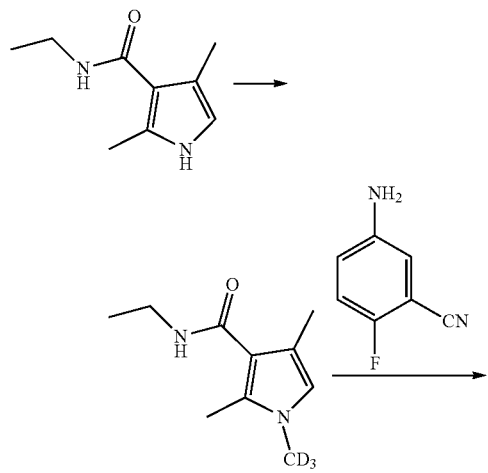

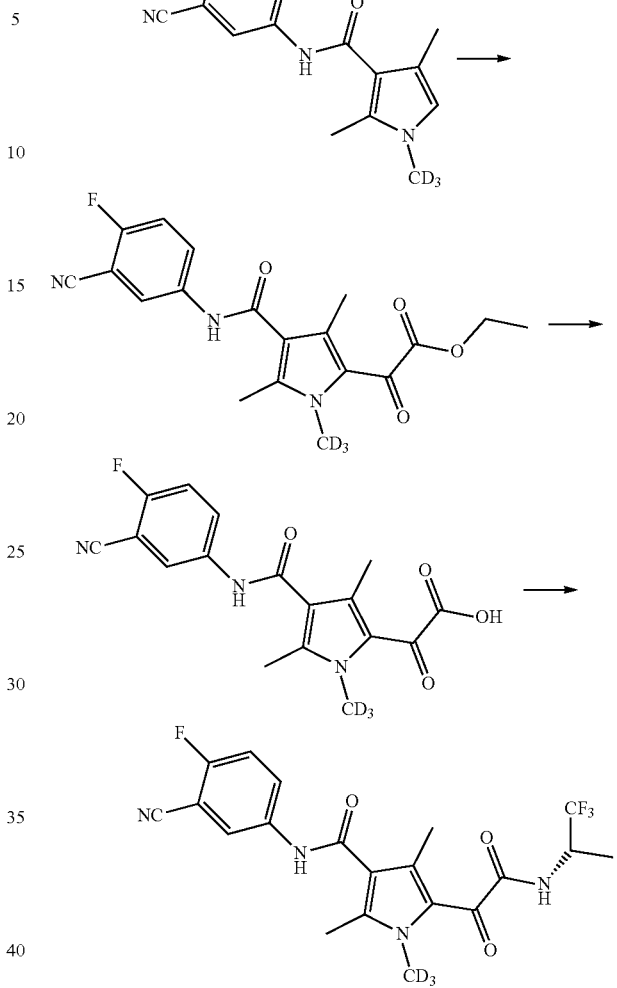

Step A: N,N-dimethylformamide (150 mL), ethyl 2,4-dimethyl-1H-pyrrole-3-carboxylate (10.0 g), and methyl iodide-d₃ (10.4 g) were added into a reaction flask under N₂ protection, followed by adding sodium hydrogen (2.857 g) in batches in an ice bath. After the addition, the reaction solution was brought to room temperature and reacted for 1.5 h. After the reaction was finished, the resulting mixture was slowly poured into 500 mL of ice-water for quenching, and then extracted with ethyl acetate (2*300 mL). The organic layers were combined, washed with a saturated sodium chloride aqueous solution, dried over anhydrous sodium sulfate, and then evaporated under reduced pressure to remove the solvent. Then the reaction mixture was separated by silica gel column chromatography (petroleum ether:ethyl acetate=50:1) to give ethyl 2,4-dimethyl-1-(methyl-d₃)-1H-pyrrole-3-carboxylate (9.7 g).

¹H-NMR (500 MHz, DMSO-d6): δ 6.44 (s, 1H), 4.19 (q, J=7.0 Hz, 2H), 2.39 (s, 3H), 2.09 (s, 3H), 1.25 (t, J=7.0 Hz, 3H). MS (ESI+, [M+H]⁺) m/z: 185.1.

Step B: Tetrahydrofuran (100 mL), ethyl 2,4-dimethyl-1-(methyl-d₃)-1H-pyrrole-3-carboxylate (9.50 g), and 5-amino-2-fluorobenzonitrile (8.7 g) were added into a reaction flask under N₂ protection, followed by slowly adding dropwise lithium bis(trimethylsilyl)amide (21.5 g, 129 mL solution in tetrahydrofuran). After the addition, the reaction solution was brought to room temperature and reacted for 4.0 h. After the reaction was finished, the resulting mixture was slowly poured into 600 mL of ice-water for quenching, and then filtered. The filter cake was refined with a mixed solvent of petroleum ether (50 mL) and ethyl acetate (50 mL) for 16.0 h, and then filtered. The filter cake was dried under vacuum to give N-(3-cyano-4-fluorophenyl)-2,4-dimethyl-1-(methyl-$d_3$)-1H-pyrrole-3-carboxamide (10.2 g).

$^1$H-NMR (500 MHz, DMSO-$d_6$): δ 9.65 (s, 1H), 8.18 (t, J=3.5 Hz, 1H), 7.93-7.96 (m, 1H), 7.48 (t, J=9.0 Hz, 1H), 6.49 (s, 1H), 2.29 (s, 3H), 2.10 (s, 3H). MS (ESI−, [M−H]$^-$) m/z: 273.3.

Step C: (Compound IV): Zinc oxide (1.48 g), and monoethyl chlorooxalate (100 g) were added into a reaction flask in an ice bath under $N_2$ protection, and stirred for 5 minutes. Then N-(3-cyano-4-fluorophenyl)-2,4-dimethyl-1-(methyl-$d_3$)-1H-pyrrole-3-carboxamide (10.0 g) was added in batches. After the addition, the reaction solution was brought to room temperature and reacted for 3.0 h. After the reaction was finished, the resulting mixture was slowly poured into 400 mL of ice water for quenching, and then extracted with dichloromethane (2*300 mL). The organic layers were combined, washed with a saturated sodium chloride, dried over anhydrous sodium sulfate, and then suction-filtered. The filtrate was rotary-evaporated under reduced pressure to remove the solvent. The reaction mixture was separated by silica gel column chromatography (dichloromethane:methanol=100:1) to give ethyl 2-(4-((3-cyano-4-fluorophenyl)carbamoyl)-3,5-dimethyl-1-(methyl-$d_3$)-1H-pyrrol-2-yl)-2-oxoacetate (4.5 g).

$^1$H-NMR (500 MHz, DMSO-$d_6$): δ 10.37 (s, 1H), 8.21-8.20 (m, 1H), 7.93 (s, 1H), 7.53 (t, J=9.0 Hz, 1H), 4.35 (d, J=7.5 Hz, 2H), 2.36 (s, 3H), 2.19 (s, 3H), 1.32 (t, J=7.0 Hz, 3H). MS (ESI+, [M+Na]$^+$) m/z: 397.2.

Step D: ethyl 2-(4-((3-cyano-4-fluorophenyl)carbamoyl)-3,5-dimethyl-1-(methyl-$d_3$)-1H-pyrrol-2-yl)-2-oxoacetate (4.5 g), and tetrahydrofuran (35 mL) were added into a reaction flask, followed by slowly adding dropwise a solution of lithium hydroxide monohydrate (1.02 g) in water (50 mL) in an ice bath. After the addition, the reaction solution was brought to room temperature and reacted for 0.2 h. Water (40 mL) and dichloromethane (50 mL) were added thereto. The resulting mixture was layered, and the organic layer was discarded. The aqueous layer was adjusted to pH about 4 with concentrated hydrochloric acid, and then filtered, and the filter cake was dried under vacuum to give 2-(4-((3-cyano-4-fluorophenyl)carbamoyl)-3,5-dimethyl-1-(methyl-$d_3$)-1H-pyrrol-2-yl)-2-oxoacetic acid (3.8 g).

$^1$H-NMR (500 MHz, DMSO-$d_6$): δ 10.34 (s, 1H), 8.21-8.19 (m, 1H), 7.96-7.94 (m, 1H), 7.52 (t, J=9.0 Hz, 1H), 2.35 (s, 3H), 2.27 (s, 3H). MS (ESI+, [M+H]$^+$) m/z: 347.1.

Step E: N,N-dimethylformamide (50 mL), 2-(4-((3-cyano-4-fluorophenyl)carbamoyl)-3,5-dimethyl-1-(methyl-$d_3$)-1H-pyrrol-2-yl)-2-oxoacetic acid (3.8 g), O-(7-azabenzotriazol-1-yl)-N,N,N',N'-tetramethyluronium hexafluorophosphate (5.4 g), and (S)-1,1,1-trifluoropropan-2-amine hydrochloride (1.96 g) were added into a reaction flask under an ice bath under $N_2$ protection, and stirred for 2 minutes, followed by adding N,N-diisopropylethylamine (3.2 g). After the addition, the reaction solution was brought to room temperature and stirred for 4.0 h, and then thereto was added water (150 mL), and the resulting mixture was extracted with ethyl acetate (2*100 mL). The organic layers were combined, washed with a saturated sodium chloride aqueous solution, dried over anhydrous sodium sulfate, and then evaporated under reduced pressure to remove the solvent. Then the reaction mixture was separated by silica gel column chromatography (dichloromethane:methanol=20:1) to give (S)—N-(3-cyano-4-fluorophenyl)-2,4-dimethyl-1-(methyl-d3)-5-(2-oxo-2-((1,1,1-trifluoroprop-2-yl) amino)acetyl)-1H-pyrrole-3-carboxamide (3.95 g).

$^1$H-NMR (500 MHz, DMSO-$d_6$): δ 10.32 (s, 1H), 9.40 (d, J=9.0 Hz, 1H), 8.20 (t, J=3.0 Hz, 1H), 7.94 (s, 1H), 7.52 (t, J=9.5 Hz, 1H), 4.74-4.79 (m, 1H), 2.36 (s, 3H), 2.21 (s, 3H), 1.31 (d, J=7.0 Hz, 3H). MS (ESI$^+$, [M+H]$^+$) m/z: 442.1.

Experimental Example 1: In Vitro Activity Study 1.1 In Vitro Cell HBV DNA Inhibitory Activity A bottle of HepG2.2.15 or HepAD38 cells in good exponential growth state was taken, washed once by adding 5 mL PBS, and then thereto was added 3 mL trypsin. After digesting at room temperature for 5 min, 2 mL trypsin was discarded, and then the sample was placed in a cell culture incubator and digested for 10 min. The cells were taken out from time to time and observed under a microscope (whether the cells were individually round and there was no adhesion between the cells). 10 mL complete medium was added to terminate the digestion. After pipetting into a single cell suspension, 10 μL of the cell suspension was taken out for cell counting with a cell counter, and then diluted with a complete medium and adjusted to a cell density of $1*10^5$ cells/mL. Then the cell suspension was seeded at 1 mL/well in a 24-well plate with a multi-channel pipette (the 24-well plate was coated with 50 μg/mL Collagen I solution in advance), and cultured in a constant temperature $CO_2$ incubator for 48 h.

Different compounds dissolved in DMSO were subjected to two-fold gradient dilution (10 concentrations in total) with complete medium. The compound was added, and fresh medium containing the compound was used to replace the spent medium every 72 hours. The cells were treated with the compound for 6 days. After the supernatant was siphoned off, 300 μL lysate (10 mM Tris-HCl, 1 mM EDTA, and 1% NP-40) was added to each well. After lysing at room temperature for 10 min, DNA was extracted, and HBV DNA in the intracellular viral capsid was measured by real-time fluorescence quantitative PCR. The inhibition rate was calculated based on the Ct value, and the EC50 value was calculated by the four-parameter method. The results are shown in Tables 1 and 2.

1.2 In Vitro Cytotoxicity

A bottle of HepG2.2.15 or HepAD38 cells in good exponential growth state was taken, washed once by adding 5 mL PBS, and then thereto was added 3 mL trypsin. The sample was digested in a cell culture incubator, and taken out from time to time and observed under a microscope. When the cells just fell off, 1 mL trypsin was discarded. The residual liquid was placed in a cell culture incubator at 37° C. and digested for 8-15 min. The cells were taken out and observed under a microscope (whether the cells were individually round and there was no adhesion between the cells). 5 mL MEM medium was added for cell resuspension. The cells were then subjected to cell counting with a cell counter, diluted with a complete medium, and adjusted to a cell density of $2*10^5$ cells/mL. Then the cells were seeded at 100 μL/well in a 96-well plate with a multi-channel pipette (the 96-well plate was coated with 50 μg/mL Collagen I solution in advance), and cultured in a constant temperature $CO_2$ incubator for 24 h. The cells were treated by drug administration, and fresh medium containing the compound was used to replace the spent medium every 3 days. To control wells was added a drug-free medium containing 0.5%

DMSO, and a control well containing a common medium was set up. 6 days after the administration, CCK-8 was added at 10 μL/well. After 1 to 2 hours, the absorbance was detected with microplate reader at 450 nm, and the inhibition rate and the CC50 were calculated. The results are shown in Table 3.

Tables 1 and 2, wherein A represents EC50≤10 nM, B represents 10 nM<EC50≤50 nM, and C represents 50 nM<EC50≤100 nM.

TABLE 1

Experimental results of anti-HBV activity in HepAD38 cells

| Examples No. | EC50 |
|---|---|
| 1 | B |
| 2 | A |
| 3 | C |
| 4 | B |
| 5 | B |
| 6 | B |
| 7 | A |
| 8 | A |
| 9 | A |
| 10 | B |
| 11 | A |
| 12 | A |
| 13 | A |
| 14 | B |
| 15 | A |
| 20 | B |
| 21 | B |
| 22 | B |
| 23 | A |
| 24 | A |
| 25 | A |
| 26 | C |
| 27 | B |
| 28 | B |
| 29 | A |
| 30 | B |
| 31 | A |
| 32 | A |
| 34 | B |
| 35 | A |
| 36 | A |
| 37 | A |
| 38 | A |
| 39 | A |
| 42 | B |
| 45 | B |
| 46 | B |
| 47 | A |
| 50 | C |
| 54 | B |
| 55 | B |
| 60 | A |

TABLE 2

Experimental results of anti-HBV activity in HepG2.2.15 cells

| Examples No. | EC50 |
|---|---|
| 1 | B |
| 2 | A |
| 6 | B |
| 7 | B |
| 8 | A |
| 9 | B |
| 11 | A |
| 12 | A |
| 15 | B |
| 16 | A |
| 17 | B |
| 20 | C |
| 21 | C |
| 22 | B |
| 23 | A |
| 24 | A |
| 25 | A |
| 26 | C |
| 27 | B |
| 29 | B |
| 30 | A |
| 38 | A |
| 39 | A |
| 42 | A |
| 45 | A |
| 46 | A |
| 47 | A |
| 54 | A |
| 55 | B |

TABLE 3

| Cells | CC50(μM) | Example No. |
|---|---|---|
| HepAD38 | >100 | 1, 2, 6, 7, 8, 9, 11, 12, 15, 16, 17, 21, 22, 23, 24, 25, 26, 27, 29, 30 |
| HepG2.2.15 | >100 | 1, 6, 7, 8, 9, 11, 12, 17, 21, 22, 23, 24, 25, 26, 27, 29, 30, 39, 42 |

1.3 CYP450 Enzyme Induction Study

500 μL of a final incubation system contains 50 μL of liver microsomes (protein concentration: 0.2 mg/mL), 1 μL of mixed CYP450 specific substrates (CYP1A2, CYP 2B6, CYP 2C9, CYP2C19, CYP 2D6, and CYP 3A4), 398 μL PBS buffer (PH7.4), 1 μL specific positive inhibitor (positive control group) or the test compound (formulated with acetonitrile), and 50 μL NADPH+MgCl$_2$. Duplicate incubation systems of 0.5 mL each were formulated for each CYP450 subtype. A total volume of 450 μL of a uniformly mixed solution of the substrate and the enzyme was formulated in each tube, and the solution and NADPH were pre-incubated at 37° C. for 5 minutes, respectively. Then 50 μL of the mixed solution of NADPH+MgCl$_2$ was added for reaction. 50 μL of the reaction solution was taken out at 30 minutes, and the reaction was terminated with 300 μL of ice acetonitrile containing an internal standard. In addition, two control groups of 500 μL each without NADPH were prepared in parallel as a negative control group.

Sample pre-treatment: To 50 μL of the incubated sample was added 300 μL of ice acetonitrile containing an internal standard, and then precipitated. After vortexing for 5 minutes, the sample was centrifugated (12000 rpm, 4° C.) for 10 minutes. 75 μL of the supernatant was pipetted, and 75 μL of ultrapure water was added thereto for dilution and mixed uniformly. 1 μL of the resulting solution was injected for analysis. The results are shown in Table 4.

TABLE 4

| Examples | Subtypes IC50 (µM) | | | | | |
|---|---|---|---|---|---|---|
| No. | 3A4 | 2D6 | 2C19 | 2C9 | 2B6 | 1A2 |
| 12 | >200 | 223.5 | 60.0 | 79.7 | 145.6 | 46.4 |
| 25 | 76.0 | 120 | 24.86 | 16.63 | 61.14 | 228.9 |

1.4 Plasma Protein Binding Assay

Formulation of plasma sample: 495 µL of blank plasmas of the corresponding species (mouse, rat, dog, monkey, and human) were drawn respectively, and thereto was added 5 µL of the corresponding test compound solution or positive control to give plasma sample solutions having a plasma drug concentration of the compound of 1 µM, and 10 µM, respectively (formulated with acetonitrile).

The pre-treated dialysis membrane was placed in a high-throughput equilibrium dialysis device, and 100 µL of the plasma sample solution and PBS buffer solution were drawn and added respectively to both sides of the dialysis membrane (sample side and buffer side) (n=3). After the equilibration device was sealed with a film, it was incubated at 37° C. overnight (100 rpm). After dialysis equilibrium was reached, 50 µL samples were drawn from the sample side and the buffer side, respectively, and the reaction was terminated by adding ice acetonitrile containing an internal standard.

Sample pre-treatment: To 50 µL of the plasma-side sample was added 450 µL of ice acetonitrile containing an internal standard, and then precipitated. After vortexing for 5 minutes, the sample was centrifugated (12000 rpm, 4° C.) for 10 minutes. 75 µL of the supernatant was pipetted, and 75 µL of ultrapure water was added thereto for dilution and mixed uniformly. 1 µL of the resulting solution was injected for analysis. To 50 µL of the PBS-side sample was added 250 µL of ice acetonitrile with an internal standard, and precipitated. After vortexing for 5 min, the sample was centrifugated (12000 rpm, 4° C.) for 10 min. 75 µL of the supernatant was pipetted, and 75 µL of ultrapure water was added thereto for dilution and mixed uniformly. 2 µL of the resulting solution was injected for analysis. The results are shown in Table 5.

TABLE 5

| Examples | | Binding rate (%) | | | | |
|---|---|---|---|---|---|---|
| No. | Concentration | Human | Rat | Mouse | Dog | Monkey |
| 12 | 1 µM | 94.0 | 82.0 | 75.3 | 85.9 | 90.7 |
|  | 10 µM | 93.7 | 79.2 | 74.5 | 85.9 | 90.6 |
| 25 | 1 µM | 92.9 | 79.5 | 76.5 | 87.0 | 87.4 |
|  | 10 µM | 92.2 | 77.0 | 74.7 | 86.8 | 85.6 |

Experimental Example 2: Stability of Liver Microsomes In Vitro

300 µL of a final incubation system contains 30 µL of liver microsomes (protein concentration: 0.15 mg/mL), 30 µL NADPH+MgCl$_2$, 3 µL substrate (formulated with acetonitrile), and 237 µL PBS buffer. Duplicate incubation systems of 0.3 mL each were formulated for each species. A total volume of 270 µL of a uniformly mixed solution of the substrate and the enzyme was formulated in each tube, the solution and NADPH were pre-incubated at 37° C. for 5 minutes, respectively. Then 30 µL of the mixed solution of NADPH+MgCl$_2$ was added for reaction. 50 µL of the reaction solution was taken out at 0, 10, 30, and 60 mins, and the reaction was terminated with 300 µL of ice acetonitrile containing an internal standard.

Sample pre-treatment: To 50 µL of the incubated sample was added 300 µL of ice acetonitrile containing diazepam as an internal standard and then precipitated. After vortexing for 5 minutes, the sample was centrifugated (12000 rpm, 4° C.) for 10 minutes. 75 µL of the supernatant was pipetted into a 96-well plate, and then diluted with 75 µL ultrapure water and mixed uniformly. 0.5 µL of the resulting solution was injected and analyzed by LC-MS/MS. The results are shown in Table 6-1, 6-2, and 6-3 below.

TABLE 6-1

Stability of human liver microsomes in vitro

| Example No. | Remaining (%) at 60 min |
|---|---|
| 1 | 69 |
| 6 | 79.1 |
| 7 | 83.8 |
| 8 | 70.6 |
| 12 | 78.8 |
| 29 | 99.6 |
| 42 | 102 |
| 45 | 73 |

TABLE 6-2

Stability of rat liver microsomes in vitro

| Example No. | Remaining (%) at 60 min | Example No. | Remaining (%) at 60 min |
|---|---|---|---|
| 1 | 44 | 12 | 65.0 |
| 6 | 74.9 | 17 | 44.9 |
| 7 | 70.5 | 25 | 52.0 |
| 8 | 52.0 | 29 | 88.7 |
| 11 | 56.8 | 42 | 85.3 |
| 45 | 47 | | |

TABLE 6-3

Stability of mouse liver microsomes in vitro

| Example No. | Remaining (%) at 60 min |
|---|---|
| 6 | 55 |
| 7 | 81.6 |
| 11 | 47.7 |
| 12 | 67.1 |
| 17 | 47.4 |
| 25 | 50.8 |
| 29 | 99.2 |
| 42 | 61.9 |

Experimental Example 3: Solubility in PBS Buffer at pH 7.4

1000 µL of a final system contains 990 µL of pH 7.4 PBS buffer, and 10 µL of the test compound (formulated with acetonitrile). After standing at 25° C. for 16 hours, the system was centrifugated (12000 rpm, room temperature) for 10 min. 20 µL of the supernatant was taken out, and the reaction was terminated with 400 µL of acetonitrile containing an internal standard (diazepam 20 ng/mL). 30 µL of the supernatant was pipetted, and 150 µL of 50% acetonitrile aqueous solution was added thereto for dilution and mixed uniformly. 0.5 μL of the resulting solution was injected for analysis. The results are shown in Table 7.

TABLE 7

| Examples No. | Solubility (μM) |
|---|---|
| 2 | 22.1 |
| 6 | 81.8 |
| 7 | 19.8 |
| 8 | 80.9 |
| 9 | 9.6 |
| 11 | 7.5 |
| 12 | 8.1 |
| 15 | 4.9 |

Experimental Example 4: In Vivo Animal Efficacy 4.1 Antiviral Effect Evaluation in AAV Mouse Model 6-8 week old male C57BL/6 mice were injected with rAAV8-1.3HBV virus (adr subtype) at tail vein at a dose of $1\times10^{11}$ vg. Blood was collected from the orbits of the mice on week 2 and 4 after the virus injection. The serum was separated, and the expression levels of HBeAg and HBsAg in the serum and the HBV DNA copy number were detected to evaluate whether the model was successfully established. According to the results of quantitative detection of serological HBeAg, HBsAg and HBV DNA, the mice having HBV DNA expression level greater than $1\times10^{4}$ IU/mL, HBeAg expression level greater than $1\times10^{3}$ NCU/mL and HBsAg expression level greater than $1\times10^{3}$ ng/mL were selected. The mice were grouped into a blank control group, a vehicle control group, and a test substance group. The mice in each group were continuously administered intragastrically once daily for 2-3 weeks. During the experiment, blood was collected from the orbits every other week, serum was separated, and the DNA content was detected by fluorescent quantitative PCR method.

TABLE 8

Reduction levels (log10) of HBV DNA in serum (administration for 24 days, dose: 30 mpk)

| Examples No. | Day 7 | Day 14 | Day 21 | Day 28 |
|---|---|---|---|---|
| 12 | 2.42 | 3.46 | 5.08 | 2.48 |
| 25 | 1.16 | 1.76 | 2.89 | 1.28 |

4.2 Antiviral Effect Evaluation in HDI Mouse Model 6-8 week old male C57BL/6 mice was used, and each mouse was injected with purified recombinant plasmid pHBV 1.3 (10 μg) dissolved in PBS equivalent to a volume of about 10% of its body weight through the tail vein within 3-8 s. Blood was collected from the orbits of the mice at 24 hours after the plasmid injection to detect serum HBV DNA. The model mice having uniform serum DNA were selected and divided into: a blank control group, a vehicle control group, and a test substance group. Mice in each group were continuously administered intragastrically once daily for 6 days at a dose of 30 mg/kg. The mouse serum was taken on day 1, 3, 5, and 7 after the injection, and the mice were sacrificed on day 7 to take liver tissue samples. The HBV DNA copy numbers in serum and liver of the mice were detected by fluorescent quantitative PCR method. The results are shown in Table 9.

TABLE 9

| Examples No. | Reduction levels (log10) of HBV DNA in serum on day 5 |
|---|---|
| 12 | 2.17 |
| 25 | 1.73 |

Experimental Example 5: In Vivo Pharmacokinetics 5.1 In Vivo Pharmacokinetics (PK) Study in Mice ICR mice, weighing 18-20 g, were randomly divided into groups of three mice each after 3 to 5 days' acclimatization, and a series of the compounds were administered intragastrically to each group at a dose of 30 mg/kg.

The test animals (ICR mice) were fasted for 12 hours before the administration and fed 4 hours after the administration. They were free to access water before and after the experiment.

After the intragastric administration, about 0.1 mL of blood was collected from the orbits. Within 30 minutes after anticoagulation with EDTA-K2, the plasma was separated by centrifugation at 4° C. and 4000 rpm for 10 minutes. Immediately after collecting all plasma, it was stored at −20° C. for testing.

20 μL of the plasma sample to be tested and standard curve sample were pipetted, and then thereto was added 200 μL of an acetonitrile solution containing an internal standard (diazepam 20 mg/mL). The resulting mixture was oscillated and mixed uniformly for 5 min, and then centrifuged at 12000 rpm for 10 min. 75 μL supernatant was pipetted, and 75 μL ultrapure water was added thereto for dilution, and mixed evenly. 1 μL of the resulting solution was pipetted for LC/MS/MS determination. The results are shown in Tables 10 and 11.

TABLE 10

| Example No. | Mode of administration | Dose (mg/kg) | Plasma $AUC_{(0-8\,h)}$ (ng/mL) | Liver $AUC_{(0-8\,h)}$ (ng/g) | Liver to blood ratio |
|---|---|---|---|---|---|
| 25 | po | 30 | 37732 | 315435 | 8.36 |

Note:
The time point of taking blood is 0.25 h, 3 h, and 8 h.

TABLE 11

| Example No. | Mode of administration | Dose (mg/kg) | Plasma $AUC_{(0-6\,h)}$ (ng/mL) | Liver $AUC_{(0-6\,h)}$ (ng/g) | Liver to blood ratio |
|---|---|---|---|---|---|
| 13 | po | 30 | 1759 | 5834 | 3.32 |

Note:
The time point of taking blood is 0.25 h, 1 h, and 6 h.

5.2 In Vivo Pharmacokinetics (PK) Study in Rats

SD rats, weighing 180~220 g, were randomly divided into groups of three mice each after 3 to 5 days' acclimatization, and a series of the compounds were administered intragastrically to each group at a dose of 20 mg/kg.

The test animals (SD rats) were fasted for 12 hours before administration and fed 4 hours after the administration. They were free to access water before and after the experiment.

After the administration, about 0.2 mL of blood from the orbits was collected at 0 min, 15 min, 30 min, 1 h, 2 h, 4 h, 6 h, 8 h, 10 h, 24 h, 30 h, and 48 h. Within 30 minutes after anticoagulation with EDTA-K2, the plasma was separated by centrifugation at 4° C. and 4000 rpm for 10 minutes. Immediately after collecting all plasma, it was stored at −20° C. for testing.

50 μL of the plasma sample to be tested and standard curve sample were pipetted, and then thereto was added 500 μL of an acetonitrile solution containing an internal standard (diazepam 20 mg/mL). The resulting mixture was oscillated and mixed uniformly for 5 min, and then centrifugated at 12000 rpm for 10 min. 75 μL supernatant was pipetted, and 75 μL ultrapure water was added thereto for dilution, and mixed evenly. 1 μL of the resulting solution was pipetted for LC/MS/MS determination. The results are shown in Table 12.

TABLE 12

|  | Example No. 12 | |
| --- | --- | --- |
| Mode of administration and dosage | IV 5 mg/kg | PO 20 mg/kg |
| $T_{1/2}$ (h) | 3.41 | 3.65 |
| Vz (mL/kg) | 914 | NA |
| Cl (mL/h/kg) | 186 | NA |
| Cmax (ng/mL) | 6274 | 5019 |
| $AUC_{(0-48\,h)}$(ng*h/mL) | 27082 | 62040 |
| $AUC_{(0-\infty)}$(ng*h/mL) | 27146 | 62340 |
| F (%) | NA | 57% |

NA means not detected.

5.3 In Vivo Pharmacokinetic (PK) Study in Beagle Dog

Beagle dogs, weighing 9 to 11 kg, were randomly divided into two groups of 3 dogs each, compound 12 was given by intragastric administration to each group at a dose of 5 mg/kg.

The test animals (Beagle dogs) were fasted for 12 hours before the administration, and fed 4 hours after the administration. They were free to access water before and after the experiment.

After the intragastric administration, about 0.5 mL of whole blood was collected from the veins of the left forelimb in an EDTA-K2 anticoagulated vacuum blood collection tube at 0 min, 15 min, 30 min, 1 h, 2 h, 4 h, 6 h, 8 h, 10 h, 24 h, 48 h, and 72 h. Within 30 minutes after collection, the plasma was separated by centrifugation at 4° C. and 4000 rpm for 10 minutes. Immediately after collecting all plasma, it was stored at −20° C. for testing.

50 μL of the plasma sample to be tested and standard curve sample were pipetted, and then thereto was added 500 μL of an acetonitrile solution containing an internal standard (diazepam 20 mg/mL). The resulting mixture was oscillated and mixed uniformly for 5 min, and then centrifugated at 12000 rpm for 10 min, 75 μL of the supernatant was pipetted, and 75 μL of ultrapure water was added for dilution and mixed evenly. 1 μL of the resulting solution was pipetted for LC/MS/MS determination. The results are shown in Table 13.

TABLE 13

|  | Example No. 12 |
| --- | --- |
| Mode of administration and dosage | PO 5 mg/kg |
| $T_{max}$ (h) | 1.67 |
| $C_{max}$ (ng/mL) | 1282 |
| $AUC_{(0-72\,h)}$(ng*h/mL) | 61881 |
| $AUC_{(0-\infty)}$(ng*h/mL) | 162075 |

TABLE 13-continued

|  | Example No. 12 |
| --- | --- |
| T1/2 (h) | 105.2 |
| MRT(0-t) (h) | 32.9 |

What is claimed:

1. A compound of Formula I, a stereoisomer, a tautomer, a geometric isomer, a solvate, a hydrate, or a pharmaceutically acceptable salt thereof,

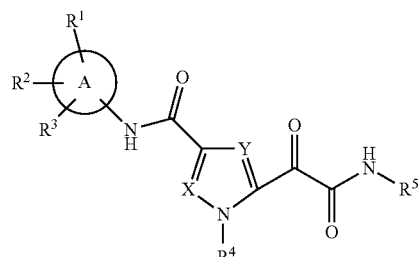

wherein,

X and Y each independently represent $CR^7$, and said $R^7$ is independently selected from the group consisting of hydrogen, $C_{3-4}$ cycloalkyl, —CN, fluoro, chloro, bromo and $C_{1-3}$ alkyl, wherein said $C_{1-3}$ alkyl is optionally substituted with one or more fluoro;

ring A is selected from the group consisting of phenyl and 5- to 10-membered heteroaryl;

$R^1$, $R^2$ and $R^3$ are each independently selected from the group consisting of hydrogen, fluoro, chloro, bromo, —$CHF_2$, —$CH_2F$, —$CF_3$, —CN, and $C_{1-3}$ alkyl;

$R^4$ is selected from the group consisting of hydrogen, $C_{1-3}$ alkyl and $C_{3-4}$ cycloalkyl;

$R^5$ is selected from the group consisting of $C_{1-6}$ alkyl, $C_{2-6}$ alkenyl, $C_{2-6}$ alkynyl, 3- to 7-membered cycloalkyl and 3- to 7-membered heterocycloalkyl, wherein said $C_{1-6}$ alkyl, $C_{2-6}$ alkenyl, $C_{2-6}$ alkynyl, 3- to 7-membered cycloalkyl and 3- to 7-membered heterocycloalkyl are optionally substituted with the group(s) selected from the group consisting of halo, 3- to 4-membered cycloalkyl, 3- to 4-membered heterocycloalkyl, —$OR^8$, oxo, —CN, —$C(O)OR^8$, —$SO_2R^8$, —$C(O)N(R^8)_2$, and $C_{1-3}$ alkyl, wherein $C_{1-3}$ alkyl is optionally substituted with one or more groups selected from the group consisting of fluoro, —CN and —OH; and each $R^8$ is independently selected from the group consisting of hydrogen and $C_{1-3}$ alkyl.

2. The compound of Formula I, a stereoisomer, a tautomer, a geometric isomer, a solvate, a hydrate, or a pharmaceutically acceptable salt thereof according to claim 1, wherein:

X and Y each independently represent $CR^7$, and said $R^7$ is independently selected from the group consisting of hydrogen, fluoro, chloro, bromo and $C_{1-3}$ alkyl, wherein the $C_{1-3}$ alkyl is optionally substituted with one or more fluoro;

alternatively, $R^7$ is independently selected from the group consisting of hydrogen, fluoro, chloro, bromo, and $C_{1-3}$ alkyl;

alternatively, $R^7$ is independently selected from the group consisting of hydrogen, fluoro, chloro, bromo, and methyl; and alternatively, $R^7$ is independently selected from the group consisting of hydrogen, chloro, bromo, and methyl.

3. The compound of Formula I, a stereoisomer, a tautomer, a geometric isomer, a solvate, a hydrate, or a pharmaceutically acceptable salt thereof according to claim 1, wherein:
ring A is selected from the group consisting of phenyl, 5-membered heteroaryl, 6-membered heteroaryl, 7-membered heteroaryl, 8-membered heteroaryl, 9-membered heteroaryl and 10-membered heteroaryl;
alternatively, ring A is selected from the group consisting of phenyl and 6-membered heteroaryl;
alternatively, ring A is selected from phenyl; and
alternatively, the "heteroaryl" in the above definitions of ring A contains 1 or 2 N atoms.

4. The compound of Formula I, a stereoisomer, a tautomer, a geometric isomer, a solvate, a hydrate, or a pharmaceutically acceptable salt thereof according to claim 1, wherein:
$R^1$ is selected from the group consisting of hydrogen, fluoro, chloro, —$CHF_2$, —CN, —$CF_3$ and methyl; and
alternatively, $R^1$ is selected from the group consisting of hydrogen and fluoro.

5. The compound of Formula I, a stereoisomer, a tautomer, a geometric isomer, a solvate, a hydrate, or a pharmaceutically acceptable salt thereof according to claim 1, wherein:
$R^2$ is selected from the group consisting of hydrogen, fluoro, chloro, and bromo; and
alternatively, $R^2$ is selected from the group consisting of hydrogen and fluoro.

6. The compound of Formula I, a stereoisomer, a tautomer, a geometric isomer, a solvate, a hydrate, or a pharmaceutically acceptable salt thereof according to claim 1, wherein:
$R^3$ is selected from the group consisting of hydrogen, fluoro, chloro, —$CHF_2$, —CN, —$CF_3$, and methyl;
alternatively, $R^3$ is selected from the group consisting of hydrogen, fluoro, chloro, —CN, and methyl.

7. The compound of Formula I, a stereoisomer, a tautomer, a geometric isomer, a solvate, a hydrate, or a pharmaceutically acceptable salt thereof according to claim 1, wherein:
$R^1$ is selected from the group consisting of hydrogen, fluoro, chloro, —$CHF_2$, —CN, —$CF_3$ and methyl, and at least one of $R^1$ and $R^3$ is fluoro or hydrogen.

8. The compound of Formula I, a stereoisomer, a tautomer, a geometric isomer, a solvate, a hydrate, or a pharmaceutically acceptable salt thereof according to claim 1, wherein:
one of $R^1$ and $R^3$ is selected from the group consisting of hydrogen and fluoro, and the other is selected from the group consisting of hydrogen, fluoro, chloro, —$CHF_2$, —CN, —$CF_3$, and methyl;
alternatively, one of $R^1$ and $R^3$ is hydrogen, and the other is selected from the group consisting of fluoro, chloro, —$CHF_2$, —CN, —$CF_3$ and methyl;
alternatively, $R^2$ is fluoro, and one of $R^1$ and $R^3$ is hydrogen, and the other is selected from the group consisting of fluoro, chloro and —CN;
alternatively, $R^2$ is fluoro, $R^1$ is hydrogen, and $R^3$ is —CN or chloro; and
alternatively, $R^2$ is fluoro, $R^1$ is hydrogen, and $R^3$ is —CN.

9. The compound of Formula I, a stereoisomer, a tautomer, a geometric isomer, a solvate, a hydrate, or a pharmaceutically acceptable salt thereof according to claim 1, wherein:
$R^4$ is selected from the group consisting of hydrogen and $C_{1-3}$ alkyl; and/or $R^8$ is selected from the group consisting of hydrogen and methyl;
alternatively, $R^4$ is methyl or hydrogen; and
alternatively, $R^4$ is methyl.

10. The compound of Formula I, a stereoisomer, a tautomer, a geometric isomer, a solvate, a hydrate, or a pharmaceutically acceptable salt thereof according to claim 1, wherein:
$R^5$ is selected from the group consisting of $C_{1-4}$ alkyl, $C_{2-4}$ alkenyl, $C_{2-4}$ alkynyl, 3- to 6-membered cycloalkyl and 4- to 6-membered heterocycloalkyl, wherein said $C_{1-4}$ alkyl, $C_{2-4}$ alkenyl, $C_{2-4}$ alkynyl, 3- to 6-membered cycloalkyl or 4- to 6-membered heterocycloalkyl is optionally substituted with the group(s) selected from the group consisting of halo, 3- to 4-membered cycloalkyl, 3- to 4-membered heterocycloalkyl, —$OR^8$, oxo, —CN, —$C(O)OR^8$, —$SO_2R^8$, —$C(O)N(R^8)_2$, and $C_{1-3}$ alkyl, wherein $C_{1-3}$ alkyl is optionally substituted with one or more groups selected from the group consisting of fluoro, —CN and —OH;
alternatively, $R^5$ is selected from the group consisting of $C_{1-4}$ alkyl, $C_{2-4}$ alkenyl, $C_{2-4}$ alkynyl, 4- to 6-membered cycloalkyl and 4- to 6-membered heterocycloalkyl, wherein said $C_{1-4}$ alkyl, $C_{2-4}$ alkenyl, $C_{2-4}$ alkynyl, 4- to 6-membered cycloalkyl or 4- to 6-membered heterocycloalkyl is optionally substituted with the group(s) selected from the group consisting of halo, 3- to 4-membered cycloalkyl, 3- to 4-membered heterocycloalkyl, —$OR^8$, oxo, —CN, —$C(O)OR^8$, —$SO_2R^8$, —$C(O)N(R^8)_2$, and $C_{1-3}$ alkyl, wherein $C_{1-3}$ alkyl is optionally substituted with one or more groups selected from the group consisting of fluoro, —CN and —OH;
alternatively, $R^5$ is selected from the group consisting of $C_{1-4}$ alkyl, $C_{2-4}$ alkenyl, $C_{2-4}$ alkynyl, 3- to 6-membered cycloalkyl and 4- to 6-membered heterocycloalkyl, wherein said $C_{1-4}$ alkyl, $C_{2-4}$ alkenyl, $C_{2-4}$ alkynyl, 3- to 6-membered cycloalkyl or 4- to 6-membered heterocycloalkyl is optionally substituted with the group(s) selected from the group consisting of halo, oxo, —OH, —CN, —$C(O)OR^8$, —$C(O)N(R^8)_2$, and $C_{1-3}$ alkyl, wherein $C_{1-3}$ alkyl is optionally substituted with one or more groups selected from the group consisting of fluoro and OH;
alternatively, $R^5$ is selected from the group consisting of $C_{1-4}$ alkyl, $C_{2-4}$ alkenyl, $C_{2-4}$ alkynyl, 3- to 6-membered cycloalkyl and 4- to 6-membered heterocycloalkyl, wherein said $C_{1-4}$ alkyl, $C_{2-4}$ alkenyl, $C_{2-4}$ alkynyl, 3- to 6-membered cycloalkyl or 4- to 6-membered heterocycloalkyl is optionally substituted with the group(s) selected from the group consisting of halo, —OH, —CN, —$C(O)OR^8$, —$C(O)N(R^8)_2$, and $C_{1-3}$ alkyl, wherein $C_{1-3}$ alkyl is optionally substituted with one or more groups selected from the group consisting of fluoro and OH;
alternatively, $R^5$ is selected from the group consisting of $C_{1-4}$ alkyl, $C_{2-4}$ alkenyl, $C_{2-4}$ alkynyl, 4- to 6-membered cycloalkyl and 4- to 6-membered heterocycloalkyl, wherein said $C_{1-4}$ alkyl, $C_{2-4}$ alkenyl, $C_{2-4}$ alkynyl, 4- to 6-membered cycloalkyl or 4- to 6-membered heterocycloalkyl is optionally substituted with the group(s) selected from the group consisting of halo, —OH, —CN, —$C(O)OR^8$, —$C(O)N(R^8)_2$, and $C_{1-3}$ alkyl, wherein C$_{1-3}$ alkyl is optionally substituted with one or more groups selected from the group consisting of fluoro and OH;

alternatively, R$^5$ is selected from the group consisting of C$_{1-4}$ alkyl, C$_{2-4}$ alkynyl, 3- to 6-membered cycloalkyl and 4- to 6-membered heterocycloalkyl, wherein said C$_{1-4}$ alkyl, C$_{2-4}$ alkynyl, 3- to 6-membered cycloalkyl or 4- to 6-membered heterocycloalkyl is optionally substituted with the group(s) selected from the group consisting of halo, oxo, —OH, —C(O)N(R$^8$)$_2$, —C(O)OR$^8$, and C$_{1-3}$ alkyl, wherein C$_{1-3}$ alkyl is optionally substituted with one or more groups selected from the group consisting of OH and fluoro;

alternatively, R$^5$ is selected from the group consisting of C$_{1-4}$ alkyl, C$_{2-4}$ alkynyl, 3- to 6-membered cycloalkyl and 4- to 6-membered heterocycloalkyl, wherein said C$_{1-4}$ alkyl, C$_{2-4}$ alkynyl, 3- to 6-membered cycloalkyl or 4- to 6-membered heterocycloalkyl is optionally substituted with the group(s) selected from the group consisting of halo, —OH, —C(O)N(R$^8$)$_2$, —C(O)OR$^8$, and C$_{1-3}$ alkyl, wherein C$_{1-3}$ alkyl is optionally substituted with the group(s) selected from the group consisting of OH and fluoro;

alternatively, R$^5$ is selected from the group consisting of C$_{1-4}$ alkyl, C$_{2-4}$ alkynyl, 4- to 6-membered cycloalkyl and 4- to 6-membered heterocycloalkyl, wherein said C$_{1-4}$ alkyl, C$_{2-4}$ alkynyl, 4- to 6-membered cycloalkyl or 4- to 6-membered heterocycloalkyl is optionally substituted with the group(s) selected from the group consisting of halo, —OH, —C(O)OR$^8$, and C$_{1-3}$ alkyl, wherein C$_{1-3}$ alkyl is optionally substituted with OH;

alternatively, R$^5$ is selected from the group consisting of C$_{1-4}$ alkyl, C$_{2-4}$ alkynyl, 3- to 6-membered cycloalkyl and 4- to 6-membered heterocycloalkyl, wherein said C$_{1-4}$ alkyl is optionally substituted with the group(s) selected from the group consisting of halo, —OH and —C(O)OR$^8$, wherein the 3- to 6-membered cycloalkyl or 4- to 6-membered heterocycloalkyl is optionally substituted with the group(s) selected from the group consisting of: oxo, —OH, fluoro, —C(O)N(R$^8$)$_2$, and C$_{1-3}$ alkyl, wherein C$_{1-3}$ alkyl is optionally substituted with one or more groups selected from the group consisting of OH and fluoro;

alternatively, R$^5$ is selected from the group consisting of C$_{1-4}$ alkyl, C$_{2-4}$ alkynyl, 3- to 6-membered cycloalkyl and 4- to 6-membered heterocycloalkyl, wherein said C$_{1-4}$ alkyl is optionally substituted with the group(s) selected from the group consisting of halo, —OH and —C(O)OR$^8$, wherein the 3- to 6-membered cycloalkyl or 4- to 6-membered heterocycloalkyl is optionally substituted with the group(s) selected from the group consisting of —OH, fluoro, —C(O)N(R$^8$)$_2$, and C$_{1-3}$ alkyl, wherein C$_{1-3}$ alkyl is optionally substituted with the group(s) selected from the group consisting of OH and fluoro;

alternatively, R$^5$ is selected from the group consisting of C$_{1-4}$ alkyl, C$_3$ alkynyl, 3- to 6-membered cycloalkyl and 4- to 6-membered heterocycloalkyl, wherein said C$_{1-4}$ alkyl group is optionally substituted with the group(s) selected from the group consisting of fluoro, —OH and —C(O)OCH$_3$, wherein said 3- to 6-membered cycloalkyl or 4- to 6-membered heterocycloalkyl is optionally substituted with the group(s) selected from the group consisting of oxo, —OH, fluoro, —C(O)NHCH$_3$, and methyl, wherein methyl is optionally substituted with one or more groups selected from the group consisting of OH and fluoro;

alternatively, R$^5$ is selected from the group consisting of C$_{1-4}$ alkyl, C$_3$ alkynyl, 3- to 6-membered cycloalkyl and 4- to 6-membered heterocycloalkyl, wherein said C$_{1-4}$ alkyl is optionally substituted with the group(s) selected from the group consisting of fluoro, —OH and —C(O)OCH$_3$, wherein said 3- to 6-membered cycloalkyl or 4- to 6-membered heterocycloalkyl is optionally substituted with the group(s) selected from the group consisting of —OH, fluoro, —C(O)NHCH$_3$, and methyl, wherein methyl is optionally substituted with the group(s) selected from the group consisting of OH and fluoro; and alternatively, the "heterocycloalkyl" in the definitions of R$^5$ contains 1 or 2 heteroatoms selected from the group consisting of N, O and S.

11. The compound of Formula I, a stereoisomer, a tautomer, a geometric isomer, a solvate, a hydrate, or a pharmaceutically acceptable salt thereof according to claim 1, wherein:

the structural unit

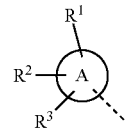

is selected from the group consisting of

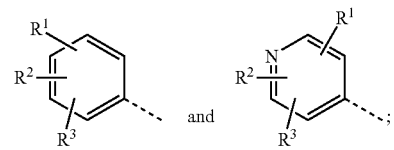

alternatively, the structural unit

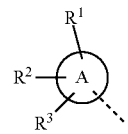

is selected from

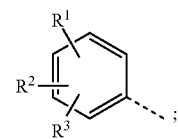

alternatively, the structural unit

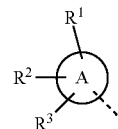

is selected from

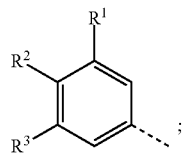

alternatively, the structural unit

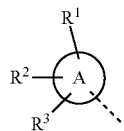

is selected from

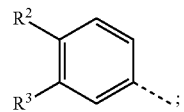

alternatively, the structural unit

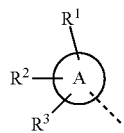

is selected from the group consisting of

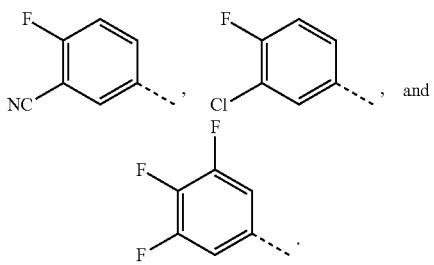

12. The compound of Formula I, a stereoisomer, a tautomer, a geometric isomer, a solvate, a hydrate, or a pharmaceutically acceptable salt thereof according to claim 1, wherein:
the structural unit

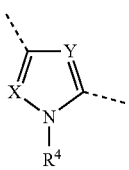

is selected from

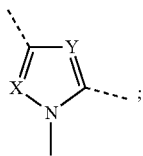

alternatively, the structural unit

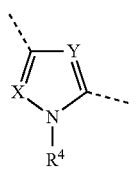

is selected from the group consisting of

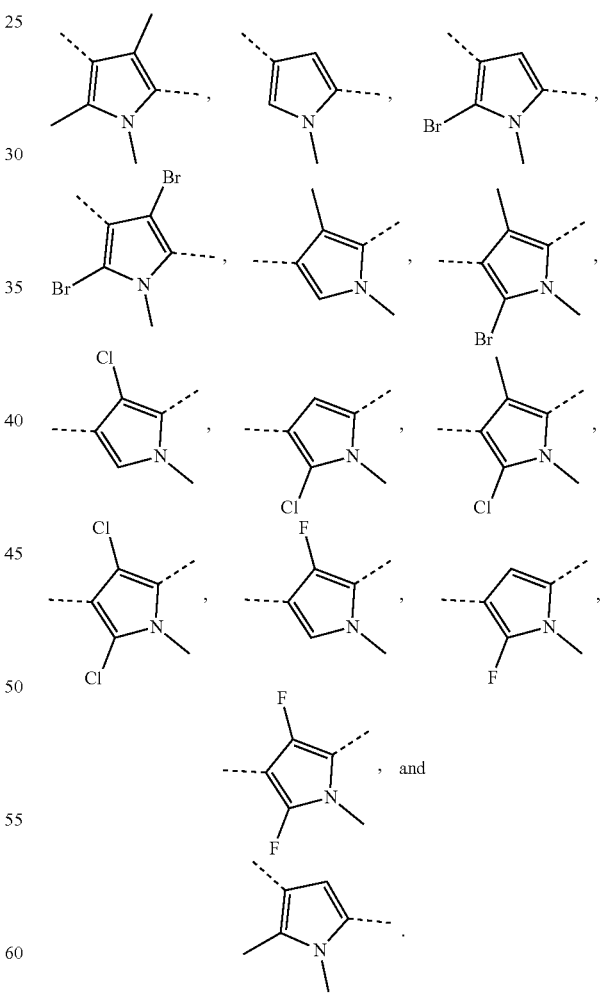

13. The compound of Formula I, a stereoisomer, a tautomer, a geometric isomer, a solvate, a hydrate, or a pharmaceutically acceptable salt thereof according to claim 1, wherein:

137
the structural unit
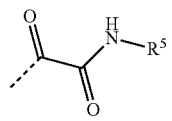
is selected from the group consisting of
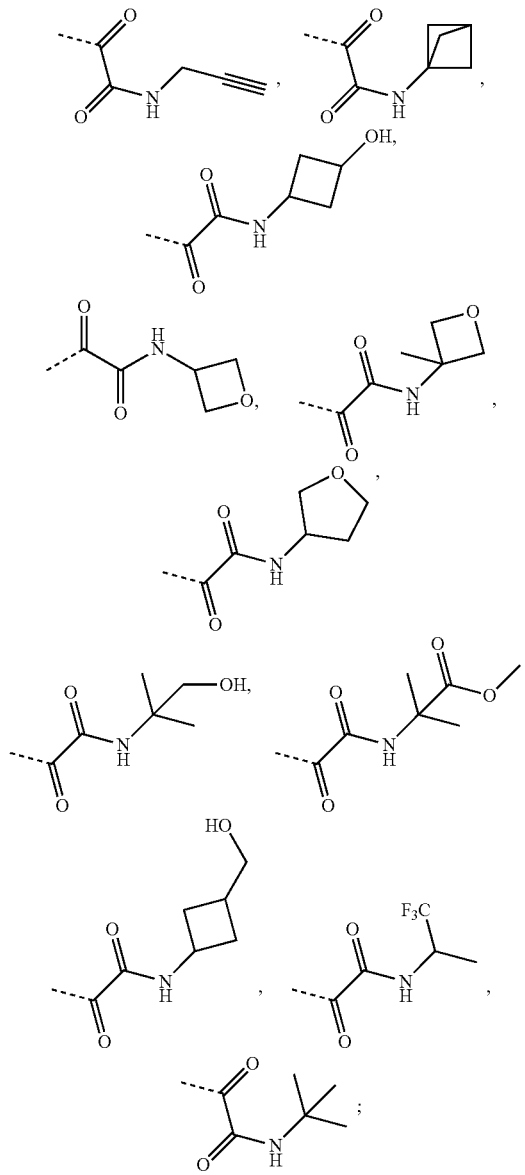
alternatively, the structural unit
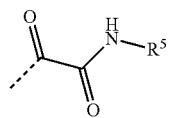
138
is selected from the group consisting of
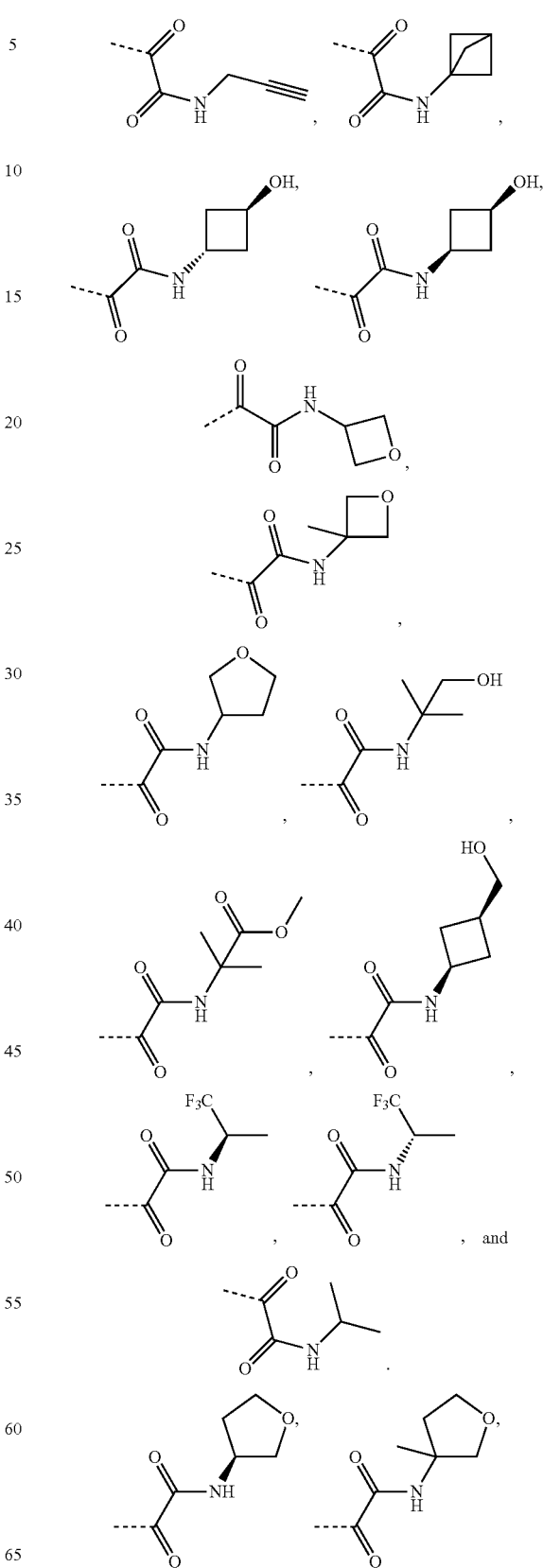

-continued

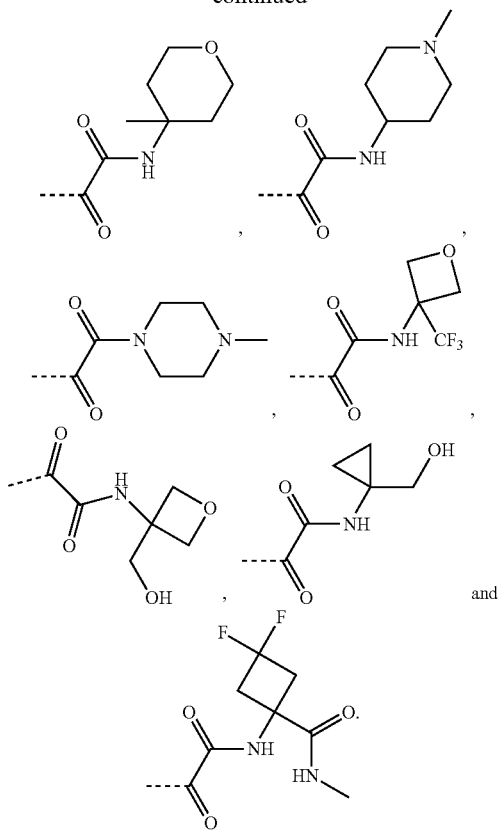

14. The compound of Formula I, a stereoisomer, a tautomer, a geometric isomer, a solvate, a hydrate, or a pharmaceutically acceptable salt thereof according to claim 1, wherein, the compound of Formula I, a stereoisomer, a tautomer, a geometric isomer, a solvate, a hydrate, or a pharmaceutically acceptable salt thereof is selected from a compound of Formula II, a stereoisomer, a tautomer, a geometric isomer, a solvate, a hydrate, or a pharmaceutically acceptable salt thereof,

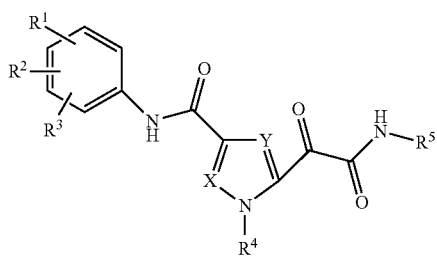

II wherein $R^1$, $R^2$, $R^3$, $R^4$, $R^5$, X, and Y are as defined in claim 1.

15. The compound of Formula I, a stereoisomer, a tautomer, a geometric isomer, a solvate, a hydrate, or a pharmaceutically acceptable salt thereof according to claim 1, wherein, $R^2$ is selected from the group consisting of fluoro, chloro, and bromo, and one of $R^1$ and $R^3$ is hydrogen, and the other is selected from the group consisting of hydrogen, fluoro, chloro, —$CHF_2$, —CN, —$CF_3$ and methyl.

16. The compound of Formula I, a stereoisomer, a tautomer, a geometric isomer, a solvate, a hydrate, or a pharmaceutically acceptable salt thereof according to claim 1, wherein: $R^5$ is selected from the group consisting of $C_{1-4}$ alkyl, $C_{2-4}$ alkynyl, 4- to 6-membered cycloalkyl and 4- to 6-membered heterocycloalkyl, wherein said $C_{1-4}$ alkyl is optionally substituted with the group(s) selected from the group consisting of halo, —OH and —C(O)$OR^8$, wherein the 4- to 6-membered cycloalkyl or 4- to 6-membered heterocycloalkyl is optionally substituted with the group(s) selected from the group consisting of —OH, and $C_{1-3}$ alkyl, wherein $C_{1-3}$ alkyl is optionally substituted with OH.

17. The compound of Formula I, a stereoisomer, a tautomer, a geometric isomer, a solvate, a hydrate, or a pharmaceutically acceptable salt thereof according to claim 1, wherein, the compound of Formula I, a stereoisomer, a tautomer, a geometric isomer, a solvate, a hydrate, or a pharmaceutically acceptable salt thereof is selected from a compound of Formula III, a stereoisomer, a tautomer, a geometric isomer, a solvate, a hydrate, or a pharmaceutically acceptable salt thereof,

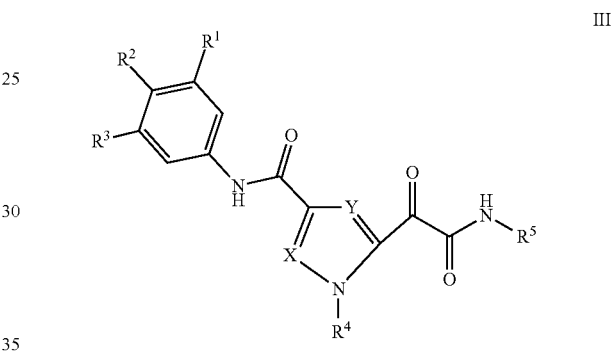

III wherein $R^1$, $R^2$, $R^3$, $R^4$, $R^5$, X, and Y are as defined in claim 1.

18. The compound of Formula I, a stereoisomer, a tautomer, a geometric isomer, a solvate, a hydrate, or a pharmaceutically acceptable salt thereof according to claim 1, wherein, the compound of Formula I, a stereoisomer, a tautomer, a geometric isomer, a solvate, a hydrate, or a pharmaceutically acceptable salt thereof is selected from a compound of Formula IV, a stereoisomer, a tautomer, a geometric isomer, a solvate, a hydrate, or a pharmaceutically acceptable salt thereof,

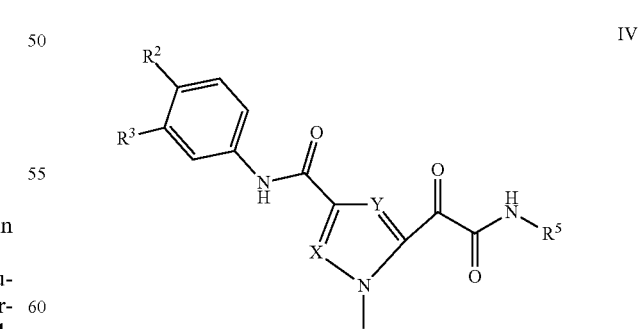

IV wherein $R^2$, $R^3$, $R^5$, X, and Y are as defined in claim 1.

19. A pharmaceutical composition comprising a compound of Formula I, a stereoisomer, a tautomer, a geometric isomer, a solvate, an active metabolite, a hydrate, a prodrug or a pharmaceutically acceptable salt thereof according to claim 1; optionally, the pharmaceutical composition further comprises a pharmaceutically acceptable excipient.

20. A method for treating a disease caused by hepatitis B virus (HBV) infection, comprising administering to a mammal in need of such treatment a therapeutically effective amount of a compound of Formula I, a stereoisomer, a tautomer, a geometric isomer, a solvate, a hydrate, or a pharmaceutically acceptable salt thereof according to claim 1.

\* \* \* \* \*